(12) United States Patent
Nakade et al.

(10) Patent No.: US 7,825,109 B2
(45) Date of Patent: Nov. 2, 2010

(54) COMPOUND CAPABLE OF BINDING S1P RECEPTOR AND PHARMACEUTICAL USE THEREOF

(75) Inventors: Shinji Nakade, Tsukuba (JP); Hirotaka Mizuno, Tsukuba (JP); Takeji Ono, Tsukuba (JP); Masashi Minami, Tsukuba (JP); Hiroshi Saga, Tsukuba (JP); Hiroshi Hagiya, Tsukuba (JP); Takaki Komiya, Tsukuba (JP); Hiromu Habashita, Mishima-gun (JP); Haruto Kurata, Mishima-gun (JP); Kazuhiro Ohtsuki, Mishima-gun (JP); Kensuke Kusumi, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1095 days.

(21) Appl. No.: 10/569,831

(22) PCT Filed: Aug. 27, 2004

(86) PCT No.: PCT/JP2004/012768

§ 371 (c)(1),
(2), (4) Date: Feb. 28, 2006

(87) PCT Pub. No.: WO2005/020882

PCT Pub. Date: Mar. 10, 2005

(65) Prior Publication Data

US 2007/0167425 A1  Jul. 19, 2007

(30) Foreign Application Priority Data

| Aug. 29, 2003 | (JP) | .......................... P. 2003-306088 |
| Apr. 2, 2004 | (JP) | .......................... P. 2004-110573 |
| Jun. 8, 2004 | (JP) | .......................... P. 2004-169958 |
| Jul. 5, 2004 | (JP) | .......................... P. 2004-198523 |

(51) Int. Cl.
*C07D 205/00* (2006.01)
*A61K 31/397* (2006.01)

(52) U.S. Cl. .................................. 514/210.17; 548/953

(58) Field of Classification Search ........................ None
See application file for complete search history.

(56) References Cited

U.S. PATENT DOCUMENTS

2003/0139597 A1  7/2003  Xue et al.

FOREIGN PATENT DOCUMENTS

| EP | 0635492 A1 | 1/1995 |
| WO | WO 96/13497 A1 | 5/1996 |
| WO | 98/38156 A1 | 9/1998 |
| WO | 01/21577 A2 | 3/2001 |
| WO | WO 02/18377 A1 | 3/2002 |
| WO | WO 02/092068 A1 | 11/2002 |
| WO | WO 03/061567 A2 | 7/2003 |
| WO | WO 03/062248 A2 | 7/2003 |
| WO | WO 03/062252 A1 | 7/2003 |
| WO | 03/091219 A1 | 11/2003 |
| WO | 2004/026305 A1 | 4/2004 |
| WO | 2004/113330 A1 | 12/2004 |

OTHER PUBLICATIONS

Shen et al, Archiv der Pharmazie, 1995, 328(2), 197-201.*
West, Anthony R., Solid State Chemistry and its Applications, Wiley, New York, 1988, pp. 358 & 365.*
Warrener et al, Journal of the Chemical Society, Chemical Communications (1981), (21), 1100-1.*
Wu et al., Toxicology, 236, pp. 1-6, 2007.*
Matthew J. Fischer, et al.; "Dihydroisoquinolone RGD MIMICS. Exploration of the Asparate Isostere"; Bioorganic & Medicinal Chemistry Letters; vol. 7 No. 19, pp. 2537-2542; Elsevier Science Ltd., 1997.
Russian Office Action dated Oct. 9, 2009 in Application No. 20070126654.
M.D. Mashkovsky, "Lekarstvennie Sredstva," Moskva, vol. 1, p. 8 (1993), Partial English Translation.
"Khimicheskii Enciklopedicheskii Slovar," Moskva, "Sovetskaya Enciklopediya," pp. 130-131 (1983), Partial English Translation.
Office Action issued on May 3, 2010 in the co-pending U.S. Appl. No. 11/721,601.
Chawla G., et al., "Challenges in Polymorphism of Pharmaceuticals", CRIPS vol. 5, No. 1; Jan.-Mar. 2004; pp. 9-12.
Newman A. W., et al., "Solid-state analysis of the active pharmaceutical ingredient in drug products"; DDT vol. 8, No. 19; Oct. 2003; pp. 898-905.
Nakade S., et al., Caplus an 2005:216595, RN 847585-40-4.
International Search Report dated Feb. 15, 2005.

* cited by examiner

*Primary Examiner*—Zinna N Davis
(74) *Attorney, Agent, or Firm*—Sughrue Mion, PLLC

(57) ABSTRACT

A compound having an ability to bind to an S1P receptor (particularly EDG-6, preferably EDG-1 and EDG-6), for example, the compound represented by formula (I) of the present invention, a salt thereof, a solvate thereof or a prodrug thereof is useful for prevention and/or treatment of rejection of transplantation, graft-versus-host disease, autoimmune disease, allergic disease and the like.

(I)

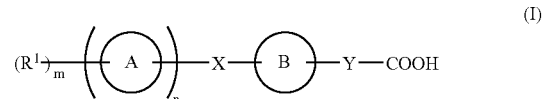

wherein ring A is a cyclic group; ring B is a cyclic group which may have substituent(s); X is a spacer having 1 to 8 atoms in its main chain, etc.; Y is a spacer having 1 to 10 atoms in its main chain, etc.; n is 0 or 1, wherein when n is 0, m is 1 and $R^1$ is a hydrogen atom or a substituent, and wherein when n is 1, m is 0 or an integer of 1 to 7 and $R^1$ is a substituent, and wherein m is 2 or more, $R^1$s are the same or different.

21 Claims, No Drawings

COMPOUND CAPABLE OF BINDING S1P RECEPTOR AND PHARMACEUTICAL USE THEREOF

This application is a 371 PCT/JP04/12768 filed Aug. 27, 2004 which claims priority to JP 2003-306088 filed Aug. 29, 2003.

TECHNICAL FIELD

The present invention relates to a compound having an ability to bind to a sphingosine-1-phosphate (hereinafter referred to as S1P in some cases) receptor which is useful as a medicament and a medicament containing the same as an active ingredient.

More specifically, the present invention relates to:
(1) a compound having an ability to bind to an S1P receptor (in particular, EDG-6, preferably EDG-1 and EDG-6);
(2) a medicament containing the compound as an active ingredient;
(3) a compound represented by the following formula (I):

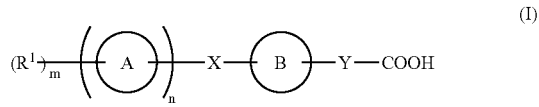

wherein all symbols have the same meanings as described below;
a prodrug thereof and a salt thereof; and
(4) a medicament containing the compound represented by formula (I), a prodrug thereof and a salt thereof as an active ingredient.

BACKGROUND ART

Sphingosine-1-phosphate (S1P) having the structural formula represented by formula (A) is a lipid that is produced by the intracellular metabolic turnover of sphingolipids or the extracellular action of secretory sphingosine kinase. It is pointed out that S1P acts as an intercellular and intracellular messenger (*Biochem. Pharm.*, 58, 201 (1999)).

As biological action of S1P, inhibition of migration of smooth muscle cells or cancer cells, platelet aggregation, induction of cell chemotaxis, inhibition of cell chemotaxis and the like are known in vitro experiments, and as the results of in vivo experiments, it is known that S1P shows effects of controlling blood pressure, promoting angiogenesis, reducing renal blood flow, inhibiting lung fibrosis, promoting the lymphocyte homing into lymphatic organs and the like. It is considered that these various physiological effects are mediated by S1P receptors existing in cell membrane. However, it has been scarcely clarified excluding some cases which subtypes of S1P receptors mediate these effects in practice.

Recently, from the study for EDG-1 knock-out mice, it is strongly indicated that S1P induced angiogenesis via EDG-1 (Yujing Liu, et al., *J. Clin. Invest.*, 106, 951 (2000)). Therefore, it is suggested that EDG-1 agonist is used as a treating agent for disease caused by anangioplasia. For example, it is used as an agent for prevention and/or treatment of peripheral arterial disease such as arteriosclerosis obliterans, thromboangiitis obliterans, Buerger's disease or diabetic neuropathy; varicose vein such as hemorrhoid, anal fissure, anal fistula; dissecting aneurysm of the aorta, sepsis, inflammatory disease such as angiitis, nephritis or pneumonia, various edematous disease caused by ischemia of various organ or increase of the blood permeability, for example, myocardial infarction, cerebral infarction, angina, DIC (disseminated intravascular coagulation), pleuritis, congestive heart failure or multiple organ failure. Furthermore, it is used as an accentuation agent for healing of wound in cornea, skin, digestive organs or the like, for example, an agent for prevention and/or treatment for bedsore, burn, chronic ulcerative colitis or Crohn's disease. In addition, it is used as a preoperative, postoperative and/or prognostic activator for blood vessel accompanying transplantation of various organs, for example, as an adhesion activator of transplanted organs such as heart transplantation, renal transplantation, dermal transplantation or liver transplantation.

Different from other EDG receptors, on the other hand, EDG-6 is localized and strongly expressed in cells of the lymphatic and hematopoietic systems including spleen, leukocytes, lymph gland, thymus, bone marrow, lung and the like, which suggests the possibility of closely relating to the

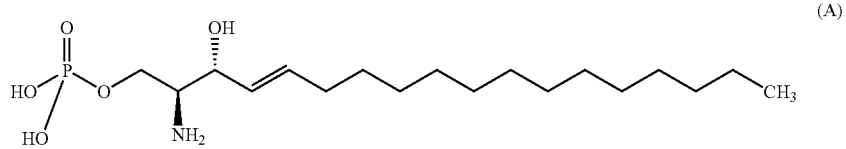

(A)

As receptors of S1P, EDG-1 which is a G protein-coupled receptor and its analogous molecules, EDG-3, EDG-5, EDG-6 and EDG-8 (also called $S1P_1$, $S1P_3$, $S1P_2$, $S1P_4$ and $S1P_5$, respectively) are known. They are called EDG receptor family together with EDG-2, EDG-4 and EDG-7 which are receptors of lysophosphatidic acid (LPA). S1P receptors binds to S1P and deliver signals into cells via G-protein coupled with the receptors. Gs, Gi, Gq and $G_{12/13}$ are known as G-proteins to which S1P receptor can couple, and it is considered that the receptor relates to responses such as increase of cell proliferation, suppression of cell proliferation, induction of cell chemotaxis and inhibition of cell chemotaxis.

effects of S1P in the course of inflammation or in the immune system (*Biochem. Biophys. Res. Commun.*, 268, 583 (2000)).

Moreover, it is known that the EDG-6 polypeptide or its homolog is concerned with immunomodulation, antiinflammation and the like, which brings about the potential usability of these substances in treating autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, arteriosclerosis, diseases associated with lymphocyte infiltration into a tissue and the like.

Accordingly, it appears that drugs acting against EDG-6 are useful as preventives and/or remedies for rejection in transplantation, rejection of a transplanted organ, transplantation versus host disease, autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, arteriosclerosis, diseases associated with lymphocyte infiltration into a tissue and the like.

It is known that 2-amino-2-[2-(4-octylphenyl)ethyl]-1,3-propanediol hydrochloride (CAS Registration No. 162359-56-0, hereinafter referred to as "FTY720") having a sphingosine-like structure has an immune suppressive effect. However, the target molecule thereof has remained unknown for a long time. Recently, it is clarified that FTY720 is phosphorylated in vivo and the phosphorylated FT-720 binds to an S1P receptor (see *Science,* 296, 346 (2002); and *J. Biol. Chem.,* 277, 21453 (2002)). As the results of detailed studies, it is found out that phosphorylated FTY720 binds to multiple subtypes of the S1P receptors, i.e., EDG-1, EDG-3, EDG-6 and EDG-8.

FTY720 is one of 2-amino-1,3-propanediol compounds represented by formula (Y):

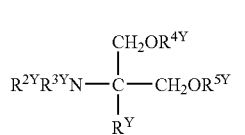

wherein $R^Y$ represents a linear or branched carbon chain which may have a substituent(s), aryl which may have a substituent(s), cycloalkyl which may have a substituent(s), etc; and $R^{2Y}$, $R^{3Y}$, $R^{4Y}$ and $R^{5Y}$ are the same or different and each represents a hydrogen atom, alkyl, aralkyl, acyl or alkoxycarbonyl (only necessary parts of the definitions of the symbols are extracted). It is disclosed that these compounds are useful as immunosuppressants (see WO 94/008943).

As the results of a recent clinical trial on FTY720 in human kidney transplantation, it is reported that FTY720 has an effect of significantly lowering the incidence rate of acute rejection. It is found out that FTY720 exerts the major effect of reducing the lymphocyte count in the peripheral blood without suppressing the proliferation or activation, the memory function and the ability to recognize a foreign matter in viral infection of lymphocytes. Thus, it is indicated that FTY720 is useful in treating diseases such as rejection in transplantation.

However, it is also reported that FTY720 has a side effect of causing bradycardia after administration (*J. Am. Soc. Nephrol.,* 13, 1073 (2002)). Therefore, attention should be sufficiently given in using it. Accordingly, there has been required a highly safe drug which shows a high therapeutic effect and yet has little side effect.

Recently, it is reported that an EDG-1 agonist is useful as an immunosuppressant. However, it has never been stated that an EDG-6 agonist or antagonist is useful as an immunosuppressant (see WO 03/061567).

Moreover, it is disclosed that a compound represented by formula (S):

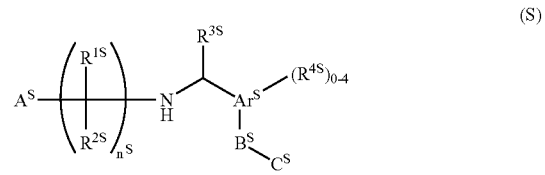

wherein $Ar^S$ represents phenyl or naphthyl; $A^S$ represents carboxy, etc.; $n^S$ represents 2, 3 or 4; $R^{1S}$ and $R^{2S}$ each independently represents a hydrogen atom, a halogen atom, hydroxy, carboxy, C1-6 alkyl which may be substituted with 1 to 3 halogen atoms or phenyl which may be substituted with 1 to 3 halogen atoms; $R^{3S}$ represents a hydrogen atom or C1-4 alkyl which may be substituted with 1 to 3 hydroxy or halogen atoms; $R^{4S}$s each independently represents hydroxy, a halogen atom, carboxy, etc.; $C^S$ represents C1-8 alkyl, C1-8 alkoxy, phenyl, etc. or $C^S$ is nil; and $B^S$ represents phenyl, C5-16 alkyl, etc. (only necessary parts of the definitions of the symbols are extracted);

a pharmaceutically acceptable salt thereof and a hydrate thereof, and a compound represented by formula (T):

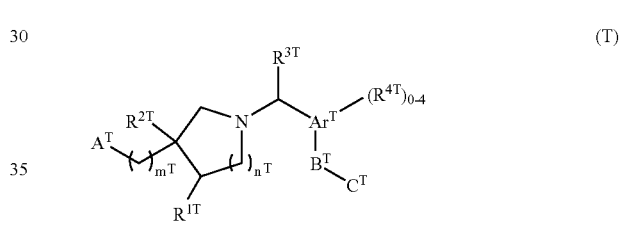

wherein $Ar^T$ represents phenyl or naphthyl; $A^T$ represents carboxy, etc.; $m^T$ represents 0 or 1; $n^T$ represents 0 or 1; $R^{1T}$ and $R^{2T}$ each independently represents a hydrogen atom, a halogen atom, hydroxy, carboxy, C1-4 alkyl or phenyl which may be substituted with a halogen atom, etc.; $R^{3T}$ represents a hydrogen atom, C1-4 alkyl which may be substituted with hydroxy or a halogen atom, etc.; $R^{4T}$'s each independently represents a halogen atom, C1-4 alkyl, C1-3 alkoxy, etc.; $C^T$ represents C1-8 alkyl, C1-8 alkoxy, phenyl, etc. or $C^T$ is nil; and $B^T$ represents phenyl, C5-16 alkyl, etc. (only necessary parts of the definitions of the symbols are extracted);

a pharmaceutically acceptable salt thereof and a hydrate thereof are useful as EDG-1 agonists (see WO 03/062248 and WO 03/062252).

Also, as an EDG-1 agonist, known is a carboxylic acid derivative represented by formula (Z):

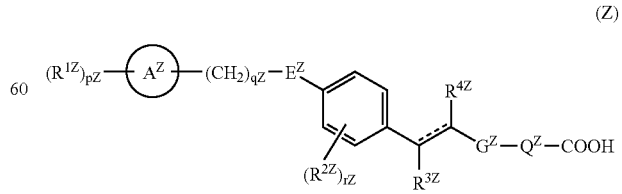

wherein $R^{1Z}$ represents C1-8 alkyl, C1-8 alkoxy, a halogen atom, nitro or trifluoromethyl; ring $A^Z$ represents a C5-7 monocyclic carbocyclic group or a 5- to 7-membered monocyclic heterocyclic group containing one or two nitrogen atoms, one oxygen atom and/or one sulfur atom; $E^Z$ represents —$CH_2$—, —O—, —S— or —$NR^{6Z}$—, in which $R^{6Z}$ represents a hydrogen atom or C1-8 alkyl; $R^{2Z}$ represents C1-8 alkyl, C1-8 alkoxy, a halogen atom, nitro or trifluoromethyl; $R^{3Z}$ represents a hydrogen atom or C1-8 alkyl; $R^{4Z}$ represents a hydrogen atom or C1-8 alkyl, or $R^{2Z}$ and $R^{4Z}$ may be taken together to form —$CH_2CH_2$— or —CH=CH—; $G^Z$ represents —$CONR^{7Z}$—, —$NR^{7Z}CO$—, —$SO_2NR^{7Z}$—, —$NR^{7Z}SO_2$—, —$CH_2NR^{7Z}$— or —$NR^{7Z}CH_2$—, in which $R^{7Z}$ represents a hydrogen atom, C1-8 alkyl or the like; $Q^Z$ represents C1-4 alkylene or the like; $p^Z$ represents 0 or an integer of 1 to 5; $q^Z$ represents an integer of 4 to 6; $r^Z$ represents 0 or an integer of 1 to 4; ----- represents a single bond or a double bond, a prodrug thereof or a non-toxic salt thereof (WO02/092068).

DISCLOSURE OF THE PRESENT INVENTION

Immunosuppressants are useful in preventing and/or treating inflammatory diseases, allergic diseases and/or rejection in transplantation. However, it is known that many of immunosuppressants used at present have severe side effects at a considerably high frequency. Furthermore, they suffer from reduction in the effects thereof within a short period of time. It is feared that FTY720 as described above is also affected by a metabolic enzyme. Moreover, it is reported that FTY720 actually shows side effects including bradycardia at clinical trials. Therefore, it has been urgently required to develop a drug which exhibits a prolonged pharmacological effect, has little side effects, shows a high safety and is never affected by metabolic enzymes.

As the results of intensive studies on sphigosine-1-phosphate (S1P) receptors being useful as medicines, the present inventors unexpectedly found out that the present invention compounds have a strong ability to bind to EDG-6. They also found out that some of the present invention compounds have a strong agonistic activity against EDG-1. They have further found out that these invention compounds having an ability to bind to EDG-6, in particular, the present invention compounds having the agonistic activity against EDG-1 have additional effects of reducing lymphocytes in the peripheral blood and immunosuppressive action. Furthermore, they have surprisingly found out that the pharmacological activities of these invention compounds can be sustained over a long time, thereby completing the present invention.

The present invention relates to the followings:

1. A compound represented by formula (I):

$$(R^1)_m - \left(\!\!\left(A\right)\!\!\right)_n - X - \left(B\right) - Y - COOH \tag{I}$$

wherein ring A represents a cyclic group;

ring B represents a cyclic group which may further have a substituent(s);

X represents a bond or a spacer having 1 to 8 atoms in its main chain in which one atom in the spacer may be taken together with a substituent on ring B to form a ring group which may have a substituent(s);

Y represents a bond or a spacer having 1 to 10 atoms in its main chain in which one atom in the spacer may be taken together with a substituent on ring B to form a ring group which may have a substituent(s);

n represents 0 or 1, wherein when n is 0, m is 1 and $R^1$ represents a hydrogen atom or a substituent, and when n is 1, m is 0 or an integer of 1 to 7 and $R^1$ represents a substituent in which when m is 2 or more, plural $R^1$s are the same or different, a salt thereof, a solvate thereof or a prodrug thereof 2. The compound according to the above item 1, which is a compound represented by formula (I):

$$(R^1)_m - \left(\!\!\left(A\right)\!\!\right)_n - X - \left(B\right) - Y - COOH \tag{I}$$

wherein all symbols have the same meanings as in the above item 1, and wherein a compound represented by formula (Ia) is excluded:

$$(R^{1a})_p - \left(A^a\right) - (CH_2)_q - E^a - \underset{(R^{2a})_r}{\overset{R^{4a}}{\diagdown}} \underset{R^{3a}}{\diagdown} G^a - Q^a - COOH \tag{Ia}$$

wherein $R^{1a}$ represents C1-8 alkyl, C1-8 alkoxy, a halogen atom, nitro or trifluoromethyl;

ring $A^a$ represents a C5-7 monocyclic carbocyclic group or a 5- to 7-membered monocyclic heterocyclic group containing one or two nitrogen atoms, one oxygen atom and/or one sulfur atom;

$E^a$ represents —$CH_2$—, —O—, —S— or —$NR^{6a}$—, in which $R^{6a}$ represents a hydrogen atom or C1-8 alkyl;

$R^{2a}$ represents C1-8 alkyl, C1-8 alkoxy, a halogen atom, nitro or trifluoromethyl;

$R^{3a}$ represents a hydrogen atom or C1-8 alkyl;

$R^{4a}$ represents a hydrogen atom or C1-8 alkyl, or $R^{2a}$ and $R^{4a}$ may be taken together to form —$CH_2CH_2$— or —CH=CH—;

$G^a$ represents —$CONR^{7a}$—, —$NR^{7a}CO$—, —$SO_2NR^{7a}$—, —$NR^{7a}SO_2$—, —$CH_2NR^{7a}$— or —$NR^{7a}CH_2$—, in which $R^{7a}$ represents a hydrogen atom, C1-8 alkyl, Cyc1 or C1-8 alkyl substituted with Cyc1, and Cyc1 represents a C5-7 monocyclic carbocyclic group or a 5- to 7-membered monocyclic heterocyclic group containing one or two nitrogen atoms, one oxygen atom and/or one sulfur atom;

$Q^a$ represents C1-4 alkylene or $$\underset{(R^{5a})_s}{\overset{J^1}{\diagup}\!\!\overset{}{\underset{J^2}{\diagdown}}\!\!\overset{}{\underset{J^3}{\diagup}}\!\!\overset{J^4}{\diagdown}}$$

wherein $J^1$, $J^2$, $J^3$ and $J^4$ each independently represents a carbon atom or a nitrogen atom in which the number of the nitrogen atom(s) is 2 or less; $R^{5a}$ represents (1) C1-8 alkyl, (2)

a halogen atom, (3) nitro, (4) cyano, (5) trifluoromethyl, (6) trifluoromethoxy, (7) phenyl, (8) tetrazolyl, (9) —OR$^{9a}$, (10) —SR$^{10a}$, (11) —COOR$^{11a}$, (12) —NR$^{12a}$R$^{13a}$, (13) —CONR$^{14a}$R$^{15a}$, (14) —SO$_2$NR$^{16a}$R$^{17a}$, (15) —NR$^{18a}$COR$^{19a}$, (16) —NR$^{20a}$SO$_2$R$^{21a}$, (17) SO$_2$R$^{22a}$, or (18) —OP(O)(OR$^{23a}$)$_2$, in which R$^{9a}$ to R$^{18a}$, R$^{20a}$ and R$^{23a}$ each independently represents a hydrogen atom, C1-8 alkyl, Cyc2 or C1-8 alkyl substituted with Cyc2, or R$^{12a}$ and R$^{13a}$, R$^{14a}$ and R$^{15a}$, or R$^{16a}$ and R$^{17a}$ may be taken together with a nitrogen atom to which they are bound, to form a 5- to 7-membered monocyclic heterocyclic group containing one or two nitrogen atoms, one oxygen atom and/or one sulfur atom, in which the heterocyclic group may be substituted with C1-8 alkyl, hydroxy or amino; R$^{19a}$ and R$^{21a}$ each independently represents C1-8 alkyl, Cyc2 or C1-8 alkyl substituted with Cyc2; R$^{22a}$ represents hydroxy, C1-8 alkyl, Cyc2 or C1-8 alkyl substituted with Cyc2; and Cyc2 represents a C5-7 monocyclic carbocyclic group or a 5- to 7-membered monocyclic heterocyclic group containing one or two nitrogen atoms, one oxygen atom and/or one sulfur atom;

p represents 0 or an integer of 1 to 5;
q represents an integer of 4 to 6;
r represents 0 or an integer of 1 to 4;
s represents 0 or an integer of 1 to 4; and
----- represents a single bond or a double bond.

3. The compound according to the above item 2, which is represented by formula (IA):

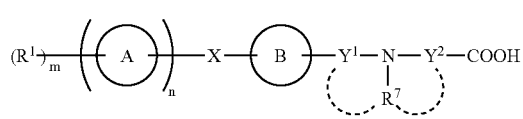

(IA)

wherein Y$^1$ and Y$^2$ each independently represents a bond or a spacer having 1 to 9 atoms in its main chain in which the total atom number of the main chains of Y$^1$ and Y$^2$ is 9 or less;

R$^7$ represents a hydrogen atom or a substituent, or may be taken together with one atom in the spacer represented by Y$^1$ and/or Y$^2$ to form a nitrogen-containing heterocyclic group which may have a substituent(s); and other symbols have the same meanings as described in the above item 1.

4. The compound according to the above item 2, which is represented by formula (IB):

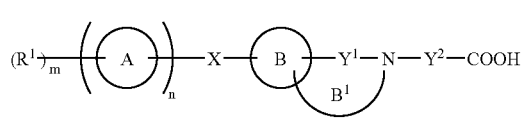

(IB)

wherein ring B$^1$ represents a nitrogen-containing heterocyclic group which may have a substituent(s) in which a nitrogen atom in the spacer represented by Y is taken together with a substituent on ring B and Y$^1$; and other symbols have the same meanings as described in the above items 1 and 3.

5. The compound according to the above item 2, wherein ring A is a benzene, indane, indene or naphthalene ring.

6. The compound according to the above item 2, wherein ring B is a C5-12 monocyclic or bicyclic carbocyclic group which may have a substituent(s).

7. The compound according to the above item 6, wherein ring B is a benzene or naphthalene ring which may have a substituent(s).

8. The compound according to the above item 2, wherein ring B is a 5- to 12-membered monocyclic or bicyclic heterocyclic group which contains 1 to 3 hetero atoms selected from an oxygen atom, a nitrogen atom and a sulfur atom and may be partially or fully saturated.

9. The compound according to the above item 2, wherein ring B is a dihydronaphthalene, indene, 6,7-dihydro-5H-benzo[7]annulene, pyridine, indole, chromene, benzofuran, benzothiophene, benzoxazole, dihydrobenzoxepine, tetrahydroisoquinoline, isoindoline or tetrahydrobenzazepine ring which may have a substituent(s).

10. The compound according to the above item 4, wherein the nitrogen-containing heterocyclic group represented by ring B$^1$ is a pyrrole, tetrahydropyridine, dihydropyrrole or tetrahydroazepine ring.

11. The compound according to the above item 2, wherein X is a divalent group having 1 to 8 atoms in its main chain which is 1 to 4 combinations selected from the group consisting of C1-8 alkylene which may be substituted, C2-8 alkenylene which may be substituted, a nitrogen atom which may be substituted, —CO—, —O—, C3-6 cycloalkylene which may be substituted and phenylene which may be substituted.

12. The compound according to the above item 11, wherein X is —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —H$_2$—O—, —(CH$_2$)$_2$—O—, —(CH$_2$)$_3$—O—, —(CH$_2$)$_4$—O—, —(CH$_2$)$_5$—O—, —CH═CH—CH$_2$—O— or -cyclopropylene-CH$_2$—O—, which each may be substituted, in which the right side of each group is bound to ring B.

13. The compound according to the above item 2, wherein Y is a divalent group having 1 to 10 atoms in its main chain which is 1 to 4 combinations selected from the group consisting of C1-10 alkylene which may be substituted, C2-10 alkenylene which may be substituted, C2-10 alkynylene which may be substituted, a nitrogen atom which may be substituted, —CO—, —O—, —S—, phenylene which may be substituted, -(aziridine which may be substituted)-, -(azetidine which may be substituted)-, -(pyrrolidine which may be substituted)-, -(piperidine which may be substituted)-, -(piperazine which may be substituted)- and -(tetrahydropyridine which may be substituted)-.

14. The compound according to the above item 13, wherein Y is —(CH$_2$)$_3$—NHCH$_2$—, —(CH$_2$)$_3$—NCH$_3$—CH$_2$—, —(CH$_2$)$_3$—NH—(CH$_2$)$_2$—, —(CH$_2$)$_2$—NH—(CH$_2$)$_2$—, —(CH$_2$)$_2$—CONHCH$_2$—, —(CH$_2$)$_2$—CONH-(m-phenylene)-, —CR$^{Y1}$═CH—CH$_2$—NH—(CH$_2$)$_4$—, —CR$^{Y1}$═CH—CH$_2$—NH—(CH$_2$)$_5$—, —CR$^{Y1}$═CH—CH$_2$—NH—(CH$_2$)$_2$—, —CH═CR$^{Y1}$-CH$_2$—NH—(CH$_2$)$_2$—, —CR$^{Y1}$═CH—CH$_2$—NH—CH$_2$—, —CH$_2$— (azetidine)-, —(CH$_2$)$_2$-(azetidine)-, —(CH$_2$)$_3$-(azetidine)-, —CR$^{Y1}$═CH—CH$_2$— (azetidine)-, —CH═CR$^{Y1}$—CH$_2$— (azetidine)-, —(CH$_2$)$_3$-(piperidine)- or —CR$^{Y1}$═CH—CH$_2$-(piperidine)-, which each may be substituted, in which R$^{Y1}$ represents a hydrogen atom, a halogen atom or C1-4 alkyl which may be substituted with 1 to 3 halogen atoms, and the right side of each group is bound to ring B.

15. The compound according to the above item 3, wherein Y$^1$ is a divalent group having 1 to 4 atoms in its main chain which is 1 to 4 combinations selected from the group consisting of C1-3 alkylene and —CO—.

16. The compound according to the above item 15, wherein Y¹ is —CH₂—, —(CH₂)₂—, —(CH₂)₂—CO—, —CO—(CH₂)₂— or —(CH₂)₃—, which each may be substituted.

17. The compound according to the above item 3, wherein Y² is a divalent group having 1 to 5 atoms in its main chain which is 1 to 4 combinations selected from the group consisting of C1-3 alkylene which may be substituted and phenylene which may be substituted.

18. The compound according to the above item 17, wherein Y² is —CH₂—, —(CH₂)₂— or -(m-phenylene)-, which each may be substituted.

19. The compound according to the above item 2, wherein the substituent represented by R¹ is a halogen atom, C1-20 alkyl which may be substituted, or C1-20 alkyloxy which may be substituted.

20. The compound according to the above item 19, wherein the substituent represented by R¹ is fluoro, chloro, bromo, methyl, trifluoromethyl or methoxy.

21. The compound according to the above item 3, wherein R⁷ is a hydrogen atom or C1-20 alkyl which may be substituted.

22. The compound according to the above item 2, which is a compound represented by formula (I-S-3a):

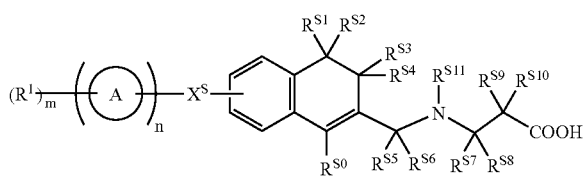

(I-S-3a)

wherein $X^S$ has the same meaning as X described in the above item 1, in which $X^S$ is not —(CH₂)$_q$-E$^a$-; $R^{S0}$, $R^{S1}$, $R^{S2}$, $R^{S3}$, $R^{S4}$, $R^{S5}$, $R^{S6}$, $R^{S7}$, $R^{S8}$, $R^{S9}$, $R^{S10}$ and $R^{S11}$ each independently represents a hydrogen atom, a halogen atom, or C1-4 alkyl which may be substituted with 1 to 3 halogen atoms; E$^a$, q and other symbols have the same meanings as described in the above items 1 and 2, or formula (I-S-7a):

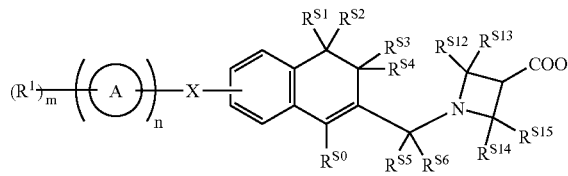

(I-S-7a)

wherein $R^{S0}$, $R^{S1}$, $R^{S2}$, $R^{S3}$, $R^{S4}$, $R^{S5}$ and $R^{S6}$ each has the same meaning as described above; $R^{S12}$, $R^{S13}$, $R^{S14}$ and $R^{S15}$ each independently represents a hydrogen atom, a halogen atom, or C1-4 alkyl which may be substituted with 1 to 3 halogen atoms; E$^a$, q and other symbols have the same meanings as described in the above items 1 and 2.

23. The compound according to the above item 2, which is a compound represented by formula (I-T):

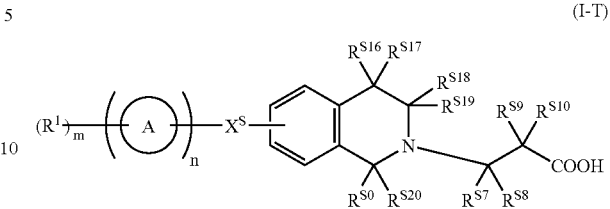

(I-T)

wherein $R^{S16}$, $R^{S17}$, $R^{S18}$, $R^{S19}$ and $R^{S20}$ each independently represents a hydrogen atom, a halogen atom, or C1-4 alkyl which may be substituted with 1 to 3 halogen atoms; and other symbols have the same meanings as described in the above items 1, 2 and 22.

24. The compound according to the above item 2, which is a compound represented by formula (I-U):

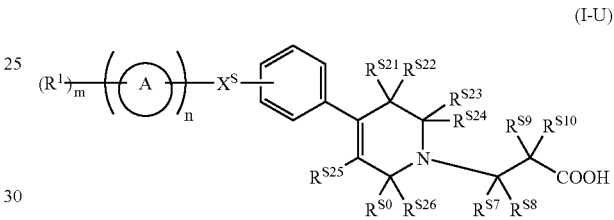

(I-U)

wherein $R^{S21}$, $R^{S22}$, $R^{S23}$, $R^{S24}$, $R^{S25}$ and $R^{S26}$ each independently represents a hydrogen atom, a halogen atom, or C1-4 alkyl which may be substituted with 1 to 3 halogen atoms; and other symbols have the same meanings as described in the above items 1, 2 and 22.

25. The compound according to the above item 2, which is
(1) N-{(2E)-3-[4-(3-phenylpropoxy)phenyl]prop-2-enyl}-β-alanine,
(2) N-{[6-(3-phenylpropoxy)-2-naphthyl]methyl}-β-alanine,
(3) 1-{[6-(3-phenylpropoxy)-2-naphthyl]methyl}azetidine-3-carboxylic acid,
(4) 1-{[6-(3-phenylpropoxy)-2-naphthyl]methyl}piperidine-4-carboxylic acid,
(5) N-{(2E)-3-[2-methyl-4-(3-phenylpropoxy)phenyl]prop-2-enyl}-β-alanine,
(6) 1-{(2E)-3-[4-(3-phenylpropoxy)phenyl]-2-propenyl}piperidine-4-carboxylic acid,
(7) 1-{(2E)-3-[4-(3-phenylpropoxy)phenyl]-2-propenyl}azetidine-3-carboxylic acid,
(8) N-{3-[4-(3-phenylpropoxy)phenyl]propyl})-β-alanine,
(9) 3-({(2E)-3-[4-(3-phenylpropyl)phenyl]-2-butenyl}amino)propanoic acid,
(10) 3-({(2E)-3-[4-(3-cyclohexylpropoxy)-2-methylphenyl]-2-propenyl}amino)propanoic acid,
(11) 1-{[1-methyl-6-(4-phenylbutoxy)-3,4-dihydro-2-naphthalenyl]methyl}-3-azetidinecarboxylic acid,
(12) N-{[1-(5-phenylpentyl)-1H-indol-5-yl]methyl}-β-alanine,
(13) 3-[4-[4-(3-phenylpropoxy)phenyl]-3,6-dihydropyridin-1(2H)-yl]propanoic acid,
(14) 1-(6-[3-(4-chlorophenyl)propoxy]-1-methyl-3,4-dihydro-2-naphthalenylmethyl)-3-azetidinecarboxylic acid, or
(15) 1-(6-[3-(4-fluorophenyl)propoxy]-1-methyl-3,4-dihydro-2-naphthalenylmethyl)-3-azetidinecarboxylic acid.

26. The compound according to the above item 1, which is
(1) N-((2E)-3-{2-methyl-4-[(5-phenylpentyl)oxy]phenyl}prop-2-enyl)-β-alanine,
(2) N-((2E)-3-{4-[(5-phenylpentyl)oxy]phenyl}-2-propenyl)-β-alanine, or
(3) 3-({[1-methyl-6-(4-phenylbutoxy)-3,4-dihydro-2-naphthalenyl]methyl}amino)propanoic acid.

27. A pharmaceutical composition which comprises a compound represented by formula (I) in the above item 1, a salt thereof, a solvate thereof or a prodrug thereof 28. The pharmaceutical composition according to the above item 27, which is an S1P receptor binding agent.

29. The pharmaceutical composition according to the above item 28, which is an EDG-6 binding agent which may have an ability to bind to EDG-1.

30. The pharmaceutical composition according to the above item 29, wherein the EDG-6 binding agent which may have an ability to bind to EDG-1 is an EDG-6 agonist which may have an agonistic activity against EDG-1.

31. The pharmaceutical composition according to the above 27, which is an agent for preventing and/or treating a disease related to EDG-1 and/or EDG-6.

32. The pharmaceutical composition according to the above 31, wherein the disease related to EDG-1 and/or EDG-6 is rejection in transplantation, autoimmune disease and/or allergic disease.

33. The pharmaceutical composition according to the above 31, wherein the disease related to EDG-1 and/or EDG-6 is rejection in transplantation of kidney, liver, heart, lung, dermal graft, cornea, bone, bone marrow cells and/or pancreatic islet cells, collagen disease, systemic lupus erythematosus, rheumatoid arthritis, multiple sclerosis, psoriasis, inflammatory bowel disease, Crohn's disease, autoimmune diabetes, lung fibrosis, atopic dermatitis and/or asthma.

34. The pharmaceutical composition according to the above item 27, which is an immunosuppressant agent.

35. The pharmaceutical composition according to the above item 27, which is an agent causing lymphopenia.

36. The pharmaceutical composition according to any one of the above 28, 31, 34 and 35, which comprises
(1) 2-[3-(4-(5-phenylpentyloxy)phenyl)propanoylamino]acetic acid,
(2) 3-[3-(4-(5-phenylpentyloxy)phenyl)propylamino]propanoic acid,
(3) 3-[2-(4-(5-phenylpentyloxy)phenyl)ethylamino]propanoic acid,
(4) 2-[3-(4-(5-phenylpentyloxy)phenyl)propylamino]acetic acid,
(5) 2-[N-methyl-3-(4-(5-phenylpentyloxy)phenyl)propylamino]acetic acid,
(6) N-((2E)-3-{2-methyl-4-[(5-phenylpentyl)oxy]phenyl}prop-2-enyl)-β-alanine,
(7) N-((2E)-3-{4-[(5-phenylpentyl)oxy]phenyl}-2-propenyl)-β-alanine,
(8) 3-({[1-methyl-6-(4-phenylbutoxy)-3,4-dihydro-2-naphthalenyl]methyl}amino)propanoic acid,
(9) 3-carboxyl-5-[3-(4-(5-phenylpentyloxy)phenyl)propanoylamino]benzoic acid, or
(10) 2-chloro-5-[3-(2-fluoro-4-(5-phenylpentyloxy)phenyl)propanoylamino]benzoic acid,
a salt thereof, a solvate thereof or a prodrug thereof 37. A medicament comprising the compound represented by formula (I) according to the above item 1, a salt thereof, a solvate thereof or a prodrug thereof in combination with one or at least two selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent and an antifungal agent.

38. An immunosuppressant agent and/or an agent causing lymphopenia, which comprises a compound which has an ability to bind to EDG-6 and may have an ability to bind to EDG-1.

39. The immunosuppressant agent and/or the agent causing lymphopenia according to the above 38, which is an agent for preventing and/or treating rejection in transplantation, autoimmune disease and/or allergic disease.

40. A method for preventing and/or treating a disease related to EDG-1 and/or EDG-6 in a mammal, which comprises administering to a mammal an effective amount of the compound represented by formula (I) according to the above item 1, a salt thereof, a solvate thereof or a prodrug thereof 41. A method for immune suppression and/or lymphopenia in a mammal, which comprises administering to a mammal an effective amount of the compound represented by formula (I) according to the above item 1, a salt thereof, a solvate thereof or a prodrug thereof.

42. Use of the compound represented by formula (I) according to the above item 1, a salt thereof, a solvate thereof or a prodrug thereof for the manufacture of a medicament for preventing and/or treating a disease related to EDG-1 and/or EDG-6.

43. Use of the compound represented by formula (I) according to the above item 1, a salt thereof, a solvate thereof or a prodrug thereof for the manufacture of an immunosuppressant agent and/or an agent causing lymphopenia.

44. A medicament comprising a compound having an ability to bind to S1P receptor.

45. The medicament according to the above item 44, which is an immunosuppressant agent and/or an agent causing lymphopenia.

46. The medicament according to the above item 45, wherein the S1P receptor is EDG-1 and EDG-6.

47. The medicament according to the above item 45, wherein the S1P receptor is EDG-6.

48. The medicament according to the above item 46, wherein the compound having an ability to bind to EDG-1 and EDG-6 is an EDG-1 agonist and an EDG-6 agonist.

49. The medicament according to the above item 47, wherein the compound having an ability to bind to EDG-6 is an EDG-6 agonist.

50. The medicament according to the above item 45, which is an agent for preventing and/or suppressing rejection.

51. The medicament according to the above item 50, wherein the rejection is rejection of transplantation, T-cell mediated rejection, acute rejection and/or chronic rejection.

52. The medicament according to the above item 51, wherein the transplantation is transplantation of organ, tissue and/or cells.

53. The medicament according to the above item 52, wherein the organ is kidney, liver, heart, and/or lung, the tissue is dermal graft, cornea, and/or bone, and the cells are bone marrow cells and/or pancreatic islet cells.

54. The medicament according to the above item 45, which is an agent for preventing and/or treating autoimmune disease and/or allergic disease.

55. The medicament according to the above item 54, wherein the allergic disease is atopic dermatitis.

56. The medicament according to the above item 45, wherein the agent causing lymphopenia is an agent for promoting the lymphocytes homing into a secondary lymphatic tissue, an agent for suppressing the recirculation of lymphocytes from lymph nods into the blood, or an agent for protecting lymphocytes in the peripheral blood during cancer therapy.

57. A medicament comprising a compound having an ability to bind to S1P receptor in combination with one or at least two selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent and an antifungal agent.

58. A production process of the compound represented by formula (I), a salt thereof, a solvate thereof or a prodrug thereof; and the like.

In the present specification, S1P means sphingosine-1-phosphate ((2S,3R,4E)-2-amino-3-hydroxyoctadec-4-enyl-1-phosphate). EDG means endothelial differentiation gene which is a generic term including from EDG-1 to EDG-8. Among these EDGs, EDG-1, EDG-3, EDG-5, EDG-6 and EDG-8 (separately named $S1P_1$, $S1P_3$, $S1P_2$, $S1P_4$ and $S1P_5$, respectively) are regarded as S1P receptors.

In the present specification, the "compound having an ability to bind to receptor" includes agonists, antagonists and inverse agonists.

In the present specification, the agonist includes full agonists and partial agonists.

In the present specification, the disease related to EDG-6 includes, for example, rejection in transplantation, rejection of a transplanted organ, transplantation versus host disease, autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, arteriosclerosis, diseases associated with lymphocyte infiltration into a tissue and the like.

In the present specification, the disease related to EDG-1 includes, for example, acute heart failure, angina, stroke, traumatic injury, genetic diseases, peripheral arterial disease such as arteriosclerosis obliterans, thromboangiitis obliterans, Buerger's disease, or diabetic neuropathy, sepsis, angiitis, nephritis, pneumonia, cerebral infarction, myocardial infarction, edematous diseases, varicose vein such as hemorrhoid, anal fissure, anal fistula, dissecting aneurysm of the aorta, DIC, pleuritis, congestive heart failure, multiple organ failure, bedsore, burn, chronic ulcerative colitis, Crohn's disease, osteoporosis, lung fibrosis, interstitial pneumonia, chronic hepatitis, cirrhosis hepatis, chronic renal failure, glomerulosclerosis and the like. EDG-1 also participates in preoperative, postoperative and/or prognostic activation for blood vessel accompanying transplantation of various organs, for example, an adhesion activation of transplanted organs such as heart transplantation, renal transplantation, dermal transplantation or liver transplantation.

In the present specification, the rejection in transplantation means an acute rejection occurring within 3 months after transplanting a graft, chronic rejection occurring thereafter and transplantation versus host disease.

In the present specification, the graft means a transplanted organ (for example, kidney, liver, heart, lung, small intestine, etc.), a transplanted tissue (for example, a dermal graft (for example, a full-thickness-skin graft, an epidermal graft, a dermis graft, a Davis graft, etc.), cornea, bone, a fetal tissue, etc.) or transplanted cells (for example, bone marrow cells, hematopoietic stem cells, peripheral blood stem cells, cord blood stem cells, pancreatic islet cells, Langerhans cells being part thereof, hepatocytes, neuronal cells, intestinal epithelial cells, etc.). As preferable organs, kidney, liver, heart and lung may be cited. As preferable tissues, a dermal graft and cornea may be cited. As preferable cells, bone marrow cells and pancreatic islet cells may be cited.

In the present specification, the T cell-mediated means that T cells participate in some step in the formation, exacerbation or continuation of a disease.

In the present specification, the autoimmune disease includes, for example, collagen disease, systemic lupus erythematosus, rheumatoid arthritis, multiple sclerosis, nephrotic syndrome, lupus nephritis, Sjoegren's syndrome, scleroderma, multiple myositis, psoriasis, inflammatory bowel disease, Crohn's disease, mixed connective tissue disease, primary myxedema, Addison's disease, hypolastic anemia, autoimmune hemolytic anemia, autoimmune thrombopenia, autoimmune diabetes (type I diabetes), uveitis, antireceptor disease, myasthenia gravis, thyrotoxicosis, thyroiditis, Hashimoto's disease and the like.

In the present specification, the allergic disease includes, for example, atopic dermatitis, asthma, rhinitis, conjunctivitis, hay fever and the like. As a preferable allergic disease, atopic dermatitis may be cited.

In the present specification, the immunosuppressant means a drug which is to be used for preventing and/or treating rejection in transplantation, autoimmune diseases, various malignant tumors, cancer, allergic diseases, etc. As such a drug, use may be made of an antimetabolite, an alkylating agent, a T cell activation inhibitor (a T cell function suppressor), a calcineurin inhibitor, a proliferation signal inhibitor, a steroid, an antibody used in immune suppression, other remedies for rejection and the like.

In the present specification, the agent causing lymphopenia means a drug having effects of reducing lymphocytes in the peripheral blood, reducing circulating lymphocytes, reducing the amount of permeated lymphocytes, promoting the lymphocytes homing into a secondary lymphatic tissue, suppressing the recirculation of lymphocytes from lymph nods into the blood, inhibiting an enzyme in the nucleic acid synthesis pathway of lymphocytes (the pyrimidine metabolic system and the purine metabolic system) and the like.

In the present specification, the secondary lymphatic tissue includes, for example, lymph nods, Peyer's patch (an intestinal lymphatic tissue), spleen and the like.

In the present specification, the effect of promoting the lymphocytes homing into a secondary lymphatic tissue means promotion of the migration of lymphocytes into a secondary lymphatic tissue, enhancement of the separation of lymphocytes in a secondary lymphatic tissue, prolongation of the sustention of lymphocytes in a secondary lymphatic tissue and the like. Owing to these effects, lymphocytes can be reduced in a site suffering from inflammation or rejection, etc.

In the present specification, the effect of protecting lymphocytes in the peripheral blood during cancer therapy means an effect of preliminarily homing lymphocytes in the peripheral blood into a secondary lymphatic tissue before a cancer therapy (in particular, chemotherapy, radiotherapy, etc.) to thereby protect the lymphocytes. This effect includes the protection of lymphocytes in pre-transplantation step of administering a large amount of an anticancer agent. It is known that the treatment of cancer by a chemotherapy, etc. with the use of an anticancer agent is accompanied by serious side effects such as the hypofunction of hematopoietic cells, thereby making a patient infectible. Such side effects can be lessened by the above-described function.

In the present specification, the cyclic group is, for example, a carbocyclic group or a heterocyclic group.

In the present specification, the carbocyclic group is, for example, a C3-15 carbocyclic group. The C3-15 carbocyclic group includes C3-15 mono-, bi- or tricyclic carbocyclic aryl, a partially or fully saturated carbocyclic group, a bicyclic carbocyclic group having a spiro bond and a bridged bicyclic carbocyclic group. Examples include cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7]annulene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, and noradamantane rings, and the like.

In the present specification, the C5-12 monocyclic or bicyclic carbocyclic group is, for example, C5-12 monoclyclic or bicyclic carbocyclic aryl which partially or fully saturated. Examples include cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7]annulene, heptalene, and perhydroheptalene rings, and the like.

In the present specification, the C5-7 monocyclic carbocyclic group is, for example, a C5-7 monocyclic carbocyclic aryl which may partially or fully saturated. Examples include cyclopentane, cyclohexane, cycloheptane, cyclopentene, cyclohexene, cycloheptene, cyclopentadiene, cyclohexadiene, cycloheptadiene, and benzene rings, and the like.

In the present specification, the heterocyclic group is, for example, a 3- to 15-membered heterocyclic group containing 1 to 5 hetero atoms selected from an oxygen atom, a nitrogen atom and a sulfur atom. The 3- to 15-membered heterocyclic group containing 1 to 5 hetero atoms selected from an oxygen atom, a nitrogen atom and a sulfur atom includes, for example, a 3- to 15-membered, monocyclic, bicyclic or tricyclic heterocyclic aryl, a bicyclic heterocyclic group having a spiro bond and a bridged bicyclic heterocyclic group, which each contains 1 to 5 hetero atoms selected from an oxygen atom, a nitrogen atom and a sulfur atom and may be partially or fully saturated. Examples includes pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dcihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chromene, chroman, benzodithiolane, and benzodithiane rings, and the like.

In the present specification, the 5- to 12-membered, monocyclic or bicyclic heterocyclic aryl, which contains 1 to 3 hetero atoms selected from an oxygen atom, a nitrogen atom and a sulfur atom and may be partially or fully saturated is, for example, 5- to 12-membered monocyclic or bicyclic heterocyclic aryl, a bicyclic heterocyclic group having a spiro bond or a bridged, bicyclic heterocyclic group, which each contains 1 to 3 hetero atoms selected from an oxygen atom, a nitrogen atom and a sulfur atom and may be partially or fully saturated. Examples include pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, phthalazine, naphthyridine, quinoxaline, quinazoline, cinnoline, benzoxazole, benzothiazole, benzimidazole, chromene, benzoxepine, dihydrobenzoxepine, benzoxazepine, benzoxadiazepine, benzothiepine, benzothiazepine, benzothiadiazepine, benzazepine, benzodiazepine, benzofurazane, benzothiadiazole, benzotriazole, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dioxolane, dioxane, dithiolane, dithiane, dioxaindan, benzodioxane, chroman, benzodithiolane, and benzodithiane rings, and the like.

In the present specification, the 5- to 7-membered monocyclic heterocyclic group containing one or two nitrogen atoms, one oxygen atom and/or one sulfur atom is, for example, a 5- to 7-membered monocyclic heterocyclic aryl containing one or two nitrogen atoms, one oxygen atom and/or one sulfur atom, which may be partially or fully saturated. Examples include pyrrole, imidazole, pyrazole, pyridine, pyrazine, pyrimidine, pyridazine, azepine, diazepine, furan, pyran, oxepine, thiophene, thiaine (thiopyran), thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, and thiomorpholine rings, and the like.

In the present specification, the 5- to 7-membered monocyclic heterocyclic group containing one or two nitrogen atoms, one oxygen atom and/or one sulfur atom, formed by substituents and a nitrogen atom bound thereto is, for example, a 5- to 7-membered monocyclic heterocyclic aryl containing one or two nitrogen atoms, one oxygen atom and/or one sulfur atom, which may be partially or fully saturated. Examples include pyrrole, imidazole, pyrazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole, tetrahydroisoxazole, tetrahydrothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxadiazepine, perhydrooxazepine, perhydrooxadiazepine, tetrahydrothiadiazepine, perhydrothiazepine, perhydrothiadiazepine, morpholine, and thiomorpholine rings, and the like.

In the present specification, the cyclic group in the cyclic group which may further have a substituent(s), the cyclic group which may be substituted and "substituted with a cyclic group" has the same meaning as the cyclic group described above.

In the present specification, the substituent in "which may have a substituent(s)" is not particularly limited, so long as it is a substituent. Examples include C1-20 alkyl which may be substituted, C2-20 alkenyl which may be substituted, C2-20 alkynyl which may be substituted, C1-20 alkylidene which may be substituted, a cyclic group which may be substituted, oxo, hydroxy, C1-20 alkyloxy which may be substituted, C2-20 alkenyloxy which may be substituted, C2-20 alkynyloxy which may be substituted, hydroxy which may be protected by a cyclic group which may be substituted, C1-20 acyloxy which may be substituted, thioxo, mercapto, C1-20 alkylthio which may be substituted, C2-20 alkenylthio which may be substituted, C2-20 alkynylthio which may be substituted, mercapto substituted with a cyclic group which may be substituted, C1-20 alkylsulfinyl which may be substituted, C2-20 alkenylsulfinyl which may be substituted, C2-20 alkynylsulfinyl which may be substituted, sulfinyl substituted with a cyclic group which may be substituted, C1-20 alkylsulfonyl which may be substituted, C2-20 alkenylsulfonyl which may be substituted, C2-20 alkynylsulfonyl which may be substituted, sulfonyl substituted with a cyclic group which may be substituted, sulfino which may be substituted, sulfo which may be substituted, sulfamoyl which may be substituted (when the substituents are two, they may be taken together with a nitrogen atom to which they are bound to form a 5- to 7-membered monocyclic heterocyclic group containing one or two nitrogen atoms, one oxygen atom and/or one sulfur atom (this heterocyclic group may be substituted with C1-8 alkyl, hydroxy or amino)), carbonyl which may be substituted, carboxy which may be substituted, C1-20 acyl which may be substituted, carbamoyl which may be substituted (when the substituents are two, they may be taken together with a nitrogen atom to which they are bound to form a 5- to 7-membered monocyclic heterocyclic group containing one or two nitrogen atoms, one oxygen atom and/or one sulfur atom (this heterocyclic group may be substituted with C1-8 alkyl, hydroxy or amino)), cyano, amidino which may be substituted (when the substituents are two, they may be taken together with a nitrogen atom to which they are bound to form a 5- to 7-membered monocyclic heterocyclic group containing one or two nitrogen atoms, one oxygen atom and/or one sulfur atom (this heterocyclic group may be substituted with C1-8 alkyl, hydroxy or amino)), nitro, nitroso, imino which may be substituted, amino which may be substituted (when the substituents are two, they may be taken together with a nitrogen atom to which they are bound to form a 5- to 7-membered monocyclic heterocyclic group containing one or two nitrogen atoms, one oxygen atom and/or one sulfur atom (this heterocyclic group may be substituted with C1-8 alkyl, hydroxy or amino)), a halogen atom and the like.

In the present specification, the substituent represented by $R^1$, $R^7$, $R^{27}$, $R^{29}$, $R^{30}$ and $R^{31}$ has the same meaning as the substituent in the cyclic group which may further have a substituent(s) described above.

In the present specification, the substituent in "which may be substituted" is, for example, C1-20 alkyl, C2-20 alkenyl, C2-20 alkynyl, C1-20 alkylidene, a cyclic group, C1-20 alkyl substituted with a cyclic group, oxo, hydroxy, C1-20 alkyloxy, C2-20 alkenyloxy, C2-20 alkynyloxy, hydroxy which may be protected by a cyclic group, C1-20 acylthio, thioxo, mercapto, C1-20 alkylthio, C2-20 alkenylthio, C2-20 alkynylthio, mercapto substituted with a cyclic group, C1-20 alkylsulfinyl, C2-20 alkenylsulfinyl, C2-20 alkynylsulfinyl, sulfinyl substituted with a cyclic group, C1-20 alkylsulfonyl, C2-20 alkenylsulfonyl, C2-20 alkynylsulfonyl, sulfonyl substituted with a cyclic group, C1-20 alkylsulfonyl substituted with a cyclic group, sulfino, sulfo, sulfamoyl, carboxy, C1-20 acyl, C1-20 acyl substituted with a cyclic group, carbonyl substituted with a cyclic group, carbamoyl, cyano, amidino, nitro, nitroso, imino, amino, a halogen atom or the like. They are substituted at any position which can be substituted with any number which can be substituted.

In the present specification, the C1-20 alkyl includes, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, and isomers thereof.

In the present specification, the C1-8 alkyl includes, for example, methyl, ethyl, propyl, butyl, pentyl, hexyl, heptyl, octyl, and isomers thereof.

In the present specification, the C2-20 alkenyl includes, for example, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, and isomers thereof.

In the present specification, the C2-20 alkynyl includes, for example, ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, and iomers thereof.

In the present specification, the C1-20 alkylidene includes, for example, methylidene, ethylidene, propylidene, butylidene, pentylidne, hexylidene, heptylidene, octylidene, nonylidene, decylidene, undecylidene, dodecylidene, tridecylidene, tetradecylidene, pentadecylidene, hexadecylidene, heptadecylidene, octadecylidene, nonadecylidene, icosylidene, and isomers thereof.

In the present specification, the C1-20 alkyloxy includes, for example, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, icosyloxy, and isomers thereof.

In the present specification, the C1-8 alkoxy includes, for example, methoxy, ethoxy, propoxy, butoxy, pentyloxy, hexyloxy, heptyloxy, octyloxy, and isomers thereof.

In the present specification, the C2-20 alkenyloxy includes, for example, ethenyloxy, propenyloxy, butenyloxy, pentenyloxy, hexenyloxy, heptenyloxy, octenyloxy, nonenyloxy, decenyloxy, undecenyloxy, dodecenyloxy, tridecenyloxy, tetradecenyloxy, pentadecenyloxy, hexadecenyloxy, heptadecenyloxy, octadecenyloxy, nonadecenyloxy, icosenyloxy, and isomers thereof.

In the present invention, the C2-20 alkynyloxy includes, for example, ethynyloxy, propynyloxy, butynyloxy, pentynyloxy, hexynyloxy, heptynyloxy, octynyloxy, nonynyloxy, decynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy, icosynyloxy, and isomers thereof.

In the present specification, the C1-20 alkylthio includes, for example, methylthio, ethylthio, propylthio, butylthio, pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio, icosylthio, and isomers thereof.

In the present specification, the C2-20 alkenylthio includes, for example, ethenylthib, propenylthio, butenylthib, pentenylthio, hexenylthio, heptenylthio, octenylthio, nonenylthio, decenylthio, undecenylthio, dodecenylthio, tridecenylthio, tetradecenylthio, pentadecenylthio, hexadecenylthio, heptadecenylthio, octadecenylthio, nonadecenylthio, icosenylthio, and isomers thereof.

In the present specification, the C2-20 alkynylthio includes, for example, ethynylthio, propynylthio, butynylthio, pentynylthio, hexynylthio, heptynylthio, octynylthio, nonynylthio, decynylthio, undecynylthio, dodecynylthio, tridecynylthio, tetradecynylthio, pentadecynylthio, hexadecynylthio, heptadecynylthio, octadecynylthio, nonadecynylthio, icosynylthio, and isomers thereof.

In the present specification, the C1-20 alkylsulfinyl includes, for example, methylsulfinyl, ethylsulfinyl, propylsulfinyl, butylsulfinyl, pentylsulfinyl, hexylsulfinyl, heptylsulfinyl, octylsulfinyl, nonylsulfinyl, decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl, icosylsulfinyl, and isomers thereof.

In the present specification, the C2-20 alkenylsulfinyl includes, for example, ethenylsulfinyl, propenylsulfinyl, butenylsulfinyl, pentenylsulfinyl, hexenylsulfinyl, heptenylsulfinyl, octenylsulfinyl, nonenylsulfinyl, decenylsulfinyl, undecenylsulfinyl, dodecenylsulfinyl, tridecenylsulfinyl, tetradecenylsulfinyl, pentadecenylsulfinyl, hexadecenylsulfinyl, heptadecenylsulfinyl, octadecenylsulfinyl, nonadecenylsulfinyl, icosenylsulfinyl, and isomers thereof.

In the present specification, the C2-20 alkynylsulfinyl includes, for example, ethynylsulfinyl, propynylsulfinyl, butynylsulfinyl, pentynylsulfinyl, hexynylsulfinyl, heptynylsulfinyl, octynylsulfinyl, nonynylsulfinyl, decynylsulfinyl, undecynylsulfinyl, dodecynylsulfinyl, tridecynylsulfinyl, tetradecynylsulfinyl, pentadecynylsulfinyl, hexadecynylsulfinyl, heptadecynylsulfinyl, octadecynylsulfinyl, nonadecynylsulfinyl, icosynylsulfinyl, and isomers thereof.

In the present specification, the C1-20 alkylsulfonyl includes, for example, methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl, icosylsulfonyl, and isomers thereof.

In the present specification, the C2-20 alkenylsulfonyl includes, for example, ethenylsulfonyl, propenylsulfonyl, butenylsulfonyl, pentenylsulfonyl, hexenylsulfonyl, heptenylsulfonyl, octenylsulfonyl, nonenylsulfonyl, decenylsulfonyl, undecenylsulfonyl, dbdecenylsulfonyl, tridecenylsulfohyl, tetradecenylsulfonyl, pentadecenylsulfonyl, hexadecenylsulfonyl, heptadecenylsulfonyl, octadecenylsulfonyl, nonadecenylsulfonyl, icosenylsulfonyl, and isomers thereof.

In the present specification, the C2-20 alkynylsulfonyl includes, for example, ethynylsulfonyl, propynylsulfonyl, butynylsulfonyl, pentynylsulfonyl, hexynylsulfonyl, heptynylsulfonyl, octynylsulfonyl, nonynylsulfonyl, decynylsulfonyl, undecynylsulfonyl, dodecynylsulfonyl, tridecynylsulfonyl, tetradecynylsulfonyl, pentadecynylsulfonyl, hexadecynylsulfonyl, heptadecynylsulfonyl, octadecynylsulfonyl, nonadecynylsulfonyl, icosynylsulfonyl, and isomers thereof.

In the present specification, the C1-20 acyl includes, for example, methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, and isomers thereof.

In the present specification, the C1-20 acyloxy includes, for example, methanoyloxy, ethanoyloxy, propanoyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy, icosanoyloxy, and isomers thereof.

In the present specification, the protecting group for hydroxy which may be protected has the same meaning as the substituent for "which may be substituted" described above.

In the present specification, the halogen atom includes, for example, fluorine, chlorine, bromine and iodine.

In the present specification, the bond means that the atoms are directly bound through no other atom.

In the present specification, the spacer having 1 to 10 atoms in its main chain means spacing in which 1 to 10 atoms are continuously linked in its main chain. In this case, the number of atoms as a main chain should be counted such that the atoms in its main chain become minimum. The spacer having 1 to 10 atoms in its main chain includes, for example, a divalent group having 1 to 10 atoms in its main chain which is 1 to 4 combinations selected from C1-10 alkylene which may be substituted, C2-10 alkenylene which may be substituted, C2-10 alkynylene which may be substituted, a nitrogen atom which may be substituted (—NH—), —CO—, —O—, —S—, —SO—, —SO$_2$—, -(carbocyclic group which may be substituted)-, -(heterocyclic group which may be substituted)-, and the like.

In the present specification, the C1-10 alkylene includes, for example, menthylene, ethylene, trimethylene, tetramethylene, -pentamethylene, hexamethylene, heptamethylene, octamethylene, nonamethylene, decamethylene, and isomers thereof.

In the present specification, the C2-10 alkenylene includes, for example, ethenylene, propenylene, butenylene, pentenylene, hexenylene, heptenylene, octenylene, nonenylene, decenylene, and isomers thereof.

In the present specification, the C2-10 alkynylene includes, for example, ethynylene, propynylene, butynylene, pentynylene, hexynylene, heptynylene, octynylene, nonynylene, decynylene, and isomers thereof.

In the present specification, the spacer having 1 to 9 atoms in its main chain means spacing in which 1 to 9 atoms are continuously linked in its main chain. In this case, the number of atoms as a main chain should be counted such that the atoms in its main chain become minimum. The spacer having 1 to 9 atoms in its main chain includes, for example, a divalent group having 1 to 9 atoms in its main chain which is 1 to 4 combinations selected from C1-9 alkylene which may be substituted, C2-9 alkenylene which may be substituted, C2-9 alkynylene which may be substituted, a nitrogen atom which may be substituted (—NH—), —CO—, —O—, —S—, —SO—, —SO$_2$—, -(carbocyclic group which may be substituted)-, -(heterocyclic group which may be substituted)-, and the like.

In the present specification, the C1-9 alkylene includes, for example, methylene, ethylene, trimethylene, tetramethylene, pentamethylene, hexamethylene, heptamethylene, octamethylene, nonamethylene, and isomers thereof.

In the present specification, the C2-9 alkenylene includes, for example, ethenylene, propenylene, butenylene, pentenylene, hexenylene, heptenylene, octenylene, nonenylene, and isomers thereof.

In the present specification, the C2-9 alkynylene includes, for example, ethynylene, propynylene, bytynylene, pentynylene, hexynylene, heptynylene, octynylene, nonylene, and isomers thereof.

In the present specification, the spacer having 1 to 8 atoms in its main chain means spacing in which 1 to 9 atoms are continuously linked in its main chain. In this case, the number of atoms as a main chain should be counted such that the atoms in its main chain become minimum. The spacer having 1 to 8 atoms in its main chain includes, for example, a divalent group having 1 to 8 atoms in its main chain which is 1 to 4 combinations selected from C1-8 alkylene which may be substituted, C2-8 alkenylene which may be substituted, C2-8 alkynylene which may be substituted, a nitrogen atom which may be substituted (—NH—), —CO—, —O—, —S—, —SO—, —SO$_2$—, -(carbocyclic group which may be substituted)-, -(heterocyclic group which may be substituted)-, and the like.

In the present specification, the C1-8 alkylene includes, for example, methylene, ethylene, trimethylene, tetramethylene, pentamethylene, hexamethylene, heptamethylene, octamethylene, and isomers thereof.

In the present specification, the C2-8 alkenylene, includes, for example, ethenylene, propenylene, butenylene, pentenylene, hexenylene, heptenylene, octenylene, and isomers thereof.

In the present specification, the C2-8 alkynylene includes, for example, ethynylene, propynylene, bytynylene, pentynylene, hexynylene, heptynylene, octynylene, and isomers thereof.

In the present specification, the C1-3 alkylene includes, for example, methylene, ethylene, trimethylene, and isomers thereof.

In the present specification, the C3-6 cycloalkylene includes, for example, cyclopropylene, cyclobutylene, cyclopenylene, cyclohexylene, and isomers thereof.

In the present specification, the ring group which may have a substituent(s) formed by taking one atom in the spacer represented by X together with a substituent on ring B means a ring group which may have a substituent(s) formed by taking one atom in the spacer represented by X together with one substituent on ring B. The ring group which may have a substituent(s) has the same meaning as the cyclic group which may further have a substituent(s).

In the present specification, the ring group which may have a substituent(s) formed by taking one atom in the spacer represented by Y together with a substituent on ring B means a ring group which may have a substituent(s) formed by taking one atom in the spacer represented by Y together with one substituent on ring B. The ring group which may have a substituent(s) has the same meaning as the cyclic group which may further have a substituent(s).

In the present specification, the nitrogen-containing heterocyclic group which may have a substituent(s) formed by taking one atom in the spacer represented by $Y^1$ and/or $Y^2$ together with $R^7$ means a nitrogen-containing heterocyclic group which may have a substituent(s) formed by taking one atom in the spacer represented by $Y^1$ and/or $Y^2$ together with $R^7$ and a nitrogen atom to which $Y^1$ or $Y^2$ is bound. The nitrogen-containing heterocyclic group in the nitrogen-containing heterocyclic group which may have a substituent(s) includes, for example, a 3- to 15-membered heterocyclic group which contain one nitrogen atom and may further contain 1 to 4 hetero atoms selected from an oxygen atom, a nitrogen atom and a sulfur atom, and the like. The 3- to 15-membered heterocyclic group which contain one nitrogen atom and may further contain 1 to 4 hetero atoms selected from an oxygen atom, a nitrogen atom and a sulfur atom includes a 3- to 15-membered monocyclic, bicyclic or tricyclic heterocyclic aryl, a bicyclic heterocyclic group and a bridged bicyclic heterocyclic group, which each contains one nitrogen atom, may further contain 1 to 4 hetero atoms selected from an oxygen atom, a nitrogen atom and a sulfur atom, and may be partially or fully saturated. Examples include pyrrole, imidazole, triazole, tetrazole, pyrazole, azepine, diazepine, indole, isoindole, indazole, purine, pyrrolopyridine, benzimidazole, benzazepine, benzodiazepine, benzotriazole, carbazole, β-carboline, phenothiazine, phenoxazine, pyrazoloisoquinoline, pyrazolonaphthyridine, pyrimidoindole, indolydinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, dihydrobenzooxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine (2,3,4,5-tetrahydro-1H-2-benzazepine, 2,3,4,5-tetrahydro-1H-3-benzazepine, etc.), dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, tetrapyridonaphthyridine, tetrahydro-β-carboline, dihydroazepinoindole, hexahydroazepinoindole, tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiadinoindole, tetrahydrothiadinoindole, dihydrooxadinoindole, tetrahydrooxadinoindole, hexahydroindolydinoindole, dihydroindolobenzodiazepine, octahydroindoloquinolizine, hexahydroimidazopyridoindole, hexahydropyrrolothiazepinoindole, azaspiro[4.4]nonane, oxazaspiro[4.4]nonane, oxazaspiro[2.5]octane, azaspiro[4.5]decane, 1,3,8-triazaspiro[4.5]decane, 2,7-diazaspiro[4.5]decane, 1,4,9-triazaspiro[5.5]undecane, oxazaspiro[4.5]decane, azaspiro[5.5]undecane, azabicyclo[2.2.1]heptane, azabicyclo[3.1.1]heptane, azabicyclo[3.2.1]octane (8-azabicyclo[3.2.1]octane, etc.), azabicyclo[2.2.2]octane (2-azabicyclo[2.2.2]octane, etc.), azabicyclo[2.1.1]hexane (5-azabicyclo[2.1.1]hexane, etc.), and the like.

In the present invention, the nitrogen-containing heterocyclic group which may have a substituent(s) formed by taking one nitrogen atom in the spacer represented by $Y^1$ together with a substituent on ring B means the same meaning as the above-described nitrogen-containing heterocyclic group which may have a substituent(s).

In the present invention, ring A is preferably a C3-15 carbocyclic group, more preferably a C5-12 monocyclic or bicyclic carbocyclic group, and more preferably a benzene, indane, indene or naphthalene ring.

In the present invention, the cyclic group in the cyclic group which may have a substituent(s) represented by ring B is preferably a C3-15 carbocyclic group or a 3- to 15-membered heterocyclic group, more preferably a C5-12 monocyclic or bicyclic carbocyclic group or a 5- to 12-membered monocyclic or bicyclic heterocyclic group which contain 1 to 3 hetero atoms selected from an oxygen atom, a nitrogen atom and a sulfur atom and may be partially or fully saturated, and most preferably a benzene, indene, naphthalene, dihydronaphthalene, 6,7-dihydro-5H-benzo[7]annulene, pyridine, indole, chromene, benzofuran, benzothiophene, benzoxazole, dihydrobenzoxepine, tetrahydroisoquinoline, isoindoline or tetrahydrobenzazepine ring.

In the present invention, the nitrogen-containing heterocyclic group represented by ring $B^1$ is preferably pyrrole, tetrahydropyridine, dihydropyrrole, tetrahydroazepine or the like.

In the present invention, the substituent in the cyclic group which may have a substituent(s) represented by ring B is preferably C1-20 alkyl which may be substituted, C1-20 alkyloxy which may be substituted, carboxy which may be substituted, or a halogen atom, and is more preferably methyl, ethyl, propyl, isopropyl, tert-butyl, methoxy, carboxy, fluoro, chloro, or trifluoromethyl.

In the present invention, X is preferably a divalent group having 1 to 8 atoms in its main chain which is 1 to 4 combinations selected from C1-8 alkylene which may be substituted, C2-8 alkenylene which may be substituted, a nitrogen atom which may be substituted (—NH—), —CO—, —O—, C3-6 cycloalkylene which may be substituted, phenylene which may be substituted, and the like, and more preferably —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH$_2$—O—, —(CH$_2$)$_2$—O—, —(CH$_2$)$_3$—O—, —(CH$_2$)$_4$—O—, —(CH$_2$)$_5$—O—, —CH═CH—CH$_2$—O—, or -cyclopropylene-CH$_2$—O—, which each may be substituted, in which the right side of each group binds to ring B.

In the present invention, Y is preferably a divalent group having 1 to 10 atoms in its main chain which is 1 to 4 combinations selected from C1-10 alkylene which may be substituted, C2-10 alkenylene which may be substituted, C2-10 alkynylene which may be substituted, a nitrogen atom which may be substituted (—NH—), —CO—, —O—, —S—, phenylene which may be substituted, -(aziridine which may be substituted)-, -(azetidine which may be substituted)-, -(pyrrolidine which may be substituted)-, -(piperidine which may be substituted)-, -(piperazine which may be substituted)-, -(morpholine which may be substituted)-, -(azabicyclo[3.2.1]octane which may be substituted)-, -(azabicyclo[2.2.2]octane which may be substituted)-, -(azabicyclo[2.1.1]hexane which may be substituted)-, -(tetrahydropyridine which may be substituted)-, and the like, and more preferably —(CH$_2$)$_3$—NHCH$_2$—, —(CH$_2$)—NCH$_3$—CH$_2$—, —(CH$_2$)$_3$—NH—(CH$_2$)$_2$—, —(CH$_2$)$_2$—NH—(CH$_2$)$_2$—, —(CH$_2$)$_2$—CONHCH$_2$—, —(CH$_2$)$_2$—CONH-(m-phenylene)-, —CR$^{Y1}$═CH—CH$_2$—NH—(CH$_2$)$_4$—, —CR$^{Y1}$═CH—CH$_2$—NH—(CH$_2$)$_5$—, —CR$^{Y1}$═CH—CH$_2$—NH—(CH$_2$)$_2$—, —CH═CR$^{Y1}$—CH$_2$—NH—(CH$_2$)$_2$—, —CR$^{Y1}$═CH—CH$_2$—NH—CH$_2$—, —CH$_2$— (azetidine)-, —(CH$_2$)$_2$-(azetidine)-, —(CH$_2$)$_3$-(azetidine)-, —CR$^{Y1}$═CH—CH$_2$— (azetidine)-, —CH═CR$^{Y1}$—CH$_2$—(azetidine)-, —(CH$_2$)$_3$-(piperidine)-, —CR$^{Y1}$═CH—CH$_2$—(piperidine)-, in which R$^{Y1}$ represents a hydrogen atom, a halogen atom, or C1-4 alkyl which may be substituted with 1 to 3 halogen atoms, and the right side of each group binds to ring B.

In the present invention, $Y^1$ is preferably a divalent group having 1 to 4 atoms in its main chain which is 1 to 4 combinations selected from C1-3 alkylene which may be substituted and —CO—, and more preferably —CH$_2$—, —(CH$_2$)$_2$—, —(CH$_2$)$_2$—CO— or —(CH$_2$)$_3$—, which each may be substituted.

In the present invention, $Y^2$ is preferably a divalent group having 1 to 5 atoms in its main chain which is 1 to 4 combinations selected from C1-3 alkylene which may be substituted, phenylene which may be substituted and the like, and is more preferably —CH$_2$—, —(CH$_2$)$_2$— or -(m-phenylene)-, which each may be substituted.

In the present invention, the substituent represented by $R^1$ is preferably a halogen atom, C1-20 alkyl which may be substituted, or C1-20 alkyloxy which may be substituted, and more preferably fluoro, chloro, bromo, methyl, trifluoromethyl or methoxy.

In the present invention, $R^7$ is preferably a hydrogen atom or C1-20 alkyl which may be substituted, and more preferably a hydrogen atom or methyl.

In the present invention, the nitrogen-containing heterocyclic group which may have a substituent(s) formed by taking one atom in the spacer represented by $Y^1$ together with $R^7$ is preferably piperidine, tetrahydropyridine or pyrazine, which each may be substituted, or the like, and more preferably tetrahydropyridine which may have a substituent(s).

In the present invention, the nitrogen-containing heterocyclic group which may have a substituent(s) formed by taking one atom in the spacer represented by $Y^2$ together with $R^7$ is azetidine, pyrrolidine, piperidine, or tetrahydropyridine which may be substituted, or the like, and more preferably azetidine which may have a substituent(s).

In the present invention, m is preferably 0, 1 or 2.

In the present invention, n is preferably 0 or 1.

As the compound of the present invention having an ability to bind to an S1P receptor, a compound which is having an ability to bind to EDG-6 and which may have an ability to bind to EDG-1 is preferred. It is more preferable that the action of binding to EDG-1 of the compound is an agonistic activity.

Among the compounds represented by formula (I) in the present invention, preferable compounds are carboxylic acid derivatives represented by formula (IA-1):

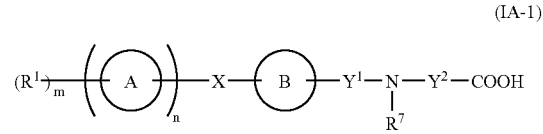

(IA-1)

wherein all symbols have the same meanings as described above;

formula (IA-2):

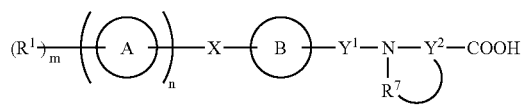

(IA-2)

wherein all symbols have the same meanings as described above;

formula (IA-3):

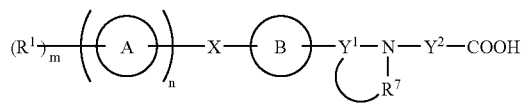

(IA-3)

wherein all symbols have the same meanings as described above;

formula (IA-4):

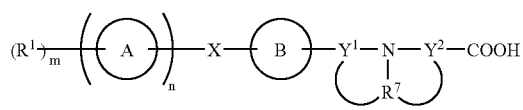

(IA-4)

wherein all symbols have the same meanings as described above; and formula (IB):

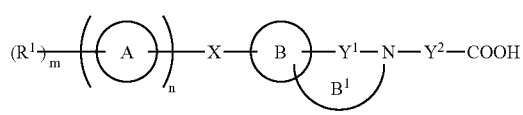

(IB)

wherein all symbols have the same meanings as described above;

a prodrug thereof and a salt thereof.

More preferable compounds are carboxylic acid derivatives represented by formula (IA-1-1):

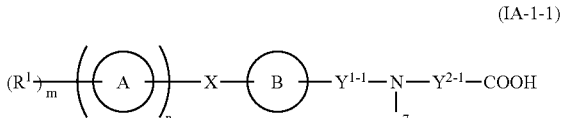

(IA-1-1)

wherein $Y^{1-1}$ represents ethylene which may have a substituent(s), propylene which may have a substituent(s) or propenylene which may have a substituent(s); $Y^{2-1}$ represents ethylene which may have a substituent(s); and other symbols have the same meanings as described above;

formula (IA-1-2):

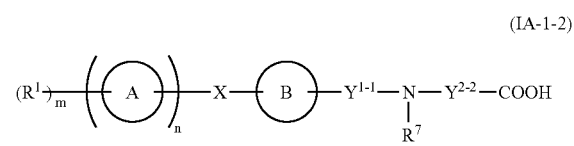

(IA-1-2)

wherein $Y^{2-2}$ represents methylene which may have a substituent(s); and other symbols have the same meanings as described above;

formula (IA-1-3):

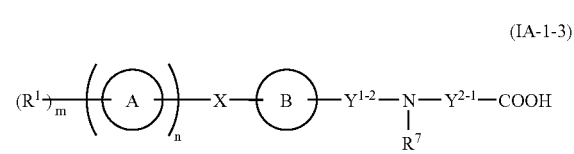

(IA-1-3)

wherein $Y^{1-2}$ represents methylene which may have a substituent(s); and other symbols have the same meanings as described above;

formula (IA-2-1):

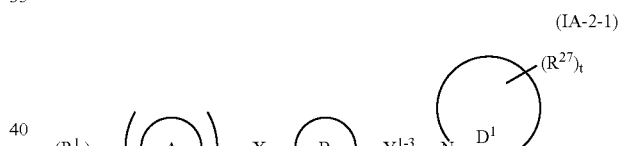

(IA-2-1)

wherein ring $D^1$ represents a nitrogen-containing heterocyclic group; $Y^{1-3}$ represents methylene which may have a substituent(s), ethylene which may have a substituent(s), propylene which may have a substituent(s) or propenylene which may have a substituent(s); $R^{27}$ represents a hydrogen atom or a substituent; t is 0 or an integer of 1 to 5; and other symbols have the same meanings as described above;

formula (IA-2-2):

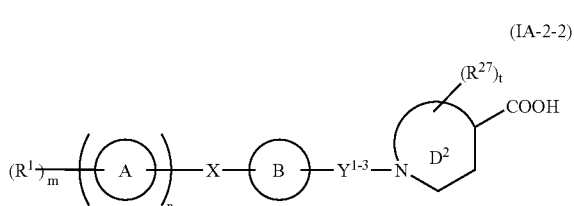

(IA-2-2)

wherein ring $D^2$ represents a nitrogen-containing heterocyclic group; and other symbols have the same meanings as described above;

formula (IA-3-1):

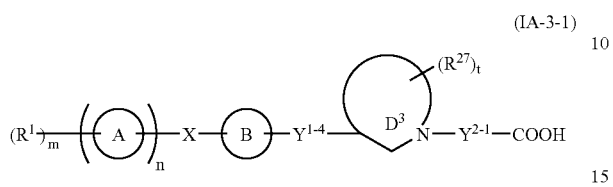

wherein ring $D^3$ represents a nitrogen-containing heterocyclic group; $Y^{1-4}$ represents a bond or methylene which may have a substituent(s); and other symbols have the same meanings as described above;

formula (IA-3-2):

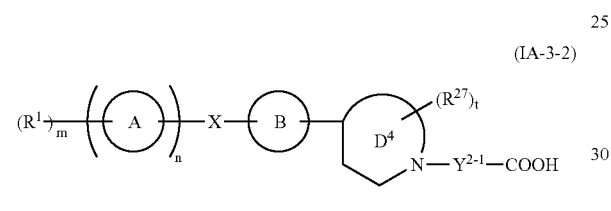

wherein ring $D^4$ represents a nitrogen-containing heterocyclic group; and other symbols have the same meanings as described above;

formula (IA-3-3):

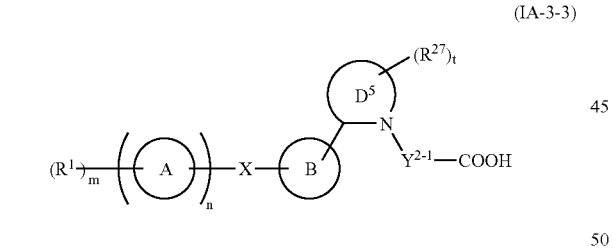

wherein ring $D^5$ represents a nitrogen-containing heterocyclic group; and other symbols have the same meanings as described above;

formula (IB-1-1):

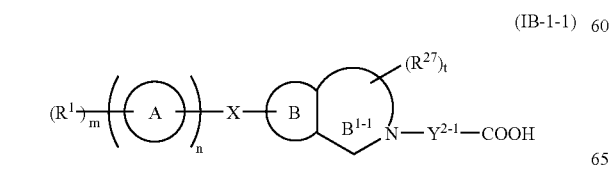

wherein ring $B^{1-1}$ represents a nitrogen-containing heterocyclic group; and other symbols have the same meanings as described above;

formula (IB-1-2):

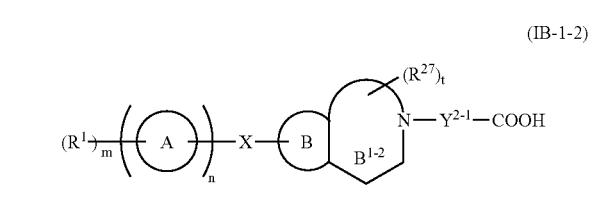

wherein ring $B^{1-2}$ represents a nitrogen-containing heterocyclic group; and other symbols have the same meanings as described above;

formula (I-1):

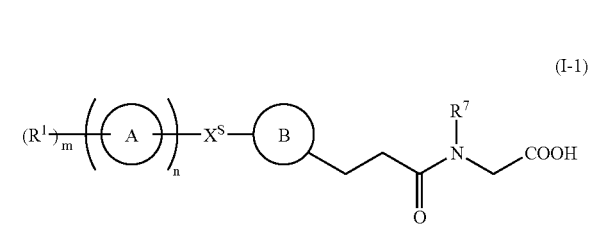

wherein all symbols have the same meanings as described above;

formula (I-2):

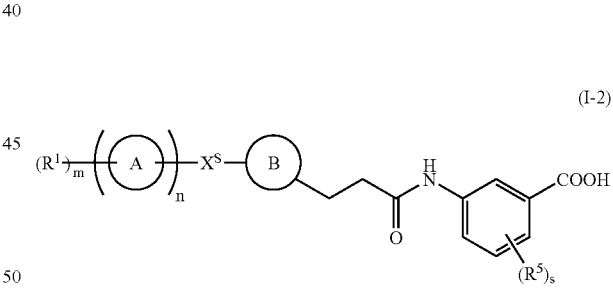

wherein all symbols have the same meanings as described above;

formula (I-S-1):

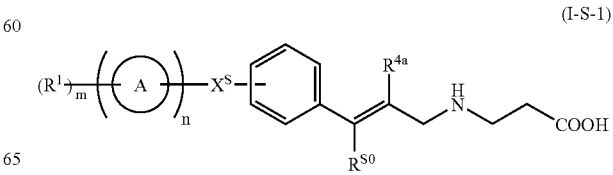

wherein all symbols have the same meanings as described above;
formula (I-S-2):

(I-S-2)

wherein all symbols have the same meanings as described above;
formula (I-S-3):

(I-S-3)

wherein all symbols have the same meanings as described above;
formula (I-S-3a):

(I-S-3a)

wherein all symbols have the same meanings as described above;
formula (I-S-4):

(I-S-4)

wherein all symbols have the same meanings as described above;
formula (I-S-5):

(I-S-5)

wherein all symbols have the same meanings as described above;
formula (I-S-6):

(I-S-6)

wherein all symbols have the same meanings as described above;
formula (I-S-7):

(I-S-7)

wherein all symbols have the same meanings as described above;
formula (I-S-7a):

(I-S-7a)

wherein all symbols have the same meanings as described above;
formula (I-T):

(I-T)

wherein all symbols have the same meanings as described above; and formula (I-U):

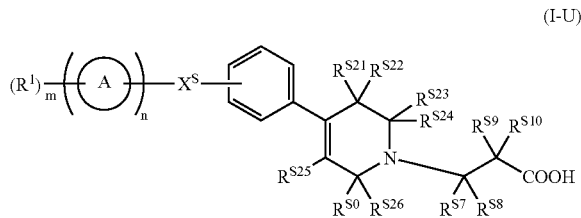

wherein all symbols have the same meanings as described above;

prodrugs thereof and salts thereof.

In the present invention, $R^{S0}$ is preferably a hydrogen atom, fluoro, chloro, methyl or trifluoromethyl, and more preferably a hydrogen atom, methyl or trifluoromethyl.

The nitrogen containing heterocyclic group represented by ring $D^1$, ring $D^3$ and ring $D^5$ includes, for example, 3- to 9-membered monocyclic heterocyclic aryl and bridged bicyclic heterocyclic group which each contains one nitrogen atom, may further contain one or two hetero atoms selected from an oxygen atom, a nitrogen atom and a sulfur atom and may be partially or fully saturated, and the like. Examples include pyrrole, imidazole, triazole, pyrazole, aziridine, azetidine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, azabicyclo[2.2.1]heptane, azabicyclo[3.1.1]heptane, azabicyclo[3.2.1]octane (8-azabicyclo[3.2.1]octane, etc.), azabicyclo[2.2.2]octane (2-azabicyclo[2.2.2]octane, etc.), diazabicyclo[2.2.2]octane, azabicyclo[2.1.1]hexane (5-azabicyclo[2.1.1]hexane, etc.), and the like.

The nitrogen containing heterocyclic group represented by ring $D^2$ and ring $D^4$ includes, for example, 4- to 9-membered monocyclic aryl and bridged heterocyclic group which each contains one nitrogen atom, may further contain one to two hetero atoms selected from an oxygen atom, a nitrogen atom and a sulfur atom and which may be partially or fully saturated. Examples include pyrrole, pyrazole, azetidine, pyrroline, pyrrolidine, pyrazoline, pyrazolidine, dihydropyridine, tetrahydropyridine, piperidine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydroisoxazole, tetrahydroisoxazole (isoxazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrooxadiazepine, tetrahydrooxadiazepine, perhydrooxadiazepine, dihydrothiazine, tetrahydrothiazine, dihydrothiazepine, tetrahydrothiazepine, perhydrothiazepine, dihydrothiadiazepine, tetrahydrothiadiazepine, perhydrothiadiazepine, azabicyclo[2.2.1]heptane, azabicyclo[3.1.1]heptane, azabicyclo[3.2.1]octane (8-azabicyclo[3.2.1]octane, etc.), azabicyclo[2.2.2]octane (2-azabicyclo[2.2.2]octane, etc.), diazabicyclo[2.2.2]octane, azabicdclo[2.1.1]hexane (5-azabicyclo[2.1.1]hexane), and the like.

The nitrogen-containing heterocyclic group represented by ring $B^{1-1}$ includes, for example, 4- to 9-membered monocyclic heterocyclic aryl which contains one nitrogen atom, may further contain one or two hetero atoms selected from an oxygen atom, a nitrogen atom and a sulfur atom and may be partially or fully saturated, and the like. Examples include pyrrole, imidazole, triazole, pyrazole, azetidine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxazine, tetrahydrooxazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiazine, tetrahydrothiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, and the like.

The nitrogen-containing heterocyclic group represented by ring $B^{1-2}$ includes, for example, 5- to 9-membered monocyclic heterocyclic aryl which contains one nitrogen atom, may further contain one or two hetero atoms selected from an oxygen atom, a nitrogen atom and a sulfur atom and may be partially or fully saturated, and the like. Examples include pyrrole, pyrazole, pyrroline, pyrrolidine, imidazoline, imidazolidine, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrooxadiazepine, tetrahydrooxadiazepine, perhydrooxadiazepine, dihydrothiazine, tetrahydrothiazine, tetrahydrothiadiazine, dihydrothiazepine, tetrahydrothiazepine, perhydrothiazepine, dihydrothiadiazepine, tetrahydrothiadiazepine, perhydrothiadiazepine, morphdline, thidmorpholine, and the like.

Specific examples of
in formula (IA-2-1) include
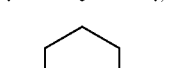
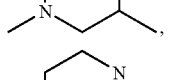
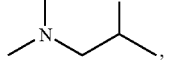
and the like.
Specific examples of
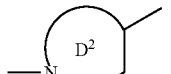
in formula (IA-2-2) include
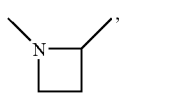
and the like.
Specific examples of
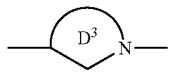
in formula (IA-3-1) include
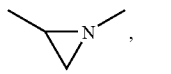
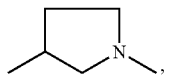
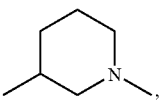
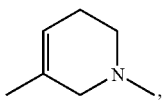
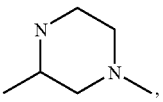
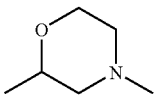
and the like.
Specific examples of
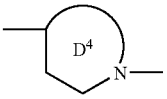
in formula (IA-3-2) include
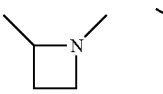
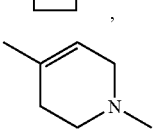
and the like.
Specific examples of
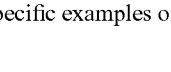
in formula (IA-3-3) include
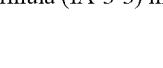
and the like.
Specific examples of
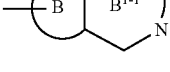

in formula (IB-1-1) include

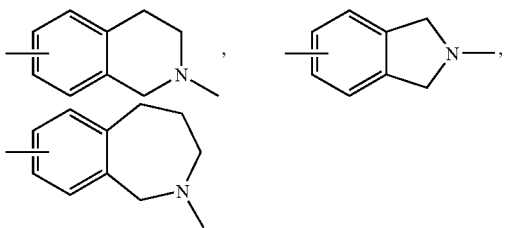

and the like.

Specific examples of

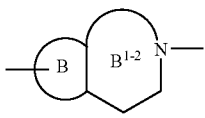

in formula (IB-1-2) include

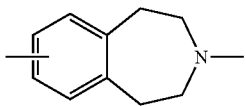

and the like.

In a compound represented by formula (Ia) for producing a pharmaceutical composition, $R^{1a}$ is preferably C1-8 alkyl, C1-8 alkoxy or a halogen atom, more preferably methyl, methoxy, chloro or fluoro; ring $A^a$ is preferably a C5-7 monocyclic carbocyclic group, more preferably a benzene ring; $E^a$ is preferably —O—, —S— or —NR$^{6a}$, and more preferably —O—; $R^{2a}$ is preferably C1-8 alkyl, C1-8 alkoxy or a halogen atom, and more preferably methyl, methoxy, chloro or fluoro; $R^{3a}$ is preferably a hydrogen atom, C1-4 alkyl or a halogen atom, and more preferably a hydrogen atom, methyl or chloro; $R^{4a}$ is preferably a hydrogen atom; the group formed by taking $R^{2a}$ together with $R^{4a}$ is preferably —CH$_2$CH$_2$—; $G^a$ is preferably —CONR$^{7a}$—, NR$^{7a}$CO—, NR$^{7a}$SO$_2$—, —CH$_2$NR$^{7a}$— or —NR$^{7a}$CH$_2$, and more preferably —CONR$^{7a}$—, —CH$_2$NR$^{7a}$— or —NR$^{7a}$CH$_2$; $R^{7a}$ is preferably a hydrogen atom or C1-8 alkyl, and more preferably a hydrogen atom or methyl; $Q^a$ is preferably C1-4 alkylene or

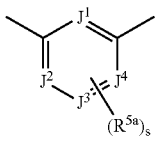

wherein all symbols have the same meanings as described above, and more preferably methylene, ethylene or phenylene; $J^1$, J, $J^3$ and $J^4$ each is preferably a carbon atom or a nitrogen atom, and more preferably a carbon atom; $R^{5a}$ is preferably a halogen atom or —COOR$^{11a}$, and more preferably chloro or —COOH; p is preferably 0, 1 or 2, and more preferably 0 or 1; q is preferably 4, 5 or 6; r is preferably 0 or 1; and s is preferably 0 or 1.

In the present invention, all of the compounds of formula (I) containing combinations of the preferable groups and the preferable rings as cited above are preferred. In particular, more preferred compounds are those described in Examples and 2-[3-(4-(5-phenylpentyloxy)phenyl)propanoylamino] acetic acid, 3-[3-(4-(5-phenylpentyloxy)phenyl)propylamino]propanoic acid, 3-[2-(4-(5-phenylpentyloxy)phenyl) ethylamino]propanoic acid, 2-[3-(4-(5-phenylpentyloxy) phenyl)propylamino]acetic acid, 2-[N-methyl-3-(4-(5-phenylpentyloxy)phenyl)propylamino]acetic acid, 3-carboxy-5-[3-(4-(5-phenylpentyloxy)phenyl)propanoylamino]benzoic acid or 2-chloro-5-[3-(2-fluoro-4-(5-phenylpentyloxy)phenyl)propanoylamino]benzoic acid, N-{(2E)-3-[4-(3-phenylpropoxy)phenyl]prop-2-enyl}-β-alanine, N-{[6-(3-phenylpropoxy)-2-naphthyl]methyl)}-β-alanine, 1-{[6-(3-phenylpropoxy)-2-naphthyl]methyl}azetidine-3-carboxylic acid, 1-{[6-(3-phenylpropoxy)-2-naphthyl] methyl}piperidine-4-carboxylic acid, N-{(2E)-3-[2-methyl-4-(3-phenylpropoxy)phenyl]prop-2-enyl}-β-alanine, 1-{(2E)-3-[4-(3-phenylpropoxy)phenyl]-2-propenyl}piperidine-4-carboxylic acid, 1-{(2E)-3-[4-(3-phenylpropoxy)phenyl]-2-propenyl}azetidine-3-carboxylic acid, N-{3-[4-(3-phenylpropoxy)phenyl]propyl}-β-alanine, N-((2E)-3-{2-methyl-4-[(5-phenylpentyl)oxy]phenyl}prop-2-enyl)-β-alanine, N-((2E)-3-{4-[(5-phenylpentyl)oxy]phenyl}-2-propenyl)-alanine, a prodrug thereof or a salt thereof, More specific embodiments include the following compounds, salts thereof, solvates thereof and prodrugs thereof, compounds described in Examples and the like.

(1) 4-{3-[4-(4-phenylbutoxy)phenyl]propyl}morpholine-2-carboxylic acid,
(2) 4-((2E)-3-{4-[4-(4-chlorophenyl)butyl]-2-methylphenyl}-2-propenyl)-1-methylpiperazine-2-carboxylic acid,
(3) 5-oxo-1-{[6-(5-phenylpentanoyl)-2-naphthyl] methyl}pyrrolidine-3-carboxylic acid,
(4) 1-(3-{2-methyl-4-[(5-phenylpentyl)oxy]phenyl}-3-oxopropyl)piperidine-4-carboxylic acid,
(5) 4-hydroxy-1-(2-{6-[(4-isobutylbenzyl)oxy]-1-naphthyl}ethyl)piperidine-4-carboxylic acid,
(6) 1-(2-{5-[3-(2,4-dichlorophenyl)propoxy]-1H-indol-1-yl}ethyl)azetidine-3-carboxylic acid,
(7) 1-((2E)-3-{4-[(5-phenylpentyl)oxy]phenyl}-2-propenyl) aziridine-2-carboxylic acid,
(8) N-({6-[4-(3-chlorophenyl)butoxy]-2-naphthyl}methyl)-N-(2-hydroxyethyl)-β-alanine,
(9) 5-{(2E)-3-[2-methyl-4-(4-phenylbutoxy)phenyl]-2-propenyl}-5-azabicyclo[2.1.1]hexane-6-carboxylic acid,
(10) 8-{[6-(4-phenylbutoxy)-3,4-dihydronaphthalen-2-yl] methyl}-8-azabicyclo[3.2.1]octane-3-carboxylic acid,
(11) 1-({7-[4-(4-chlorophenyl)butyl]-4-oxo-4H-chromen-3-yl}methyl)pyrrolidine-3-carboxylic acid,
(12) N-{[6-(3-phenylpropoxy)-3,4-dihydronaphthalen-2-yl] methyl}-O-alanine,
(13) 1-({2-[4-(2-chlorophenyl)butyl]-1-benzothien-5-yl}methyl)azetidine-3-carboxylic acid,
(14) 1-({2-[4-(2-naphthyl)butyl]-1,3-benzoxazol-5-yl}methyl)piperidine-4-carboxylic acid,
(15) N-(2-hydroxyethyl)-N-({5-[(7E)-8-phenyl-7-octenoyl] pyridin-2-yl}methyl)-β-alanine,
(16) N-({3-[3-(2,4-dimethylphenyl)propoxy]-6,7-dihydro-5H-benzo[7]annulen-8-yl}methyl)-β-alanine,
(17) 1-{[8-(4-phenylbutoxy)-2,3-dihydro-1-benzoxepin-4-yl]methyl}pyrrolidine-3-carboxylic acid,

(18) 1-({2-[(3-isobutylbenzyl)oxy]-5-oxo-5H-benzo[7]annulen-6-yl}methyl)azetidine-3-carboxylic acid,
(19) N-[(5-nonyl-1-benzothien-2-yl)methyl]-β-alanine,
(20) 3-{4-[4-(3-phenylpropoxy)phenyl]piperidin-1-yl}propanoic acid,
(21) 3-[5-[4-(3-cyclohexylpropoxy)benzyl]-3,6-dihydropyridin-1(2H)-yl]propanoic acid,
(22) 3-[5-{3-[(6-phenylhexyl)oxy]phenyl}-3,6-dihydropyridin-1(2H)-yl]propanoic acid,
(23) 3-{4-[3-({5-[4-(trifluoromethyl)phenyl]pentyl}oxy)phenyl]-2-azabicyclo[2.2.2]-2-octyl}propanoic acid,
(24) 3-(4-{3-[3-(3-isobutylphenyl)propoxy]phenyl}-2-azabicyclo[2.2.2]-2-octyl)propanoic acid,
(25) 3-[3-(3-{2-[3-(2-phenylethoxy)phenyl]ethoxy}phenyl)piperidin-1-yl]propanoic acid,
(26) 3-{4-[3-(octyloxy)phenyl]piperidin-1-yl}propanoic acid,
(27) 3-(3-{6-[2-(2-chloro-6-methylphenyl)ethoxy]-2-naphthyl}pyrrolidin-1-yl)propanoic acid,
(28) 3-(2-{4-[(5-phenylpentyl)oxy]phenyl}azetidin-1-yl)propanoic acid,
(29) 3-(3-{3-[(5-methylhexyl)oxy]phenyl}azetidin-1-yl)propanoic acid,
(30) 3-methyl-3-[6-{3-[4-(trifluoromethyl)phenyl]propoxy}-3,4-dihydroisoquinolin-2(1H)-yl]butanoic acid,
(31) 3-(5-chloro-6-{3-[4-chloro-2-(trifluoromethyl)phenyl]propoxy}-1,3-dihydro-2H-isoindol-Z-yl)propanoic acid,
(32) 3-[6-methoxy-5-(octyloxy)-1-oxo-1,3-dihydro-2H-isoindol-2-yl]propanoic acid,
(33) 3-[7-(3-cyclohexylpropoxy)-1,3,4,5-tetrahydro-2H-2-benzazepin-2-yl]propanoic acid,
(34) 3-{7-[2-(1,1'-biphenyl-3-yl)ethyl]-8-chloro-1,2,4,5-tetrahydro-3H-3-benzazepin-3-yl}propanoic acid.

Isomers:

Unless otherwise specifically mentioned, all isomers are included in the present invention. For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl and acyloxy include straight chain and branched ones. Moreover, all of isomers due to double bond, ring and fused ring (E-, Z-, cis- and trans-forms), isomers due to presence of asymmetric carbon(s) etc. R-, S-, α- and β-configuration, enantiomer and diastereomer), optically active compounds having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

In the present invention, unless otherwise specified, the symbol  means that the α-configuration substituent, the symbol  means that the β-configuration substituent, the symbol  means α-configuration, β-configuration or a mixture of α-configuration and β-configuration by an appropriate ratio, and the symbol  means a mixture of α-configuration and β-configuration by an appropriate ratio as would be clear to the person skilled in the art.

Salt and Solvate:

The compound of the present invention can be converted into a salt by known methods. The salt is preferably a non-toxic and water-soluble salt.

The salt of the present invention includes, for example, salts of alkali metal (such as potassium, sodium and lithium), salts of alkaline earth metal (such as calcium and magnesium), ammonium salts (such as tetramethylammonium salt and tetrabutylammonium salt), salts of organic amine (such as triethylamine, methylamine, dimethylamine, cyclopentylamine, benzylamine, phenethylamine, piperidine, monoethanolamine, diethanolamine, tris(hydroxymethyl) methylamine, lysine, arginine and N-methyl-D-glucamine) and acid addition salts [such as inorganic acid salts (e.g., hydrochloride, hydrobromide, hydroiodide, sulfate, phosphate and nitrate) and organic acid salts (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate), etc.].

The compound of the present invention or a salt thereof can be converted into a solvate by known methods. The solvate is preferably a non-toxic and water-soluble solvate.

The solvate of the present invention includes, for example, solvates of water, alcohols (e.g., methanol, ethanol, etc.), and the like.

Prodrugs:

A prodrug of the compound represented by formula (I) means a compound which is converted to the compound represented by formula (I) by reaction with an enzyme, gastric acid or the like in the living body. For example, with regard to a prodrug of the compound represented by formula (I), when the compound represented by formula (I) has an amino group, compounds in which the amino group is, for example, acylated, alkylated or phosphorylated (e.g., compounds in which the amino group of the compound represented by formula (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, acetoxymethylated, tert-butylated, etc.); when the compound represented by formula (I) has a hydroxy group, compounds where the hydroxy group is, for example, acylated, alkylated, phosphorylated or borated (e.g., compounds in which the hydroxy group of the compound represented by formula (I) is acetylated, palmitoylated, propanoylated, pivaloylated, succinylated, fumarylated, alanylated or dimethylaminomethylcarbonylated); and when the compound represented by formula (I) has a carboxy group, compounds where the carboxy group of the compound represented by formula (I) is, for example, esterified or amidated (e.g., compounds in which the carboxy group of the compound represented by formula (I) is made into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be prepared by a known method per se. The prodrug of the compound represented by formula (I) may be either a hydrate or a non-hydrate. A prodrug of the compound represented by formula (I) may also be a compound which is converted to the compound represented by formula (I) under physiologic condition as described in "*Iyakuhin no kaihatsu*, Vol. 7 (Bunshi-sekkei), pp. 163-198 (Hirokawa-Shoten), 1990". Also, the compound represented by formula (I) may also be labeled by a radio isotope (such as $^3$H, $^{14}$C, $^{35}$S, $^{125}$I etc,).

Examples of the prodrug of the compound represented by formula (I) in the present invention include a compound represented by the following formula (I-A):

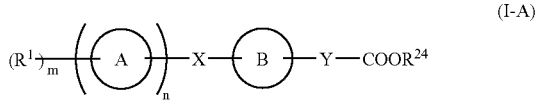

(I-A)

wherein $R^{24}$ represents C1-8 alkyl or C1-8 alkyl substituted with one or two of hydroxy or amino; and other symbols have the same meanings as described above;

a compound represented by the following formula (I-B):

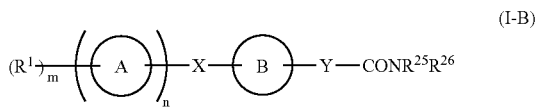

(I-B)

wherein $R^{25}$ and $R^{26}$ each independently represents a hydrogen atom, C1-8 alkyl or C1-8 alkyl substituted with one or two of hydroxy or amino; and other symbols have the same meanings as described above; and a compound represented by the following formula (I-C):

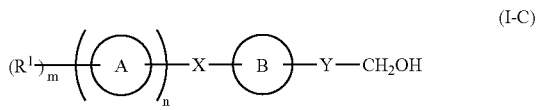

(I-C)

wherein all symbols have the same meanings as described above.

The compounds represented by formula (I) in the present invention are excellent in solubility and absorbability, exhibit a prolonged action (ability to bind to an S1P receptor (in particular, EDG-6, preferably EDG-1 and EDG-6)), are little affected by drug-metabolic enzymes and have low toxicity. These characteristics are the most important physical, chemical and pharmaceutical characteristics required in developing drugs. Because of fulfilling these requirements, therefore, the compounds represented by formula (I) in the present invention are likely usable as highly excellent drugs (see *The Merck Manual of Diagnosis and Therapy*, 17th Ed., Merck & Co.).

It can be assessed that the compound represented by formula (I) in the present invention is useful as a drug by various experimental methods described below, methods described in Biological Examples, and their methods which properly improved. It can be also easily assessed that the compound of the present invention has a good pharmacokinetic property such as a length of serum half-life, a stability in the gastrointestinal tract, an absorption of oral preparations, bioavailability, etc. by known methods, for example, a method described in *Yakubutsu bioavailability* (*Hyouka to kaizen no kagaku*), Jul. 6, 1998, Gendaiiryou-sha, etc.

(I) Experiments for Evaluating the Properties of Compound

Evaluation of the Solubility of the Present Invention Compound

Method:

About 3 to 5 mg of a test compound having been heated to 37° C. (measured with a thermometer in practice) is sampled into a test tube. Then, a solvent (Official Solution I as specified in The Japanese Pharmacopoeia, Official Solution II as specified in The Japanese Pharmacopoeia and Official Solution II added by bovine bile acid in artificial bile juice (0.5% (w/w), SIGMA)), a pH 7.4 buffer solution (prepared by diluting 4-fold McIlvaine buffer), a pH 4.0 buffer solution (prepared by diluting 4-fold McIlvaine buffer), purified water and saline, having been heated to 37° C. in a water bath, are added thereto to respectively give concentrations of 1.5 mg/mL. After stirring at a constant temperature of 37° C. for 30 minutes, the mixture is filtered through a filter (in general, DISMIC-13 cp, cellulose acetate, hydrophilic, 0.20 μm, Advantec). Immediately thereafter, the filtrate is diluted 2-fold with an organic solvent in which the test compound is highly soluble (acetonitrile or methanol) and stirred. The solubility of the test compound can be evaluated by concentrating its concentration by the external standard method with the use of HPLC.

Absorption Test of the Present Invention Compound in Oral Administration to Dog

Method:

To fasted adult beagle dogs, pentagastrin (10 μg/kg) is intramuscularly (i.m.) injected. Fifteen minutes thereafter, each test compound is orally administered (100 mg/body) with water (20 mL). Fifteen minutes thereafter, pentagastrin (10 μg/kg) is intramuscularly (i.m.) injected. Next, 15 and 30 minutes and 1, 2, 3, 4, 6, 8 and 10 hours after the administration of the test compound, the blood of the animal is collected and extracted with acetonitrile. Then, the concentration of the compound in the plasma is measured by high-performance liquid chromatography (the internal standard method). By using the concentrations of the blood in the plasma thus obtained, it is possible to determine the area under the plasma concentration curve (AUC, μg min/mL) and the maximum concentration in the plasma ($C_{max}$, ng/mL).

(II) Experiments for Evaluating the Efficacy of the Present Invention Compound (Measurement of Cytokines)

The effects of the present invention compounds on cytokine production can be confirmed by the following experiments. For example, the effects of the present invention compounds can be evaluated in cytokine production systems with the use of THP-1 (a human monocyte cell line), diluted whole human blood, mouse or rat. An example of the experiment for evaluating the effect of inhibiting the production of TNF-α, which is one of cytokines, will be illustrated.

Effect of Inhibiting TNF-α Production Using Human Cell Line

Method:

To a 96-well plate for cell incubation, 50 μL portions of lipopolysaccharide (LPS; Difco #3120-25-0) adjusted to 40 ng/mL by using RPMI-1640 medium containing 10% of fetal bovine serum (hereinafter referred to as RPMI-1640) and RPMI-1640 containing a test compound are added. Further, 100 μL of a THP-1 (DAINIPPON PHARMA #06-202) cell suspension adjusted to 2×10⁶ cells/mL by using RPMI-1640 is added, followed by incubation for 90 minutes at 37° C. (5% $CO_2$, 95% air). After the completion of the reaction, the culture supernatant is collected and the amount of the TNF-α thus produced is measured by using an ELISA kit (Invitrogen #850090192).

The activity of inhibiting the TNF-α production can be calculated as an inhibition ratio (%) in accordance with the following formula.

$$\text{Inhibition ratio } (\%) = \{(A_C - A_X)/(A_C - A_B)\} \times 100$$

$A_B$: value measured without LPS-elicitation.

$A_C$: value measured under LPS-elicitation in the absence of test compound.

PA$_X$: value measured under LPS-elicitation in the presence of test compound.

The inhibition ratios of the compound are measured at various concentrations. Thus, the concentration at which the compound shows an inhibition ratio of 50% (IC$_{50}$) can be determined from the inhibition curve.

Effect of Inhibiting TNF-α Production Using Diluted Whole Human Blood

Method:

Human peripheral blood is obtained by collecting the heparinized blood of a male healthy volunteer. The peripheral blood thus collected is finally diluted 10-fold with RPM1640 medium (manufactured by Gibco BRL) before using.

To a 96-well plate for cell incubation, a lipopolysaccharide (LPS) solution (final concentration 100 ng/ml) (Bacto W. *E. coli* 055:B5; manufactured by DIFCO Lab.), a solution of a test compound and diluted whole blood are added. After incubating the mixture at 37° C. for 6 hours, the 96-well plate is centrifuged and the supernatant is collected. Then, the amount of the TNF-α thus produced in the supernatant is measured by using an ELISA kit (manufactured by R&D system). By referring the difference in the TNF-α level between an untreated group and the LPS-elicitation group as to 100%, the inhibition ratio (%) of the test compound is determined and the 50% inhibition concentration (IC$_{50}$) is calculated.

Effect of Inhibiting TNF-α Production in Mice (Intravenous Administration)

Method:

The activity of inhibiting TNF-α production can be measured by a method reported in a document (ed. by Kazuo Ouchi, *Seibutsu Kagaku Jikken Koza* 12, 707 (1994), Hirokawa Shoten, Tokyo) with an appropriate modification. For example, a test compound is intravenously administered at various concentrations to female mice (BALB/c, 7-week-old) and then LPS (100 µg/mouse) (Bacto W. *E. coli* 055:B5; manufactured by DIFCO Lab.) is intraperitoneally administered. Ninety minutes after the LPS administration, heparinized blood is collected from the aorta abdominalis under ether anesthesia. Then, the plasma is immediately prepared and stored at –80° C. The TNF-α content in the plasma is determined by using a mouse cytokine ELISA kit (manufactured by Genzyme). By referring the difference in the TNF-α content in the plasma between an untreated group and the LPS-elicitation group as to 100%, the inhibition ratio (%) of the test compound is determined and the 50% inhibition concentration (IC$_{50}$) is calculated.

Effect of Inhibiting TNF-α Production in Mice (Oral Administration)

Method:

A test compound suspended in a vehicle is orally administered to mice (male C57BL/6). Half an hour thereafter, lipopolysaccharide (LPS, 055:B5, Sigma) is intraperitoneally administered in a dose of 60 mg/kg. To a control group, vehicle is orally administered. Sixty minutes after the LPS treatment, heparinized blood is collected from the aorta abdominalis under ether anesthesia. Then, the blood is centrifuged (12000 r.p.m.) at 4° C. for 3 minutes to give the plasma. The obtained plasma samples are stored at –80° C. before using. The TNF-α content in the plasma is determined by using an ELISA kit (R&D systems).

Effect of Inhibiting TNF-α Production in Rats (Oral Administration)

Method:

A test compound contained in a vehicle is orally administered to female Lew rats (CHARLES RIVER LABORATORIES, JAPAN). Two hours thereafter, lipopolysaccharide (LPS, 055:B6, Difco) is intravenously administered in a dose of 10 µg/kg (each group having 5 animals). To a control group, vehicle is orally administered (5 animals). Ninety minutes after the LPS treatment, heparinized blood is collected from the aorta abdominalis under ether anesthesia. Then, the blood is centrifuged (12,000 r.p.m., 3 min, 4° C.) to give the plasma. The obtained plasma samples are stored at –80° C. before using. The TNF-α content in the plasma is determined by using an ELISA kit (Genzyme/Techne, #10516).

The activity of inhibiting the TNF-α production can be calculated as an inhibition ratio (%) in accordance with the following formula.

$$\text{Inhibition ratio (\%)} = \{(A_C - A_X)/A_C\} \times 100$$

A$_B$: value measured under LPS-elicitation without the administration of test compound.

A$_C$: value measured under LPS-elicitation with the administration of test compound.

In the case of using another cytokine as a substitute for TNF-α, the effects of the present invention compounds on the cytokine production can be evaluated by appropriately modifying the methods as described above. For example, assay can be made by incubating a commercially available ELISA kit for another cytokine (for example, a Th1 type or Th2 type cytokine such as IL-1, IL-2, IL-4, IL-5, IL-6, IL-8, IL-12, TGF-β, interferon γ, etc.) as a substitute for the ELISA kits for TNF-α for a period of time suitable for each cytokine and using a substance capable of inducing each cytokine (for example, phorbol-12-myristate-13-acetate (PMA), concanavalin A (ConA), etc.).

(III) Experiments for Evaluating the Efficacy of the Present Invention Compound (Animal Model of Diseases)

It can be confirmed by using the following experiments that the present invention compounds have preventive and/or therapeutic effects on allergic diseases. For example, the preventive and/or therapeutic effects on atopic dermatitis or allergic rhinitis can be confirmed by the following experiments.

Mouse Delayed Dermatitis Model

Method:

The abdominal hair of 14-week-old male BALB/cAnCrj mice (CHARLES RIVER LABORATORIES, JAPAN) is shaven. On the next day, 0.1 mL of a 7% solution of picryl chloride (PC, Tokyo Kasei Kogyo, cat. C0307) in ethanol is applied to the whole shaven part with a pippette to thereby sensitize the animal. Four days thereafter, 0.02 mL/ear of a 2% PC solution in olive oil is applied to the front and back faces of both ear auricles by using a pippette and thus mouse delayed dermatitis is elicited. Twenty hours thereafter, the thicknesses of both ear auricles are measured with Dial Thickness Gauge (Ozaki Seisakusho) and the mean is calculated to thereby evaluate edema in the ear auricles. A test compound is suspended in a 0.5% methylcellulose solution 30 minutes before the elicitation and then orally administered once or administered as an application agent.

As the hapten, it is also possible to use 4-ethoxymethylene-2-phenyl-2-oxazolin-5-one; oxalone) or the like as a substitute for picryl chloride.

Mouse DTH Model

Method:

The abdominal hair of mice (male BALB/c) is shaven with clippers and a 7% (w/v) solution of 2,4,6-trinitrochlorobenzene (TNCB) in ethanol (100 μl) is applied to the abdomen to thereby sensitize the animals. Seven days after the sensitization, a 1% (w/v) TNCB solution in olive oil is applied to an ear auricle (right, both faces) of the mouse for elicitation. A test compound is dissolved in a vehicle and then orally administered or applied to both faces of the right ear (20 μL) before the application of TNCB. To the control group, the vehicle is applied. Immediately before the administration of the test compound and 24 hours after the TNCB application, the thickness of the mouse ear auricle is measured with Dial Thickness Gauge (Ozaki Seisakusho) as an indication of the efficacy to the mouse DTH model.

As the hapten, it is also possible to use 4-ethoxymethylene-2-phenyl-2-oxazolin-5-one; oxalone) or the like as a substitute for TNCB.

Mouse Model of Dermatitis Caused by Continuous Application of Hapten

Method:

A 1% (w/v) TNCB solution (acetone:olive oil=4:1) is applied (20 μl) to an ear auricle (right, both faces) of mice (male Balb/c) to perform the primary sensitization. Seven days after the sensitization, a 1% (w/v) TNCB solution (acetone:olive oil=4:1) is applied (20 μl) for elicitation (day 0). The same procedure as the day 0 is repeated on the days 2, 4, 6, 8, 10, 12, 14 and 16. A test compound is dissolved in a vehicle and then orally administered or applied to both faces of the right ear (20 μL) before the application of TNCB. To the control group, the vehicle is applied. Immediately before the administration of the test compound and 24 hours after the TNCB application, the thickness of the mouse ear auricle is measured with Dial Thickness Gauge (Ozaki Seisakusho) as an indication of the efficacy to the mouse model of dermatitis induced by the continuous application of hapten.

As the hapten, it is also possible to use 4-ethoxymethylene-2-phenyl-2-oxazolin-5-one; oxalone) or the like as a substitute for TNCB.

Inhibitory Effect of Invention Compound on Spontaneous Scratching Behavior of NC Mouse with Spontaneous Onset of Dermatitis Method:

Male NC mice suffering from the spontaneous onset of dermatitis are employed. The mice are put into a monitoring cage and allow to acclimatize to the environment for 30 minutes. Then, scratching behaviors within an hour are videotaped in an unmanned room. By replaying the video, a series of movements of scratching the face, ears, back neck and around these parts with hinder legs are regarded as a single scratching behavior and these behaviors are counted. A test compound or a control (0.5% aqueous solution of methylcellulose) is orally administered 3 to 5 times in total at intervals of 30 minutes. Immediately after the second administration, the scratching behaviors are videotaped and counted for 1 to 3 hours, thereby making evaluation.

Inhibitory Effect on Spontaneous Scratching Behavior of BN Rat with DNFB-induced Dermatitis Firstly, 0.3% dinitrofluorobenzene (DNFB) is repeatedly applied to the scalp of Brown Norway (BN) rats to elicit dermatitis. Then, an increase in scratching behaviors is observed 24 to 27 hours after the application. The effect of the present invention compound on the scratching behaviors can be evaluated.

Method:

To the shaven scalp of male BN rats, 0.3% DNFB dissolved in a mixed solvent of acetone and olive oil is applied as a hapten. To a non-elicitation group, the mixed solvent of acetone and olive oil is applied. One week thereafter, these substances are applied to the scalp again and the application procedures are repeated thrice every other day. Then, 24 to 27 hours after the fourth application, the rats are videotaped in an unmanned room. By replaying the video, a series of movements of scratching around the hapten-application site with hinder legs are regarded as a single scratching behavior and these behaviors are counted. A test compound or a control (0.5% aqueous solution of methylcellulose) is orally administered 12 to 48 hours after the third to sixth administrations. To a non-elicited group, 0.5% aqueous solution of methylcellulose is orally administered. From 30 minutes after the administration, the scratching behaviors are videotaped for 3 hours and counted, thereby making evaluation.

Allergic Rhinitis Model

Method:

To male Crj Hartley guinea pigs (6-week-old), ovalbumin is administered in the procedure as shown in Table 1 to thereby construct an allergic rhinitis model.

TABLE 1

| Day | Dose | Administration route |
| --- | --- | --- |
| 0 | 0.5 mg/0.5 mL | Intraperitoneal |
| 2 | 1.0 mg/0.5 mL | Intraperitoneal |
| 22 | 0.1% 40 μL | Nasal (both sides) |
| 24 | 0.2% 40 μL | Nasal (both sides) |
| 27 | 0.4% 40 μL | Nasal (both sides) |
| 31 | 0.5% 40 μL | Nasal (both sides) |
| 36 | 1.0% 40 μL | Nasal (both sides) |
| 41 | 1.0% 40 μL | Nasal (both sides) |

After the initiation for 42 days, a tube is inserted into the airway of each guinea pig under anesthesia and maintained at a constant temperature by a heat pat. Then, 40 μL of a test compound or saline is dropped into the both nasal cavities. Ten minutes thereafter, 40 μL of 1% ovalbumin is dropped into the both nasal cavities. Thirty minutes after the dropping of ovalbumin, the moisture in the nose is eliminated with absorbent cotton. Fifteen minutes thereafter, the absorbent cotton having been weighed is inserted into the nose for 15 minutes. The difference between the absorbent cotton weights is referred as the nasal secretion, thereby making evaluation.

It can be confirmed by using the following experiment that the present invention compounds have immunosuppressant effects. For example, the therapeutic effects of the present invention compounds on rejection in transplantation can be confirmed by using heart, kidney, liver, pancreas, lung, bone marrow and dermal graft models or the like. As an example, a heart transplantation model will be illustrated below.

Rat Ectopic Heart Transplantation Model

Method:

Using rats, the heart is taken out from a donor rat and transplanted into the abdomen of a recipient rat. By orally administering a test compound for a preventive purpose, the heart transplantation survival days are estimated and the therapeutic effect can be thus evaluated.

It can be confirmed by using the following experiments that the present invention compounds have preventive and/or therapeutic effects on autoimmune diseases. For example, the preventive and/or therapeutic effects on rheumatoid arthritis (for example, arthritis, arthritis deformans, etc.) can be confirmed by using the following experiments.

Effect on Rat Collagen-induced Arthritis Model

Method:

Eight-week-old female DA rats (SLC) are used. Throughout the experimental period, the animals are fed in a feeding room artificially conditioned at a temperature of 24±2° C. and a humidity of 55±5% and cyclically illuminated 12 hours per day. The animals are maintained on a solid feed (CE-2; CLEA Japan) and tap water ad libitum. After pre-feeding for 1 week, the animals are used in the experiment. A model of collagen-induced arthritis is constructed in the following manner. Namely, bovine type II collagen (a 0.3% solution, COLLAGEN GIJUTSU KENSHUKAI; #K-41, lot. 11214, hereinafter referred to as CII) and adjuvant incomplete freund (DIDCO #0639-60, hereinafter referred to as IFA) are mixed at a ratio of CII:saline:IFA of 1:1:2 and the mixture is ultrasonically treated (20 sec.×3 times at intervals of 1 min) to prepare an emulsion. This emulsion (0.75 mg of CII/mL) is subcutaneously injected in 0.1 mL portions to 4 sites in the back of the rat. For additional sensitization, 0.15 mL thereof emulsion is subcutaneously administered into the tail root to induce arthritis. A test compound is suspended in a 0.5% carboxymethylcellulose solution and orally administered by force into the stomach with the use of an oral sonde twice a day (in the morning and evening) from the administration day to the day 28. The arthritis is evaluated by scoring the arthritis degree in accordance with the method of Ostermann T., et al. (*Inflamm. Res.*, 44, 258-263 (1995)). The foot volume of each individual animal can be measured by using a plethysmometer (UNICOM, TK-101 CMP).

Mouse Antibody Cocktail-induced Arthritis

Method:

An antibody cocktail against type II collagen is intravenously administered to male DBA/1 JNCrj mice in a dose of 2 mg/0.5 mL/mouse. Three days thereafter, lipopolysaccharide is intraperitoneally administered in a dose of 25 μg/0.1 mL/mouse to elicit arthritis. On the day 10, four legs of each animal can be evaluated by scoring in 4-grades depending on the intensities of erythema and enlargement. A test compound is dissolved in an equimolar 0.02 mol/L sodium hydroxide solution, then diluted with distilled water and orally administered thrice a day from 30 minutes before the lipopolysaccharide administration.

Adjuvant-induced Arthritis Model

Method:

Evaluation is made by using 7 weeks male or female Lewis rats. After measuring the volume of the left hinder leg of a rat, a 600 μg/100 μL suspension of dry *Mycobacterium butyricum* cells (Difco), which is employed as an adjuvant, in liquid paraffin is subcutaneously injected into the right hinder foot pad. Thus, a rat adjuvant-induced arthritis model is constructed. By comparing a test group to which a test compound has been orally administered with a control group of non-administration, the therapeutic or preventive effect is evaluated.

Effect of the Present Invention Compound on Pain Response of Adjuvant-induced Arthritis Model The inhibitory effect of a test compound on a pain response of an adjuvant-induced arthritis model (i.e., a chronic arthritis pain model) can be evaluated by using the abnormal phonation response as an indication.

Method:

Seven week male Lewis rats can be used. After measuring the volume of the left hinder leg of a rat, a 600 μg/100 μL suspension of dry *Mycobacterium butyricum* cells (Difco), which is employed as an adjuvant, in liquid paraffin is subcutaneously injected into the right hinder foot pad. Thus, a rat adjuvant-induced arthritis model is constructed. Twenty-two days after the adjuvant injection, the knee joint of the left hinder leg is bent and stretched 5 times before orally administering a test compound. Individuals showing the abnormal phonation response every time are employed in the experiment. Based on the edema volume in the left hinder leg in the previous day, the rats are divided into groups each having 10 animals. A test compound at various doses and 5 mL/kg of an aqueous methylcellulose solution (control) are orally administered. One, two, three and four hours after the administration, the abnormal phonation responses are observed. The analgesic effects are evaluated by bending and stretching the knee joint of the left hinder leg 5 times at each observation point and individuals showing no abnormal phonation response every time are regarded as negative in the abnormal phonation response, while individuals showing negative abnormal phonation response at one or more evaluation points are regarded as positive in the analgesic effect.

Rabbit Outer Meniscus Removal Model

Method:

Rabbits (female Kbs: NZW (Healthy) rabbits) are preliminarily fed for 1 week and then subjected to the removal of meniscus by the following method.

A 2% Seractal injection (0.05 ml/kg) is subcutaneously administered into the back neck of the rabbits. Then, the animals are anesthetized by intravenously administering a Nembutal injection (20 mg/kg) to the auricular edge. The right knee is disinfected with 5-fold iodine tincture dilution, if necessary, the animals are topically anesthetized by dropping a 2% xylocalne injection into the incised part.

Next, the outer epithelium and articular capsule of the right hinder leg are incised at an angle of 90° to the patellar ligament. The outer collateral ligament is excised and then the sesamoid ligament is excised. In this step, Bosmine injection is dropped for hemostasis. The tissue bound to the anterior tissue of the outer meniscus is picked up with forceps and the meniscus is pulled forward and cut at ⅓ in the center. The surgical site is washed with saline injection and the synovial membrane and the articular capsule are stitched. Further the muscular layer and the outer skin are individually stitched.

After the surgical operation, crystalline penicillin G potassium (5000 U/animal) and streptomycin sulfate (100 mg/animal) are intramuscularly injected into the left hinder leg to prevent infection. The rabbits are fed until they are sacrificed on the day 7 after the surgical operation. During the feeding period, a test compound is administered at each defined dose twice a day.

The animals are anesthetized by intravenously injecting a Nembutal injection (40 mg/kg) into the articular edge and then killed by exsanguination. The right knee joint is collected. The knee joint is incised and the thigh bone and the tibial capital are collected and stored in a 10% neutral buffer Formalin at room temperature. After collecting all samples, the thigh bone and the tibial capital are masked. Then, the invaded area is measured by using a stereoscopic microscope.

Evaluation can be made by a statistically processing method of comparing the invaded cartilage area of the control (vehicle) group with that of the test compound-administered group by Williams's multiple comparison (EXSAS, Ver 5.00).

The above-described experimental model, in which cartilage fracture closely similar to human arthritis deformans can be induced, has been generally accepted as an OA model.

It can be confirmed by using the following experiments that the present invention compounds have preventive and/or therapeutic effects on autoimmune diseases. For example, the preventive and/or therapeutic effects on nerve diseases (multiple sclerosis), inflammatory bowel disease and hepatitis can be confirmed by the following experiments.

EAE Model (Experimental Allergic Encephalomyelitis)

Method:

Using Lewis rats, experimental allergic encephalomyelitis is induced by using various antigens such as spinal cord or MOG (myelin oligodendrocyte elycoprotein). By comparing a group to which a test compound is orally administered with a non-administered group, a therapeutic or preventive effect can be evaluated.

Acetic Acid-induced Colitis Model

Method:

A required amount of a 5% acetic acid solution is packed into a 1 mL syringe provided with a disposable oral sonde (for mouse). Under Somnopentyl anesthesia, the sonde (to 5 cm from the tip) is inserted from the anus into the large intestine to into 7-week-old male SD(CD)IGS rats. After the insertion, the 5% acetic acid solution (0.25 mL) is injected into the large intestine over 10 seconds. Then, the sonde is drawn and the anus is closed for about 1 minute. A required amount of saline is packed into a 50 mL syringe provided with a disposable oral sonde (for mouse). Then, the sonde (to 8 cm from the tip) is inserted from the anus into the large intestine. After the insertion, the intestinal tract is washed with the saline (about 10 mL).

A test compound and a vehicle are orally administered each in a definite amount 30 minutes before the elicitation of colitis and 8 hours after the elicitation.

Twenty hours after the elicitation, the animals are sacrificed and the whole large intestine (from the anus to the cecum root) is taken out. The contents of the large intestine are washed with saline. After trimming the large intestine having been taken out and washed, a part 9 cm apart from the anus is excised. From the large intestine piece thus excised, excessive moisture is wiped off and the wet weight is determined by using an electronic balance. The injured area ($mm^2$) of the excised large intestine is calculated by image analysis.

TNBS-induced Colitis Model

Method:

Under Somnopentyl anesthesia, a flexible oral sonde (to 8 cm from the tip) is inserted from the anus into the large intestine of male SD(CD)IGS rats (7-week-old). Then, 50 mg TNBS (2,4,6-trinitrobenzenesulfonic acid)/20% ethanol/ 0.25 mL/rat or 20% ethanol/0.25 mL/rat is injected. After closing the injection site, the animals are allowed to stand for about 2 hours to thereby elicit colitis. A test compound is orally administered 30 minutes before the elicitation and 8 hours thereafter on the elicitation day and twice a day (in the morning and evening) from the next day. Three days after the elicitation, the rats are killed by exsanguination under ether anesthesia. The large intestine is taken out and the contents of the large intestine are washed with saline. Then, the length of the whole large intestine is measured. After trimming the large intestine, a part 9 cm apart from the anus is excised. From the large intestine piece thus excised, excessive moisture is wiped off and the wet weight is determined by using an electronic balance.

Chronic Ulcerative Colitis Model

Method:

Under pentobarbital anesthesia, 1% aqueous solution of acetic acid (10 ml/kg) is injected from the anus into the large intestinal cavity of male Syrian hamsters (6 to 7-week-old) by using a flexible oral sonde for rat. Then, the anus is clipped for 30 minutes to thereby elicit colitis. To a normal group, distilled water is injected in the same manner. A test compound is orally administered 18 hours and an hour before the elicitation of colitis and 6 hours after the elicitation, i.e., thrice in total. Twenty hours after the elicitation, the animals are sacrificed and a large intestine piece (7 cm from the anus) is collected. The collected sample is incised along the intestinal tract membrane attached site and the inside of the intestinal membrane is washed with saline (5 ml). The incised large intestine is photographed and the ulcer area ratio (total ulcer area×100/total large intestine area) is calculated. The supernatant of the large intestine washing liquor is used in an occult blood test.

Effect of Inhibiting Chronic Ulcerative Colitis

Method:

Male C57BL/6 mice are maintained on 7% aqueous solution of dextran sulfate sodium (hereinafter referred to as DSS) ad libitum. From the initiation of the aqueous DSS solution intake, the body weight and clinical score are measured every other day. The clinical score is calculated as the sum of diarrhea score (normal: 0, loose stool: 2, diarrhea: 4) and hematochezia score (normal: 0, hemorrhage: 2, serious hemorrhage: 4). On the day 10 of the aqueous DSS solution intake, heparinized blood is collected from the postcava under ether anesthesia. By using a blood cell counter, the hematocrit value is measured. From the day 0 to the day 10 of the aqueous DSS solution intake, a test compound is orally administered repeatedly in a definite dose twice a day.

Inhibitory Effect on Galactosamine/LPS-induced Hepatopathy Model

Method:

A test compound at various concentrations is administered to male mouse (BALB/c, 7 to 8-week-old) having been fasted overnight. Thirty minutes thereafter, a solution of a mixture of galactosamine (700 mg/kg) and LPS (10 μg/kg) (Bacto W. *E. coli* 055:B5; manufactured by DIFCO Lab.) is intraperitoneally administered to elicit hepatopathy. Each test compound is suspended in 0.5% methylcellulose.

Seven hours after the elicitation, heparinized blood is collected from the aorta abdominalis under ether anesthesia. Then, the plasma is immediately prepared. The extent of hepatopathy is evaluated by using an increase in plasma GPT as an indication. The plasma GPT is measured with an autoanalyzer with the use of a GPT measurement reagent (manufactured by Wako Pure Chemicals). By referring a difference in plasma GPT level between an untreated group and the hepatopathy-induced group as to 100%, the inhibitory ratio (%) of the test compound can be calculated.

It can be confirmed that the present invention compounds have preventive and/or therapeutic effects on multiple organ failure and sepsis by using the following experiment.

Multiple Organ Failure Model

Method:

Rats having been fasted for about 24 hours are anesthetized by intravenously administering pentobarbital (40 mg/kg). After fitting catheters to both femoral veins and an alar needle to the tail vein, lipopolysaccharide (LPS; 0.3 mg/kg/h) and a test compound or a vehicle for the administration of the test compound (in the case of a control group) are continuously administered via an arbitrary vein. During the administration period, the animals are additionally anesthetized, if necessary depending on the wakening. Six hours after the initiation of the continuous intravenous administration, the blood is collected from the aorta abdominalis. Then, elastase activity, coagulation fibrinolysis parameters (fibrinogen, FDP, platelet count, etc.) and biochemical parameters of blood (GOT, GPT, creatinine, BUN, etc.) are measured. Further, an indication of lung injury is determined by taking out lungs and measuring the wet weight or measuring the leakage protein which is systemically administering a fluorescent labeled protein into the lung.

(IV) Experiments for Evaluating the Inhibitory Effect of the Present Invention Compound on Drug Metabolic Enzyme and/or the Inhibitory Effect on the Induction of Drug Metabolic Enzyme CYP1A2 Inhibitory Effect Using Expression Microsome Method:

A CYP1A2 expression microsome (Gentest) prepared by expressing in human lymphoblast cells is employed as an enzyme system. As a fluorescent substrate, 3-cyano-7-ethoxycoumarin (CEC, Molecular Probes) is employed.

As a reaction system, use is made of a phosphate buffer (100 mmol/l, 200 µl; pH 7.4) containing the CYP1A2 expression microsome (0.05 mg/ml), $MgCl_2$ (5 mmol/l) and NADPH (1 mmol/l). To this reaction system, the fluorescent substrate CEC (final concentration 10 µmol/l) and a test compound (final concentration 3, 10 or 30 µmol/l) or α-naphthoflavone (final concentration 0.003 or 0.01 µmol/l; TOKYO KASEI) employed as a positive control inhibitor are added and the reaction is performed at 37° C. for 30 minutes. The fluorescent intensity (Ex=409 nm, Em=409 nm) of a metabolite of the substrate is measured (fluorescence detector: Spectra Max Geminin (Molecular Devices)).

The inhibitory effect is evaluated in the inhibition ratio (%) by referring the inhibition of the formation of the metabolite by the test compound as an indication.

Inhibitory Activity Against Human CYP2C9

Method:

Inhibitory activity against human CYP2C9 of the compound of the present invention can be evaluated by a method of Sato, et al. (*Yakubutsudotai* (*Xenobio. Metabol. and Dispos.*), 16(2), 115-126 (2001)), which is improved in assaying accuracy and/or assaying sensitivity.

Inhibitory Activity Against Human CYP3A4

Method:

Inhibitory activity against human CYP3A4 of the compound of the present invention can be evaluated by an improved method described in *Drug Metabolism and Disposition,* 28(12), 1440-1448 (2000).

For example, a reaction solution consisted of potassium phosphate buffer (pH 7.4) (final concentration: 200 mM), magnesium chloride hexahydrate (final concentration: 5 mM), substrate (7-benzyloxyquinoline (7-BQ), final concentration: 40 µM), and expression system microsome (Daiichikagakuyakuhin, final concentration: 0.25 mg/mL) is prepared. Then, 100 µL of the reaction solution is dispensed in 96 well plate, and added by 50 µL of an aqueous solution containing test a compound and 0.8% acetonitrile, to carry out 10 minutes of preincubation at 37° C. Then, 50 µL of a reduced nicotinamide adenine dinucleotide phospate (NADPH, 4 mM) is added to initiate a reaction. The fluorescence intensity of each well is measured at the time when NADPH is added and after incubated for 30 minutes. Excitation wavelength at 409 nm and emission wavelength at 530 nm of quinolinol, which is metabolite of substrate, is measured. Inhibition ratio (%) of the test compound is calculated by the following calculation formula to obtain $IC_{50}$ value.

Inhibition ratio (%)=[1−{(measured value when a test compound is added)−(blank value)/(control value−blank value)}]×100

Human CYP3A4 Inducing Effect

Method:

HepG2 cells are cultured in an incubator at 37° C. and 5% $CO_2$ by using a medium (MEM(+)) prepared by mixing minimum essential medium Eagle (MOD.) with Earle's salts without L-glutathione (manufactured by ICN, product No. 1210254) with 1/100 times as much non-essential amino acids for MEM Eagle (100×) (manufactured by ICN, product No. 1681049), Antibiotic-Antimycotic ((100×), manufactured by GIBCO, product No. 15240-096), L-glutamine-200 mM ((100×), GIBCO, prdduct No. 25030-081) and 1/10 times as much fetal bovine serum (Sigma, product No. F9423). The medium is replaced at intervals of 2 to 3 days and an about 1/5 portion of the cells attaining a confluence are subcultured once a week. Almost confluent HepG2 cells having been cultured in a culture flask (225 $cm^2$) are seeded in a 24-well plate (IWAKI, product No. 3820-024) at a density of 5×10$^4$ cells/MEM(+) 500 µL/well and cultured in an incubator at 37° C. and 5% $CO_2$ for 2 days. Subsequently, transduction is carried out as follows. Per well (MEM 100 µl) of the 24-well plate, a solution containing autogenously prepared hPXR vector (10 ng), CYP3A4 vector (200 ng) and pRL-TK vector (200 ng) and preliminarily prepared Tfx (Tradename)-20 reagent (0.75 µL, Promega, product No. E2391, prepared in accordance with the attached manual) are added. After mixing by upsetting several times, the mixture is allowed to stand at room temperature for 15 minutes (DNA-liposome mixture solution). Cells having been cultured for 2 days are washed with PBS(−) (1 mL per well) and then the DNA-liposome mixture solution prepared above (100 µl) is added. After culturing the cells in an incubator at 37° C. and 5% $CO_2$ for 1 hour, MEM(+) (440 µL/well) and a test compound (adjusted to a 10-fold concentration of the final concentration by using MEM(+) containing 1% DMSO, 60 µl/well) is added and the cells are cultured in an incubator at 37° C. and 5% $CO_2$ for additional 2 days. Then, the cells having been cultured for 2 days after the addition of the test compound are washed with PBS(−) (1 mL per well) once and a passive lysis buffer (PLB) (100 µl/well) is added. The mixture is allowed to stand at room temperature for 15 minutes or longer (lysis solution). A 20 µl/well portion of the lysis solution thus prepared is transferred into a 96-well white plate (Perkin Elmer, product No.

23300) and a luciferase assay reagent II (LARII) (100 μl/well) is added. After 2 to 24 seconds, a stop & glo reagent (100 μl/well) is added and then each chemical luminescence is measured for 2 to 14 seconds by using a luminometer (Microlumat LB96P, Berthold JAPAN). The reagents employed (PLB, LARII and the stop & glo reagent) are prepared and handled in accordance with the manual attached to Dual-Luciferase$^R$ Reporter Assay System (Promega, product No. EI910).

The CYP3A4 inducing activity is calculated by referring an increase in the CYP3A4 transcriptional activity in the case of using Rifampicin (10 μmol/L) as a positive control as to 100%.

(V) Experiments for Evaluating the Toxicity of the Present Invention Compound Mutagenicity Test The mutagencities of the present invention compounds can be evaluated in accordance with the method described in *Anei-ho ni Okeru Henigensei Shiken-Tesuto Gaidorain to GLP* (*Mutagenicity Test according to Occupational Health and Safety Law-Test Guideline and GLP-*) (Ed. by Chemical Substance Investigation Division, Industrial Safety and Health Department, Ministry of Labor; Japan Industrial Safety and Health Association, 1991, chapter 4).

Single Acute Toxicity Test in Rat

The test compound is administered to six-week-old Crj:CD (SD) rat by single intravenous dose or single oral administration. Toxicity can be evaluated by contrast with value at no addition of the test compound. Basic evaluation of toxicity can be done by, for example, observation of performance status or locomotor activity, etc.

Cardiotoxicity to Rat (Bradycardia)

Using SD rats, catheters are inserted into the jugular vein and the carotid artery (or the femoral vein and the femoral artery) under anesthesia. The tip of the arterial cannula is connected to a pressure transducer (DX-100, NIHON KOHDEN) and the blood pressure and the heart rate are measured respectively via a strain pressure amplifier (AP-641G, NIHON KOHDEN) and an instant heart rate meter (AT-601G, NIHON KOHDEN). Under anesthesia or promoting wakening, a test compound is intravenously or orally administered and changes in the blood pressure and heart rate are monitored.

(ii) Evaluation of the Activity of the Compound of the Present Invention Against hERG $I_{Kr}$ Current Method According to the report by Zou, et al. (*Biophys. J.*, 74, 230-241 (1998)), using HEK293 cell overexpressed of human ether-a-go-go-related gene (hERG), max tale current of HERG $I_{Kr}$ current induced by depolarization pulse, followed by repolarization pulse is measured by patch-clamp recording. Rate of change (inhibition ratio) is calculated by comparison max tale current between before addition of the test compound and 10 minutes after. The influence of the test compound against hERG $I_{Kr}$ current can be evaluated by the inhibition ratio.

Processes for the Preparation of the Compound of the Present Invention:

The compound represented by formula (I) in the present invention can be prepared by methods which properly improved and combined known methods, such as methods described in WO02/092068, *Synth. Commun.*, 23(19), 3347 (2003), *Comprehensive Organic Transformations: A Guide to Functional Group Preparations*, 2nd Ed., (Richard C. Larock, John Wiley & Sons Inc. (1999)) and the like, methods described below and/or method according thereto, or methods described in Examples. In each method described below, a starting material can be used as a salt thereof. An example of the salt includes a variety of salt described as a salt of compound represented by formula (I) described above.

Among the compounds represented by formula (I), a compound wherein X is bound to ring B via oxygen, i.e., a compound represented by formula (I-D):

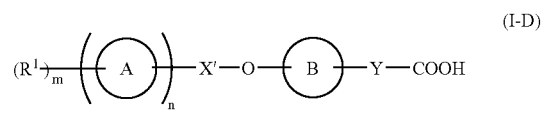

wherein X' represents a bond or a spacer having 1 to 7 atoms in its main chain; and other symbols have the same meanings as described above;

can be prepared by the following method (1) or (2).

(1) A compound represented by formula (I-D) can be prepared by subjecting a compound represented by formula (II):

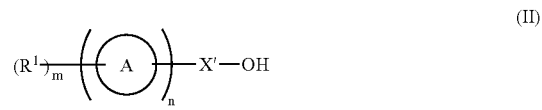

wherein all symbols have the same meanings as described above;

and a compound represented by formula (III):

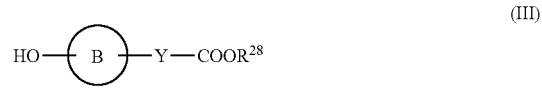

wherein $R^{28}$ represents a hydrogen atom or a group for protecting a carboxy group; and other symbols have the same meanings as described above;

to Mitsunobu reaction, followed by a removal of the protecting group, if necessary. This Mitsunobu reaction, which is publicly known, is carried out by, for example, reacting these compounds at 0 to 60° C. in an organic solvent (dichloromethane, diethyl ether, tetrahydrofuran, acetonitrile, benzene, toluene, etc.) in the presence of an azo compound (diethyl azodicarboxylate (DEAD), diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, polymer supported triphenylphosphine, etc.). The removal of the group for protecting a carboxy group can be carried out by a known method, for example, the method described in WO 02/092068 or a similar method and/or the method described in *Protective Groups in Organic Synthesis*, T. W. Greene, John Wiely & Sons Inc. (1999). The group for protecting a carboxy group is not particularly restricted and use may be made of an arbitrary one in addition to the above-described groups so long as it can be easily and selectively removed.

(2) A compound represented by formula (I-D) can be prepared by subjecting a compound represented by formula (II):

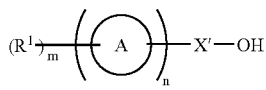
(II)

wherein all symbols have the same meanings as described above;

and a compound represented by formula (IV):

(IV)

wherein L represents a leaving group such as a halogen atom, rmethanesulfonyloxy (OMs), toluenesulfonyloxy (OTs), trifluoromethanesulfonyloxy (OTf), alkylthio, alkylsulfinyl, alkylsulfonyl or hydroxysulfonyl; and other symbols have the same meanings as described above;

or a compound represented by formula (V):

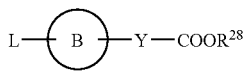
(V)

wherein all symbols have the same meanings as described above;

and a compound represented by formula (III):

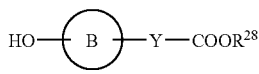
(III)

wherein all symbols have the same meanings as described above;

respectively to etherifying reactions, followed by a removal of the protecting group, if necessary. These etherifying reactions, which have been publicly known, are carried out by, for example, reacting the compounds at 0 to 100° C. in an organic solvent (N,N-dimethylformamide, dimethyl sulfoxide, chloroform, dichloromethane, diethyl ether, tetrahydrofuran, methyl t-butyl ether, etc.) in the presence of an alkali metal hydroxide (sodium hydroxide, potassium hydroxide, lithium hydroxide, etc.), an alkaline earth metal hydroxide (barium hydroxide, calcium hydroxide, etc.) or a carbonate (sodium carbonate, potassium carbonate, cesium carbonate, etc.), an aqueous solution thereof or a mixture thereof. The removal of the protecting group can be carried out by a similar method to those described above.

Among the present invention compounds represented by formula (I), a compound wherein Y represents:

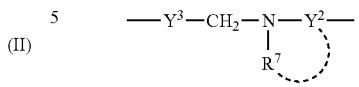

wherein $Y^2$ and $Y^3$ each independently represents a bond or a spacer having 1 to 8 atoms in its main chain (provided that the sum of the atoms in its main chains of $Y^2$ and $Y^3$ does not exceed 8); and $R^7$ represents a hydrogen atom or a substituent or an atom in the spacer represented by $Y^2$ may be taken together with $R^7$ to form a heterocyclic group which may have a substituent(s);

namely, a compound represented by formula (I-E):

(I-E)

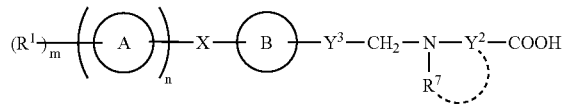

wherein all symbols have the same meanings as described above;

can be prepared by subjecting a compound represented by formula (VI):

(VI)

wherein all symbols have the same meanings as described above;

and a compound represented by formula (VII):

(VII)

wherein all symbols have the same meanings as described above;

to a reductive amination reaction, followed by a removal of the protecting group, if necessary. This reductive amination reaction, which has been publicly known, is carried out by, for example, reacting the compounds at a temperature of 0 to 100° C. in an organic solvent (N,N-dimethylformamide, dichloromethane, etc. either alone or as a mixed solvent comprising two or more of these solvent at an arbitrary mixing rate) in the presence or absence of an organic acid (acetic acid, etc.) or in the presence or absence of an organic base (triethylamine, sodium hydrogencarbonate, etc.) with the use of a reducing agent (sodium triacetoxyborohydride, sodium cyanoborohydride, tetrabutylammonium borohydride, etc.). The removal of the protecting group can be carried out by a similar method to those described above.

Among the present invention compounds represented by formula (I), a compound wherein Y represents:

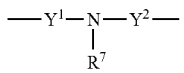

wherein all symbols have the same meanings as described above;
namely, a compound represented by formula (I-F):

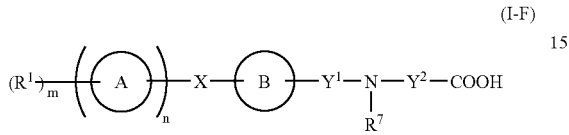

wherein all symbols have the same meanings as described above;
can be prepared by subjecting a compound represented by formula (VIII):

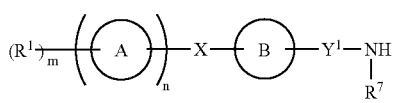

wherein all symbols have the same meanings as described above;
and a compound represented by formula (IX):

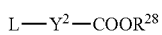

(IX)

L—Y²—COOR²⁸ wherein all symbols have the same meanings as described above;
or a compound represented by formula (X):

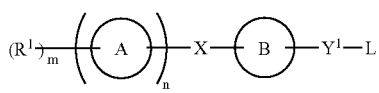

wherein all symbols have the same meanings as described above;
and a compound represented by formula (X):

(XI)

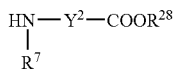

wherein all symbols have the same meanings as described above;
respectively to alkylation reactions, followed by a removal of the protecting group, if necessary. These alkylation reactions, which have been publicly known, are carried out by, for example, reacting the compounds at 0 to 100° C. in an organic solvent (N,N-dimethylformamide, dimethyl sulfoxide, chloroform, dichloromethane, diethyl ether, tetrahydrofuran, methyl t-butyl ether, etc.) in the presence of an alkali metal hydroxide (sodium hydroxide, potassium hydroxide, lithium hydroxide, etc.), an alkaline earth metal hydroxide (barium hydroxide, calcium hydroxide, etc.) or a carbonate (sodium carbonate, potassium carbonate, cesium carbonate, etc.), an aqueous solution thereof or a mixture thereof. The removal of the protecting group can be carried out by a similar method to those described above.

Among the present invention compounds represented by formula (I), a compound wherein Y represents:

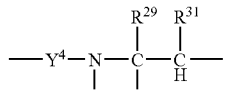

wherein $Y^4$ represents a bond or a spacer having 1 to 7 atoms in its main chain; $R^{29}$, $R^{30}$ and $R^{31}$ each independently represents a hydrogen atom or a substituent; and other symbols have the same meanings as described above;
namely, a compound represented by formula (I-G):

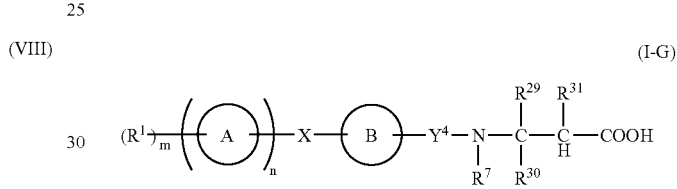

wherein all symbols have the same meanings as described above;
can be prepared by subjecting a compound represented by formula (XII):

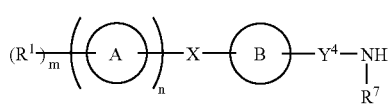

wherein all symbols have the same meanings as described above;
and a compound represented by formula (XIII):

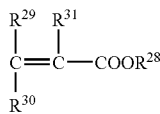

wherein all symbols have the same meanings as described above;
to an addition reaction to amine, followed by a removal of the protecting group, if necessary. The addition reaction to amine, which has been publicly known, is carried out by, for example, reacting the compounds at a temperature of −78° C. to the reflux temperature in an organic solvent (for example, methanol, ethanol, propanol, benzene, toluene, diethyl ether, tetrahydrofuran, dimethoxyethane, etc.) or without solvent. The removal of the protecting group can be carried out by a similar method to those described above.

The compounds represented by the formulae (II) to (XIII) which are used as the starting materials in the present invention are either publicly known per se or can be easily prepared by publicly known methods.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Application to Pharmaceuticals:

The compounds having an ability to bind to an S1P receptor (in particular, EDG-6, preferably EDG-1 and EDG-6) are useful as immunosuppressants. The binding manner to EDG-1 is preferably an agonistic action.

The present invention compounds represented by formula (I), salts thereof, solvates thereof or prodrugs thereof are compounds having an ability to bind to EDG-6 and exhibit prolonged pharmacological action. Therefore, they are useful as preventives and/or remedies in mammals, in particular, humans for rejection in transplantation, rejection of a transplanted organ, transplantation versus host disease, autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, arteriosclerosis, acute heart failure, angina, stroke, traumatic injury, genetic diseases and the like.

In addition to the ability to bind to EDG-6, some of the present invention compounds have an agonistic activity against EDG-1 and, therefore, show an immunosuppressant effect and prolonged pharmacological action. Owing to these characteristics, they are more useful as preventives and/or remedies for rejection in transplantation, transplantation versus host disease, autoimmune diseases, allergic diseases and the like.

When the compound represented by formula (I) in the present invention or a combination preparation of the compound of the present invention represented by formula (I) and other drug(s) is used for the purpose above described, it may be normally administered systemically or locally, usually by oral or parenteral administration. The doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 100 mg, by parenteral administration, up to several times per day, or continuous administration from 1 to 24 hours per day from vein. As described above, the doses to be used depend upon various conditions. Therefore, there are cases in which doses lower than or greater than the ranges specified above may be used.

When the compound represented by formula (I) in the present invention or a combination preparation of the compound of the present invention represented by formula (I) and other drug(s) is administered, it is used in the form of solid for oral administration, liquid forms for oral administration, injections, liniments, suppositories, eye drops or inhalant for parenteral administration or the like.

Solid forms for oral administration include compressed tablets, pills, capsules, dispersible powders, and granules. Capsules include hard capsules and soft capsules. Tablets include sublingual tablets, buccal adhesive tablets, buccal quick disintegration tablets and or the like. Also, in such solid forms, one, two or more active compound(s) may be admixed with a vehicle (such as lactose, mannitol, glucose, microcrystalline cellulose or starch), a binder (such as hydroxypropylcellulose, polyvinylpyrrolidone or magnesium metasilicate aluminate), a disintegrant (such as cellulose calcium glycolate), lubricants (such as magnesium stearate), a stabilizing agent, and a solution adjuvant (such as glutamic acid or aspartic acid) and prepared according to methods well known in normal pharmaceutical practice. The solid forms may, if desired, be coated with a coating agent (such as sugar, gelatin, hydroxypropylcellulose or hydroxypropylmethylcellulose phthalate), or be coated with two or more films. Furthermore, coating may include containment within capsules of absorbable materials such as gelatin.

The sublingual tablets are produced in accordance with a conventionally known method. For example, one, two or more active substance(s) are used after making into pharmaceutical preparations by the law of the art by mixing with an vehicle (such as lactose, mannitol, glucose, microcrystalline cellulose, colloidal silica, starch, etc.), a binder (such as hydroxypropylcellulose, polyvinylpyrrolidone, magnesium aluminometasilicate, etc.), a disintegrant (such as starch, L-hydroxypropylcellulose, carboxymethylcellulose, croscarmellose sodium, cellulose calcium glycolate, etc.), a lubricant (such as magnesium stearate, etc.), a swelling agent (such as hydroxypropylcellulose, hydroxypropylmethylcellulose, carbopol, carboxymethylcellulose, polyvinyl alcohol, xanthan gum, guar gum, etc.), a swelling adjuvant (such as glucose, fructose, mannitol, xylitol, erythritol, maltose, trehalose, phosphate, citrate, silicate, glycine, glutamic acid, arginine, etc.), a stabilizing agent, a solubilizing agent (such as polyethylene glycol, propylene glycol, glutamic acid, aspartic acid, etc.), a flavoring agent (such as orange, strawberry, mint, lemon, vanilla, etc.) and the like. Also, if necessary, they may be coated with a coating agent (such as sucrose, gelatin, hydroxypropylcellulose, hydroxypropylmethylcellulose phthalate, etc.), or coated with two or more films. In addition, if necessary, a preservative, an antioxidant, a colorant, a sweetening agent and the like generally used additive agents can also be added thereto.

The buccal adhesive tablets are produced in accordance with a conventionally known method. For example, one, two or more active substance(s) are used after making into pharmaceutical preparations by the law of the art by mixing with an vehicle (such as lactose, mannitol, glucose, microcrystalline cellulose, colloidal silica, starch, etc.), a binder (such as hydroxypropylcellulose, polyvinylpyrrolidone, magnesium aluminometasilicate, etc.), a disintegrant (such as starch, L-hydroxypropylcellulose, carboxymethylcellulose, croscarmellose sodium, cellulose calcium glycolate, etc.), a lubricant (such as magnesium stearate, etc.), an adhesive agent (such as hydroxypropylcellulose, hydroxypropylmethylcellulose, carbopol, carboxymethylcellulose, polyvinyl alcohol, xanthan gum, guar gum, etc.), an adhesive adjuvant (such as glucose, fructose, mannitol, xylitol, erythritol, maltose, trehalose, phosphate, citrate, silicate, glycine, glutamic acid, arginine, etc.), a stabilizing agent, a solubilizing agent (such as polyethylene glycol, propylene glycol, glutamic acid, aspartic acid, etc.), a flavoring agent (such as orange, strawberry, mint, lemon, vanilla, etc.) and the like. Also, if necessary, they may be coated with a coating agent (such as sucrose, gelatin, hydroxypropylcellulose, hydroxypropylmethylcellulose phthalate, etc.), or coated with two or more layers. In addition, if necessary, a preservative, an antioxidant, a colorant, a sweetening agent and the like generally used additive agents can also be added thereto.

The buccal quick disintegration tablets are produced in accordance with a conventionally known method. For example, one, two or more active substance(s) are used as such or after making into pharmaceutical preparations by the law of the art by mixing the active substances, prepared by coating the material powder or granulated material particles with an appropriate coating agent (such as ethyl cellulose, hydroxypropylcellulose, hydroxypropylmethylcellulose, acrylate-methacrylate copolymer, etc.) and a plasticizer (such as polyethylene glycol, triethyl citrate, etc.), with an vehicle (such as lactose, mannitol, glucose, microcrystalline cellulose, colloidal silica, starch, etc.), a binder (such as hydroxypropylcellulose, polyvinylpyrrolidone, magnesium aluminometasilicate, etc.), a disintegrant (such as starch, L-hydroxypropylcellulose, carboxymethylcellulose, croscarmellose sodium, cellulose calcium glycolate, etc.), a lubricant (such as magnesium stearate, etc.), a dispersing adjuvant (such as glucose, fructose, mannitol, xylitol, erythritol, maltose, trehalose, phosphate, citrate, silicate, glycine, glutamic acid, arginine, etc.), a stabilizing agent, a solubilizing agent (such as polyethylene glycol, propylene glycol, glutamic acid, aspartic acid, etc.), a flavoring agent (such as orange, strawberry, mint, lemon, vanilla, etc.) and the like. Also, if necessary, they may be coated with a coating agent (such as sucrose, gelatin, hydroxypropylcellulose, hydroxypropylmethylcellulose phthalate, etc.), or coated with two or more layers. In addition, if necessary, a preservative, an antioxidant, a colorant, a sweetening agent and the like generally used additive agents can also be added thereto.

Liquid forms for oral administration include pharmaceutically acceptable solutions, suspensions, emulsions, syrups and elixirs. In such forms, one, two or more active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

The agent for parenteral administration may be in the form of, e.g., ointment, gel, cream, wet compress, paste, liniment, nebula, inhalant, spray, eye drops, collunarium or the like. These agents each contain one or more active materials and are prepared by any known method or commonly used formulation.

The ointment is prepared by any known or commonly used formulation. For example, one, two or more active materials are titurated or dissolved in a base to prepare such an ointment. The ointment base is selected from known or commonly used materials. In some detail, higher aliphatic acid or higher aliphatic acid ester (e.g., myristic acid, palmitic acid, stearic acid, oleic acid, myristic acid ester, palmitic acid ester, stearic acid ester, oleic acid ester), wax (e.g., beeswax, whale wax, ceresin), surface active agent (e.g., polyoxyethylene-alkyletherphosphoric acid ester), higher alcohol (e.g., cetanol, stearyl alcohol, setostearyl alcohol), silicon oil (e.g., dimethyl polysiloxane), hydrocarbon (e.g., hydrophilic petrolatum, white petrolatum, purified lanolin, liquid paraffin), glycol (e.g., ethylene glycol, diethylene glycol, propylene glycol, polyethylene glycol, macrogol), vegetable oil (e.g., castor oil, olive oil, sesame oil, turpentine oil), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one, two or more active materials are dissolved in a base to prepare such a gel. The gel base is selected from known or commonly used materials. For example, lower alcohol (e.g., ethanol, isopropyl alcohol), gelling agent (e.g., carboxymethylcellulose, hydroxyethylcellulose, hydroxypropylcellulose, ethylcellulose), neutralizing agent (e.g., triethanolamine, diisopropanolamine), surface active agent (e.g., polyethylene glycol monostearate), gum, water, absorption accelerator, and rash preventive are used singly or in admixture of two or more thereof. The gel base may further comprise a humectant, an antioxidant, a perfume, etc.

The cream is prepared by any known or commonly used formulation. For example, one, two or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol), higher alcohol (e.g., 2-hexyldecanol, cetanol), emulsifier (e.g., polyoxyethylene alkyl ether, aliphatic acid ester), water, absorption accelerator, and rash preventive are used singly or in admixture of two or more thereof. The cream base may further comprise a humectant, an antioxidant, a perfume, etc.

The wet compress is prepared by any known or commonly used formulation. For example, one, two or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methylcellulose), wetting agent (e.g., urea, glycerin, propylene glycol), filler (e.g., kaolin, zinc oxide, talc, calcium, magnesium), water, dissolution aid, tackifier, and rash preventive may be used singly or in admixture of two or more thereof. The wet compress base may further comprise a humectant, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a humectant, an antioxidant, a perfume, etc.

The liniment is prepared by any known or commonly used formulation. For example, one, two or more active materials are dissolved, suspended or emulsified in water, alcohol (e.g., ethanol, polyethylene glycol), higher aliphatic acid, glycerin, soap, emulsifier, suspending agent, etc., singly or in combination of two or more thereof, to prepare such a liniment. The liniment may further comprise a humectant, an antioxidant, a perfume, etc.

The nebula, inhalant, spray and aerosol each may comprise a stabilizer such as sodium hydrogensulfite and a buffer capable of providing isotonicity such as isotonic agent (e.g., sodium chloride, sodium citrate, citric acid). For the process for the preparation of spray, reference can be made to U.S. Pat. Nos. 2,868,691 and 3,095,355.

The injection for parenteral administration may be in the form of solution, suspension, emulsion or solid injection to be dissolved or suspended in a solvent in use. The injection is prepared by dissolving, suspending or emulsifying one, two or more active materials in a solvent. As such a solvent there may be used distilled water for injection, saline, vegetable oil, alcohol such as propylene glycol, polyethylene glycol and ethanol, etc., singly or in combination. The injection may further comprise a stabilizer, a dissolution aid (e.g., glutamic acid, aspartic acid, Polysolvate 80 (trade name)), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvent before use.

The eye drops for parenteral administration may be in the form of liquid, suspension, emulsion or ointment or may be dissolved in a solvent in use. These eye drops are prepared by any known method. For example, one, two or more active materials are dissolved, suspended or emulsified in a solvent. As such a solvent for eye drops there may be used sterilized purified water, saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalant for parenteral administration may be in the form of aerosol, powder for inhalation or liquid for inhalation. The liquid for inhalation may be dissolved or suspended in water or other proper medium in use. These inhalants are prepared by an known method. For example, the liquid for inhalation is prepared from materials properly selected from preservatives (e.g., benzalconium chloride, Paraben), colorants, buffering agents (e.g., sodium phosphate, sodium acetate), isotonic agents (e.g., sodium chloride, concentrated glycerin), thickening agents (e.g., carboxyvinyl polymer), absorption accelerators, etc. as necessary.

The powder for inhalation is prepared from materials properly selected from glidants (e.g., stearic acid and salt thereof), binders (e.g., starch, dextrin), vehicles (e.g., lactose, cellulose), colorants, preservatives (e.g., benzalconium chloride, Paraben), absorption accelerators, etc., if necessary.

In order to administer the liquid fof inhalation, a sprayer (e.g., atomizer, nebulizer) is normally used. In order to administer the powder for inhalation, a powder inhaler is normally used.

Other examples of the composition for oral administration include sublingual medication for sublingual administration, suppository for rectal administration and pessary for vaginal administration prepared by an ordinary formulation comprising one or more active materials.

The compound of the present invention of formula (I) may be administered as a combined preparation by combining with other pharmaceuticals for the purpose of 1) supplement and/or enhancing of prevention and/or treatment effect of the compound,
2) improvement in pharmacokinetics and absorption and reduction of dose of the compound, and/or
3) reduction of side effect of the compound.

The combined preparation of the compound of the present invention of formula (I) with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention of formula (I) may be firstly administered, followed by administering the other pharmaceutical or the other pharmaceutical may be administered firstly, followed by administering the compound of the present invention of formula (I). Methods for each of the administration are the same or different.

The combination preparation with other pharmaceuticals which supplement and/or enhance the prevention and/or treatment effect of the compound of the present invention is not limited to those exemplified in the present invention. Also, the combination preparation with other pharmaceuticals which supplement and/or enhance the prevention and/or treatment effect of the compound of the present invention, not only that which has been found up to now but also that which will be found in future on the basis of the above-described mechanism are included.

The diseases against which the combined drugs as described above have preventive and/or therapeutic effects are not particularly restricted. Namely, they may be diseases by which the preventive and/or therapeutic effects of the present invention compounds represented by formula (I) can be complemented and/or enhanced. For example, other immunosuppressants, antibiotics, etc. may be cited as drugs to be used for complementing and/or enhancing the preventive and/or therapeutic effects on rejection in transplantation to which an EDG-6 agonist is applicable. Steroids, nonsteroidal anti-inflammatory drugs (NSAIDs), disease modifying antirheumatic diseases (DMARDs, slow-acting antirheumatic drugs), other immunosuppressants, T cell inhibitors, anti-inflammatory enzyme preparations, cartilage protecting agents, prostaglandins, prostaglandin synthase inhibitors, IL-1 inhibitors, IL-6 inhibitors (including protein preparations such as an anti-IL-6 receptor antibody), TN-$\alpha$ inhibitors (including protein preparations such as an anti-TNF-$\alpha$ antibody), interferon $\gamma$ agonists, phosphodiesterase inhibitors, metalloproteinase inhibitors and the like can be cited as drugs to be used in preventing and/or treating autoimmune diseases. EDG-6 agonists can be used in combination with them. Concerning drugs to be used for complementing and/or enhancing the preventive and/or therapeutic effects on allergic diseases, examples of drugs to be used for complementing and/or enhancing the preventive and/or therapeutic effects on atopic dermatitis include immunosuppressants, steroids, nonsteroidal anti-inflammatory drugs, prostaglandins, antiallergic agents, mediator release inhibitors, antihistaminic drugs, forskolin preparations, phosphodiesterase inhibitors, cannabinoid-2 receptor stimulants and the like.

Examples of the immunosuppressants include azathioprine (trade name: IMULAN and AZANIN), mizoribine (trade name: BREDININ), methotrexate (trade name: METHOTREXATE, RHEUMATREX), mycophenolate mofetil (trade name: CELLCEPT), cyclophosphamide (trade name: ENDOXAN P), ciclosporin A (trade name: NEORAL, SANDIMMUN), tacrolimus (FK506, trade name: PROGRAF), sirolimus (RAPAMYCIN), everolimus (trade name: CERTICAN), prednisolone (trade name: PREDONIN), methylprednisolone (trade name: MEDROL), orthoclone OKT3 (trade name: MUROMONAB CD3), anti human lymphocyte globulin (ALe; trade name: ALBULIN), deoxyspergualin (DSG, gusperimus hydrochloride, trade name: SPANIDIN) and the like.

Examples of antibiotics include cefuroxime sodium, meropenem trihydrate, netilmicin sulfate, sisomicin sulfate, ceftibuten, PA-1806, IB-367, tobramycin, PA-1420, doxorubicin, astromicin sulfate, or cefetamet pivoxil hydrochloride, etc.

Examples of antibiotics as an inhalant include PA-1806, IB-367, tobramycin, PA-1420, doxorubicin, astromicin sulfate, or cefetamet pivoxil hydrochloride, etc.

Regarding the steroid, in the case of external preparations, examples include clobetasol propionate, diflorasone diacetate, fluocinonide, mometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propianate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone dipropionate, clobetasone butyrate, prednisolone, beclometasone dipropionate, fludroxycortide and the like. Examples of internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, triamcinolone acetonide, dexamethasone, dexamethasone acetate, dexamethasone sodium phosphate, dexamethasone palmitate, paramethasone acetate, betamethasone and the like. Examples of inhalations include beclometasone dipropionate, fluticasone propionate, budesonide, flunisolide, triamcinolone, ST-126P, ciclesonide, dexamethasone palmitate, mometasone furoate, sodium prasterone sulfate, deflazacort, methylprednisolone suleptanate, methylprednisolone sodium succinate and the like.

Examples of the nonsteroidal antiinflammatory drug (NSAID) include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics, etc.

Examples of the disease modifying anti-rheumatic drug (DMARDs, slow-acting anti-rheumatic drug) include, for example, gold thioglucose, aurothiomalate sodium, auranofin, actarit, D-penicillamine preparations, lobenzarit disodium, bucillamine, hydroxychloroquine, salazosulfapyridine, methotrexate, and leflunomide, etc.

Examples of the antiinflammatory enzyme preparations include, for example, lysozyme chloride, bromelain, pronase, serrapeptase, or streptokinase-streptodornase, etc.

Examples of the chondroprotective agents include, for example, hyaluronate sodium, glucosamine, chondroitin sulfate, and glucosaminoglycan polysulfate, etc.

Examples of the prostaglandins (hereinafter referred to as "PG") include PG receptor agonist, and PG receptor antagonist, etc. Examples of the PG receptor include PGE receptor (EP1, EP2, EP3, EP4), PGD receptor (DP, CRTH2), PGF receptor (FP), PGI receptor (IP), or TX receptor (TP), etc.

Examples of the prostaglandin synthase inhibitor include, for example, salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen, etc.

Examples of IL-1 inhibitor (including protein preparation such as human IL-1 receptor antagonist) include, for example, anakinra, etc.

Examples of IL-6 inhibitor (including protein preparation such as anti-IL-6 receptor antibody) include, for example, MRA, etc.

Examples of the TNF-α inhibitors (including a protein preparation such as anti-TNF-α antibody) include, for example, infliximab, adalimumab, etanercept, etc.

Examples of the phosphodiesterase inhibitor include, for example, rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4386, IC-485, or ONO-6126 as PDE-4 inhibitor, etc.

Examples of the mediator releasing inhibitor include tranilast, sodium cromoglicate, anlexanox, repirinast, ibudilast, tazanolast, and pemilolast sodium, etc.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin, etc.

Toxicity:

The present invention compounds have low toxicities and, therefore, they are considered as sufficiently safe when used as drugs.

Effect of the Present Invention

The compounds having an ability to bind to an S1P receptor (in particular, EDG-6, preferably EDG-1 and EDG-6) are useful as immunosuppressants.

The present invention compounds represented by formula (I), salts thereof, solvates thereof or prodrugs thereof are compounds having an ability to bind to EDG-6 and exhibit prolonged pharmacological action. Therefore, they are useful as preventives and/or remedies in mammals, in particular, humans for rejection in transplantation, rejection of a transplanted organ, transplantation versus host disease, autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, arteriosclerosis, diseases associated with lymphocyte infiltration into a tissue and the like.

In addition to the ability to bind to EDG-6, some of the present invention compounds have an agonistic activity against EDG-1 and, therefore, show an immunosuppressant effect and prolonged pharmacological action. Owing to these characteristics, they are more useful as preventives and/or remedies for rejection in transplantation, transplantation versus host disease, autoimmune diseases, allergic diseases and the like.

BEST MODE FOR CARRYING OUT THE PRESENT INVENTION

The present invention will be described in greater detail by the following Examples. However, the present invention is not construed as being restricted thereto. Concerning chromatographic separation or TLC, a solvent in parentheses corresponds to an eluting solvent or a developing solvent employed and a ratio is expressed in volume. Aqueous ammonia used in TLC is a commercially available 28% aqueous ammonia. Concerning N, a solvent in parentheses corresponds to a solvent for the measurement. Unless otherwise noted, MS was performed by using the ESI (electrospray ionization) method and only cationic ions (pos.) were detected.

The nomenclature the compounds in the present invention, was carried out by a computerized system to denominate a compound generally according to IUPAC nomenclature system such as ACD/Name (registered trade name, manufactured by Advanced Chemistry Development Inc.) or ACD/Name Batch (registered trade name, manufactured by Advanced Chemistry Development Inc.), or according to TUPAC nomenclature system.

EXAMPLE 1 methyl 3-[4-(3-phenylpropoxy)phenyl]propanoate

To a solution of methyl 3-(4-hydroxyphenyl)propanoate (2.50 g) and 3-phenylpropan-1-ol (2.8 mL) in tetrahydrofuran (70 mL), triphenylphosphine (5.46 g) was added at room temperature. Next, diethyl azodicarboxylate (9.4 mL, 40% toluene solution) was added dropwise thereto, followed by stirring at room temperature for 2 hours. Then, the reaction mixture was concentrated and the obtained residue was purified by silica gel column chromatography (hexane:ethyl acetate=30:1 to 5:1) to give the title compound (3.02 g) having the following physical properties.

TLC: Rf 0.45 (hexane:ethyl acetate=5:1);
$^1$H-NMR (CDCl$_3$): δ 2.09 (m, 2H), 2.60 (t, 2H), 2.80 (m, 2H), 2.89 (t, 2H), 3.67 (s, 3H), 3.94 (t, 2H), 6.82 (d, 2H), 7.10 (d, 2H), 7.20 (m, 3H), 7.29 (m, 2H).

EXAMPLE 2

3-[4-(3-phenylpropoxy)phenyl]propanal

To a solution of the compound (1.0 g) prepared in Example 1 in dry dichloromethane (15 mL), diisobutylaluminum hydride (3.5 mL; 0.95 M n-hexane solution) was dropped at −78° C. and the mixture was stirred at −78° C. for 30 minutes. To the reaction mixture, methanol (0.5 mL) was dropped, followed by stirring at room temperature for 40 minutes. The reaction mixture was filtered through Celite (trade name) and the filtrate was concentrated. Then, the obtained residue was purified by silica gel column chromatography (hexane:ethyl acetate=10:1 to 6:1) to give the title compound (614 mg) having the following physical properties.

TLC: Rf 0.20 (hexane:ethyl acetate=7:1);
$^1$H-NMR (CDCl$_3$): δ 2.09 (m, 2H), 2.77 (m, 4H), 2.90 (t, 2H), 3.94 (t, 2H), 6.82 (d, 2H), 7.09 (d, 2H), 7.20 (m, 3H), 7.27 (m, 2H), 9.82 (t, 1H).

EXAMPLE 3

N-{3-[4-(3-phenylpropoxy)phenyl]propyl}alanine

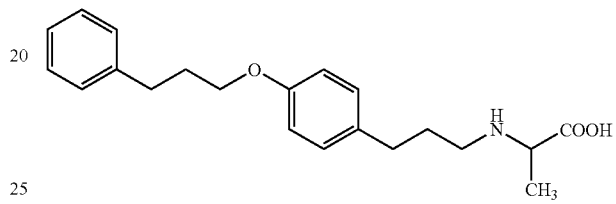

To a suspension of alanine (7.1 mg) in methanol (0.30 mL), sodium hydroxide (3.4 mg) was added at room temperature. Then, the compound (30 mg) prepared in Example 2 was added and the mixture was stirred at room temperature for 15 minutes. To the reaction mixture, sodium borohydride (4.0 mg) was added at 0° C. and the mixture was stirred at 0° C. for an hour. The reaction mixture was purified by silica gel column chromatography (chloroform:methanol:aqueous ammonia=80:20:4) to give the title compound (14 mg) having the following physical properties.

TLC: Rf 0.24 (chloroform:methanol:aqueous ammonia=80:20:4);
$^1$H-NMR (DMSO-d$_6$): δ 1.23 (d, 3H), 1.81 (m, 2H), 1.98 (m, 2H), 2.53 (m, 2H), 2.72 (m, 4H), 3.14 (q, 1H), 3.91 (t, 2H), 6.83 (d, 2H), 7.09 (d, 2H), 7.23 (m, 5H).

EXAMPLES 3(1) to 3(38)

The procedure of Example 3 was similarly carried out, except for using a corresponding amine compound as a substitute for alanine while using the compound prepared in Example 2 or a corresponding aldehyde compound as a substitute therefor, followed by the conversion into a corresponding salt by a known method, if necessary. Thus, the following compounds were obtained.

EXAMPLE 3(1)

N-{3-[4-(3-phenylpropoxy)phenyl]propyl}glycine

TLC: Rf 0.52 (ethyl acetate:acetic acid:water=3:1:1);
$^1$H-NMR (CD$_3$OD): δ 2.03 (m, 4H), 2.64 (t, 2H), 2.78 (m, 2H), 2.96 (m, 2H), 3.45 (s, 2H), 3.92 (t, 2H), 6.83 (d, 2H), 7.18 (m, 7H).

EXAMPLE 3(2)

4-({3-[4-(3-phenylpropoxy)phenyl]propyl}amino)butanoic acid

TLC: Rf 0.25 (chloroform:methanol:aqueous ammonia=80:20:4);
$^1$H-NMR (CD$_3$OD): δ 1.83 (m, 2H), 1.94 (m, 2H), 2.04 (m, 2H), 2.37 (m, 2H), 2.65 (t, 2H), 2.78 (m, 2H), 2.93 (m, 2H), 3.00 (m, 2H), 3.92 (t, 2H), 6.83 (d, 2H), 7.19 (m, 7H).

EXAMPLE 3(3)

5-({3-[4-(3-phenylpropoxy)phenyl]propyl}amino)pentanoic acid

TLC: Rf 0.28 (chloroform:methanol:aqueous ammonia=80:20:4);
$^1$H-NMR (CD$_3$OD): δ 1.66 (m, 4H), 2.03 (m, 4H), 2.21 (t, 2H), 2.65 (t, 2H), 2.78 (m, 2H), 2.94 (m, 4H), 3.92 (t, 2H), 6.83 (d, 2H), 7.18 (m, 7H).

EXAMPLE 3(4)

2-methyl-N-{3-[4-(3-phenylpropoxy)phenyl]propyl}alanine

TLC: Rf 0.36 (chloroform:methanol:aqueous ammonia=80:20:4);
$^1$H-NMR (CDCl$_3$: CD$_3$OD=5:1): δ 1.34 (s, 6H), 1.89 (m, 2H), 2.03 (m, 2H), 2.57 (m, 2H), 2.73 (m, 4H), 3.87 (t, 2H), 6.76 (d, 2H), 7.01 (d, 2H), 7.13 (m, 3H), 7.20 (m, 2H).

EXAMPLE 3(5)

N-{3-[4-(3-phenylpropoxy)phenyl]propyl}valine

TLC: Rf 0.42 (chloroform:methanol:aqueous ammonia=80:20:4);
$^1$H-NMR (CDCl$_3$: CD$_3$OD=5:1): δ 0.94 (m, 6H), 1.89 (m, 2H), 2.01 (m, 2H), 2.12 (m, 1H), 2.54 (m, 2H), 2.72 (m, 4H), 3.13 (d, 1H), 3.86 (t, 2H), 6.75 (d, 2H), 6.99 (d, 2H), 7.12 (m, 3H), 7.20 (m, 2H).

EXAMPLE 3(6)

N-{3-[4-(3-phenylpropoxy)phenyl]propyl}phenylalanine

TLC: Rf 0.41 (chloroform:methanol:aqueous ammonia=80:20:4);
$^1$H-NMR (CDCl$_3$: CD$_3$OD=5:1): δ 1.72 (m, 2H), 2.02 (m, 2H), 2.41 (m, 2H), 2.62 (m, 4H), 2.87 (m, 1H), 3.20 (m, 1H), 3.46 (m, 1H), 3.88 (m, 2H), 6.71 (d, 2H), 6.89 (d, 2H) 7.16 (m, 10H).

EXAMPLE 3(7)

N-{3-[4-(3-phenylpropoxy)phenyl]propyl}serine

TLC: Rf 0.12 (chloroform:methanol:aqueous ammonia=80:20:4);
$^1$H-NMR (CDCl$_3$: CD$_3$OD=5:1): δ 2.10 (m, 4H), 2.67 (m, 2H), 2.81 (t, 2H), 3.01 (m, 2H), 3.44 (t, 1H), 3.93 (m, 4H), 6.84 (d, 2H), 7.10 (d, 2H), 7.22 (m, 3H), 7.29 (m, 2H).

EXAMPLE 3(8)

N-{3-[4-(3-phenylpropoxy)phenyl]propyl}homoserine

TLC: Rf 0.18 (chloroform:methanol:aqueous ammonia=80:20:4);
$^1$H-NMR (CDCl$_3$: CD$_3$OD=5:1): δ 1.99 (m, 6H), 2.57 (t, 2H), 2.73 (m, 2H), 2.91 (m, 2H), 3.43 (m, 1H), 3.72 (m, 2H), 3.87 (t, 2H), 6.76 (d, 2H), 7.01 (d, 2H), 7.12 (m, 3H), 7.20 (m, 2H).

EXAMPLE 3(9)

2-hydroxy-3-({3-[4-(3-phenylpropoxy)phenyl]propyl}amino)propanoic acid

TLC: Rf 0.12 (chloroform:methanol:aqueous ammonia=80:20:4);
$^1$H-NMR (CDCl$_3$: CD$_3$OD=5:1): δ 2.06 (m, 4H), 2.65 (t, 2H), 2.81 (m, 2H), 2.97 (m, 3H), 3.25 (m, 1H), 3.97 (m, 2H), 4.03 (t, 1H), 6.84 (d, 2H), 7.09 (d, 2H), 7.22 (m, 3H), 7.29 (m, 2H).

EXAMPLE 3(10)

2-methyl-N-{3-[4-(3-phenylpropoxy)phenyl]propyl}serine

TLC: Rf 0.22 (chloroform:methanol:aqueous ammonia=80:20:4);
$^1$H-NMR (CDCl$_3$: CD$_3$OD=5:1): δ 1.34 (s, 3H), 2.07 (m, 4H), 2.67 (t, 2H), 2.81 (m, 2H), 2.92 (m, 2H), 3.54 (d, 1H), 3.94 (m, 3H), 6.84 (d, 2H), 7.10 (d, 2H), 7.21 (m, 3H), 7.29 (m, 2H).

EXAMPLE 3(11)

N-{[6-(3-phenylpropoxy)-2-naphthyl]methyl}glycine

TLC: Rf 0.13 (chloroform:methanol:aqueous ammonia=80:20:4);
$^1$H-NMR (CDCl$_3$: CD$_3$OD=5:1): δ 2.19 (m, 2H), 2.87 (t, 2H), 3.43 (s, 2H), 4.10 (t, 2H), 4.22 (s, 2H), 7.12 (d, 1H), 7.27 (m, 6H), 7.44 (dd, 1H), 7.77 (d, 2H), 7.82 (d, 1H).

EXAMPLE 3(12)

4-({[6-(3-phenylpropoxy)-2-naphthyl]methyl}amino)butanoic acid

TLC: Rf 0.17 (chloroform:methanol:aqueous ammonia=80:20:4);
$^1$H-NMR (CDCl$_3$: CD$_3$OD=5:1): δ 1-0.84 (m, 2H), 2.18 (m, 2H), 2.44 (m, 2H), 2.86 (m, 2H), 2.97 (m, 2H), 4.09 (t, 2H), 4.13 (s, 2H), 7.11 (d, 1H), 7.27 (m, 6H), 7.43 (dd, 1H), 7.76 (m, 3H).

EXAMPLE 3(13)

2-hydroxy-3-({[6-(3-phenylpropoxy)-2-naphthyl]methyl}amino)propanoic acid

TLC: Rf 0.11 (chloroform:methanol:aqueous ammonia=80:20:4);

¹H-NMR (CDCl₃: CD₃OD=5:1): δ 2.19 (m, 2H), 2.87 (m, 2H), 3.11 (dd, 1H), 3.20 (dd, 1H), 4.09 (m, 3H), 4.23 (d, 1H), 4.29 (d, 1H), 7.12 (d, 1H), 7.27 (m, 6H), 7.44 (dd, 1H), 7.77 (d, 2H), 7.82 (s, 1H).

EXAMPLE 3(14)

N-{(2E)-3-[4-(3-phenylpropoxy)phenyl]prop-2-enyl}-β-alanine

TLC: Rf 0.13 (chloroform:methanol:aqueous ammonia=80:20:4);

¹H-NMR (CD₃OD): δ 2.07 (m, 2H), 2.49 (t, 2H), 2.79 (t, 2H), 3.16 (t, 2H), 3.76 (dd, 2H), 3.96 (t, 2H), 6.12 (dt, 1H), 6.78 (d, 1H), 6.88 (d, 2H), 7.20 (m, 5H), 7.39 (d, 21).

EXAMPLE 3(15)

1-{3-[4-(3-phenylpropoxy)phenyl]propyl}azetidine-3-carboxylic acid acetate

TLC: Rf 0.44 (ethyl acetate:acetic acid:water=3:1:1);

¹H-NMR (CD₃OD): δ 1.71-1.92 (m, 2H), 1.98 (s, 3H), 1.99-2.12 (m, 2H), 2.61 (t, 2H), 2.78 (t, 2H), 3.09-3.20 (m, 2H), 3.32-3.46 (m, 1H), 3.92 (t, 2H), 4.09-4.26 (m, 4H), 6.79-6.88 (m, 2H), 7.07-7.13 (m, 2H), 7.14-7.29 (m, 5H).

EXAMPLE 3(16)

1-{3-[4-(3-phenylpropoxy)phenyl]propyl}proline

TLC: Rf 0.46 (ethyl acetate:acetic acid:water=3:1:1);

¹H-NMR (CD₃OD): δ 1.82-2.19 (m, 7H), 2.32-2.48 (m, 1H), 2.64 (t, 2H), 2.78 (t, 2H), 2.96-3.16 (m, 2H), 3.15-3.29 (m, 1H), 3.61-3.77 (m, 1H), 3.80 (dd, 1H), 3.91 (t, 2H), 6.76-6.90 (m, 2H), 7.07-7.13 (m, 2H), 7.14-7.35 (m, 5H).

EXAMPLE 3(17)

1-{3-[4-(3-phenylpropoxy)phenyl]propyl}pyrrolidine-3-carboxylic acid

TLC: Rf 0.46 (ethyl acetate:acetic acid:water=3:1:1);

¹H-NMR (CD₃OD): δ 1.92-2.12 (m, 4H), 2.13-2.38 (m, 2H), 2.64 (t, 2H), 2.78 (t, 2H), 2.98-3.09 (m, 1H), 3.10-3.20 (m, 2H), 3.22-3.47 (m, 3H), 3.52-3.65 (m, 1H), 3.92 (t, 2H), 6.84 (d, 2H), 7.12 (d, 2H), 7.16-7.33 (m, 5H).

EXAMPLE 3(18)

1-{3-[4-(3-phenylpropoxy)phenyl]propyl}piperidine-2-carboxylic acid

TLC: Rf 0.51 (ethyl acetate:acetic acid:water=3:1:1);

¹H-NMR (CD₃OD): δ 1.44-1.64 (m, 1H), 1.65-1.91 (m, 4H), 1.97-2.12 (m, 4H), 2.12-2.27 (m, 1H), 2.49-2.70 (m, 2H), 2.78 (t, 2H), 2.83-3.06 (m, 2H), 3.16-3.29 (m, 1H), 3.34-3.47 (m, 1H), 3.47-3.62 (m, 1H), 3.92 (t, 2H), 6.77-6.87 (m, 2H), 7.08-7.14 (m, 2H), 7.14-7.31 (m, 5H).

EXAMPLE 3(19)

1-{3-[4-(3-phenylpropoxy)phenyl]propyl}piperidine-3-carboxylic acid

TLC: Rf 0.44 (ethyl acetate:acetic acid:water=3:1:1);

¹H-NMR (CD₃OD): δ 1.66-1.99 (m, 4H), 1.99-2.15 (m, 4H), 2.57-2.71 (m, 3H), 2.78 (t, 2H), 2.88-3.39 (m, 6H), 3.92 (t, 2H), 6.77-6.89 (m, 2H), 7.10-7.17 (m, 2H), 7.16-7.31 (m, 5H).

EXAMPLE 3(20)

1'-{3-[4-(3-phenylpropoxy)phenyl]propyl}piperidine-4-carboxylic acid

TLC: Rf 0.51 (ethyl acetate:acetic acid:water=3:1:1);

¹H-NMR (CD₃OD): δ 1.78-2.15 (m, 8H), 2.31-2.47 (m, 1H), 2.63 (t, 2H), 2.78 (t, 2H), 2.88-3.08 (m, 4H), 3.34-3.50 (m, 2H), 3.92 (t, 2H), 6.79-6.88 (m, 2H), 7.09-7.15 (m, 2H), 7.14-7.31 (m, 5H).

EXAMPLE 3(21)

N-{[6-(3-phenylpropoxy)-2-naphthyl]methyl}-O-alanine

TLC: Rf 0.13 (chloroform:methanol:aqueous ammonia=80:20:4);

¹H-NMR (CDCl₃): δ 2.14-2.24 (m, 2H), 2.47 (t, 2H), 2.87 (t, 2H), 3.09 (t, 2H), 4.10 (t, 2H), 4.23 (s, 2H), 7.12 (d, 1H), 7.18-7.33 (m, 6H), 7.43 (dd, 1H), 7.75-7.82 (m, 3H).

EXAMPLE 3(22)

N-{[6-(3-phenylpropoxy)-2-naphthyl]methyl}-β-alanine hydrochloride

TLC: Rf 0.13 (chloroform:methanol:aqueous ammonia=80:20:4);

¹H-NMR (CD₃OD): δ 2.09-2.19 (m, 2H), 2.76 (t, 2H), 2.84 (t, 2H), 3.30-3.34 (m, 2H), 4.09 (t, 2H), 4.36 (s, 2H), 7.13-7.29 (m, 7H), 7.50 (dd, 1H), 7.79-7.86 (m, 2H), 7.91 (s, 1H).

EXAMPLE 3(23)

1-{[6-(3-phenylpropoxy)-2-naphthyl]methyl}azetidine-3-carboxylic acid hydrochloride TLC: Rf 0.20 (chloroform:methanol:aqueous ammonia=80:20:4);

¹H-NMR (CD₃OD): δ 2.09-2.19 (m, 2H), 2.84 (t, 2H), 3.64-3.76 (m, 1H), 4.09 (t, 2H), 4.28-4.38 (m, 4H), 4.52 (s, 2H), 7.13-7.29 (m, 7H), 7.45 (dd, 1H), 7.81-7.85 (m, 2H), 7.90 (s, 1H).

EXAMPLE 3(24)

1-{[6-(3-phenylpropoxy)-2-naphthyl]methyl}piperidine-4-carboxylic acid hydrochloride TLC: Rf 0.21 (chloroform:methanol:aqueous ammonia=80:20:4);

¹H-NMR (CD₃OD): δ 1.75-1.93 (m, 2H), 2.09-2.27 (m, 4H), 2.56-2.65 (m, 1H), 2.84 (t, 2H), 3.03-3.14 (m, 2H), 3.53-3.61 (m, 2H), 4.10 (t, 2H), 4.43 (s, 2H), 7.13-7.29 (m, 7H), 7.50 (dd, 1H), 7.81-7.87 (m, 2H), 7.93 (s, 1H).

Example 3(25)

N-{(2E)-3-[2-methyl-4-(3-phenylpropoxy)phenyl]prop-2-enyl}-β-alanine hydrochloride TLC: Rf 0.21 (chloroform:methanol:aqueous ammonia=80:20:4);

$^1$H-NMR (CD$_3$OD): δ 1.99-2.12 (m, 2H), 2.34 (s, 3H), 2.74-2.81 (m, 4H), 3.27-3.31 (m, 2H), 3.83 (d, 2H), 3.95 (t, 2H), 6.02 (dt, 1H), 6.71-6.76 (m, 2H), 7.07 (d, 1H), 7.12-7.29 (m, 5H), 7.44 (d, 1H).

EXAMPLE 3(26)

N-((2E)-3-{2-methyl-4-[(5-phenylpentyl)oxy]phenyl}prop-2-enyl)-β-alanine hydrochloride TLC: Rf 0.21 (chloroform:methanol:aqueous ammonia=80:20:4);

$^1$H-NMR (CD$_3$OD): δ 1.44-1.55 (m, 2H), 1.61-1.84 (m, 4H), 2.34 (s, 3H), 2.63 (t, 2H), 2.76 (t, 2H), 3.25-3.30 (m, 2H), 3.82 (d, 2H), 3.95 (t, 2H), 6.02 (dt, 1H), 6.70-6.74 (m, 2H), 7.06 (d, 1H), 7.10-7.26 (m, 5H), 7.43 (d, 1H).

EXAMPLE 3(27)

1-{(2E)-3-[4-(3-phenylpropoxy)phenyl]-2-propenyl}piperidine-4-carboxylic acid hydrochloride TLC: Rf 0.20 (chloroform:methanol:aqueous ammonia=80:20:4);

$^1$H-NMR (CD$_3$OD): δ 1.81-2.16 (m, 6H), 2.36-2.48 (m, 1H), 2.79 (t, 2H), 2.90-3.07 (m, 2H), 3.38-3.51 (m, 2H), 3.78 (d, 2H), 3.97 (t, 2H), 6.07-6.18 (m, 1H), 6.80 (d, 1H), 6.89 (d, 2H), 7.11-7.29 (m, 5H), 7.41 (d, 2H).

EXAMPLE 3(28)

1-{(2E)-3-[4-(3-phenylpropoxy)phenyl]-2-propenyl}azetidine-3-carboxylic acid hydrochloride TLC: Rf 0.10 (chloroform:methanol:aqueous ammonia=80:20:4);

$^1$H-NMR (CD$_3$OD): δ 2.01-2.12 (m, 2H), 2.79 (t, 2H), 3.63-3.71 (m, 1H), 3.92-3.99 (m, 4H), 4.23-4.40 (m, 4H), 5.97-6.09 (m, 1H), 6.81-6.92 (m, 3H), 7.11-7.28 (m, 5H), 7.40 (d, 2H).

EXAMPLE 3(29)

N-((2E)-3-{4-[(5-phenylpentyl)oxy]phenyl}-2-propenyl)-β-alanine hydrochloride

TLC: Rf 0.20 (chloroform:methanol:aqueous ammonia=80:20:4);

$^1$H-NMR (CD$_3$OD): δ 1.41-1.57 (m, 2H), 1.61-1.74 (m, 2H), 1.74-1.85 (m, 2H), 2.63 (t, 2H), 2.76 (t, 2H), 3.25-3.33 (m, 2H), 3.80 (d, 2H), 3.97 (t, 2H), 6.11 (dt, 1H), 6.81 (d, 1H), 6.88 (d, 2H), 7.08-7.30 (m, 5H), 7.39 (d, 2H).

EXAMPLE 3(30)

N-({6-[(5-phenylpentyl)oxy]-2-naphthyl}methyl-β-alanine hydrochloride

TLC: Rf 0.17 (chloroform:methanol:aqueous ammonia=80:20:4);

$^1$H-NMR (CD$_3$OD): δ 1.48-1.63 (m, 2H), 1.64-1.79 (m, 2H), 1.80-1.94 (m, 2H), 2.65 (t, 2H), 2.76 (t, 2H), 3.18-3.42 (m, 2H), 4.10 (t, 2H), 4.35 (s, 2H), 7.07-7.29 (m, 7H), 7.50 (dd, 1H), 7.80 (d, 1H), 7.85 (d, 1H), 7.88-7.93 (m, 1H).

EXAMPLE 3(31)

1-({6-[(5-phenylpentyl)oxy]-2-naphthyl}methyl)azetidine-3-carboxylic acid hydrochloride TLC: Rf 0.14 (chloroform:methanol:aqueous ammonia=80:20:4);

$^1$H-NMR (CD$_3$OD): δ 1.46-1.64 (m, 2H), 1.64-1.79 (m, 2H), 1.79-1.95 (m, 2H), 2.65 (t, 2H), 3.58-3.76 (m, 1H), 4.09 (t, 2H), 4.26-4.39 (m, 4H), 4.51 (s, 2H), 7.06-7.29 (m, 7H), 7.45 (dd, 1H), 7.81 (d, 1H), 7.85 (d, 1H), 7.88-7.92 (m, 1H).

EXAMPLE 3(32)

1-({6-[(5-phenylpentyl)oxy]-2-naphthyl}methyl)piperidine-4-carboxylic acid hydrochloride TLC: Rf 0.16 (chloroform:methanol:aqueous ammonia=80:20:4);

$^1$H-NMR (CD$_3$OD): δ 1.46-1.64 (m, 2H), 1.63-1.79 (m, 2H), 1.79-1.97 (m, 4H), 2.10-2.32 (m, 2H), 2.55-2.74 (m, 1H), 2.65 (t, 2H), 2.98-3.23 (m, 2H), 3.45-3.65 (m, 2H), 4.10 (t, 2H), 4.43 (s, 2H), 7.07-7.30 (m, 7H), 7.50 (dd, 1H), 7.82 (d, 1H), 7.87 (d, 1H), 7.90-7.97 (m, 1H).

EXAMPLE 3(33)

N-{[6-(4-phenylbutoxy)-2-naphthyl]methyl})-β-alanine hydrochloride

TLC: Rf 0.17 (chloroform:methanol:aqueous ammonia=80:20:4);

$^1$H-NMR (CD$_3$OD): δ 1.78-1.95 (m, 4H), 2.64-2.79 (m, 4H), 3.23-3.36 (m, 2H), 4.07-4.16 (m, 2H), 4.35 (s, 2H), 7.09-7.31 (m, 7H), 7.50 (dd, 1H), 7.80 (d, 1H), 7.85 (d, 1H), 7.87-7.92 (m, 1H).

EXAMPLE 3(34)

1-{[6-(4-phenylbutoxy)-2-naphthyl]methyl}azetidine-3-carboxylic acid hydrochloride TLC: Rf 0.13 (chloroform:methanol:aqueous ammonia=80:20:4);

$^1$H-NMR (CD$_3$OD): δ 1.79-1.94 (m, 4H), 2.64-2.77 (m, 2H), 3.65-3.77 (m, 1H), 4.06-4.17 (m, 2H), 4.22-4.42 (m, 4H), 4.52 (s, 2H), 7.08-7.30 (m, 7H), 7.46 (dd, 1H), 7.83 (t, 2H), 7.88-7.94 (m, 1H).

EXAMPLE 3(35)

1-{[6-(4-phenylbutoxy)-2-naphthyl]methyl}piperidine-4-carboxylic acid hydrochloride TLC: Rf 0.14 (chloroform:methanol:aqueous ammonia=80:20:4).

EXAMPLE 3(36)

N-({6-[3-(4-chlorophenyl)propoxy]-2-naphthyl}methyl)-β-alanine hydrochloride

TLC: Rf 0.14 (chloroform:methanol:aqueous ammonia=80:20:4);
$^1$H-NMR (CD$_3$OD): δ 2.03-2.24 (m, 2H), 2.76 (t, 2H), 2.84 (t, 2H), 3.25-3.36 (m, 2H), 4.09 (t, 2H), 4.36 (s, 2H), 7.16-7.30 (m, 6H), 7.50 (dd, 1H), 7.83 (t, 2H), 7.88-7.94 (m, 1H).

EXAMPLE 3(37)

1-({6-[3-(4-chlorophenyl)propoxy]-2-naphthyl}methyl)azetidine-3-carboxylic acid hydrochloride TLC: Rf 0.11 (chloroform:methanol:aqueous ammonia=80:20:4);
$^1$H-NMR (CD$_3$OD): δ 2.05-2.21 (m, 2H), 2.84 (t, 2H), 3.60-3.79 (m, 1H), 4.09 (t, 2H), 4.24-4.40 (m, 4H), 4.52 (s, 2H), 7.17-7.31 (m, 6H), 7.46 (dd, 1H), 7.79-7.87 (m, 2H), 7.88-7.94 (m, 1H).

EXAMPLE 3(38)

1-({6-[3-(4-chlorophenyl)propoxy]-2-naphthyl}methyl)piperidine-4-carboxylic acid hydrochloride TLC: Rf 0.15 (chloroform:methanol:aqueous ammonia=80:20:4);
$^1$H-NMR (CD$_3$OD): δ 1.72-1.97 (m, 2H), 2.03-2.32 (m, 4H), 2.52-2.71 (m, 1H), 2.83 (t, 2H), 2.95-3.20 (m, 2H), 3.47-3.69 (m, 2H), 4.09 (t, 2H), 4.43 (s, 2H), 7.13-7.32 (m, 6H), 7.52 (dd, 1H), 7.76-7.90 (m, 2H), 7.90-7.99 (m, 1H).

EXAMPLE 4 tert-butyl N-[3-(4-hydroxyphenyl)propyl]-β-alaninate

To a methanol solution (25 mL) of 4-(3-aminopropyl)phenol (1.83 g), tert-butyl acrylate (1.7 mL) was added dropwise thereto at room temperature, followed by stirring at room temperature overnight. The reaction mixture was concentrated. The residue was purified by silica gel column chromatography (ethyl acetate→ethyl acetate:methanol=3:1) to give the title compound (1.55 g) having the following physical properties. TLC: Rf 0.24 (ethyl acetate:methanol 5:1);

$^1$H-NMR (CDCl$_3$): δ 1.45 (s, 9H), 1.79 (m, 2H), 2.44 (t, 2H), 2.60 (m, 4H), 2.83 (t, 2H), 6.68 (d, 2H), 6.99 (d, 2H).

EXAMPLE 5 tert-butyl N-(tert-butoxycarbonyl)-N-[3-(4-hydroxyphenyl)propyl]-β-alaninate

To a tetrahydrofuran (30 mL) solution of the compound (1.55 g) prepared in Example 4, a tetrahydrofliran (3 mL) solution of di-tert-butyl dicarbonate (1.15 g) was added dropwise thereto at 0° C., followed by stirring at 0° C. for 2 hours. The reaction mixture was concentrated and the residue was purified by silica gel column chromatography (hexane:ethyl acetate=6:1 to 3:1) to give the title compound (1.57 g) having the following physical properties.

TLC: Rf 0.45 (hexane:ethyl acetate=2:1);
$^1$H-NMR (CDCl$_3$): δ 1.43 (m, 18H), 1.79 (m, 2H), 2.51 (m, 4H), 3.22 (m, 2H), 3.42 (m, 2H), 4.92 (s, 1H), 6.75 (d, 2H), 7.03 (d, 2H).

EXAMPLE 6 tert-butyl N-(tert-butoxycarbonyl)-N-{3-[4-(3-phenylpropoxy)phenyl]propyl}-β-alaninate To a solution of the compound (3.6 g) prepared in Example 5 in dimethylformamide (36 mL), potassium carbonate (4.20 g) was added at room temperature and (3-bromopropyl)benzene (2.31 mL) was added dropwise thereto, followed by stirring at room temperature overnight. The reaction mixture was poured into ice-water and extracted with a mixed solvent (hexane:ethyl acetate=2:1, twice). The organic layer was successively washed with water and a saturated aqueous sodium chloride solution, dried over anhydrous magnesium sulfate and concentrated. The residue was purified by silica gel column chromatography (hexane:ethyl acetate=30:1 to 4:1) to give the title compound (4.44 mg) having the following physical properties.

TLC: Rf0.18 (hexane:ethyl acetate=10:1);
$^1$H-NMR (CDCl$_3$): δ 1.43 (s, 18H), 1.81 (m, 2H), 2.09 (m, 2H), 2.52 (m, 4H), 2.81 (t, 2H), 3.22 (m, 2H), 3.42 (m, 2H), 3.94 (t, 2H), 6.81 (d, 2H), 7.08 (d, 2H), 7.21 (m, 3H), 7.29 (m, 2H).

EXAMPLE 7

N-{3-[4-(3-phenylpropoxy)phenyl]propyl}-β-alanine hydrochloride

To a solution of the compound (4.68 g) prepared in Example 6 in 1,4-dioxane (9 mL), a 4N hydrogen chloride-1,4-dioxane solution (38 mL) was added at room temperature, followed by stirring at room temperature overnight. The precipitate was collected by filtration and dried. Thus, the title compound (2.87 g) having the following physical properties was obtained.

TLC: Rf 0.31 (chloroform:methanol:aqueous ammonia=80:20:4);
$^1$H-NMR (CD$_3$OD): δ 2.02 (m, 4H), 2.65 (t, 2H), 2.71 (t, 2H), 2.78 (t, 2H), 3.01 (m, 2H), 3.24 (t, 2H), 3.92 (t, 2H), 6.84 (d, 2H), 7.12 (d, 2H), 7.20 (m, 5H).

EXAMPLES 8 to 8(3)

The procedures of Examples 6 and 7 were followed but using a corresponding derivative as a substitute for (3-bromopropyl)benzene, followed by the conversion into a corresponding salt by a known method, if necessary. Thus, the following compounds were obtained.

EXAMPLE 8

N-(3-{4-[3-(4-methoxyphenyl)propoxy]phenyl}propyl)-β-alanine hydrochloride

TLC: Rf 0.25 (chloroform:methanol:aqueous ammonia=80:20:4);
$^1$H-NMR (CD$_3$OD): δ 2.00 (m, 4H), 2.69 (m, 6H), 3.01 (m, 2H), 3.23 (t, 2H), 3.74 (s, 3H), 3.90 (t, 2H), 6.82 (m, 4H), 7.11 (m, 4H).

EXAMPLE 8(1)

N-(3-{4-[3-(3,4-dimethoxyphenyl)propoxy]phenyl}propyl)-β-alanine acetate

TLC: Rf 0.25 (chloroform:methanol:aqueous ammonia=80:20:4);
$^1$H-NMR (CD$_3$OD): δ 1.90 (s, 3H), 2.02 (m, 4H), 2.47 (t, 2H), 2.64 (t, 2H), 2.73 (t, 2H), 2.96 (m, 2H), 3.11 (t, 2H), 3.73 (s, 3H), 3.78 (s, 3H), 3.91 (t, 2H), 6.76 (m, 2H), 6.84 (m, 3H), 7.12 (d, 2H).

EXAMPLE 8(2)

N-(3-{4-[3-(4-chlorophenyl)propoxy]phenyl}propyl)-β-alanine hydrochloride

TLC: Rf 0.25 (chloroform:methanol:aqueous ammonia=80:20:4);
$^1$H-NMR (CD$_3$OD): δ 2.02 (m, 4H), 2.65 (t, 2H), 2.72 (t, 2H), 2.78 (t, 2H), 3.01 (m, 2H), 3.24 (t, 2H), 3.92 (t, 2H), 6.84 (d, 2H), 7.12 (d, 2H), 7.18 (d, 2H), 7.25 (d, 2H).

EXAMPLE 8(3)

N-(3-{4-[(7-chloroquinolin-2-yl)methoxy]phenyl}propyl)-β-alanine hydrochloride

TLC: Rf 0.14 (chloroform:methanol:aqueous ammonia=80:20:4);
$^1$H-NMR (DMSO-d$_6$): δ 1.84 (m, 2H), 2.56 (t, 2H), 2.65 (t, 2H), 2.86 (m, 2H), 3.08 (m, 2H), 5.34 (s, 2H), 6.99 (d, 2H), 7.14 (d, 2H), 7.66 (dd, 1H), 7.69 (d, 1H), 8.06 (m, 2H), 8.47 (d, 1H), 8.66 (s, 2H).

EXAMPLE 9 methyl N-[2-(4-hydroxyphenyl)ethyl]-N-(trifluoroacetyl)-β-alaninate

To a solution of tyramine (3.0 g) in methanol (40 mL), acrylate (0.98 mL) in methanol (5.0 mL) was dropped at room temperature, followed by stirring at room temperature for 13 hours. Then, the mixture was concentrated and azeotropically distilled with toluene. The residue was dissolved in dichloromethane (30 mL) and trifluoroacetic anhydride (4.6 mL) and pyridine (2.6 mL) were added at 0° C., followed by stirring at room temperature for 2 hours. Then, chloroform (30 mL) was added to the reaction mixture. The organic layer was successively washed with a saturated aqueous ammonium chloride solution, water and 1N hydrochloric acid, dried over anhydrous magnesium sulfate and concentrated. The residue was punrified by silica gel column chromatography (chloroform:methanol=40:1) to give the title compound (1.43 mg) having the following physical properties.

TLC: Rf 0.63 (chloroform:methanol:aqueous ammonia=8:1:0.1);
$^1$H-NMR (DMSO-d$_6$): δ 2.63 (t, 2H), 2.77 (t, 2H), 2.90-2.96 (m, 3H), 3.55 (t, 2H), 3.59-3.68 (m, 2H), 6.71 (d, 2H), 7.01 (d, 2H), 8.83 (s, 1H).

EXAMPLE 10 methyl N-(2-{4-[(3-phenylprop-2-ynyl)oxy]phenyl}ethyl)-N-(trifluoroacetyl)-β-alaninate The procedure of Example 1 was similarly carried out, except for using the compound prepared in Example 9 as a substitute for methyl 3-(4-hydroxyphenyl)propanoate while using 3-phenylprop-2-yn-1-ol as a substitute for 3-phenylpropan-1-ol. Thus, the title compound having the following physical properties was obtained.

TLC: Rf 0.43 (hexane:ethyl acetate=3:1);
$^1$H-NMR (CDCl$_3$): δ 2.55 (t, 1.2H), 2.68 (t, 0.8H), 2.79-2.92 (m, 2H), 3.51-3.70 (m, 4H), 3.67-3.70 (m, 3H), 4.90 (s, 2H), 6.93-7.04 (m, 2H), 7.08-7.19 (m, 2H), 7.27-7.35 (m, 3H), 7.39-7.47 (m, 2H).

EXAMPLE 11

N-(2-{4-[(3-phenylprop-2-ynyl)oxy]phenyl}ethyl)-β-alanine

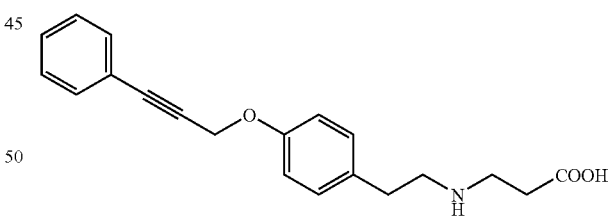

To a solution of the compound (39 mg) prepared in Example 10 in a mixture of tetrahydrofuran (1 mL) and methanol (0.5 mL), 1 N aqueous sodium hydroxide solution (0.5 mL) was added, followed by stirring for 3 hours. Then, the reaction mixture was concentrated. The residue was purified by silica gel column chromatography (chloroform:methanol:formic acid=15:1:0.5) to give the title compound (18 mg) having the following physical properties.

TLC: Rf 0.26 (chloroform:methanol:formic acid=10:1:0.5);
$^1$H-NMR (CD$_3$OD): δ 2.48 (t, 2H), 2.95 (t, 2H), 3.11-3.26 (m, 4H), 4.93 (s, 2H), 7.02 (d, 2H), 7.24 (d, 2H), 7.27-7.35 (m, 3H), 7.35-7.43 (m, 2H).

EXAMPLES 12 to 12(2)

The procedures of Examples 1 and 11 were followed but using a corresponding alcohol compound as a substitute for methyl 3-(4-hydroxyphenyl)propanoate while using a corresponding alcohol compound as a substitute for 3-phenylpropan-1-ol, followed by the conversion into a corresponding salt by a known method, if necessary. Thus, the following compounds were obtained.

EXAMPLE 12

N-[2-(4-{[(2E)-3-phenylprop-2-enyl]oxy}phenyl)ethyl]-β-alanine formate

TLC: Rf 0.28 (chloroform:methanol: formic acid=10:1:0.5);
$^1$H-NMR (CD$_3$OD): δ 2.52 (t, 2H), 2.93 (t, 2H), 3.14-3.27 (m, 4H), 4.69 (dd, 2H), 6.43 (dt, 1H), 6.73 (d, 1H), 6.96 (d, 2H), 7.14-7.26 (m, 3H), 7.30 (t, 2H), 7.41 (d, 2H), 8.32 (s, 1H).

EXAMPLE 12(1)

N-(3-{4-[(3-phenylprop-2-ynyl)oxy]phenyl}propyl)-β-alanine

TLC: Rf 0.31 (chloroform:methanol:formic acid=10:1:0.5);
$^1$H-NMR (CD$_3$OD): δ 1.89-2.05 (m, 2H), 2.58 (t, 2H), 2.67 (t, 2H), 2.94-3.05 (n, 2H), 3.17 (t, 2H), 4.91 (s, 2H), 6.98 (d, 2H), 7.17 (d, 2H), 7.28-7.35 (m, 3H), 7.35-7.42 (m, 2H).

EXAMPLE 12(2)

N-[3-(4-{[(2E)-3-phenylprop-2-enyl]oxy}phenyl)propyl]-β-alanine

TLC: Rf 0.35 (chloroform:methanol:formic acid=10:1:0.5);
$^1$H-NMR (CD$_3$OD): δ 1.83-2.06 (m, 2H), 2.51 (t, 2H), 2.67 (t, 2H), 2.92-3.05 (m, 2H), 3.14 (t, 2H), 4.68 (dd, 2H), 6.43 (dt, 1H), 6.73 (d, 1H), 6.92 (d, 2H), 7.15 (d, 2H), 7.19-7.26 (m, 1H), 7.27-7.34 (m, 2H), 7.37-7.45 (m, 2H).

EXAMPLE 13 ethyl (2E)-2-cyano-3-[4-(3-phenylpropoxy)phenyl]acrylate 4-(3-phenylpropoxy)benzaldehdye (240 mg), ethyl cyanoacetate (0.094 mL) and ammonium acetate (74 mg) were mixed and reacted under microwave irradiation (50 W, 100° C., 10 minutes). Then, water was added to the reaction mixture, followed by extraction with ethyl acetate. The organic layer was dried over anhydrous magnesium sulfate and concentrated. The above procedure was repeated thrice to give three residues. The residues were combined and purified by silica gel column chromatography (hexane:ethyl acetate=20:1 to 7:1) to give the title compound (629 mg) having the following physical properties.

TLC: Rf 0.28 (hexane:ethyl acetate=5:1);
$^1$H-NMR (CDCl$_3$): δ 1.39 (t, 3H), 2.15 (m, 2H), 2.83 (m, 2H), 4.04 (t, 2H), 4.37 (q, 2H), 6.97 (d, 2H), 7.21 (m, 3H), 7.29 (m, 2H), 7.99 (d, 2H), 8.17 (s, 1H).

EXAMPLE 14 ethyl 2-cyano-3-[4-(3-phenylpropoxy)phenyl]propanoate

Under an argon atmosphere, ethanol (1 mL) was added to palladium carbon containing 10% moisture (250 mg). Next, a solution of the compound (620 mg) prepared in Example 13 in a mixture of ethanol (4 mL) and ethyl acetate (4 mL) was added thereto. After purging with hydrogen, the mixture was stirred at room temperature for 2 hours. Then, the reaction mixture was filtered through Celite (trade name). The filtrate was concentrated to give the title compound (594 mg) having the following physical properties.

TLC: Rf 0.26 (hexane:ethyl acetate=5:1);
$^1$H-NMR (CDCl$_3$): δ 1.28 (t, 3H), 2.10 (m, 2H), 2.81 (m, 2H), 3.18 (m, 2H), 3.67 (dd, 1H), 3.95 (t, 2H), 4.24 (q, 2H), 6.85 (d, 2H), 7.19 (m, 5H), 7.28 (m, 2H).

EXAMPLE 15

3-amino-2-[4-(3-phenylpropoxy)benzyl]propan-1-ol

To lithium aluminum hydride (131 mg) was added dry tetrahydrofuran (10 mL). Then, a solution of the compound (290 mg) prepared in Example 14 in dry tetrahydrofuran (15 mL) was added dropwise thereto, followed by stirring at 60° C. for 3 hours. To the reaction mixture, 1 N hydrochloric acid was added at 0° C., followed by stirring at room temperature for 1 hour. Anhydrous sodium sulfate was added to the reaction mixture and the mixture was filtered through Celite (trade name). The filtrate was concentrated to give the title compound (284 mg) having the following physical properties as a crude product. The obtained compound was used in the next reaction without further purification.

TLC: Rf 0.43 (chloroform:methanol:aqueous ammonia=80:20:4).

EXAMPLE 16

N-{3-hydroxy-2-[4-(3-phenylpropoxy)benzyl]propyl}-β-alanine

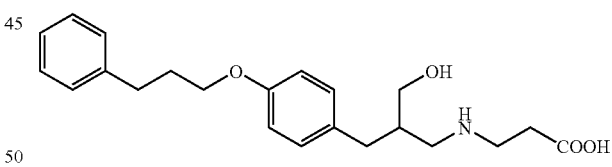

To a solution of tert-butyl N-{3-hydroxy-2-[4-(3-phenylpropoxy)benzyl]propyl}-β-alaninate (65 mg; prepared by following the procedure of Example 4 using the compound prepared in Example 15 as a substitute for 4-(3-aminopropyl)phenol) in dichloromethane (3 mL), trifluoroacetic acid (3 mL) was dropped at 0° C., followed by stirring at room temperature for 2 hours. Then, the reaction mixture was concentrated. The residue was purified by silica gel column chromatography (chloroform:methanol:aqueous ammonia=80:20:4). The crude product thus obtained was washed with diethyl ether to give the title compound (38 mg) having the following physical properties.

TLC: Rf 0.56 (ethyl acetate:acetic acid:water=3:1:1);
$^1$H-NMR (DMSO-d$_6$): δ 1.86 (m, 1H), 1.99 (m, 2H), 2.18 (t, 2H), 2.59 (m, 1H), 2.71 (m, 3H), 2.80 (t, 2H), 3.37 (m, 4H), 3.91 (t, 2H), 6.83 (d, 2H), 7.09 (d, 2H), 7.23 (m, 5H).

EXAMPLE 17 cyano[4-(3-phenylpropoxy)phenyl]methyl acetate

To dry dichloromethane (3 mL), a solution of titanium tetraisopropoxide (0.074 mL) and 4-(3-phenylpropoxy)benzaldehyde (300 mg) in dry dichloromethane (3 mL) and trimethylsilyl cyanide were successively dropped, followed by stirring at room temperature overnight. To the reaction mixture, 1 N hydrochloric acid (3 mL) was added at 0° C., followed by stirring at room temperature for 6.5 hours. After adding water, the reaction mixture was extracted with dichloromethane. The organic layer was washed with a saturated aqueous sodium chloride solution, dried over anhydrous magnesium sulfate and filtered. To the filtrate, acetic anhydride (0.24 mL) and pyridine (0.20 mL) were successively dropped at room temperature, followed by stirring at room temperature overnight. Then, the reaction mixture was concentrated. The residue was purified by silica gel column chromatography (hexane:ethyl acetate=10:1) to give the title compound (160 mg) having the following physical properties.

TLC: Rf 0.30 (hexane:ethyl acetate=5:1);
$^1$H-NMR (CDCl$_3$): δ 2.05-2.20 (m, 5H), 2.81 (t, 2H), 3.98 (t, 2H), 6.35 (s, 1H), 6.93 (d, 2H), 7.16-7.24 (m, 3H), 7.27-7.34 (m, 2H), 7.44 (d, 2H).

EXAMPLE 18

3-hydroxy-3-[4-(3-phenylpropoxy)phenyl]propanenitrile

To dry tetrahydrofuran (14 mL), n-butyl lithium (0.94 mL; a 1.6 M hexane solution) and dry acetonitrile (0.082 mL) were successively dropped at −78° C. After stirring for 30 minutes, a solution of 4-(3-phenylpropoxy)benzaldehyde (300 mg) in dry tetrahydrofuran (3 mL) was dropped into the mixture at −78° C. The reaction mixture was stirred at room temperature for 1 hour, then poured into ice-water and extracted with ethyl acetate. The organic layer was successively washed with water and a saturated aqueous sodium chloride solution, dried over anhydrous magnesium sulfate and concentrated. The residue was washed with a mixed solvent of diethyl ether and hexane and filtered to give the title compound (238 mg) having the following physical properties.

TLC: Rf 0.52 (hexane:ethyl acetate=1:1);
$^1$H-NMR (CDCl$_3$): δ 2.11 (m, 2H), 2.18 (d, 1H), 2.76 (m, 4H), 3.97 (t, 2H), 5.00 (td, 1H), 6.91 (d, 2H), 7.20 (m, 3H), 7.30 (m, 4H).

Examples 19 to 19(1)

By using the compound prepared in Example 17 or 18 as a substitute for the compound prepared in Example 14, the procedures of Example 15, Example 4 and Example 11 were followed in this order to thereby give the following compounds.

EXAMPLE 19

N-{2-hydroxy-2-[4-(3-phenylpropoxy)phenyl]ethyl})-β-alaninate sodium salt

TLC: Rf 0.55 (ethyl acetate:acetic acid:water=3:1:1);
$^1$H-NMR (CD$_3$OD): δ 2.00-2.10 (m, 2H), 2.38 (t, 2H), 2.68-2.90 (m, 6H), 3.94 (t, 2H), 4.70 (dd, 1H), 6.86 (d, 2H), 7.12-7.28 (m, 7H).

EXAMPLE 19(1)

N-{3-hydroxy-3-[4-(3-phenylpropoxy)phenyl]propyl}-β-alanine

TLC: Rf 0.48 (ethyl acetate:acetic acid:water=3:1:1);
$^1$H-NMR (CD$_3$OD): δ 1.98-2.10 (m, 4H), 2.48 (t, 2H), 2.78 (t, 2H), 3.04-3.20 (m, 4H), 3.94 (t, 2H), 4.78 (t, 1H), 6.89 (d, 2H), 7.12-7.31 (m, 7H).

EXAMPLE 20

1-[4-(3-phenylpropoxy)phenyl]prop-2-en-1-ol

To a solution of 4-(3-phenylpropoxy)benzaldehyde (10.4 g) in dry tetrahydrofuran (100 mL), a solution of bromo(vinyl) magnesium in tetrahydrofuran (14%, about 1 M) was added at 0° C. After stirring for 15 minutes, the reaction mixture was added to a cold saturated aqueous ammonium chloride solution and extracted with ethyl acetate. The organic layer was successively washed with water and a saturated aqueous sodium chloride solution, dried over anhydrous magnesium sulfate and concentrated. The residue was purified by silica gel column chromatography (hexane:ethyl acetate=20:1 to 3:1) to give the title compound (10.01 g) having the following physical properties.

TLC: Rf 0.24 (hexane:ethyl acetate=4:1);
$^1$H-NMR (CDCl$_3$): δ 1.85 (d, 1H), 2.04-2.17 (m, 2H), 2.81 (t, 2H), 3.96 (t, 2H), 5.14-5.21 (m, 2H), 5.34 (dt, 1H), 6.05 (ddd, 1H), 6.88 (d, 2H), 7.16-7.23 (m, 3H), 7.25-7.32 (m, 4H).

EXAMPLE 21 oxiran-2-yl[4-(3-phenylpropoxy)phenyl]methanol

To a solution of the compound (3.0 g) prepared in Example 20, m-chloroperbenzoic acid (7.67 g; mCPBA) was added at room temperature. After stirring for 4 hours, the reaction mixture was poured into a cold 0.1 N aqueous sodium hydroxide solution and extracted with a mixed solvent (hexane:ethyl acetate=1:5). The organic layer was successively washed with water and a saturated aqueous sodium chloride solution, dried over anhydrous magnesium sulfate and concentrated. The residue was purified by silica gel column chromatography (hexane:ethyl acetate=10:1 to 2:1) to give the title compound (1.96 g) having the following physical properties.

TLC: Rf 0.29 (hexane:ethyl acetate=2:1);
$^1$H-NMR (CDCl$_3$): δ 2.06-2.15 (m, 2H), 2.23 (d, 0.5H), 2.76-2.89 (m, 3.5H), 2.98 (dd, 0.5H), 3.17-3.27 (m, 1H), 3.97 (t, 2H), 4.43 (t, 0.5H), 4.89 (d, 0.5H), 6.87-6.93 (m, 2H), 7.16-7.24 (m, 3H), 7.26-7.36 (m, 4H).

EXAMPLE 22

N-{2,3-dihydroxy-3-[4-(3-phenylpropoxy)phenyl]propyl}-β-alanine

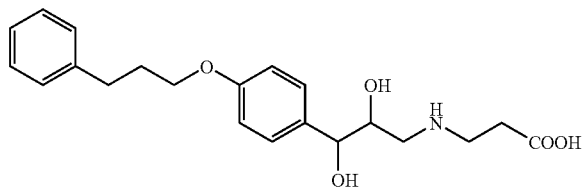

To a 2.5 N aqueous sodium hydroxide solution (2.2 mL) of O-alanine (550 mg), a solution of the compound (350 mg) prepared in Example 21 in 2-propanol (2.2 mL) was dropped, followed by stirring at 50° C. for 2 hours. Then, the reaction mixture was cooled and 1 N hydrochloric acid (5.5 mL) was added thereto at 0° C., followed by concentration. The residue was purified by silica gel column chromatography (chloroform:methanol aqueous ammonia=80:20:4) to give the title compound (313 mg) having the following physical properties.

TLC: Rf 0.16 (chloroform:methanol:aqueous ammonia=80:40:4);

$^1$H-NMR (CD$_3$OD): δ 2.01-2.10 (m, 2H), 2.42-2.51 (m, 2H), 2.78 (t, 2H), 2.85-3.18 (m, 4H), 3.84-3.97 (m, 3H), 4.52 (d, 0.5H), 4.59 (d, 0.5H), 6.88-6.92 (m, 2H), 7.11-7.26 (m, 5H), 7.26-7.34 (m, 2H).

EXAMPLE 23

N-{2-hydroxy-3-[4-(3-phenylpropoxy)phenyl]propyl}-O-alanine

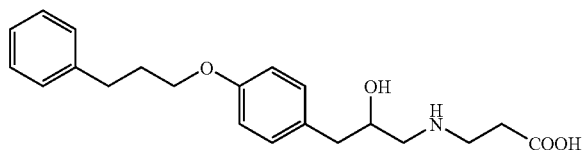

By using 1-allyl-4-(3-phenylpropoxy)benzene as a substitute for the compound prepared in Example 20, the procedures of Example 21 and Example 22 were followed to thereby give the title compound having the following physical properties.

TLC: Rf 0.19 (chloroform:methanol:aqueous ammonia=80:20:4);

$^1$H-NMR (CD$_3$OD): δ 2.00-2.10 (m, 2H), 2.46 (t, 2H), 2.66-2.90 (m, 5H), 2.99-3.19 (m, 3H), 3.92 (t, 2H), 3.96-4.04 (m, 1H), 6.84 (d, 2H), 7.11-7.29 (m, 7H).

EXAMPLE 24

N-(tert-butoxycarbonyl)-N-[3-(4-hydroxyphenyl)propyl]-β-alanine

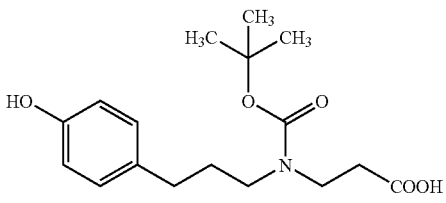

By using 3-(4-hydroxyphenyl)propanenitrile as a substitute for the compound prepared in Example 14, the procedures of Example 15, Example 4, Example 5 and Example 11 were followed in this order to thereby give the title compound having the following physical properties.

TLC: Rf 0.40 (hexane:ethyl acetate=1:3);

$^1$H-NMR (CDCl$_3$): δ 1.45 (s, 9H), 1.81 (m, 2H), 2.52 (t, 2H), 2.61 (t, 2H), 3.22 (m, 2H), 3.47 (t, 2H), 6.76 (d, 2H), 7.02 (d, 2H).

EXAMPLE 25

N-[3-(4-hydroxyphenyl)propyl]-β-alanine hydrochloride

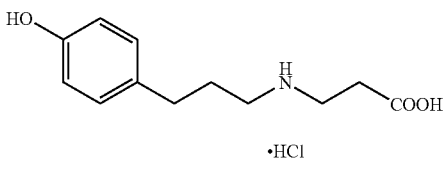

By using the compound prepared in Example 24 as a substitute for the compound prepared in Example 6, the procedure of Example 7 was followed to thereby give the title compound having the following physical properties.

TLC: Rf 0.69 (ethyl acetate:acetic acid:water=3:1:1);

$^1$H-NMR (CD$_3$OD): δ 1.95 (m, 2H), 2.62 (t, 2H), 2.72 (t, 2H), 3.00 (m, 2H), 3.24 (t, 2H), 6.71 (d, 2H), 7.03 (d, 2H).

EXAMPLE 26

N-[2-(4-{2-[4-(benzyloxy)phenyl]ethoxy}phenyl)ethyl]-β-alanine trifluoroacetate

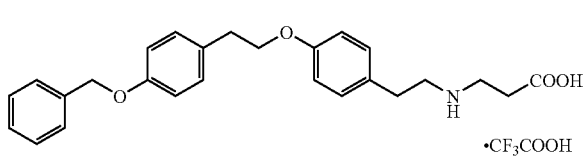

Step A:

To a suspension of Wang resin (manufactured by Argonaut Technology; Cat No. 800296) (1.06 mmol/g, 10.6 g, 11.2 mmol) in dichloromethane (100 mL), N,N-diisopropylethylamine (17.4 mL; 100 mmol) was added at −78° C. Further, acrylic acid chloride (4.06 mL; 50 mmol) was added and the mixture was shaken at room temperature overnight. After aspiration of the solvent, the obtained resin was washed with dichloromethane 4 times to give an acrylate resin (10.9 g).

Step B:

To the acrylate resin (1.5 g), a solution of 4-(2-aminoethyl) phenol (20 mmol) in N-methylpyrrolidone (20 mL) was added at room temperature and the mixture was shaken at room temperature overnight. After aspiration of the solvent, the obtained resin was washed with dichloromethane 4 times to give an phenol resin (1.78 g, 1.2 mmolg).

Step C:

To the phenol resin (50 mg, 0.060 mmol), 2-[4-(benzyloxy) phenyl]ethanol (0.30 mmol) was added at room temperature. Further, a mixed solvent (1 mL; dichloromethane:dry tetrahydrofuran=1:1) was added, followed by the addition of tri-n-butylphosphine (0.30 mmol) and 1,1'-azobis(N,N-dimethylformamide) (0.30 mmol). Then, the mixture was shaken at room temperature overnight. The resin was taken up by filtration and washed successively with a mixed solvent (dichloromethane:tetrahydrofuran=1:1) 3 times, dichloromethane 3 times, methanol 4 times, a mixed solvent (dichloromethane: methanol=3:1) 2 times and dichloromethane 3 times. Next, trifluoroacetic acid (0.5 mL) and dichloromethane (0.5 mL) were added and the mixture was shaken at room temperature for 4 hours. After filtering off the resin and washing with dichloromethane 4 times, the filtrate was concentrated to thereby give the title compound having the following physical properties.

HPLC retention time (minute): 3.67; MS (m/z): 839 (2M+ H)+, 420 (+H)+.

Unless otherwise noted, HPLC was conducted under the following conditions.
Column: Xterra (trade name) MS $C_{18}$ 5 μm, 4.6×50 mm I.D.
Flow rate: 3 ml/min
Solvent A: 0.1% aqueous solution of trifluoroacetic acid
Solvent B: 0.1% solution of trifluoroacetic acid in acetonitrile Within 0.5 minute following the initiation of the measurement, the mixing rate of the solution A to the solution B was fixed to 95/5. Subsequently, the mixing ratio of the solution A to the solution B was linearly changed to 0/100 within 2.5 minutes, and fixed to 0/100 during 0.5 minute. In the subsequent 0.01 minute, the mixing rate of the solution A to the solution B was linearly changed to 95/5.

EXAMPLES 26(1) to 26(244)

The procedure of Example 26 was similarly carried out, except for using 4-(2-aminoethyl)phenol or a corresponding derivative as a substitute therefor and 2-[4-(benzyloxy)phenyl]ethanol or a corresponding derivative as a substitute therefor to thereby give the following compounds.

EXAMPLE 26(1)

N-{2-[4-(2-phenoxyethoxy)phenyl]ethyl}-β-alanine trifluoroacetate

HPLC retention time (minute): 3.34; MS (m/z): 659 (2M+ H)+, 330 (M+H)+, 266.

Example 26(2)

N-{2-[4-(3-phenylpropoxy)phenyl]ethyl}-β-alanine trifluoroacetate

HPLC retention time (minute): 3.48; MS (m/z): 655 (2M+ H)+, 328 (M+H)+.

EXAMPLE 26(3)

N-{2-[4-(4-phenylbutoxy)phenyl]ethyl}-O-alanine trifluoroacetate

HPLC retention time (minute): 3.58; MS (m/z): 683 (2M+ H)+, 342 (M+H)+.

EXAMPLE 26(4)

N-(2-{4-[4-(4-methoxyphenyl)butoxy] phenyl}ethyl)-β-alanine trifluoroacetate

HPLC retention time (minute): 3.54; MS (m/z): 743 (2M+ H)+, 372 (M+H)+.

EXAMPLE 26(5)

N-(2-{4-[2-(benzylsulfanyl)ethoxy]phenyl}ethyl)-β-alanine trifluoroacetate

HPLC retention time (minute): 3.48; MS (m/z): 719 (2M+ H)+, 360 (M+H)+.

EXAMPLE 26(6)

N-{2-[4-(3-phenoxypropoxy)phenyl]ethyl}-β-alanine trifluoroacetate

HPLC retention time (minute): 3.45; MS (m/z): 687 (2M+ H)+, 344 (M+H)+.

EXAMPLE 26(7)

N-{2-[4-(cyclohexylmethoxy)phenyl]ethyl}-β-alanine trifluoroacetate

HPLC retention time (minute): 3.56; MS (m/z): 611 (2M+ H)+, 306 (M+H)+.

EXAMPLE 26(8)

N-(2-{4-[2-(2,4-difluorophenyl)ethoxy] phenyl}ethyl)-β-alanine trifluoroacetate

HPLC retention time (minute): 3.46; MS (m/z): 699 (2M+ H)+, 350 (M+H)+.

EXAMPLE 26(9)

N-(2-{4-[(3-phenoxybenzyl)oxy]phenyl}ethyl)-β-alanine trifluoroacetate

HPLC retention time (minute): 3.62; MS (m/z): 783 (2M+ H)+, 392 (M+H)+.

EXAMPLE 26(10)

N-{2-[4-(2-cyclohexylethoxy)phenyl]ethyl}-β-alanine trifluoroacetate

HPLC retention time (minute): 3.64; MS (m/z): 639 (2M+H)$^+$, 320 (M+H)$^+$.

EXAMPLE 26(11)

N-{2-[4-(benzyloxy)phenyl]ethyl}-β-alanine trifluoroacetate

HPLC retention time (minute): 3.34; MS (m/z): 599 (2M+H)$^+$, 300 (M+H)$^+$.

EXAMPLE 26(12)

N-{2-[4-(2-phenylethoxy)phenyl]ethyl}-β-alanine trifluoroacetate

HPLC retention time (minute): 3.41; MS (m/z): 627 (2M+H)$^+$, 314 (M+H)$^+$.

EXAMPLE 26(13)

N-{2-[4-(3,3-dimethylbutoxy)phenyl]ethyl})-β-alanine trifluoroacetate

HPLC retention time (minute): 3.51; MS (m/z): 587 (2M+H)$^+$, 294 (M+H)$^+$.

EXAMPLE 26(14)

N-{2-[4-(3-cyclohexylpropoxy)phenyl]ethyl}-β-alanine trifluoroacetate

HPLC retention time (minute): 3.77; MS(m/z): 667 (2M+H)$^+$, 334 (M+H)$^+$.

EXAMPLE 26(15)

N-(2-{4-[(4-tert-butylbenzyl)oxy]phenyl}ethyl)-β-alanine trifluoroacetate

HPLC retention time (minute): 3.50; MS (m/z): 711 (2M+H)$^+$, 356 (M+H)$^+$.

EXAMPLE 26(16)

N-(2-{4-[(4-cyclohexylbenzyl)oxy]phenyl}ethyl)-β-alanine trifluoroacetate

HPLC retention time (minute): 3.65; MS (m/z): 763 (2M+H)$^+$, 382 (M+H)$^+$.

EXAMPLE 26(17)

N-{3-[4-(2-phenylethoxy)phenyl]propyl}-β-alanine trifluoroacetate

HPLC retention time (minute): 3.39; MS (m/z): 655 (2M+H)$^+$, 328 (M+H)$^+$.

EXAMPLE 26(18)

N-(3-{4-[2-(2-methylphenyl)ethoxy]phenyl}propyl)-β-alanine trifluoroacetate

HPLC retention time (minute): 3.46; MS (m/z): 683 (2M+H)$^+$, 342 (M+H)$^+$.

EXAMPLE 26(19)

N-(3-{4-[2-(3-methylphenyl)ethoxy]phenyl}propyl)-β-alanine trifluoroacetate

HPLC retention time (minute): 3.47; MS (m/z): 683 (2M+H)$^+$, 342 (M+H)$^+$.

EXAMPLE 26(20)

N-(3-{4-[2-(4-methylphenyl)ethoxy]phenyl}propyl)-β-alanine trifluoroacetate

HPLC retention time (minute): 3.48; MS (m/z): 683 (2M+H)$^+$, 342 (ME+H)$^+$.

EXAMPLE 26(21)

N-{3-[4-(benzyloxy)phenyl]propyl}-β-alanine trifluoroacetate

HPLC retention time (minute): 3.30; MS (m/z): 627 (2M+H)$^+$, 314 (M+H)$^+$.

EXAMPLE 26(22)

N-(4-{2-[4-(benzyloxy)phenyl]ethoxy}benzyl)-β-alanine trifluoroacetate

HPLC retention time (minute): 3.56; MS (m/z): 406 (M+H)$^+$.

EXAMPLE 26(23)

N-[4-(2-phenoxyethoxy)benzyl]-β-alanine trifluoroacetate

HPLC retention-time (minute): 3.22; MS (m/z): 316 (M+H)$^+$, 227.

EXAMPLE 26(24)

N-{4-[2-(benzyloxy)ethoxy]benzyl}-β-alanine trifluoroacetate

HPLC retention time (minute): 3.21; MS (m/z): 330 (M+H)$^+$, 241.

EXAMPLE 26(25)

N-[4-(3-phenylpropoxy)benzyl]-β-alanine trifluoroacetate

HPLC retention time (minute): 3.35; MS (m/z): 314 (M+H)$^+$, 225.

EXAMPLE 26(26)

N-[4-(4-phenylbutoxy)benzyl]-β-alanine trifluoroacetate

HPLC retention time (minute): 3.43; MS (m/z): 328 (M+H)$^+$, 239.

EXAMPLE 26(27)

N-{4-[(5-phenylpentyl)oxy]benzyl)}-β-alanine trifluoroacetate

HPLC retention time (minute): 3.54; MS (m/z): 342 (M+H)$^+$, 253.

EXAMPLE 26(28)

N-[4-(2-thien-2-ylethoxy)benzyl]-β-alanine trifluoroacetate

HPLC retention time (minute): 3.21; MS (m/z): 306 (M+H)$^+$, 217.

EXAMPLE 26(29)

N-{4-[2-(benzylsulfanyl)ethoxy]benzyl}-β-alanine trifluoroacetate

HPLC retention time (minute): 3.33; MS (m/z): 346 (M+H)$^+$, 151.

EXAMPLE 26(30)

N-{4-[(6-phenylhexyl)oxy]benzyl}-β-alanine trifluoroacetate

HPLC retention time (minute): 3.61; MS (m/z): 356 (M+H)$^+$.

EXAMPLE 26(31)

N-{4-[3-(benzyloxy)propoxy]benzyl}-β-alanine trifluoroacetate

HPLC retention time (minute): 3.28; MS (m/z): 344 (M+H)$^+$, 255.

EXAMPLE 26(32)

N-{4-[(7-phenylheptyl)oxy]benzyl}-β-alanine trifluoroacetate

HPLC retention time (minute): 3.72; MS (m/z): 370 (M+H)$^+$.

EXAMPLE 26(33)

N-[4-(3-phenoxypropoxy)benzyl]-β-alanine trifluoroacetate

HPLC retention time (minute): 3.32; MS (m/z): 330 (M+H)$^+$, 241.

EXAMPLE 26(34)

N-{4-[(9-phenylnonyl)oxy]benzyl}-β-alanine trifluoroacetate

HPLC retention time (minute): 3.91; MS (m/z): 398 (M+H)$^+$, 309.

EXAMPLE 26(35)

N-{4-[(8-phenyloctyl)oxy]benzyl})-β-alanine trifluoroacetate

HPLC retention time (minute): 3.82; MS (m/z): 384 (M+H)$^+$, 295.

EXAMPLE 26(36)

N-[4-(cyclohexylmethoxy)benzyl]-β-alanine trifluoroacetate

HPLC retention time (minute): 3.41; MS (m/z): 292 (M+H)$^+$, 203.

EXAMPLE 26(37)

N-[4-(2-cyclopentylethoxy)benzyl]-β-alanine trifluoroacetate

HPLC retention time (minute): 3.41; MS (m/z): 292 (M+H)$^+$, 203.

EXAMPLE 26(38)

N-(4-{[5-(benzyloxy)pentyl]oxy}benzyl)-β-alanine trifluoroacetate

HPLC retention time (minute): 3.43; MS (m/z): 372 (M+H)$^+$, 283.

EXAMPLE 26(39)

N-{4-[4-(benzyloxy)butoxy]benzyl}-O-alanine trifluoroacetate

HPLC retention time (minute): 3.36; MS (m/z): 358 (M+H)$^+$, 269.

EXAMPLE 26(40)

N-{4-[(3-phenoxybenzyl)oxy]benzyl})-β-alanine trifluoroacetate

HPLC retention time (minute): 3.48; MS (m/z): 378 (M+H)$^+$, 289.

EXAMPLE 26(41)

N-[4-(2-cyclohexylethoxy)benzyl]-β-alanine trifluoroacetate

HPLC retention time (minute): 3.50; MS (m/z): 306 (M+H)$^+$, 217.

EXAMPLE 26(42)

N-(4-butoxybenzyl)-β-alanine trifluoroacetate

HPLC retention time (minute): 3.15; MS (m/z): 252 (M+H)$^+$, 163.

EXAMPLE 26(43)

N-[4-(cyclopentylmethoxy)benzyl]-β-alanine trifluoroacetate

HPLC retention time (minute): 3.31; MS (m/z): 278 (M+H)$^+$, 189.

EXAMPLE 26(44)

N-[4-(benzyloxy)benzyl]-β-alanine trifluoroacetate

HPLC retention time (minute): 3.18; MS (m/z): 286 (M+H)$^+$, 197.

EXAMPLE 26(45)

N-[4-(2-phenylethoxy)benzyl]-β-alanine trifluoroacetate

HPLC retention time (minute): 3.26; MS (m/z): 300 (M+H)$^+$, 211.

EXAMPLE 26(46)

N-(4-isobutoxybenzyl)-β-alanine trifluoroacetate

HPLC retention time (minute): 3.17; MS (m/z): 252 (M+H)$^+$, 163.

EXAMPLE 26(47)

N-{4-[(4-methylpentyl)oxy]benzyl}-O-alanine trifluoroacetate

HPLC retention time (minute): 3.38; MS (m/z): 280 (M+H)$^+$, 191.

EXAMPLE 26(48)

N-[4-(3,3-dimethylbutoxy)benzyl]-β-alanine trifluoroacetate

HPLC retention time (minute): 3.34; MS (m/z): 280 (M+H)$^+$, 191.

EXAMPLE 26(49)

N-{4-[(2-propylpentyl)oxy]benzyl}-β-alanine trifluoroacetate

HPLC retention time (minute): 3.59; MS (m/z): 308 (M+H)$^+$, 219.

EXAMPLE 26(50)

N-[4-(3-cyclohexylpropoxy)benzyl]-β-alanine trifluoroacetate

HPLC retention time (minute): 3.61; MS (m/z): 320 (M+H)$^+$, 231.

EXAMPLE 26(51)

N-[4-(pentyloxy)benzyl]-β-alanine trifluoroacetate

HPLC retention time (minute): 3.29; MS (m/z): 266 (M+H)$^+$, 177.

EXAMPLE 26(52)

N-[4-(hexyloxy)benzyl]-β-alanine trifluoroacetate

HPLC retention time (minute): 3.40; MS (m/z): 280 (M+H)$^+$, 191.

EXAMPLE 26(53)

N-[4-(heptyloxy)benzyl]-β-alanine trifluoroacetate

HPLC retention time (minute): 3.50; MS (m/z): 294 (M+H)$^+$, 205.

EXAMPLE 26(54)

N-[4-(octyloxy)benzyl]-β-alanine trifluoroacetate

HPLC retention time (minute): 3.62; MS (m/z): 308 (M+H)$^+$, 219.

EXAMPLE 26(55)

N-{4-[(4-chlorobenzyl)oxy]benzyl}-β-alanine trifluoroacetate

HPLC retention time (minute): 3.32; MS (m/z): 320 (M+H)$^+$, 231.

EXAMPLE 26(56)

N-[3-(4-{2-[4-(benzyloxy)phenyl]ethoxy}phenyl)propyl]-β-alanine trifluoroacetate HPLC retention time (minute): 3.60; MS (m/z): 434 (M+H)$^+$, 219.

EXAMPLE 26(57)

N-{3-[4-(2-phenoxyethoxy)phenyl]propyl}-β-alanine trifluoroacetate

HPLC retention time (minute): 3.33; MS (m/z): 344 (M+H)$^+$.

EXAMPLE 26(58)

N-(3-{4-[2-(benzyloxy)ethoxy]phenyl}propyl)-β-alanine trifluoroacetate

HPLC retention time (minute): 3.31; MS (m/z): 358 (M+H)$^+$.

EXAMPLE 26(59)

N-{3-[4-(3-phenylpropoxy)phenyl]propyl}-β-alanine trifluoroacetate

HPLC retention time (minute): 3.45; MS (m/z): 342 (M+H)$^+$.

EXAMPLE 26(60)

N-{3-[4-(2-thien-2-ylethoxy)phenyl]propyl}-β-alanine trifluoroacetate

HPLC retention time (minute): 3.34; MS (m/z): 334 (M+H)$^+$.

Example 26(61)

N-(3-{4-[2-(benzylsulfanyl)ethoxy]phenyl}propyl)-β-alanine trifluoroacetate

HPLC retention time (minute): 3.44; MS (m/z): 374 (M+H)⁺.

EXAMPLE 26(62)

N-(3-{4-[3-(benzyloxy)propoxy]phenyl}propyl)-β-alanine trifluoroacetate

HPLC retention time (minute): 3.38; MS (m/z): 372 (M+H)⁺.

EXAMPLE 26(63)

N-{3-[4-(3-phenoxypropoxy)phenyl]propyl}-β-alanine trifluoroacetate

HPLC retention time (minute): 3.42; MS (m/z): 358 (M+H)⁺.

EXAMPLE 26(64)

N-(3-{4-[(9-phenylnonyl)oxy]phenyl}propyl)-β-alanine trifluoroacetate

HPLC retention time (minute): 4.00; MS (m/z): 426 (M+H)⁺.

EXAMPLE 26(65)

N-(3-{4-[(8-phenyloctyl)oxy]phenyl}propyl)-β-alanine trifluoroacetate

HPLC retention time (minute): 3.93; MS (m/z): 412 (M+H)⁺.

EXAMPLE 26(66)

N-{3-[4-(cyclohexylmethoxy)phenyl]propyl}-β-alanine trifluoroacetate

HPLC retention time (minute): 3.55; MS (m/z): 320 (M+H)⁺, 219.

EXAMPLE 26(67)

N-{3-[4-(2-cyclopentylethoxy)phenyl]propyl}-β-alanine trifluoroacetate

HPLC retention time (minute): 3.53; MS (m/z): 320 (M+H)⁺.

EXAMPLE 26(68)

N-[3-(4-{[5-(benzyloxy)pentyl]oxy}phenyl)propyl]-β-alanine trifluoroacetate

HPLC retention time (minute): 3.53; MS (m/z): 400 (M+H)⁺.

EXAMPLE 26(69)

N-(3-{4-[4-(benzyloxy)butoxy]phenyl}propyl)-β-alanine trifluoroacetate

HPLC retention time (minute): 3.45; MS (m/z): 386 (M+H)⁺.

EXAMPLE 26(70)

N-(3-{4-[(3-phenoxybenzyl)oxy]phenyl}propyl)-β-alanine trifluoroacetate

HPLC retention time (minute): 3.58; MS (m/z): 406 (M+H)⁺, 219.

EXAMPLE 26(71)

N-{3-[4-(2-cyclohexylethoxy)phenyl]propyl}-O-alanine trifluoroacetate

HPLC retention time (minute): 3.60; MS (m/z): 334 (M+H)⁺, 219.

EXAMPLE 26(72)

N-{3-[4-(cyclopentylmethoxy)phenyl]propyl}-O-alanine trifluoroacetate

HPLC retention time (minute): 3.44; MS (m/z): 306 (M+H)⁺.

EXAMPLE 26(73)

N-[3-(4-isobutoxyphenyl)propyl]-β-alanine trifluoroacetate

HPLC retention time (minute): 3.31; MS (m/z): 280 (M+H)⁺.

EXAMPLE 26(74)

N-(3-{4-[(4-methylpentyl)oxy]phenyl}propyl)-β-alanine trifluoroacetate

HPLC retention time (minute): 3.51; MS (m/z): 308 (M+H)⁺.

EXAMPLE 26(75)

N-{3-[4-(3,3-dimethylbutoxy)phenyl]propyl}-O-alanine trifluoroacetate

HPLC retention time (minute): 3.49; MS (m/z): 308 (M+H)⁺.

EXAMPLE 26(76)

N-(3-{4-[(2-propylpentyl)oxy]phenyl}propyl)-β-alanine trifluoroacetate

HPLC retention time (minute): 3.71; MS (m/z): 336 (M+H)⁺.

EXAMPLE 26(77)

N-{3-[4-(3-cyclohexylpropoxy)phenyl]propyl}-β-alanine trifluoroacetate

HPLC retention time (minute): 3.75; MS (m/z): 348 (M+H)$^+$.

EXAMPLE 26(78)

N-(3-{4-[(4-chlorobenzyl)oxy]phenyl}propyl)-β-alanine trifluoroacetate

HPLC retention time (minute): 3.42; MS (m/z): 350, 348 (M+H)$^+$.

EXAMPLE 26(79)

N-(3-{4-[2-(4-tert-butylphenyl)ethoxy]phenyl}propyl)-β-alanine trifluoroacetate

HPLC retention time (minute): 3.69; MS (m/z): 384 (M+H)$^+$.

EXAMPLE 26(80)

N-(3-{4-[2-(2-naphthyl)ethoxy]phenyl}propyl)-β-alanine trifluoroacetate

HPLC retention time (minute): 3.56; MS (m/z): 378 (M+H)$^+$.

EXAMPLE 26(81)

N-{3-[4-(decyloxy)phenyl]propyl}-β-alanine trifluoroacetate

HPLC retention time (minute): 3.99; MS (m/z): 364 (M+H)$^+$.

EXAMPLE 26(82)

N-{2-[4-(2-thien-2-ylethoxy)phenyl]ethyl})-β-alanine trifluoroacetate

HPLC retention time (minute): 3.27; MS (m/z): 320 (M+H)$^+$.

EXAMPLE 26(83)

N-(2-{4-[(6-phenylhexyl)oxy]phenyl}ethyl)-β-alanine trifluoroacetate

HPLC retention time (minute): 3.67; MS (m/z): 370 (M+H)$^+$, 219.

EXAMPLE 26(84)

N-(2-{4-[3-(benzyloxy)propoxy]phenyl}ethyl)-β-alanine trifluoroacetate

HPLC retention time (minute): 3.34; MS (m/z): 358 (M+H)$^+$.

EXAMPLE 26(85)

N-(2-{4-[(7-phenylheptyl)oxy]phenyl}ethyl)-β-alanine trifluoroacetate

HPLC retention time (minute): 3.77; MS (m/z): 384 (M+H)$^+$.

EXAMPLE 26(86)

N-(2-{4-[(9-phenylnonyl)oxy]phenyl}ethyl)-β-alanine trifluoroacetate

HPLC retention time (minute): 3.95; MS (m/z): 412 (M+H)$^+$.

EXAMPLE 26(87)

N-(2-{4-[(8-phenyloctyl)oxy]phenyl}ethyl)-β-alanine trifluoroacetate

HPLC retention time (minute): 3.86; MS (m/z): 398 (M+H)$^+$.

EXAMPLE 26(88)

N-{2-[4-(2-cyclopentylethoxy)phenyl]ethyl}-β-alanine trifluoroacetate

HPLC retention time (minute): 3.47; MS (m/z): 306 (M+H)$^+$.

EXAMPLE 26(89)

N-[2-(4-{[5-(benzyloxy)pentyl]oxy}phenyl)ethyl]-β-alanine trifluoroacetate

HPLC retention time (minute): 3.49; MS (m/z): 386 (M+H)$^+$.

EXAMPLE 26(90)

N-(2{-4-[4-(benzyloxy)butoxy]phenyl}ethyl)-β-alanine trifluoroacetate

HPLC retention time (minute): 3.40; MS (m/z): 372 (M+H)$^+$.

Example 26(91)

N-[2-(4-butoxyphenyl)ethyl]-β-alanine trifluoroacetate

HPLC retention time (minute): 3.23; MS (m/z): 266 (M+H)$^+$.

EXAMPLE 26(92)

N-{2-[4-(cyclopentylmethoxy)phenyl]ethyl}-β-alanine trifluoroacetate

HPLC retention time (minute): 3.38; MS (m/z): 292 (M+H)$^+$.

EXAMPLE 26(93)

N-[2-(4-isobutoxyphenyl)ethyl]-β-alanine trifluoroacetate

HPLC retention time (minute): 3.23; MS (m/z): 266 (M+H)$^+$.

EXAMPLE 26(94)

N-(2-{4-[(4-methylpentyl)oxy]phenyl}ethyl)-β-alanine trifluoroacetate

HPLC retention time (minute): 3.44; MS (m/z): 294 (M+1H)$^+$.

EXAMPLE 26(95)

N-(2-{4-[(2-propylpentyl)oxy]phenyl}ethyl)-β-alanine trifluoroacetate

HPLC retention time (minute): 3.64; MS (m/z): 322 (M4+H)$^+$, 219.

EXAMPLE 26(96)

N-{2-[4-(pentyloxy)phenyl]ethyl}-β-alanine trifluoroacetate

HPLC retention time (minute): 3.34; MS (m/z): 280 (M+H)$^+$.

EXAMPLE 26(97)

N-{2-[4-(hexyloxy)phenyl]ethyl}-β-alanine trifluoroacetate

HPLC retention time (minute): 3.45; MS (m/z): 294 (M+H)$^+$.

EXAMPLE 26(98)

N-{2-[4-(heptyloxy)phenyl]ethyl}-β-alanine trifluoroacetate

HPLC retention time (minute): 3.56; MS (m/z): 308 (M+H)$^+$, 219.

EXAMPLE 26(99)

N-{2-[4-(octyloxy)phenyl]ethyl}-β-alanine trifluoroacetate

HPLC retention time (minute): 3.67; MS (m/z): 322 (M+H)$^+$.

EXAMPLE 26(100)

N-(2-{4-[(4-chlorobenzyl)oxy]phenyl}ethyl)-β-alanine trifluoroacetate

HPLC retention time (minute): 3.38; MS (m/z): 336, 334 (M+H)$^+$.

EXAMPLE 26(101)

N-(2-{4-[2-(4-tert-butylphenyl)ethoxy]phenyl}ethyl)-β-alanine trifluoroacetate

HPLC retention time (minute): 3.66; MS (m/z): 370 (M+H)$^+$.

EXAMPLE 26(102)

N-(2-{4-[2-(2-naphthyl)ethoxy]phenyl}ethyl)-β-alanine trifluoroacetate

HPLC retention time (minute): 3.49; MS (m/z): 364 (M+H)$^+$.

EXAMPLE 26(103)

N-(2-{4-[2-(4-methylphenyl)ethoxy]phenyl}ethyl)-β-alanine trifluoroacetate

HPLC retention time (minute): 3.40; MS (m/z): 328 (M+H)$^+$.

EXAMPLE 26(104)

N-{2-[4-(nonyloxy)phenyl]ethyl}-β-alanine trifluoroacetate

HPLC retention time (minute): 3.80; MS (m/z): 336 (M+H)$^+$.

EXAMPLE 26(105)

N-(2-{4-[2-(3-methylphenyl)ethoxy]phenyl}ethyl)-β-alanine trifluoroacetate

HPLC retention time (minute): 3.40; MS (m/z): 328 (M+H)$^+$.

EXAMPLE 26(106)

N-{2-[4-(decyloxy)phenyl]ethyl}-β-alanine trifluoroacetate

HPLC retention time (minute): 3.89; MS (m/z): 350 (M+H)$^+$.

EXAMPLE 26(107)

N-(2-{4-[2-(2-methylphenyl)ethoxy]phenyl}ethyl)-β-alanine trifluoroacetate

HPLC retention time (minute): 3.40; MS (m/z): 328 (M+H)$^+$.

EXAMPLE 26(108)

N-[2-(3-{2-[4-(benzyloxy)phenyl]ethoxy}phenyl)ethyl]-β-alanine trifluoroacetate

HPLC retention time (minute): 3.58; MS (m/z): 420 (M+H)$^+$.

EXAMPLE 26(109)

N-{2-[3-(2-phenoxyethoxy)phenyl]ethyl}-O-alanine trifluoroacetate

HPLC retention time (minute): 3.27; MS (m/z): 330 (M+H)$^+$.

EXAMPLE 26(110)

N-{2-[3-(3-phenylpropoxy)phenyl]ethyl}-β-alanine trifluoroacetate

HPLC retention time (minute): 3.38; MS (m/z): 328 (M+H)$^+$.

EXAMPLE 26(111)

N-{2-[3-(4-phenylbutoxy)phenyl]ethyl}-β-alanine trifluoroacetate

HPLC retention time (minute): 3.47; MS (m/z): 342 (M+H)$^+$.

EXAMPLE 26(112)

N-(2-{3-[(5-phenylpentyl)oxy]phenyl}ethyl)-β-alanine trifluoroacetate

HPLC retention time (minute): 3.56; MS (m/z): 356 (M+H)$^+$, 219.

EXAMPLE 26(113)

N-(2-{3-[2-(benzylsulfanyl)ethoxy]phenyl}ethyl)-β-alanine trifluoroacetate

HPLC retention time (minute): 3.38; MS (m/z): 360 (M+H)$^+$.

EXAMPLE 26(114)

N-(2-{3-[(6-phenylhexyl)oxy]phenyl}ethyl)-β-alanine trifluoroacetate

HPLC retention time (minute): 3.64; MS (m/z): 370 (M+H)$^+$.

EXAMPLE 26(115)

N-(2-{3-[3-(benzyloxy)propoxy]phenyl}ethyl)-β-alanine trifluoroacetate

HPLC retention time (minute): 3.34; MS (m/z): 358 (M+H)$^+$.

EXAMPLE 26(116)

N-(2-{3-[(7-phenylheptyl)oxy]phenyl}ethyl)-β-alanine trifluoroacetate

HPLC retention time (minute): 3.75; MS (m/z): 384 (M+H)$^+$.

EXAMPLE 26(117)

N-(2-{3-[(9-phenylnonyl)oxy]phenyl}ethyl)-β-alanine trifluoroacetate

HPLC retention time (minute): 3.95; MS (m/z): 412 (M+H)$^+$.

EXAMPLE 26(118)

N-(2-{3-[(8-phenyloctyl)oxy]phenyl}ethyl)-β-alanine trifluoroacetate

HPLC retention time (minute): 3.84; MS (m/z): 398 (M+H)$^+$.

EXAMPLE 26(119)

N-{2-[3-(cyclohexylmethoxy)phenyl]ethyl}-β-alanine trifluoroacetate

HPLC retention time (minute): 3.45; MS (m/z): 320, 306 (M+H)$^+$.

EXAMPLE 26(120)

N-{2-[3-(2-cyclopentylethoxy)phenyl]ethyl})-β-alanine trifluoroacetate

HPLC retention time (minute): 3.45; MS (m/z): 306 (M+H)$^+$.

EXAMPLE 26(121)

N-[2-(3-{[5-(benzyloxy)pentyl]oxy}phenyl)ethyl]-β-alanine trifluoroacetate

HPLC retention time (minute): 3.47; MS (m/z): 386 (M+H)$^+$.

EXAMPLE 26(122)

N-(2-{3-[4-(benzyloxy)butoxy]phenyl}ethyl)-β-alanine trifluoroacetate

HPLC retention time (minute): 3.42; MS (m/z): 372 (M+H)$^+$.

EXAMPLE 26(123)

N-(2-{3-[(3-phenoxybenzyl)oxy]phenyl}ethyl)-β-alanine trifluoroacetate

HPLC retention time (minute): 3.51; MS (m/z): 392 (M+H)$^+$.

EXAMPLE 26(124)

N-{2-[3-(2-cyclohexylethoxy)phenyl]ethyl}-β-alanine trifluoroacetate

HPLC retention time (minute): 3.58; MS (m/z): 320 (M+H)$^+$, 219.

EXAMPLE 26(125)

N-[2-(3-butoxyphenyl)ethyl]-β-alanine trifluoroacetate

HPLC retention time (minute): 3.22; MS (m/z): 266 (M+H)$^+$.

EXAMPLE 26(126)

N-{2-[3-(cyclopentylmethoxy)phenyl]ethyl}-β-alanine trifluoroacetate

HPLC retention time (minute): 3.40; MS (m/z): 336, 320, 292 (M+H)$^+$.

EXAMPLE 26(127)

N-{2-[3-(benzyloxy)phenyl]ethyl}-β-alanine trifluoroacetate

HPLC retention time (minute): 3.23; MS (m/z): 300 (M+H)$^+$.

EXAMPLE 26(128)

N-{2-[3-(2-phenylethoxy)phenyl]ethyl}-D-alanine trifluoroacetate

HPLC retention time (minute): 3.33; MS (m/z): 314 (M+H)$^+$.

EXAMPLE 26(129)

N-[2-(3-isobutoxyphenyl)ethyl]-β-alanine trifluoroacetate

HPLC retention time (minute): 3.23; MS (m/z): 266 (M+H)$^+$.

EXAMPLE 26(130)

N-(2-{3-[(4-methylpentyl)oxy]phenyl}ethyl)-β-alanine trifluoroacetate

HPLC retention time (minute): 3.44; MS (m/z): 294 (M+H)$^+$.

EXAMPLE 26(131)

N-{2-[3-(3,3-dimethylbutoxy)phenyl]ethyl}-β-alanine trifluoroacetate

HPLC retention time (minute): 3.40; MS (m/z): 294 (M+H)$^+$.

EXAMPLE 26(132)

N-(2-{3-[(2-propylpentyl)oxy]phenyl}ethyl)-β-alanine trifluoroacetate

HPLC retention time (minute): 3.62; MS (m/z): 322 (M+H)$^+$.

EXAMPLE 26(133)

N-{2-[3-(3-cyclohexylpropoxy)phenyl]ethyl}-β-alanine trifluoroacetate

HPLC retention time (minute): 3.66; MS (m/z): 334 (M+H)$^+$.

EXAMPLE 26(134)

N-{2-[3-(pentyloxy)phenyl]ethyl})-β-alanine trifluoroacetate

HPLC retention time (minute): 3.33; MS (m/z): 280 (M+H)$^+$.

EXAMPLE 26(135)

N-{2-[3-(hexyloxy)phenyl]ethyl}-β-alanine trifluoroacetate

HPLC retention time (minute): 3.44; MS (m/z): 294 (M+H)$^+$.

EXAMPLE 26(136)

N-{2-[3-(heptyloxy)phenyl]ethyl})-β-alanine trifluoroacetate

HPLC retention time (minute): 3.56; MS (m/z): 308 (M+H)$^+$.

EXAMPLE 26(137)

N-{2-[3-(octyloxy)phenyl]ethyl}-β-alanine trifluoroacetate

HPLC retention time (minute): 3.67; MS (m/z): 322 (M+H)$^+$.

EXAMPLE 26(138)

N-(2-{3-[(4-chlorobenzyl)oxy]phenyl}ethyl)-β-alanine trifluoroacetate

HPLC retention time (minute): 3.37; MS (m/z): 336, 334 (M+H)$^+$.

EXAMPLE 26(139)

N-(2-{3-[2-(4-tert-butylphenyl)ethoxy]phenyl}ethyl)-β-alanine trifluoroacetate

HPLC retention time (minute): 3.62; MS (m/z): 370 (M+H)$^+$.

EXAMPLE 26(140)

N-(2-{3-[2-(2-naphthyl)ethoxy]phenyl}ethyl)-β-alanine trifluoroacetate

HPLC retention time (minute): 3.47; MS (m/z): 364 (M+H)$^+$.

EXAMPLE 26(141)

N-(2-{3-[2-(4-methylphenyl)ethoxy]phenyl}ethyl)-β-alanine trifluoroacetate

HPLC retention time (minute): 3.40; MS (m/z): 328 (M+H)$^+$.

EXAMPLE 26(142)

N-{2-[3-(nonyloxy)phenyl]ethyl}-β-alanine trifluoroacetate

HPLC retention time (minute): 3.78; MS (m/z): 336 (M+H)$^+$.

EXAMPLE 26(143)

N-(2-{3-[2-(3-methylphenyl)ethoxy]phenyl}ethyl)-β-alanine trifluoroacetate

HPLC retention time (minute): 3.40; MS (m/z): 328 (M+H)$^+$.

EXAMPLE 26(144)

N-{2-[3-(decyloxy)phenyl]ethyl)}-β-alanine trifluoroacetate

HPLC retention time (minute): 3.88; MS (m/z): 350 (M+H)$^+$.

EXAMPLE 26(145)

N-(2-{3-[2-(2-methylphenyl)ethoxy]phenyl}ethyl)-β-alanine trifluoroacetate

HPLC retention time (minute): 3.38; MS (m/z): 328 (M+H)$^+$.

EXAMPLE 26(146)

N-(3-{2-[4-(benzyloxy)phenyl]ethoxy}benzyl)-β-alanine trifluoroacetate

HPLC retention time (minute): 3.55; MS (m/z): 406 (M+H)$^+$.

EXAMPLE 26(147)

N-[3-(3-phenylpropoxy)benzyl]-β-alanine trifluoroacetate

HPLC retention time (minute): 3.33; MS (m/z): 314 (M+H)$^+$.

EXAMPLE 26(148)

N-[3-(4-phenylbutoxy)benzyl]-β-alanine trifluoroacetate

HPLC retention time (minute): 3.42; MS (m/z): 328 (M+H)$^+$.

EXAMPLE 26(149)

N-{3-[(5-phenylpentyl)oxy]benzyl})-β-alanine trifluoroacetate

HPLC retention time (minute): 3.51; MS (m/z): 342 (M+H)$^+$.

EXAMPLE 26(150)

N-{3-[2-(benzylsulfanyl)ethoxy]benzyl}-β-alanine trifluoroacetate

HPLC retention time (minute): 3.34; MS (m/z): 360, 346 (M+H)$^+$.

EXAMPLE 26(151)

N-{3-[(6-phenylhexyl)oxy]benzyl}-β-alanine trifluoroacetate

HPLC retention time (minute): 3.60; MS (m/z): 356 (M+H)$^+$.

EXAMPLE 26(152)

N-{3-[3-(benzyloxy)propoxy]benzyl}-β-alanine trifluoroacetate

HPLC retention time (minute): 3.29; MS (m/z): 344 (M+H)$^+$.

EXAMPLE 26(153)

N-{3-[(7-phenylheptyl)oxy]benzyl}-β-alanine trifluoroacetate

HPLC retention time (minute): 3.69; MS (m/z): 370 (M+H)$^+$.

EXAMPLE 26(154)

N-[3-(3-phenoxypropoxy)benzyl]-β-alanine trifluoroacetate

HPLC retention time (minute): 3.31; MS (m/z): 330 (M+H)$^+$.

EXAMPLE 26(155)

N-{3-[(9-phenylnonyl)oxy]benzyl}-β-alanine trifluoroacetate

HPLC retention time (minute): 3.88; MS (m/z): 330 (M+H)$^+$.

EXAMPLE 26(156)

N-{3-[(8-phenyloctyl)oxy]benzyl})-β-alanine trifluoroacetate

HPLC retention time (minute): 3.77; MS (m/z): 384 (M+H)$^+$.

EXAMPLE 26(157)

N-[3-(2-cyclopentylethoxy)benzyl]-β-alanine trifluoroacetate

HPLC retention time (minute): 3.38; MS (m/z): 292 (M+H)$^+$.

EXAMPLE 26(158)

N-(3-{[5-(benzyloxy)pentyl]oxy}benzyl)-β-alanine trifluoroacetate

HPLC retention time (minute): 3.42; MS (m/z): 372 (M4+H)$^+$.

EXAMPLE 26(159)

N-{3-[4-(benzyloxy)butoxy]benzyl}-β-alanine trifluoroacetate

HPLC retention time (minute): 3.33; MS (m/z): 358 (M+Ht)$^+$.

EXAMPLE 26(160)

N-{3-[(3-phenoxybenzyl)oxy]benzyl)}-1-alanine trifluoroacetate

HPLC retention time (minute): 3.45; MS (m/z): 378 (M+H)$^+$.

EXAMPLE 26(161)

N-[3-(2-cyclohexylethoxy)benzyl]-β-alanine trifluoroacetate

HPLC retention time (minute): 3.45; MS (m/z): 306 (M+H)$^+$.

EXAMPLE 26(162)

N-(3-butoxybenzyl)-β-alanine trifluoroacetate

HPLC retention time (minute): 3.14; MS (m/z): 252 (M+H)$^+$.

EXAMPLE 26(163)

N-[3-(cyclopentylmethoxy)benzyl]-β-alanine trifluoroacetate

HPLC retention time (minute): 3.29; MS (m/z): 278 (M+H)$^+$.

EXAMPLE 26(164)

N-[3-(benzyloxy)benzyl]-β-alanine trifluoroacetate

HPLC retention time (minute): 3.16; MS (m/z): 286 (M+H)$^+$.

EXAMPLE 26(165)

N-[3-(2-phenylethoxy)benzyl]-β-alanine trifluoroacetate

HPLC retention time (minute): 3.25; MS (m/z): 300 (M+H)$^+$.

EXAMPLE 26(166)

N-(3-isobutoxybenzyl)-β-alanine trifluoroacetate

HPLC retention time (minute): 3.16; MS (m/z): 252 (M+H)$^+$.

EXAMPLE 26(167)

N-{3-[(4-methylpentyl)oxy]benzyl}-β-alanine trifluoroacetate

HPLC retention time (minute): 3.36; MS (m/z): 280 (M+H)$^+$.

EXAMPLE 26(168)

N-[3-(3,3-dimethylbutoxy)benzyl]-β-alanine trifluoroacetat

HPLC retention time (minute): 3.33; MS (m/z): 280 (M+H)$^+$.

Example 26(169)

N-{3-[(2-propylpentyl)oxy]benzyl}-β-alanine trifluoroacetate

HPLC retention time (minute): 3.56; MS (m/z): 308 (M+H)$^+$.

EXAMPLE 26(170)

N-[3-(3-cyclohexylpropoxy)benzyl]-β-alanine trifluoroacetate

HPLC retention time (minute): 3.58; MS (m/z): 320 (M+H)$^+$.

EXAMPLE 26(171)

N-[3-(pentyloxy)benzyl]-β-alanine trifluoroacetate

HPLC retention time (minute): 3.25; MS (m/z): 266 (M+H)$^+$.

EXAMPLE 26(172)

N-[3-(hexyloxy)benzyl]-β-alanine trifluoroacetate

HPLC retention time (minute): 3.40; MS (m/z): 280 (M+H)$^+$.

EXAMPLE 26(173)

N-[3-(heptyloxy)benzyl]-β-alanine trifluoroacetate

HPLC retention time (minute): 3.47; MS (m/z): 294 (M+1H)$^+$.

EXAMPLE 26(174)

N-[3-(octyloxy)benzyl]-β-alanine trifluoroacetate

HPLC retention time (minute): 3.60; MS (m/z): 308 (M+H)$^+$.

EXAMPLE 26(175)

N-{3-[(4-chlorobenzyl)oxy]benzyl}-β-alanine trifluoroacetate

HPLC retention time (minute): 3.31; MS (m/z): 322, 320 (M+H)$^+$.

EXAMPLE 26(176)

N-{3-[2-(4-tert-butylphenyl)ethoxy]benzyl}-β-alanine trifluoroacetate

HPLC retention time (minute): 3.58; MS (m/z): 3.56 (M+H)$^+$.

EXAMPLE 26(177)

N-{3-[2-(2-naphthyl)ethoxy]benzyl}-β-alanine trifluoroacetate

HPLC retention time (minute): 3.42; MS (m/z): 350 (M+H)$^+$.

EXAMPLE 26(178)

N-{3-[2-(4-methylphenyl)ethoxy]benzyl)}-β-alanine trifluoroacetate

HPLC retention time (minute): 3.34; MS (m/z): 314 (M+H)$^+$.

EXAMPLE 26(179)

N-[3-(nonyloxy)benzyl]-β-alanine trifluoroacetate

HPLC retention time (minute): 3.71; MS (m/z): 322 (M+H)$^+$.

EXAMPLE 26(180)

N-{3-[2-(3-methylphenyl)ethoxy]benzyl}-β-alanine trifluoroacetate

HPLC retention time (minute): 3.34; MS (m/z): 314 (M+H)$^+$.

EXAMPLE 26(181)

N-[3-(decyloxy)benzyl]-β-alanine trifluoroacetate

HPLC retention time (minute): 3.80; MS (m/z): 336 (M+H)$^+$.

EXAMPLE 26(182)

N-{3-[2-(2-methylphenyl)ethoxy]benzyl}-β-alanine trifluoroacetate

HPLC retention time (minute): 3.33; MS (m/z): 314 (M+H)$^+$.

EXAMPLE 26(183)

N-[3-(3-{2-[4-(benzyloxy)phenyl]ethoxy}phenyl)propyl]-β-alanine trifluoroacetate HPLC retention time (minute): 3.64; MS (m/z): 434 (M+H)$^+$.

EXAMPLE 26(184)

N-{3-[3-(2-phenoxyethoxy)phenyl]propyl}-β-alanine trifluoroacetate

HPLC retention time (minute): 3.33; MS (m/z): 344 (M+H)$^+$.

EXAMPLE 26(185)

N-{3-[3-(3-phenylpropoxy)phenyl]propyl)}-β-alanine trifluoroacetate

HPLC retention time (minute): 3.45; MS (m/z): 342 (M+H)$^+$.

EXAMPLE 26(186)

N-{3-[3-(4-phenylbutoxy)phenyl]propyl}-β-alanine trifluoroacetate

HPLC retention time (minute): 3.53; MS (m/z): 356 (M+H)$^+$.

EXAMPLE 26(187)

N-(3-{3-[(5-phenylpentyl)oxy]phenyl}propyl)-β-alanine trifluoroacetate

HPLC retention time (minute): 3.64; MS (m/z): 370 (M+H)$^+$.

EXAMPLE 26(188)

N-(3-{3-[(6-phenylhexyl)oxy]phenyl}propyl)-β-alanine trifluoroacetate

HPLC retention time (minute): 3.73; MS (m/z): 384 (M+H)$^+$.

EXAMPLE 26(189)

N-(3-{3-[3-(benzyloxy)propoxy]phenyl}propyl)-β-alanine trifluoroacetate

HPLC retention time (minute): 3.40; MS (m/z): 372 (M+H)$^+$.

EXAMPLE 26(190)

N-(3-{3-[(7-phenylheptyl)oxy]phenyl}propyl)-β-alanine trifluoroacetate

HPLC retention time (minute): 3.82; MS (m/z): 398 (M+H)$^+$.

EXAMPLE 26(191)

N-(3-{3-[(9-phenylnonyl)oxy]phenyl}propyl)-β-alanine trifluoroacetate

HPLC retention time (minute): 4.00; MS (m/z): 426 (M+H)$^+$.

EXAMPLE 26(192)

N-(3-{3-[(8-phenyloctyl)oxy]phenyl}propyl)-β-alanine trifluoroacetate

HPLC retention time (minute): 3.89; MS (m/z): 412 (M+H)$^+$.

EXAMPLE 26(193)

N-{3-[3-(2-cyclopentylethoxy)phenyl]propyl}-β-alanine trifluoroacetate

HPLC retention time (minute): 3.51; MS (m/z): 320 (M+H)$^+$.

EXAMPLE 26(194)

N-[3-(3-{[5-(benzyloxy)pentyl]oxy}phenyl)propyl]-β-alanine trifluoroacetate

HPLC retention time (minute): 3.51; MS (m/z): 400 (M+H)$^+$.

EXAMPLE 26(195)

N-(3-{3-[4-(benzyloxy)butoxy]phenyl}propyl)-β-alanine trifluoroacetate

HPLC retention time (minute): 3.45; MS (m/z): 386 (M+H)$^+$.

EXAMPLE 26(196)

N-(3-{3-[(3-phenoxybenzyl)oxy]phenyl}propyl)-β-alanine trifluoroacetate

HPLC retention time (minute): 3.55; MS (m/z): 406 (M+H)$^+$.

EXAMPLE 26(197)

N-{3-[3-(2-cyclohexylethoxy)phenyl]propyl}-β-alanine trifluoroacetate

HPLC retention time (minute): 3.60; MS (m/z): 334 (M+H)$^+$.

EXAMPLE 26(198)

N-[3-(3-butoxyphenyl)propyl]-β-alanine trifluoroacetate

HPLC retention time (minute): 3.29; MS (m/z): 280 (M+H)$^+$.

Example 26(199)

N-{3-[3-(cyclopentylmethoxy)phenyl]propyl}-β-alanine trifluoroacetate

HPLC retention time (minute): 3.42; MS (m/z): 306 (M+H)$^+$.

EXAMPLE 26(200)

N-{3-[3-(benzyloxy)phenyl]propyl}-β-alanine trifluoroacetate

HPLC retention time (minute): 3.29; MS (m/z): 314 (M+H)$^+$.

EXAMPLE 26(201)

N-{3-[3-(2-phenylethoxy)phenyl]propyl}-β-alanine trifluoroacetate

HPLC retention time (minute): 3.38; MS (m/z): 328 (M+H)$^+$.

EXAMPLE 26(202)

N-[3-(3-isobutoxyphenyl)propyl]-β-alanine trifluoroacetate

HPLC retention time (minute): 3.29; MS (m/z): 280 (M+H)$^+$.

EXAMPLE 26(203)

N-(3-{3-[(4-methylpentyl)oxy]phenyl}propyl)-β-alanine trifluoroacetate

HPLC retention time (minute): 3.49; MS (m/z): 308 (M+H)$^+$.

EXAMPLE 26(204)

N-{3-[3-(3,3-dimethylbutoxy)phenyl]propyl}-β-alanine trifluoroacetate

HPLC retention time (minute): 3.45; MS (m/z): 308 (M+H)$^+$.

EXAMPLE 26(205)

N-(3-{3-[(2-propylpentyl)oxy]phenyl}propyl)-β-alanine trifluoroacetate

HPLC retention time (minute): 3.69; MS (m/z): 336 (M+H)$^+$.

EXAMPLE 26(206)

N-{3-[3-(3-cyclohexylpropoxy)phenyl]propyl}-β-alanine trifluoroacetate

HPLC retention time (minute): 3.71; MS (m/z): 348 (M+H)$^+$.

EXAMPLE 26(207)

N-{3-[3-(pentyloxy)phenyl]propyl}-β-alanine trifluoroacetate

HPLC retention time (minute): 3.42; MS (m/z): 294 (M+H)$^+$.

EXAMPLE 26(208)

N-{3-[3-(hexyloxy)phenyl]propyl}-β-alanine trifluoroacetate

HPLC retention time (minute): 3.51; MS (m/z): 308 (M+H)$^+$.

EXAMPLE 26(209)

N-{3-[3-(heptyloxy)phenyl]propyl}-β-alanine trifluoroacetate

HPLC retention time (minute): 3.60; MS (m/z): 322 (M+H)$^+$.

EXAMPLE 26(210)

N-{3-[3-(octyloxy)phenyl]propyl}-β-alanine trifluoroacetate

HPLC retention time (minute): 3.71; MS (m/z): 336 (M+H)$^+$.

EXAMPLE 26(211)

N-(3-{3-[(4-chlorobenzyl)oxy]phenyl}propyl)-β-alanine trifluoroacetate

HPLC retention time (minute): 3.42; MS (m/z): 350, 348 (M+H)$^+$.

EXAMPLE 26(212)

N-(3-{3-[2-(4-tert-butylphenyl)ethoxy]phenyl}propyl)-β-alanine trifluoroacetate

HPLC retention time (minute): 3.67; MS (m/z): 384 (M+H)$^+$.

EXAMPLE 26(213)

N-(3-{3-[2-(2-naphthyl)ethoxy]phenyl}propyl)-β-alanine trifluoroacetate

HPLC retention time (minute): 3.53; MS (m/z): 378 (M+H)$^+$.

EXAMPLE 26(214)

N-(3-{3-[2-(4-methylphenyl)ethoxy]phenyl}propyl)-β-alanine trifluoroacetate

HPLC retention time (minute): 3.45; MS (m/z): 342 (M+H)$^+$.

EXAMPLE 26(215)

N-{3-[3-(nonyloxy)phenyl]propyl}-β-alanine trifluoroacetate

HPLC retention time (minute): 3.84; MS (m/z): 350 (M+H)$^+$.

EXAMPLE 26(216)

N-(3-{3-[2-(3-methylphenyl)ethoxy]phenyl}propyl)-β-alanine trifluoroacetate

HPLC retention time (minute): 3.45; MS (m/z): 342 (M+H)$^+$.

EXAMPLE 26(217)

N-{3-[3-(decyloxy)phenyl]propyl}-β-alanine trifluoroacetate

HPLC retention time (minute): 3.93; MS (m/z): 364 (M+H)$^+$.

EXAMPLE 26(218)

N-(3-{3-[2-(2-methylphenyl)ethoxy]phenyl}propyl)-β-alanine trifluoroacetate

HPLC retention time (minute): 3.44; MS (m/z): 342 (M+H)$^+$.

EXAMPLE 26(219)

N-(3-{4-[3-(4-fluorophenyl)propoxy]phenyl}propyl)-β-alanine trifluoroacetate

HPLC retention time (minute): 3.49; MS (m/z): 360 (M+H)$^+$.

EXAMPLE 26(220)

N-(3-{4-[3-(4-bromophenyl)propoxy]phenyl}propyl)-β-alanine trifluoroacetate

HPLC retention time (minute): 3.60; MS (m/z): 422, 420 (M+H)$^+$.

EXAMPLE 26(221)

N-[3-(4-{3-[4-(trifluoromethyl)phenyl]propoxy}phenyl)propyl]-β-alanine trifluoroacetate HPLC retention time (minute): 3.62; MS (m/z): 410 (M+H)$^+$.

EXAMPLE 26(222)

N-(3-{4-[3-(3-methylphenyl)propoxy]phenyl}propyl)-β-alanine trifluoroacetate

HPLC retention time (minute): 3.55; MS (m/z): 356 (M+H)$^+$.

Example 26(223)

N-(3-{4-[3-(2-chlorophenyl)propoxy]phenyl}propyl)-β-alanine trifluoroacetate

HPLC retention time (minute): 3.55; MS (m/z): 378, 376 (M+H)$^+$.

EXAMPLE 26(224)

N-(3-{4-[3-(2,6-dichlorophenyl)propoxy]phenyl}propyl)-β-alanine trifluoroacetate HPLC retention time (minute): 3.64; MS (m/z): 412, 410 (M+H)$^+$.

EXAMPLE 26(225)

N-(3-{4-[3-(4-chlorophenyl)propoxy]phenyl}propyl)-β-alanine trifluoroacetate

HPLC retention time (minute): 3.58; MS (m/z): 378, 376 (M+H)$^+$.

EXAMPLE 26(226)

N-(3-{4-[3-(2-methylphenyl)propoxy]phenyl}propyl)-β-alanine trifluoroacetate

HPLC retention time (minute): 3.49; MS (m/z): 356 (M+H)$^+$.

EXAMPLE 26(227)

N-(3-{4-[3-(3-chlorophenyl)propoxy]phenyl}propyl)-β-alanine trifluoroacetate

HPLC retention time (minute): 3.56; MS (m/z): 378, 376 (M+H)$^+$.

EXAMPLE 26(228)

N-(3-{4-[3-(4-methoxyphenyl)propoxy]phenyl}propyl)-β-alanine trifluoroacetate

HPLC retention time (minute): 3.44; MS (m/z): 372 (M+H)$^+$.

EXAMPLE 26(229)

N-(3-{4-[3-(2-bromophenyl)propoxy]phenyl}propyl)-β-alanine trifluoroacetate

HPLC retention time (minute): 3.58; MS (m/z): 422, 420 (M+H)$^+$.

EXAMPLE 26(230)

N-(3-{4-[3-(3-nitrophenyl)propoxy]phenyl}propyl)-β-alanine trifluoroacetate

HPLC retention time (minute): 3.44; MS (m/z): 387 (M+H)$^+$.

EXAMPLE 26(231)

N-(3-{4-[3-(3-fluorophenyl)propoxy]phenyl}propyl)-β-alanine trifluoroacetate

HPLC retention time (minute): 3.49; MS (m/z): 360 (M+H)$^+$.

EXAMPLE 26(232)

N-(3-{4-[3-(3,4-dimethoxyphenyl)propoxy]phenyl}propyl)-β-alanine trifluoroacetate HPLC retention time (minute): 3.34; MS (m/z): 402 (M+H)$^+$.

EXAMPLE 26(233)

N-(3-{4-[3-(3-phenoxyphenyl)propoxy]phenyl}propyl)-β-alanine trifluoroacetate

HPLC retention time (minute): 3.71; MS (m/z): 434 (M+H)$^+$.

EXAMPLE 26(234)

N-(3-{4-[3-(3,4-difluorophenyl)propoxy]phenyl}propyl)-β-alanine trifluoroacetate HPLC retention time (minute): 3.53; MS (m/z): 378 (M+H)$^+$.

EXAMPLE 26(235)

N-(3-{4-[3-(3,4,5-trimethoxyphenyl)propoxy]phenyl}propyl)-β-alanine trifluoroacetate HPLC retention time (minute): 3.31; MS (m/z): 432 (M+H)$^+$.

EXAMPLE 26(236)

N-[3-(4-{3-[3-(trifluoromethoxy)phenyl]propoxy}phenyl)propyl]-β-alanine trifluoroacetate HPLC retention time (minute): 3.64; MS (m/z): 426 (M+H)$^+$.

EXAMPLE 26(237)

N-[3-(4-{3-[2,5-bis(trifluoromethyl)phenyl]propoxy}phenyl)propyl]-β-alanine trifluoroacetate HPLC retention time (minute): 3.69; MS (m/z): 478 (M+H)$^+$.

EXAMPLE 26(238)

N-(3-{4-[3-(3-bromophenyl)propoxy]phenyl}propyl)-β-alanine trifluoroacetate

HPLC retention time (minute): 3.60; MS (m/z): 422, 420 (M+H)$^+$.

EXAMPLE 26(239)

N-[3-(4-{3-[3,5-bis(trifluoromethyl)phenyl]propoxy}phenyl)propyl]-β-alanine trifluoroacetate HPLC retention time (minute): 3.75; MS (m/z): 478 (M+H)$^+$.

EXAMPLE 26(240)

N-[3-(4-{3-[3-(trifluoromethyl)phenyl]propoxy}phenyl)propyl]-β-alanine trifluoroacetate HPLC retention time (minute): 3.60; MS (m/z): 410 (M+H)$^+$.

EXAMPLE 26(241)

N-{3-[4-(3-phenylbutoxy)phenyl]propyl}-β-alanine trifluoroacetate

HPLC retention time (minute): 3.53; MS (m/z): 356 (M+H)$^+$.

EXAMPLE 26(242)

N-{3-[4-(bicyclo[4.2.0]octa-1,3,5-trien-7-ylmethoxy)phenyl]propyl}-β-alanine trifluoroacetate HPLC retention time (minute): 3.44; MS (m/z): 340 (M+H)$^+$.

EXAMPLE 26(243)

N-{3-[4-(2-methyl-3-phenylpropoxy)phenyl]propyl}-β-alanine trifluoroacetate

HPLC retention time (minute): 3.55; MS (m/z): 356 (M+H)$^+$.

EXAMPLE 26(244)

N-{3-[4-(3,3-diphenylpropoxy)phenyl]propyl}-β-alanine trifluoroacetate

HPLC retention time (minute): 3.62; MS (m/z): 418 (M+H)$^+$.

EXAMPLE 27

N-{3-[4-(4-phenylbutoxy)phenyl]propyl}-β-alanine hydrochloride

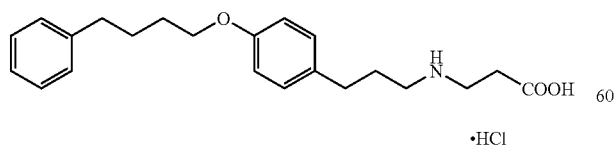

·HCl

Step A:

To a suspension of chlorotrityl resin (manufactured by Argonaut Technology; Cat No. 800380) (1.00 mmol/g, 1.0 g, 1.0 mmol) in dichloromethane (5 mL), a solution of the compound (323 mg) prepared in Example 24 in a mixed solvent of N,N-diisopropylethylamine (0.70 mL) and dichloromethane (5 mL) was dropped at 0° C. After washing with dichloromethane (2 mL), the mixture was shaken at room temperature for 5 hours. Then, the resin was taken up by filtration and washed successively with a mixed solvent (dichloromethane:methanol:diisopropylethylamine=51:6:3) 3 times, dichloromethane 3 times, N,N-dimethylformamide 2 times and dichloromethane 2 times and dried to give a phenol resin (1.195 g).

Step B:

To the phenol resin (100 mg), 4-phenylbutan-1-ol (0.42 mmol) was added at room temperature, followed by the addition of dry tetrahydrofuran (0.4 mL) and dichloromethane (0.4 mL). At room temperature, tri-n-butylphosphine (0.42 mmol) was added dropwise thereto and further 1,1'-azobis(N,N-dimethylformamide) (0.42 mmol) was added. The mixture was shaken at room temperature for 5 hours. The resin was taken up by filtration, washed with a mixed solvent (dichloromethane:tetrahydrofuran=1:1) 4 times and dichloromethane 2 times and then dried to give a phenyl ether resin (about 100 mg).

Step C:

To the phenyl ether resin (about 100 mg), acetic acid (0.2 mL), trifluoroethanol (0.2 mL) and dichloromethane (0.6 mL) were added at room temperature and the mixture was shaken at room temperature for 3 hours. The resin was taken up by filtration and washed with a mixed solvent (acetic acid:trifluoroethanol:dichloromethane=1:1:3) 2 times and dichloromethane 4 times. The filtrate was concentrated and the residue was purified by silica gel column chromatography (hexane:ethyl acetate=5:1 to ethyl acetate) to thereby give N-(tert-butoxycarbonyl)-N-{3-[4-(4-phenylbutoxy)phenyl]propyl}-β-alanine (2 mg; Boc compound).

Step D:

To the Boc compound, 4 N hydrogen chloride-ethyl acetate solution (1 mL) was added at room temperature, followed by stirring for 1 hour. The reaction mixture was concentrated to give the title compound (2 mg) having the following physical properties.

TLC: Rf 0.20 (chloroform:methanol:aqueous ammonia=80:20:4);

$^1$H-NMR (CD$_3$OD): δ 1.76 (m, 4H), 1.96 (m, 2H), 2.68 (m, 6H), 3.01 (m, 2H), 3.24 (t, 2H), 3.94 (m, 2H), 6.83 (d, 2H), 7.17 (m, 7H).

EXAMPLES 27(1) to 27(9)

The procedure of Example 27 was similarly carried out, except for using a corresponding compound as a substitute for 4-phenylbutan-1-ol to thereby give the following compounds. In the case of the compound of Example 27(9), the step D was omitted.

EXAMPLE 27(1)

N-(3-{4-[(6-phenylhexyl)oxy]phenyl}propyl)-β-alanine hydrochloride

TLC: Rf 0.29 (chloroform:methanol:aqueous ammonia=80:20:4);
$^1$H-NMR (CD$_3$OD): δ 1.42 (m, 4H), 1.64 (m, 2H), 1.74 (m, 2H), 1.96 (m, 2H), 2.66 (m, 6H), 3.01 (m, 2H), 3.24 (t, 2H), 3.91 (t, 2H), 6.83 (d, 2H), 7.13 (m, 5H), 7.22 (m, 2H).

EXAMPLE 27(2)

N-(3-{4-[(7-phenylheptyl)oxy]phenyl}propyl)-β-alanine hydrochloride

TLC: Rf 0.31 (chloroform:methanol:aqueous ammonia=80:20:4);
$^1$H-NMR (CD$_3$OD): δ 1.38 (m, 6H), 1.62 (m, 2H), 1.72 ((m, 2H), 1.96 (m, 2H), 2.66 (m, 6H), 3.01 (m, 2H), 3.23 (t, 2H), 3.92 (t, 2H), 6.83 (d, 2H), 7.12 (m, 5H), 7.23 (m, 2H).

EXAMPLE 27(3)

N-[3-(4-butoxyphenyl)propyl]-β-alanine hydrochloride

TLC: Rf 0.21 (chloroform:methanol:aqueous ammonia=80:20:4);
$^1$H-NMR (CD$_3$OD): δ 0.97 (t, 3H), 1.47 (m, 2H), 1.73 (m, 2H), 1.96 (m, 2H), 2.67 (m, 4H), 3.01 (m, 2H), 3.23 (t, 2H), 3.93 (t, 2H), 6.84 (d, 2H), 7.12 (d, 2H).

EXAMPLE 27(4)

N-{3-[4-(pentyloxy)phenyl]propyl}-β-alanine hydrochloride

TLC: Rf 0.24 (chloroform:methanol:aqueous ammonia=80:20:4);
$^1$H-NMR (CD$_3$OD): δ 0.94 (t, 3H), 1.41 (m, 4H), 1.72 (m, 2H), 1.96 (m, 2H), 2.65 (t, 2H), 2.71 (t, 2H), 3.01 (m, 2H), 3.24 (t, 2H), 3.92 (t, 2H), 6.84 (d, 2H), 7.12 (d, 2H).

EXAMPLE 27(5)

N-{3-[4-(hexyloxy)phenyl]propyl}-β-alanine hydrochloride

TLC: Rf 0.27 (chloroform:methanol:aqueous ammonia=80:20:4);
$^1$H-NMR (CD$_3$OD): δ 0.91 (m, 3H), 1.35 (m, 4H), 1.48 (m, 2H), 1.74 (m, 2H), 1.96 (m, 2H), 2.65 (t, 2H), 2.71 (t, 2H), 3.01 (m, 2H), 3.24 (t, 2H), 3.93 (t, 2H), 6.84 (d, 2H), 7.12 (d, 2H).

EXAMPLE 27(6)

N-{3-[4-(heptyloxy)phenyl]propyl}-β-alanine hydrochloride

TLC: Rf 0.29 (chloroform:methanol:aqueous ammonia=80:20:4);
$^1$H-NMR (CD$_3$OD): δ 0.90 (m, 3H), 1.32 (m, 8H), 1.72 (m, 2H), 1.96 (m, 2H), 2.65 (t, 2H), 2.70 (t, 2H), 3.01 (m, 2H), 3.23 (t, 2H), 3.92 (t, 2H), 6.84 (d, 2H), 7.12 (d, 2H).

EXAMPLE 27(7)

N-{3-[4-(octyloxy)phenyl]propyl}-β-alanine hydrochloride

TLC: Rf 0.30 (chloroform:methanol:aqueous ammonia=80:20:4);
$^1$H-NMR (CD$_3$OD): δ 0.90 (m, 3H), 1.31 (m, 10H), 1.74 (m, 2H), 1.96 (m, 2H), 2.65 (t, 2H), 2.71 (t, 2H), 3.01 (m, 2H), 3.24 (t, 2H), 3.92 (t, 2H), 6.84 (d, 2H), 7.12 (d, 2H).

EXAMPLE 27(8)

N-{3-[4-(nonyloxy)phenyl]propyl}-β-alanine hydrochloride

TLC: Rf 0.31 (chloroform:methanol:aqueous ammonia=80:20:4);
$^1$H-NMR (CD$_3$OD): δ 0.89 (m, 3H), 1.29 (m, 12H); 1.73 (m, 2H), 1.96 (m, 2H), 2.65 (t, 2H), 2.71 (t, 2H), 3.01 (m, 2H), 3.24 (t, 2H), 3.92 (t, 2H), 6.84 (d, 2H), 7.12 (d, 2H).

EXAMPLE 27(9)

N-(tert-butoxycarbonyl)-N-(3-{4-[(5-phenylpentyl)oxy]phenyl}propyl)-β-alanine

TLC: Rf 0.40 (chloroform:methanol=10:1);
$^1$H-NMR (CDCl$_3$): δ 1.45 (s, 9H), 1.67 (m, 8H), 2.53 (t, 2H), 2.64 (m, 4H), 3.23 (t, 2H), 3.47 (t, 2H), 3.92 (t, 2H), 6.81 (d, 2H), 7.07 (d, 2H), 7.18 (m, 2H), 7.27 (m, 3H).

EXAMPLE 28

N-{3-[4-(3-phenylpropoxy)phenyl]propyl}-N-(3-phenylpropyl)-β-alanine trifluoroacetate

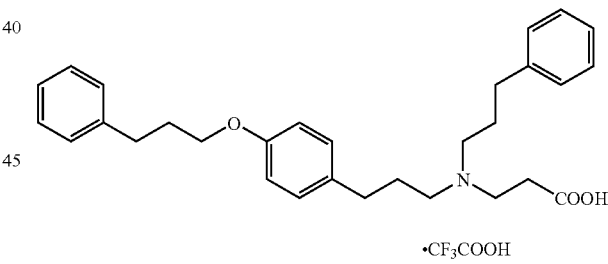

To a solution of tert-butyl N{3-[4-(4-phenylbutoxy)phenyl]propyl}-β-alaninate (8.0 mg) in dichloroethane (0.2 mL), 3-phenylpropanal (0.008 mL) and sodium triacetoxyborohydride (21 mg) were added and the mixture was shaken at room temperature for 17 hours. Then, the reaction mixture was diluted by adding methanol (1.0 mL). After adding lanthanum toluenesulfonic acid resin (manufactured by MIMOTOPE; Cat No. MIL1025) (2 pins, 0.3 mmol), the mixture was allowed to stand for 1 hour. Then, the resin was taken out from the reaction mixture, washed with dichloromethane and methanol and then dipped in a 5% triethylamine-methanol solution (1.0 mL×2) for 30 minutes. The obtained solutions were recovered, combined and then concentrated. To the residue, trifluoroacetic acid (1.0 mL) and dichloromethane (1.0 mL) were added, followed by stirring at room temperature for 16 hours and concentrated to thereby give the title compound (10 mg) having the following physical properties.

TLC: Rf 0.81 (ethyl acetate:acetic acid:water=3:1:1);

$^1$H-NMR (CD$_3$OD): δ 1.83-2.00 (m, 4H), 1.99-2.13 (m, 2H), 2.57-2.69 (m, 4H), 2.70-2.84 (m, 4H), 3.04-3.20 (m, 4H), 3.40 (t, 2H), 3.91 (t, 2H), 6.83 (d, 1H), 7.11 (d, 2H), 7.14-7.33 (m, 10H).

EXAMPLE 29

3-({(2E)-3-[4-(3-phenylpropyl)phenyl]-2-butenyl}amino)propanoic acid hydrochloride

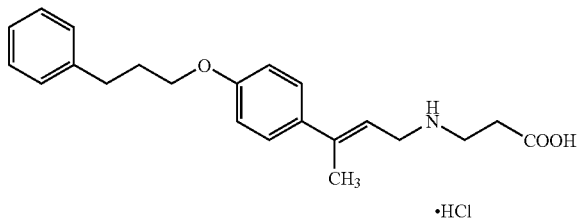

To a suspension of β-alanine (433 mg) in methanol (30 ml), sodium hydroxide (204 mg) was added. Then, trimethoxymethane (532 μl) was added to the mixture at 0° C. Further, a solution of (2E)-3-[4-(3-phenylpropoxy)phenyl]but-2-enal (1.43 g) in a mixture of methanol (30 ml) and tetrahydrofuran (10 ml) was added. The reaction mixture was stirred at 0° C. for 30 minutes. To the mixture, sodium borohydride (221 mg) was added at 0° C. The reaction mixture was stirred at 0° C. for 30 minutes. After adding 2 N hydrochloric acid (5.5 ml), the reaction mixture was concentrated. To the residue thus obtained, a mixed solvent of chloroform:methanol:aqueous ammonia=80:10:1 was added, followed by filtration. To the precipitate thus obtained, water was added and the mixture was centrifuged to give a precipitate. The obtained residue was purified by silica gel column chromatography (chloroform:methanol:aqueous ammonia=80:20:4). To a suspension of the purified product in dioxane (100 ml) and water (15 ml), a 4 mol/l hydrogen chloride-dioxane solution (0.9 ml) was added at 0° C. The reaction mixture was concentrated and the residue was washed with diethyl ether and dried to give the title compound (1.16 g) having the following physical properties.

Melting point: 181-186° C.;

TLC: Rf 0.19 (chloroform:methanol:aqueous ammonia=80:20:4);

$^1$H-NMR (CD$_3$OD): δ 7.39 (d, J=9.00 Hz, 2H), 7.11-7.28 (m, 5H), 6.88 (d, J=9.00 Hz, 2H), 5.77 (tq, J=7.50, 1.50 Hz, 1H), 3.96 (t, J=6.50 Hz, 2H), 3.88 (d, J=7.50 Hz, 2H), 3.30-3.34 (m, 2H), 2.74-2.83 (m, 4H), 2.15 (d, J=1.50 Hz, 3H), 2.00-2.11 (m, 2H).

EXAMPLES 29(1) to 29(4)

The procedure of Example 29 was similarly carried out, except for using a corresponding aldehyde compound as a substitute for (2E)-3-[4-(3-phenylpropoxy)phenyl]but-2-enal and the corresponding amine compound to thereby give invention compounds as shown below. In the case of the compound of Example 29(4), the conversion into hydrochloride was omitted.

EXAMPLE 29(1)

3-({(2E)-3-[4-(3-cyclohexylpropoxy)-2-methylphenyl]-2-propenyl}amino)propanoic acid hydrochloride TLC: Rf 0.22 (chloroform:methanol:aqueous ammonia=80:20:4);

$^1$H-NMR (CD$_3$OD): δ 0.84-1.01 (m, 2H) 1.13-1.40 (m, 6H) 1.61-1.83 (m, 7H) 2.34 (s, 3H) 2.77 (t, J=6.50 Hz, 2H) 3.22-3.29 (m, 2H) 3.82 (d, J=7.00 Hz, 2H) 3.93 (t, J=6.50 Hz, 2H) 5.95-6.09 (m, 1H) 6.68-6.76 (m, 2H) 7.06 (d, J=15.50 Hz, 1H) 7.43 (d, J=9.50 Hz, 1H).

EXAMPLE 29(2)

3-({[1-methyl-6-(4-phenylbutoxy)-3,4-dihydro-2-naphthalenyl]methyl}amino)propanoic acid hydrochloride Melting point: 162.5-163.3° C.;

TLC: Rf 0.16 (chloroform:methanol:aqueous ammonia=80:20:4);

$^1$H-NMR (CD$_3$OD): δ 7.09-7.33 (m, 6H), 6.66-6.80 (m, 2H), 3.95-4.01 (m, 2H), 3.93 (s, 2H), 3.25-3.34 (m, 2H), 2.71-2.83 (m, 4H), 2.61-2.71 (m, 2H), 2.26-2.38 (m, 2H), 2.15 (s, 3H), 1.72-1.83 (m, 4H).

EXAMPLE 29(3)

1-{[1-methyl-6-(4-phenylbutoxy)-3,4-dihydro-2-naphthalenyl]methyl}-3-azetidinecarboxylic acid hydrochloride TLC: Rf 0.14 (chloroform:methanol:aqueous ammonia=80:20:4);

$^1$H-NMR (CD$_3$OD): δ 7.03-7.39 (m, 6H), 6.64-6.82 (m, 2H), 4.20-4.48 (m, 2H), 4.16 (s, 2H), 3.92-4.06 (m, 2H), 3.57-3.82 (m, 1H), 3.24-3.36 (m, 2H), 2.61-2.79 (m, 4H), 2.17-2.29 (m, 5H), 1.72-1.83 (m, 4H);

Melting point: 121-122° C.

EXAMPLE 29(4)

N-{[1-(5-phenylpentyl)-1H-indol-5-yl]methyl}-β-alanine

TLC: Rf 0.23 (chloroform:methanol:aqueous ammonia=80:20:4);

$^1$H-NMR (CD$_3$OD): δ 7.66 (d, J=1.50 Hz, 1H), 7.46 (d, J=8.50 Hz, 1H), 7.16-7.26 (m, 4H), 7.06-7.14 (m, 3H), 6.46 (d, J=3.00 Hz, 1H), 4.25 (s, 2H), 4.18 (t, J=7.00 Hz, 2H), 3.15 (t, J=6.50 Hz, 2H), 2.53 (t, J=7.50 Hz, 2H), 2.48 (t, J=6.50 Hz, 2H), 1.78-1.90 (m, 2H), 1.54-1.66 (m, 2H), 1.23-1.36 (m, 2H).

EXAMPLE 30

3-[4-[4-(3-phenylpropoxy)phenyl]-3,6-dihydropyridin-1(2H)-yl]propanoic acid trifluoroacetate

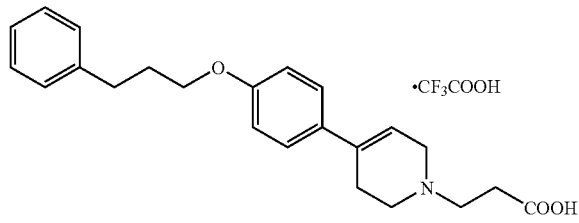

The procedures of Example 4 and Example 16 were followed in this order but using 4-[4-(3-phenylpropoxy)phenyl]-1,2,3,6-tetrahydropyridine as a substitute for 4-(3-aminopropyl)phenol to thereby give the title compound having the following physical properties.

TLC: Rf 0.24 (chloroform:methanol:aqueous ammonia=8:2:0.4);

$^1$H-NMR (CD$_3$OD): δ 7.40 (d, J=8.97 Hz, 2H), 7.10-7.30 (m, 5H), 6.90 (d, J=8.97 Hz, 2H), 5.92-6.09 (m, 1H), 3.96 (t, J=6.22 Hz, 2H), 3.89-4.00 (m, 2H), 3.52 (t, J=7.04 Hz, 2H), 3.47-3.68 (m, 2H), 2.88 (t, J=7.04 Hz, 2H), 2.83-2.92 (m, 2H), 2.79 (t, J=7.80 Hz, 2H), 1.97-2.14 (m, 2H).

EXAMPLES 31-01 to 31-94

The procedure of Example 29 was similarly carried out, except for using a corresponding amine compound as a substitute for β-alanine and a corresponding aldehyde compound as a substitute for (2E)-3-[4-(3-phenylpropoxy)phenyl]but-2-enal to thereby give an invention compound having the following physical properties.

EXAMPLE 31-01

3-({(2E)-3-[3-methyl-4-(3-phenylpropoxy)phenyl]-2-propenyl}amino)propanoic acid hydrochloride

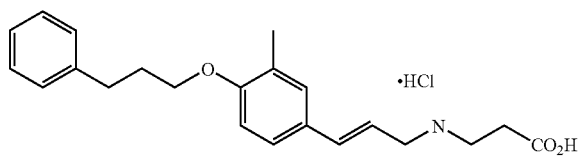

TLC: Rf 0.15 (chloroform:methanol:aqueous ammonia=80:20:4);

$^1$H-NMR (CD$_3$OD): δ 2.05-2.13 (m, 2H), 2.23 (s, 3H), 2.73-2.86 (m, 4H), 3.24-3.29 (m, 2H), 3.79 (d, J=7.50 Hz, 2H), 3.97 (t, J=6.00 Hz, 2H), 6.03-6.14 (m, 1H), 6.72-6.83 (m, 2H), 7.11-7.29 (m, 7H).

EXAMPLE 31-02

3-({(2E)-3-[3-methyl-4-(4-phenylbutoxy)phenyl]-2-propenyl}amino)propanoic acid hydrochloride TLC: Rf 0.16 (chloroform:methanol:aqueous ammonia=80:20:4);

$^1$H-NMR (CD$_3$OD): δ 1.78-1.86 (m, 4H), 2.19 (s, 3H), 2.64-2.79 (m, 4H), 3.23-3.28 (m, 2H), 3.78 (d, J=7.00 Hz, 2H), 3.96-4.03 (m, 2H), 6.03-6.14 (m, 1H), 6.76 (d, J=15.50 Hz, 1H), 6.83 (d, J=8.00 Hz, 1H), 7.09-7.28 (m, 7H).

EXAMPLE 31-03

3-[((2E)-3-{3-methyl-4-[(5-phenylpentyl)oxy]phenyl}-2-propenyl)amino]propanoic acid hydrochloride TLC: Rf 0.18 (chloroform:methanol:aqueous ammonia=80:20:4);

$^1$H-NMR (CD$_3$OD): δ 1.48-1.58 (m, 2H), 1.65-1.75 (m, 2H), 1.77-1.87 (m, 2H), 2.15 (s, 3H), 2.64 (t, J=7.50 Hz, 2H), 2.75 (t, J=6.50 Hz, 2H), 3.19-3.28 (m, 2H), 3.78 (d, J=7.50 Hz, 2H), 3.97 (t, J=6.00 Hz, 2H), 6.02-6.14 (m, 1H), 6.76 (d, J=16.00 Hz, 1H), 6.83 (d, J=8.00 Hz, 1H), 7.08-7.27 (m, 7H).

EXAMPLE 31-04

3-({(2E)-3-[4-(4-phenylbutoxy)phenyl]-2-butenyl}amino)propanoic acid hydrochloride TLC: Rf 0.20 (chloroform:methanol:aqueous ammonia=80:20:4);

$^1$H-NMR (CD$_3$OD): δ 1.76-1.82 (m, 4H), 2.14 (d, J=1.50 Hz, 3H), 2.64-2.71 (m, 2H), 2.76 (t, J=6.50 Hz, 2H), 3.30-3.35 (m, 2H), 3.87 (d, J=7.50 Hz, 2H), 3.96-4.01 (m, 2H), 5.75 (tq, J=7.50, 1.50 Hz, 1H), 6.88 (d, J=9.00 Hz, 2H), 7.09-7.28 (m, 5H), 7.38 (d, J=9.00 Hz, 2H).

EXAMPLE 31-05

3-[((2E)-3-{4-[(5-phenylpentyl)oxy]phenyl}-2-butenyl)amino]propanoic acid hydrochloride TLC: Rf 0.20 (chloroform:methanol:aqueous ammonia=80:20:4);

$^1$H-NMR (CD$_3$OD): δ 1.45-1.56 (m, 2H), 1.63-1.74 (m, 2H), 1.74-1.85 (m, 2H), 2.15 (d, J=1.50 Hz, 3H), 2.63 (t, J=7.50 Hz, 2H), 2.76 (t, J=6.50 Hz, 2H), 3.31-3.37 (m, 2H), 3.87 (d, J=7.50 Hz, 2H), 3.96 (t, J=6.50 Hz, 2H), 5.75 (tq, J=7.50, 1.50 Hz, 1H), 6.87 (d, J=9.00 Hz, 2H), 7.10-7.26 (m, 5H), 7.38 (d, J=9.00 Hz, 2H).

EXAMPLE 31-06

3-({[6-(4-phenylbutoxy)-3,4-dihydro-2-naphthalenyl]methyl}amino)propanoic acid hydrochloride TLC: Rf 0.19 (chloroform:methanol:aqueous ammonia=80:20:4);

¹H-NMR (CD₃OD): δ 1.75-1.82 (m, 4H) 2.34 (t, J=8.00 Hz, 2H) 2.63-2.71 (m, 2H) 2.77 (t, J=6.50 Hz, 2H) 2.85 (t, J=8.00 Hz, 2H) 3.23-3.28 (m, 2H) 3.79 (s, 2H) 3.97 (t, J=6.00 Hz, 2H) 6.62 (s, 1H) 6.68-6.73 (m, 2H) 7.00 (d, J=7.50 Hz, 1H) 7.11-7.28 (m, 5H).

EXAMPLE 31-07

3-({[6-(4-phenylbutoxy)-3,4-dihydro-2-naphthalenyl]methyl}amino)butanoic acid hydrochloride TLC: Rf 0.32 (chloroform:methanol:aqueous ammonia=80:20:4);

¹H-NMR (CD₃OD): δ 1.42 (d, J=7.00 Hz, 3H) 1.75-1.81 (m, 4H) 2.29-2.44 (m, 2H) 2.64-2.71 (m, 2H) 2.73-2.78 (m, 2H) 2.86 (t, J=8.00 Hz, 2H) 3.61-3.72 (m, 1H) 3.82 (s, 2H) 3.97 (t, J=6.00 Hz, 2H) 6.64 (s, 1H) 6.68-6.73 (m, 2H) 7.00 (d, J=7.50 Hz, 1H) 7.11-7.28 (m, 5H).

EXAMPLE 31-08

2-methyl-3-({[6-(4-phenylbutoxy)-3,4-dihydro-2-naphthalenyl]methyl}amino)propanoic acid hydrochloride TLC: Rf 0.29 (chloroform:methanol:aqueous ammonia=80:20:4);

¹H-NMR (CD₃OD): δ 1.30 (d, J=7.00 Hz, 3H) 1.73-1.82 (m, 4H) 2.33 (t, J=7.50 Hz, 2H) 2.63-2.71 (m, 2H) 2.81-2.95 (m, 3H) 3.06 (dd, J=13.00, 4.50 Hz, 1H) 3.21-3.29 (m, 1H) 3.79 (s, 2H) 3.97 (t, J=6.00 Hz, 2H) 6.62 (s, 1H) 6.68-6.74 (m, 2H) 7.01 (d, J=8.00 Hz, 1H) 7.10-7.28 (m, 5H).

EXAMPLE 31-09

2-fluoro-3-({[6-(4-phenylbutoxy)-3,4-dihydro-2-naphthalenyl]methyl}amino)propanoic acid hydrochloride TLC: Rf 0.16 (chloroform:methanol:aqueous ammonia=80:20:4); ¹H-NMR (CD₃OD): δ 1.74-1.82 (m, 4H) 2.35 (t, J=8.00 Hz, 2H) 2.64-2.71 (m, 2H) 2.86 (t, J=8.00 Hz, 2H) 3.47-3.72 (m, 2H) 3.85 (s, 2H) 3.97 (t, J=6.00 Hz, 2H) 5.36 (ddd, J=48.50, 8.00, 3.50 Hz, 1H) 6.64 (s, 1H) 6.67-6.76 (m, 2H) 7.01 (d, J=8.00 Hz, 1H) 7.10-7.30 (m, 5H).

EXAMPLE 31-10

3-({(2E)-3-[2-methyl-4-(4-phenylbutoxy)phenyl]-2-propenyl}amino)propanoic acid hydrochloride TLC: Rf 0.22 (chloroform:methanol:aqueous ammonia=80:20:4);

¹H-NMR (CD₃OD): δ 1.72-1.83 (m, 4H) 2.34 (s, 3H) 2.64-2.71 (m, 2H) 2.77 (t, J=6.50 Hz, 2H) 3.23-3.29 (m, 2H) 3.82 (d, J=7.00 Hz, 2H) 3.96 (t, J=6.00 Hz, 2H) 5.96-6.08 (m, 1H) 6.70-6.75 (m, 2H) 7.06 (d, J=15.50 Hz, 1H) 7.09-7.28 (m, 5H) 7.42 (d, J=9.50 Hz, 1H).

EXAMPLE 31-11

3-({(2E)-3-[4-(4-cyclohexylbutoxy)-2-methylphenyl]-2-propenyl}amino)propanoic acid hydrochloride TLC: Rf 0.23 (chloroform:methanol:aqueous ammonia=80:20:4);

¹H-NMR (CD₃OD): δ 0.81-1.00 (m, 2H) 1.13-1.35 (m, 6H) 1.41-1.54 (m, 2H) 1.62-1.80 (m, 7H) 2.34 (s, 3H) 2.77 (t, J=6.50 Hz, 2H) 3.24-3.29 (m, 2H) 3.82 (d, J=7.50 Hz, 2H) 3.95 (t, J=6.50 Hz, 2H) 5.95-6.10 (m, 1H) 6.70-6.76 (m, 2H) 7.06 (d, J=15.50 Hz, 1H) 7.43 (d, J=9.00 Hz, 1H).

EXAMPLE 31-12

3-({(2E)-3-[4-(4-phenylbutoxy)phenyl]-2-propenyl}amino)propanoic acid hydrochloride TLC: Rf 0.29 (chloroform:methanol:aqueous ammonia=80:20:4);

¹H-NMR (CD₃OD): δ 7.39 (d, J=8.79 Hz, 2H) 7.09-7.30 (m, 5H) 6.89 (d, J=8.79 Hz, 2H) 6.80 (d, J=16.11 Hz, 1H) 6.10 (dt, J=16.11, 7.32 Hz, 1H) 3.92-4.04 (m, 2H) 3.79 (dd, J=7.32, 1.01 Hz, 2H) 3.24-3.29 (m, 2H) 2.75 (t, J=6.59 Hz, 2H) 2.60-2.71 (m, 2H) 1.71-1.86 (m, 4H).

EXAMPLE 31-13

3-[((2E)-3-{4-[3-(4-chlorophenyl)propoxy]phenyl}-2-propenyl)amino]propanoic acid hydrochloride TLC: Rf 0.28 (chloroform:methanol:aqueous ammonia=80:20:4);

¹H-NMR (CD₃OD): δ 7.40 (d, J=8.79 Hz, 2H) 7.25 (d, J=8.60 Hz, 2H) 7.19 (d, J=8.60 Hz, 2H) 6.89 (d, J=8.79 Hz, 2H) 6.81 (d, J=15.74 Hz, 1H) 6.11 (dt, J=15.74, 7.14 Hz, 1H) 3.96 (t, J=6.13 Hz, 2H) 3.79 (d, J=7.14 Hz, 2H) 3.20-3.29 (m, 2H) 2.69-2.84 (m, 4H) 1.98-2.11 (m, 2H).

EXAMPLE 31-14

3-[((2E)-3-{4-[(4-methylpentyl)oxy]phenyl}-2-propenyl)amino]propanoic acid hydrochloride TLC: Rf 0.27 (chloroform:methanol:aqueous ammonia=80:20:4);

¹H-NMR (CD₃OD): δ 7.40 (d, J=8.79 Hz, 2H) 6.89 (d, J=8.79 Hz, 2H) 6.81 (d, J=15.74 Hz, 1H) 6.11 (dt, J=15.74, 7.32 Hz, 1H) 3.96 (t, J=6.50 Hz, 2H) 3.80 (d, J=7.32 Hz, 2H) 3.22-3.29 (m, 2H) 2.75 (t, J=6.59 Hz, 2H) 1.70-1.84 (m, 2H) 1.51-1.68 (m, 1H) 1.28-1.43 (m, 2H) 0.93 (d, J=6.59 Hz, 6H).

EXAMPLE 31-15

3-[((2E)-3-{2-chloro-4-[(5-phenylpentyl)oxy]phenyl}-2-propenyl)amino]propanoic acid hydrochloride TLC: Rf 0.29 (chloroform:methanol:aqueous ammonia=80:20:4);

¹H-NMR (CD₃OD): δ 7.59 (d, J=8.79 Hz, 1H) 7.08-7.28 (m, 6H) 6.95 (d, J=2.56 Hz, 1H) 6.87 (dd, J=8.79, 2.56 Hz, 1H) 6.18 (dt, J=15.70, 7.16 Hz, 1H) 3.97 (t, J=6.41 Hz, 2H) 3.85 (dd, J=7.16, 1.01 Hz, 2H) 3.25-3.34 (m, 2H) 2.77 (t,

J=6.59 Hz, 2H) 2.63 (t, J=7.69 Hz, 2H) 1.74-1.87 (m, 2H) 1.61-1.74 (m, 2H) 1.41-1.57 (m, 2H).

EXAMPLE 31-16

3-({(2E)-3-[2-chloro-4-(4-phenylbutoxy)phenyl]-2-propenyl}amino)propanoic acid hydrochloride TLC: Rf 0.29 (chloroform:methanol:aqueous ammonia=80:20:4);
$^1$H-NMR (CD$_3$OD): δ 7.58 (d, J=8.79 Hz, 1H) 7.08-7.31 (m, 6H) 6.96 (d, J=2.56 Hz, 1H) 6.88 (dd, J=8.79, 2.56 Hz, 1H) 6.18 (dt, J=15.84, 7.19 Hz, 1H) 3.93-4.04 (m, 2H) 3.85 (dd, J=7.19, 1.10 Hz, 2H) 3.25-3.33 (m, 2H) 2.77 (t, J=6.59 Hz, 2H) 2.62-2.72 (m, 2H) 1.74-1.84 (m, 4H).

EXAMPLE 31-17

3-[((2E)-3-{2-chloro-4-[3-(4-chlorophenyl)propoxy]phenyl}-2-propenyl)amino]propanoic acid hydrochloride TLC: Rf 0.29 (chloroform:methanol:aqueous ammonia=80:20:4);
$^1$H-NMR (CD$_3$OD): δ 7.59 (d, J=8.79 Hz, 1H) 7.12-7.31 (m, 5H) 6.96 (d, J=2.56 Hz, 1H) 6.88 (dd, J=8.79, 2.56 Hz, 1H) 6.18 (dt, J=15.74, 7.32 Hz, 1H) 3.97 (t, J=6.22 Hz, 2H) 3.85 (dd, J=7.32, 1.10 Hz, 2H) 3.26-3.34 (m, 2H) 2.71-2.84 (m, 4H) 1.96-2.14(m, 2H);
Melting point: 119-124° C.

EXAMPLE 31-18

3-({[6-(3-phenylpropoxy)-2-naphthyl]methyl}amino)propanoic acid

TLC: Rf 0.13 (chloroform:methanol:aqueous ammonia=80:20:4);
$^1$H-NMR (CDCl$_3$+CD$_3$OD=5:1): δ 2.19 (m, 2H) 2.47 (t, J=6.00 Hz, 2H) 2.87 (m, 2H) 3.10 (t, J=6.00 Hz, 2H) 4.10 (t, J=6.50 Hz, 2H) 4.22 (s, 2H) 7.12 (d, J=2.00 Hz, 1H) 7.26 (m, 6H) 7.43 (dd, J=8.50, 2.00 Hz, 1H) 7.79 (m, 3H).

EXAMPLE 31-19

3-[((2E)-3-{4-[(4-tert-butylbenzyl)oxy]-2-chlorophenyl}-2-propenyl)amino]propanoic acid hydrochloride TLC: Rf 0.40 (n-butanol:acetic acid:water=20:4:1);
$^1$H-NMR (CD$_3$OD): δ 7.61 (d, J=8.78 Hz, 1H) 7.41 (d, J=8.70 Hz, 2H) 7.34 (d, J=8.70 Hz, 2H) 7.17 (d, J=15.92 Hz, 1H) 7.05 (d, J=2.56 Hz, 1H) 6.96 (dd, J=8.78, 2.56 Hz, 1H) 6.21 (dt, J=15.92, 7.25 Hz, 1H) 5.06 (s, 2H) 3.86 (dd, J=7.25, 0.82 Hz, 2H) 3.25-3.35 (m, 2H) 2.78 (t, J=6.68 Hz, 2H) 1.31 (s, 9H).

EXAMPLE 31-20

3-({(2E)-3-[4-(1,1'-biphenyl-4-ylmethoxy)-2-chlorophenyl]-2-propenyl}amino)propanoic acid hydrochloride TLC: Rf 0.41 (n-butanol:acetic acid:water=20:4:1);
$^1$H-NMR (CD$_3$OD): δ 7.57-7.67 (m, 5H) 7.50 (d, J=8.40 Hz, 2H) 7.39-7.46 (m, 2H) 7.29-7.37 (m, 1H) 7.19 (d, J=15.73 Hz, 1H) 7.10 (d, J=2.38 Hz, 1H) 7.00 (dd, J=8.78, 2.38 Hz, 1H) 6.19 (dt, J=15.73, 7.25 Hz, 1H) 5.16 (s, 2H) 3.85 (dd, J=7.25, 1.10 Hz, 2H) 3.26-3.36 (m, 2H) 2.76 (t, J=6.59 Hz, 2H).

EXAMPLE 31-21

3-[((2E)-3-{2-chloro-4-[3-(2-fluorophenyl)propoxy]phenyl}-2-propenyl)amino]propanoic acid hydrochloride TLC: Rf 0.39 (n-butanol:acetic acid:water=20:4:1);
$^1$H-NMR (CD$_3$OD): δ 7.61 (d, J=8.78 Hz, 1H) 7.12-7.30 (m, 3H) 6.96-7.13 (m, 2H) 6.95 (d, J=2.38 Hz, 1H) 6.88 (dd, J=8.60, 2.38 Hz, 1H) 6.21 (dt, J=15.74, 7.32 Hz, 1H) 3.99 (t, J=6.13 Hz, 2H) 3.86 (dd, J=7.32, 1.10 Hz, 2H) 3.27-3.36 (m, 2H) 2.75-2.88 (m, 4H)-2.00-2.13 (m, 2H).

EXAMPLE 31-22

1-{[6-(4-phenylbutoxy)-3,4-dihydro-2-naphthalenyl]methyl}-3-azetidinecarboxylic acid hydrochloride TLC: Rf 0.11 (chloroform:methanol:aqueous ammonia=80:20:4);
$^1$H-NMR (CD$_3$OD): δ 1.75-1.80 (m, 4H), 2.27 (t, J=8.00 Hz, 2H), 2.63-2.71 (m, 2H), 2.82 (t, J=8.00 Hz, 2H), 3.64-3.78 (m, 1H), 3.93-4.01 (m, 4H), 4.16-4.46 (m, 4H), 6.62 (s, 1H), 6.68-6.72 (m, 2H), 7.03 (d, J=9.00 Hz, 1H), 7.10-7.27 (m, 5H);
Melting point: 152-155° C.

EXAMPLE 31-23

3-({(2E)-3-[2-methoxy-4-(3-phenylpropoxy)phenyl]-2-propenyl}amino)propanoic acid hydrochloride TLC: Rf 0.27 (n-butanol:acetic acid:water=20:4:1);
$^1$H-NMR (CD$_3$OD): δ 7.36 (d, J=8.4 Hz, 1H), 7.11-7.30 (m, 5H), 7.03 (d, J=16.1 Hz, 1H), 6.35-6.62 (m, 2H), 6.05-6.26 (m, 1H), 3.89-4.06 (m, 2H), 3.64-3.89 (m, 5H), 3.15-3.37 (m, 2H), 2.65-2.89 (m, 4H), 1.94-2.16 (m, 2H).

EXAMPLE 31-24

3-({(2E)-3-[2-methoxy-4-(4-phenylbutoxy)phenyl]-2-propenyl}amino)propanoic acid hydrochloride TLC: Rf 0.28 (n-butanol:acetic acid:water=20:4:1);
$^1$H-NMR (CD$_3$OD): δ 7.36 (d, J=8.23 Hz, 2H) 7.09-7.30 (m, 5H) 7.02 (d, J=16.28 Hz, 1H) 3.88-4.07 (m, 2H) 3.62-3.88 (m, 5H) 3.16-3.40 (m, 2H) 2.46-2.85 (m, 4H) 1.71-1.87 (m, 4H).

EXAMPLE 31-25

3-[((2E)-3-{2-methoxy-4-[(5-phenylpentyl)oxy]phenyl}-2-propenyl)amino]propanoic acid hydrochloride TLC: Rf 0.30 (n-butanol:acetic acid:water=20:4:1);
$^1$H-NMR (CD$_3$OD): δ 7.36 (d, J=8.4 Hz, 1H), 7.09-7.29 (m, 5H), 7.02 (d, J=15.9 Hz, 1H), 6.41-6.58 (m, 2H), 6.04-6.30 (m, 1H), 3.98 (t, J=6.4 Hz, 2H), 3.67-3.89 (m, 5H), 3.05-3.43 (m, 2H), 2.74 (t, J=6.6 Hz, 2H), 2.54-2.71 (m, 2H), 1.76-1.88 (m, 2H), 1.60-1.76 (m, 2H), 1.42-1.59 (m, 2H).

EXAMPLE 31-26

3-{[(6-{3-[3,5-bis(trifluoromethyl)phenyl]propoxy}-2-naphthyl)methyl]amino}propanoic acid hydrochloride TLC: Rf 0.16 (chloroform:methanol:aceetic acid=9:1:0.5);
$^1$H-NMR (CD$_3$OD): δ 7.73-7.97 (m, 6H) 7.52 (dd, J=8.32, 1.56 Hz, 1H) 7.25 (d, J=2.47 Hz, 1H) 7.19 (dd, J=8.87, 2.47 Hz, 1H) 4.37 (s, 2H) 4.14 (t, J=5.95 Hz, 2H) 3.28-3.37 (m, 2H) 3.01-3.13 (m, 2H) 2.71-2.86 (m, 2H) 2.15-2.31 (m, 2H).

EXAMPLE 31-27

3-[({6-[3-(2-chlorophenyl)propoxy]-2-naphthyl}methyl)amino]propanoic acid acetate TLC: Rf 0.17 (chloroform:methanol:aceetic acid=9:1:0.5);
$^1$H-NMR (CD$_3$OD): δ 7.89 (s, 1H) 7.82 (d, J=8.42 Hz, 1H) 7.80 (d, J=8.42 Hz, 1H) 7.49 (dd, J=8.60, 1.65 Hz, 1H) 7.33-7.39 (m, 1H) 7.27-7.33 (m, 1H) 7.11-7.26 (m, 4H) 4.31 (s, 2H) 4.12 (t, J=6.13 Hz, 2H) 3.20 (t, J=6.22 Hz, 2H) 2.92-3.04 (m, 2H) 2.52 (t, J=6.22 Hz, 2H) 2.08-2.24 (m, 2H) 1.95 (s, 3H).

EXAMPLE 31-28

3-[({6-[3-(2,6-dichlorophenyl)propoxy]-2-naphthyl}methyl)amino]propanoic acid acetate TLC: Rf 0.17 (chloroform:methanol:aceetic acid=9:1:0.5);
$^1$H-NMR (CD$_3$OD): δ 7.89 (s, 1H) 7.83 (d, J=8.50 Hz, 1H) 7.80 (d, J=8.50 Hz, 1H) 7.50 (dd, J=8.42, 1.46 Hz, 1H) 7.35 (d, J=8.50 Hz, 2H) 7.25 (d, J=2.38 Hz, 1H) 7.14-7.21 (m, 2H) 4.32 (s, 2H) 4.19 (t, J=6.04 Hz, 2H) 3.15-3.25 (m, 4H) 2.49-2.57 (m, 2H) 2.08-2.20 (m, 2H) 1.93 (s, 3H).

EXAMPLE 31-29

3-({(2Z)-3-[4-(3-phenylpropoxy)phenyl]-2-butenyl}amino)propanoic acid hydrochloride TLC: Rf 0.27 (chloroform:methanol:aqueous ammonia=80:20:4);
$^1$H-NMR (CD$_3$OD): δ 7.10-7.29 (m, 7H), 6.94 (d, J=9.00 Hz, 2H), 5.55 (tq, J=7.00, 1.50 Hz, 1H), 3.97 (t, J=6.00 Hz, 2H), 3.63 (dd, J=7.00, 1.00 Hz, 2H), 3.12 (t, J=6.50 Hz, 2H), 2.80 (t, J=7.50 Hz, 2H), 2.62 (t, J=6.50 Hz, 2H), 2.12-2.15 (m, 3H), 2.02-2.11 (m, 2H).

EXAMPLE 31-30

3-[((2E)-3-{2-chloro-4-[(4-propylbenzyl)oxy]phenyl}-2-propenyl)amino]propanoic acid hydrochloride TLC: Rf 0.25 (n-butanol:acetic acid:water=20:4:41);
$^1$H-NMR (CD$_3$OD): δ 7.59 (d, J=9.0 Hz, 1H), 7.32 (d, J=8.1 Hz, 2H), 7.14-7.23 (m, 3H), 7.06 (d, J=2.6 Hz, 1H), 6.96 (dd, J=8.8, 2.6 Hz, 1H), 6.18 (dt, J=9.0, 8.8 Hz, 1H), 5.06 (s, 2H), 3.85 (dd, J=7.3, 0.9 Hz, 2H), 3.26-3.34 (m, 2H), 2.76 (t, J=6.6 Hz, 2H), 2.55-2.63 (m, 2H), 1.56-1.71 (m, 2H), 0.93 (t, J=7.3 Hz, 3H).

EXAMPLE 31-31

3-[((2E)-3-{2-chloro-4-[(4-pentylbenzyl)oxy]phenyl}-2-propenyl)amino]propanoic acid hydrochloride TLC: Rf 0.22 (n-butanol:acetic acid:water=20:4:1);
$^1$H-NMR (CD$_3$OD): δ 7.60 (d, J=8.78 Hz, 1H) 7.32 (d, J=8.23 Hz, 2H) 7.12-7.23 (m, 3H) 7.06 (d, J=2.56 Hz, 1H) 6.96 (dd, J=8.60, 2.56 Hz, 1H) 6.09-6.31 (m, 1H) 5.06 (s, 2H) 3.85 (dd, J=7.23, 1.01 Hz, 2H) 3.22-3.39 (m, 2H) 2.76 (t, J=6.59 Hz, 2H) 2.61 (t, J=8.10 Hz, 2H) 1.54-1.68 (m, 2H) 1.25-1.42 (m, 4H) 0.89 (t, J=6.90 Hz, 3H).

EXAMPLE 31-32

3-[((2E)-3-{2-chloro-4-[(4-hexylbenzyl)oxy]phenyl}-2-propenyl)amino]propanoic acid hydrochloride TLC: Rf 0.25 (n-butanol:acetic acid:water=20:4:1);
$^1$H-NMR (CD$_3$OD): δ 7.59 (d, J=8.8 Hz, 1H), 7.32 (d, J=8.1 Hz, 2H), 7.11-7.25 (m, 3H), 7.06 (d, J=2.6 Hz, 1H), 6.96 (dd, J=8.8, 2.6 Hz, 1H), 6.06-6.30 (m, 1H), 5.06 (s, 2H), 3.85 (dd, J=7.2, 1.0 Hz, 2H), 3.19-3.40 (m, 2H), 2.76 (t, J=6.3 Hz, 2H), 2.54-2.66 (m, 2H), 1.50-1.69 (m, 2H), 1.26-1.38 (m, 6H), 0.83-0.93 (m, 3H).

EXAMPLE 31-33

3-[((2E)-3-{2-chloro-4-[(4-cyclohexylbenzyl)oxy]phenyl}-2-propenyl)amino]propanoic acid hydrochloride TLC: Rf 0.22 (n-butanol:acetic acid:water=20:4:1);
$^1$H-NMR (CD$_3$OD): δ 7.59 (d, J=8.6 Hz, 1H), 7.32 (d, J=8.4 Hz, 2H), 7.13-7.25 (m, 3H), 7.06 (d, J=2.6 Hz, 1H), 6.96 (dd, J=8.9, 2.6 Hz, 1H), 6.04-6.30 (m, 1H), 5.06 (s, 2H), 3.84 (d, J=6.6 Hz, 2H), 2.70-2.79 (m, 2H), 2.42-2.58 (m, 2H), 1.69-1.89 (m, 5H), 1.20-1.52 (m, 6H).

EXAMPLE 31-34

3-[((2E)-3-{2-chloro-4-[(4-isobutylbenzyl)oxy]phenyl}-2-propenyl)amino]propanoic acid hydrochloride TLC: Rf 0.24 (n-butanol:acetic acid:water=20:4:1);
$^1$H-NMR (CD$_3$OD): δ 7.60 (d, J=8.6 Hz, 1H), 7.32 (d, J=8.2 Hz, 2H), 7.12-7.25 (m, 3H), 7.07 (d, J=2.6 Hz, 1H), 6.97 (dd, J=9.0, 2.6 Hz, 1H), 6.18 (dt, J=15.6, 7.2 Hz, 1H), 5.06 (s, 2H), 3.85 (dd, J=7.2, 1.2 Hz, 2H), 3.25-3.35 (m, 2H), 2.75 (t, J=6.5 Hz, 2H), 2.48 (d, J=7.3 Hz, 2H), 1.76-1.95 (m, 1H), 0.89 (d, J=6.6 Hz, 6H).

EXAMPLE 31-35

3-[((2E)-3-{4-[2-(1,1'-biphenyl-4-yl)ethoxy]-2-chlorophenyl}-2-propenyl)amino]propanoic acid hydrochloride TLC: Rf 0.25 (n-butanol:acetic acid:water=20:4:1);
$^1$H-NMR (CD$_3$OD): δ 7.48-7.68 (m, 5H) 7.24-7.47 (m, 4H) 7.18 (d, J=15.92 Hz, 1H) 6.99 (d, J=2.56 Hz, 1H) 6.91 (dd, J=8.69, 2.56 Hz, 1H) 6.05-6.28 (m, 1H) 4.25 (t, J=6.68

Hz, 2H) 3.85 (dd, J=7.32, 1.10 Hz, 2H) 3.20-3.39 (m, 2H) 3.11 (t, J=6.68 Hz, 2H) 2.76 (t, J=6.68 Hz, 2H).

EXAMPLE 31-36

3-[((2E)-3-{4-[(4-butylbenzyl)oxy]-2-chlorophenyl}-2-propenyl)amino]propanoic acid hydrochloride TLC: Rf 0.20 (n-butanol:acetic acid:water=20:4:1);
$^1$H-NMR (CD$_3$OD): δ 7.60 (d, J=8.8 Hz, 1H), 7.32 (d, J=8.4 Hz, 2H), 7.11-7.24 (m, 3H), 7.06 (d, J=2.6 Hz, 1H), 6.96 (dd, J=8.8, 2.3 Hz, 1H), 6.18 (dt, J=15.9, 7.1 Hz, 1H), 5.06 (s, 2H), 3.85 (dd, J=7.1, 1.1 Hz, 2H), 3.24-3.38 (m, 2H), 2.76 (t, J=6.6 Hz, 2H), 2.61 (t, J=7.8 Hz, 2H), 1.50-1.68 (m, 2H), 1.25-1.43 (m, 2H), 0.93 (t, J=7.3 Hz, 3H).

EXAMPLE 31-37

3-{[(2E)-3-(2-chloro-4-{3-[4-(trifluoromethyl)phenyl]propoxy}phenyl)-2-propenyl]amino}propanoic acid hydrochloride TLC: Rf 0.19 (n-butanol:acetic acid:water=20:4:1);
$^1$H-NMR (CD$_3$OD): δ 7.49-7.67 (m, 3H), 7.41 (d, J=8.2 Hz, 2H), 7.18 (d, J=15.7 Hz, 1H), 6.97 (d, J=2.6 Hz, 1H), 6.89 (dd, J=8.8, 2.6 Hz, 1H), 6.07-6.29 (m, 1H), 4.00 (t, J=6.1 Hz, 2H), 3.85 (d, J=7.2 Hz, 2H), 3.17-3.41 (m, 2H), 2.89 (dd, J=8.1, 7.3 Hz, 2H), 2.68-2.82 (m, 2H), 2.01-2.19 (m, 2H).

EXAMPLE 31-38

3-({[1-methyl-6-(3-phenylpropoxy)-3,4-dihydro-2-naphthalenyl]methyl}amino)propanoic acid hydrochloride TLC: Rf 0.25 (chloroform:methanol:aqueous ammonia=80:20:4);
$^1$H-NMR (CD$_3$OD): δ 7.31 (d, J=8.50 Hz, 1H), 7.11-7.28 (m, 5H), 6.71-6.79 (m, 2H), 3.92-3.99 (m, 4H), 3.27-3.33 (m, 2H), 2.73-2.82 (m, 6H), 2.33 (t, J=7.00 Hz, 2H), 2.16 (s, 3H), 2.01-2.11 (m, 2H).

EXAMPLE 31-39

1-{[1-methyl-6-(3-phenylpropoxy)-3,4-dihydro-2-naphthalenyl]methyl}-3-azetidinecarboxylic acid hydrochloride TLC: Rf 0.20 (chloroform:methanol:aqueous ammonia=80:20:4);
$^1$H-NMR (CD$_3$OD): δ 7.32 (d, J=8.50 Hz, 1H), 7.11-7.28 (m, 5H), 6.76 (dd, J=8.50, 2.50 Hz, 1H), 6.72 (d, J=2.50 Hz, 1H), 4.20-4.45 (m, 4H), 4.16 (s, 2H), 3.96 (t, J=6.50 Hz, 2H), 3.67-3.78 (m, 1H), 2.69-2.83 (m, 4H), 2.20-2.29 (m, 5H), 2.01-2.11 (m, 2H).

EXAMPLE 31-40

3-({[6-(4-phenylbutoxy)-1H-inden-2-yl]methyl}amino)propanoic acid

TLC: Rf 0.24 (chloroform:methanol:aqueous ammonia=80:20:4);
$^1$H-NMR (CD$_3$OD): δ 7.04-7.33 (m, 7H), 6.92-6.97 (m, 1H), 6.74-6.84 (m, 1H), 4.03-4.10 (m, 2H), 3.96-4.02 (m, 2H), 3.44-3.52 (m, 2H), 3.14-3.21 (m, 2H), 2.63-2.72 (m, 2H), 2.46-2.54 (m, 2H), 1.75-1.83 (m, 4H).

EXAMPLE 31-41

3-({(2E)-2-methyl-3-[4-(3-phenylpropoxy)phenyl]-2-propenyl}amino)propanoic acid hydrochloride TLC: Rf 0.27 (chloroform:methanol:aqueous ammonia=80:20:4);
$^1$H-NMR (CD$_3$OD): δ 7.12-7.29 (m, 7H), 6.91 (d, J=8.50 Hz, 2H), 6.65-6.68 (m, 1H), 3.97 (t, J=6.00 Hz, 2H), 3.77 (s, 2H), 3.25-3.30 (m, 2H), 2.75-2.85 (m, 4H), 2.01-2.12 (m, 2H), 2.00 (d, J=1.00 Hz, 3H).

EXAMPLE 31-42

3-({(2E)-2-methyl-3-[4-(4-phenylbutoxy)phenyl]-2-propenyl}amino)propanoic acid hydrochloride TLC: Rf 0.27 (chloroform:methanol:aqueous ammonia=80:20:4);
$^1$H-NMR (CD$_3$OD): δ 7.10-7.29 (m, 7H), 6.91 (d, J=8.50 Hz, 2H), 6.64-6.67 (m, 1H), 3.97-4.02 (m, 2H), 3.76 (s, 2H), 3.25-3.29 (m, 2H), 2.78 (t, J=6.50 Hz, 2H), 2.64-2.71 (m, 2H), 2.00 (d, J=1.00 Hz, 3H), 1.76-1.82 (m, 4H).

EXAMPLE 31-43

3-[({6-[3-(4-chlorophenyl)propoxy]-1-methyl-3,4-dihydro-2-naphthalenyl}methyl)amino]propanoic acid hydrochloride TLC: Rf 0.30 (chloroform:methanol:aqueous ammonia=80:20:4);
$^1$H-NMR (CD$_3$OD): δ 7.31 (d, J=8.50 Hz, 1H), 7.25 (d, J=8.50 Hz, 2H), 7.19 (d, J=8.50 Hz, 2H), 6.75 (dd, J=8.50, 2.50 Hz, 1H), 6.72 (d, J=2.50 Hz, 1H), 3.91-3.99 (m, 4H), 3.27-3.34 (m, 2H), 2.73-2.82 (m, 6H), 2.29-2.38 (m, 2H), 2.16 (t, J=1.5 Hz, 3H), 2.00-2.11 (m, 2H).

EXAMPLE 31-44

1-({6-[3-(4-chlorophenyl)propoxy]-1-methyl-3,4-dihydro-2-naphthalenyl}methyl)-3-azetidinecarboxylic acid hydrochloride TLC: Rf 0.22 (chloroform:methanol:aqueous ammonia=80:20:4);
$^1$H-NMR (CD$_3$OD): δ 7.32 (d, J=8.50 Hz, 1H), 7.25 (d, J=8.50 Hz, 2H), 7.19 (d, J=8.50 Hz, 2H), 6.76 (dd, J=8.50, 2.50 Hz, 1H), 6.71 (d, J=2.50 Hz, 1H), 4.15-4.47 (m, 6H), 3.96 (t, J=6.00 Hz, 2H), 3.65-3.80 (m, 1H), 2.69-2.82 (m, 4H), 2.20-2.29 (m, 5H), 1.99-2.11 (m, 2H);
Melting point: 147-150° C.

EXAMPLE 31-45

3-({[6-(3-cyclohexylpropoxy)-1-methyl-3,4-dihydro-2-naphthalenyl]methyl}amino)propanoic acid hydrochloride TLC: Rf 0.30 (chloroform:methanol:aqueous ammonia=80:20:4);
$^1$H-NMR (CD$_3$OD): δ 7.30 (d, J=8.50 Hz, 1H), 6.71-6.78 (m, 2H), 3.90-3.98 (m, 4H), 3.26-3.34 (m, 2H), 2.73-2.82 (m, 4H), 2.29-2.37 (m, 2H), 2.16 (t, J=1.50 Hz, 3H), 1.61-1.83 (m, 7H), 1.12-1.40 (m, 6H), 0.84-1.01 (m, 2H).

EXAMPLE 31-46

1-{[6-(3-cyclohexylpropoxy)-1-methyl-3,4-dihydro-2-naphthalenyl]methyl}-3-azetidinecarboxylic acid hydrochloride TLC: Rf 0.22 (chloroform:methanol:aqueous ammonia=80:20:4);
$^1$H-NMR (CD$_3$OD): δ 7.32 (d, J=8.50 Hz, 1H), 6.76 (dd, J=8.50, 2.50 Hz, 1H), 6.71 (d, J=2.50 Hz, 1H), 4.18-4.48 (m, 4H), 4.16 (s, 2H), 3.94 (t, J=6.50 Hz, 2H), 3.67-3.79 (m, 1H), 2.70-2.77 (m, 2H), 2.20-2.29 (m, 5H), 1.61-1.82 (m, 7H), 1.11-1.39 (m, 6H), 0.83-1.00 (m, 2H);
Melting point: 160-163° C.

EXAMPLE 31-47

1-({1-methyl-6-[3-(4-methylphenyl)propoxy]-3,4-dihydro-2-naphthalenyl}methyl)-3-azetidinecarboxylic acid hydrochloride TLC: Rf 0.31 (chloroform:methanol:aqueous ammonia=80:20:4);
$^1$H-NMR (CD$_3$OD): δ 7.32 (d, J=8.50 Hz, 1H), 7.06-7.08 (m, 4H), 6.75 (dd, J=8.50, 2.50 Hz, 1H), 6.71 (d, J=2.50 Hz, 1H), 4.17-4.48 (m, 4H), 4.16 (s, 2H), 3.94 (t, J=6.00 Hz, 2H), 3.65-3.78 (m, 1H), 2.69-2.77 (m, 4H), 2.19-2.29 (m, 8H), 1.97-2.09 (m, 2H).

EXAMPLE 31-48

1-[(1-methyl-6-{3-[4-(trifluoromethyl)phenyl]propoxy}-3,4-dihydro-2-naphthalenyl)methyl]-3-azetidinecarboxylic acid hydrochloride TLC: Rf 0.30 (chloroform:methanol:aqueous ammonia=80:20:4); $^1$H-NMR (CD$_3$OD): δ 7.56 (d, J=8.00 Hz, 2H), 7.40 (d, J=8.00 Hz, 2H), 7.33 (d, J=8.50 Hz, 1H), 6.76 (dd, J=8.50, 2.50 Hz, 1H), 6.71 (d, J=2.50 Hz, 1H), 4.17-4.49 (m, 4H), 4.16 (s, 2H), 3.98 (t, J=6.00 Hz, 2H), 3.64-3.78 (m, 1H), 2.89 (t, J=7.50 Hz, 2H), 2.69-2.77 (m, 2H), 2.20-2.29 (m, 5H), 2.05-2.15 (m, 2H).

EXAMPLE 31-49

1-({6-[3-(2-chlorophenyl)propoxy]-1-methyl-3,4-dihydro-2-naphthalenyl}methyl)-3-azetidinecarboxylic acid hydrochloride TLC: Rf 0.30 (chloroform:methanol:aqueous ammonia=80:20:4);
$^1$H-NMR (CD$_3$OD): δ 7.25-7.38 (m, 3H), 7.13-7.24 (m, 2H), 6.77 (dd, J=8.50, 2.50 Hz, 1H), 6.73 (d, J=2.50 Hz, 1H), 4.18-4.43 (m, 4H), 4.16 (s, 2H), 3.99 (t, J=6.00 Hz, 2H), 3.65-3.76 (m, 1H), 2.90-2.97 (m, 2H), 2.70-2.77 (m, 2H), 2.20-2.29 (m, 5H), 2.02-2.13 (m, 2H).

EXAMPLE 31-50

1-({6-[3-(2-fluorophenyl)propoxy]-1-methyl-3,4-dihydro-2-naphthalenyl}methyl)-3-azetidinecarboxylic acid hydrochloride TLC: Rf 0.30 (chloroform:methanol:aqueous ammonia=80:20:4);
$^1$H-NMR(CD$_3$OD): δ 7.33 (d, J=8.50 Hz, 1H), 7.16-7.27 (m, 2H), 6.98-7.10 (m, 2H), 6.76 (dd, J=8.50, 2.50 Hz, 1H), 6.72 (d, J=2.50 Hz, 1H), 4.19-4.46 (m, 4H), 4.16 (s, 2H), 3.98 (t, J=6.00 Hz, 2H), 3.65-3.78 (, 1H), 2.83 (t, J=7.50 Hz, 2H), 2.70-2.77 (m, 2H), 2.20-2.29 (m, 5H), 2.00-2.11 (m, 2H);
Melting point: 133-135° C.

EXAMPLE 31-51

1-{[1-chloro-6-(4-phenylbutoxy)-3,4-dihydro-2-naphthalenyl]methyl}-3-azetidinecarboxylic acid hydrochloride TLC: Rf 0.15 (n-butanol:acetic acid:water=20:4:1);
$^1$H-NMR (CD$_3$OD): δ 7.56 (d, J=8.60 Hz, 1H), 7.06-7.35 (m, 5H), 6.63-6.88 (m, 2H), 4.29 (s, 2H), 4.22-4.59 (m, 4H), 3.94-4.06 (m, 2H), 3.61-3.81 (m, 1H), 2.84 (t, J=8.40 Hz, 2H), 2.60-2.75 (m, 2H), 2.47 (t, J=7.20 Hz, 2H), 1.67-1.90 (m, 4H).

EXAMPLE 31-52

3-({[1-chloro-6-(4-phenylbutoxy)-3,4-dihydro-2-naphthalenyl]methyl}amino)propanoic acid hydrochloride TLC: Rf 0.27 (n-butanol:acetic acid:water=20:4:1);
$^1$H-NMR (CD$_3$OD): δ 7.55 (d, J=8.4 Hz, 1H); 7.00-7.35 (m, 5H), 6.64-6.86 (m, 2H), 4.08 (s, 2H), 3.94-4.04 (m, 2H), 3.19-3.45 (m, 2H), 2.88 (t, J=7.5 Hz, 2H), 2.79 (t, J=6.5 Hz, 2H), 2.63-2.72 (m, 2H), 2.53 (t, J=7.5 Hz, 2H), 1.74-1.84 (m, 4H).

EXAMPLE 31-53

1-({6-[3-(4-fluorophenyl)propoxy]-1-methyl-3,4-dihydro-2-naphthalenyl}methyl)-3-azetidinecarboxylic acid hydrochloride TLC: Rf 0.26 (chloroform:methanol:aqueous ammonia=80:20:4);
$^1$H-NMR (CD$_3$OD): δ 7.32 (d, J=8.50 Hz, 1H), 7.20 (dd, J=8.50, 5.50 Hz, 2H), 6.98 (t, J=8.50 Hz, 2H), 6.76 (dd, J=8.50, 2.50 Hz, 1H), 6.72 (d, J=2.50 Hz, 1H), 4.18-4.43 (m, 4H), 4.16 (s, 2H), 3.95 (t, J=6.00 Hz, 2H), 3.66-3.75 (m, 1H), 2.69-2.82 (m, 4H), 2.20-2.28 (m, 5H), 1.99-2.10 (m, 2H);
Melting point: 135-137° C.

EXAMPLE 31-54

1-({6-[2-(4-tert-butylphenyl)ethoxy]-1-methyl-3,4-dihydro-2-naphthalenyl}methyl)-3-azetidinecarboxylic acid hydrochloride TLC: Rf 0.27 (chloroform:methanol:aqueous ammonia=80:20:4);
$^1$H-NMR (CD$_3$OD): δ 7.30-7.35 (m, 3H), 7.20 (d, J=8.50 Hz, 2H), 6.77 (dd, J=8.50, 2.50 Hz, 1H), 6.72 (d, J=2.50 Hz, 1H), 4.20-4.46 (m, 4H), 4.13-4.19 (m, 4H), 3.61-3.78 (m, 1H), 3.01 (t, J=7.00 Hz, 2H), 2.69-2.76 (m, 2H), 2.18-2.28 (m, 5H), 1.30 (s, 9H).

EXAMPLE 31-55

1-{[6-(1,1'-biphenyl-4-ylmethoxy)-1-methyl-3,4-dihydro-2-naphthalenyl]methyl}-3-azetidinecarboxylic acid hydrochloride TLC: Rf 0.28 (chloroform:methanol:aqueous ammonia=80:20:4);
$^1$H-NMR (CD$_3$OD): δ 7.58-7.64 (m, 4H), 7.49 (d, J=8.00 Hz, 2H), 7.42 (t, J=8.00 Hz, 2H), 7.29-7.36 (m, 2H), 6.87 (dd, J=8.50, 2.50 Hz, 1H), 6.83 (d, J=2.50 Hz, 1H), 5.14 (s, 2H), 4.21-4.44 (m, 4H), 4.15 (s, 2H), 3.64-3.77 (m, 1H), 2.70-2.79 (m, 2H), 2.19-2.30 (m, 5H).

EXAMPLE 31-56

1-({6-[3-(2,6-dichlorophenyl)propoxy]-1-methyl-3,4-dihydro-2-naphthalenyl}methyl)-3-azetidinecarboxylic acid hydrochloride TLC: Rf 0.17 (n-butanol:acetic acid:water=20:4:1);
$^1$H-NMR (CD$_3$OD): δ 7.30-7.37 (m, 3H), 7.14-7.20 (m, 1H), 6.77 (dd, J=8.7, 2.6 Hz, 1H), 6.72 (d, J=2.6 Hz, 1H), 4.19-4.45 (m, 4H), 4.16 (s, 2H), 4.06 (t, J=6.1 Hz, 2H), 3.62-3.78 (m, 1H), 3.07-3.18 (m, 2H), 2.68-2.78 (m, 2H), 2.22 (s, 3H), 2.19-2.29 (m, 2H), 1.97-2.10 (m, 2H).

EXAMPLE 31-57

1-[(6-{-3-[3,5-bis(trifluoromethyl)phenyl]propoxy}-1-methyl-3,4-dihydro-2-naphthalenyl)methyl]-3-azetidinecarboxylic acid hydrochloride TLC: Rf 0.20 (n-butanol:acetic acid:water=20:4:1);
$^1$H-NMR (CD$_3$OD): δ 7.82 (s, 2H), 7.77 (s, 1H), 7.33 (d, J=8.6 Hz, 1H), 6.75 (dd, J=8.6, 2.6 Hz, 1H), 6.70 (d, J=2.6 Hz, 1H), 4.19-4.45 (m, 4H), 4.16 (s, 2H), 4.00 (t, J=6.0 Hz, 2H), 3.62-3.77 (m, 1H), 2.95-3.04 (m, 2H), 2.67-2.76 (m, 2H), 2.22 (s, 3H), 2.19-2.30 (m, 2H), 2.07-2.18 (m, 2H).

EXAMPLE 31-58

1-{[1-methyl-6-(octyloxy)-3,4-dihydro-2-naphthalenyl]methyl}-3-azetidinecarboxylic acid hydrochloride TLC: Rf 0.17 (n-butanol:acetic acid:water=20:4:1);
$^1$H-NMR (CD$_3$OD): δ 7.32 (d, J=8.6 Hz, 1H), 6.76 (dd, J=8.6, 2.6 Hz, 1H), 6.72 (d, J=2.6 Hz, 1H), 4.18-4.44 (m, 4H), 4.16 (s, 2H), 3.96 (t, J=6.4 Hz, 2H), 3.63-3.77 (m, 1H), 2.69-2.77 (m, 2H), 2.22 (s, 3H), 2.17-2.31 (m, 2H), 1.68-1.81 (m, 2H), 1.23-1.53 (m, 10H), 0.84-0.95 (m, 3H).

EXAMPLE 31-59

1-{[6-(3,3-diphenylpropoxy)-1-methyl-3,4-dihydro-2-naphthalenyl]methyl}-3-azetidinecarboxylic acid hydrochloride TLC: Rf 0.27 (n-butanol:acetic acid:water=20:4:1);
$^1$H-NMR (CD$_3$OD): δ 7.10-7.37 (m, 11H), 6.63-6.73 (m, 2H), 4.19-4.45 (m, 5H), 4.15 (s, 2H), 3.88 (t, J=6.3 Hz, 2H), 3.64-3.77 (m, 1H), 2.66-2.76 (m, 2H), 2.44-2.57 (m, 2H), 2.20 (s, 3H), 2.16-2.29 (m, 2H);
Melting point: 77-83° C.

EXAMPLE 31-60

1-({1-methyl-6-[(4-propylbenzyl)oxy]-3,4-dihydro-2-naphthalenyl}methyl)-3-azetidinecarboxylic acid hydrochloride TLC: Rf 0.23 (n-butanol:acetic acid:water=20:4:1);
$^1$H-NMR (CD$_3$OD): δ 7.27-7.36 (m, 3H), 7.18 (d, J=8.1 Hz, 2H), 6.84 (dd, J=8.1, 2.7 Hz, 1H), 6.80 (d, J=2.7 Hz, 1H), 5.04 (s, 2H), 4.21-4.43 (m, 4H), 4.15 (s, 2H), 3.62-3.76 (m, 1H), 2.68-2.78 (m, 2H), 2.58 (t, J=7.8 Hz, 2H), 2.22 (s, 3H), 2.19-2.30 (m, 2H), 1.56-1.71 (m, 2H), 0.93 (t, J=7.3 Hz, 3H);
Melting point: 144-150° C.

EXAMPLE 31-61

1-({6-[(4-isobutylbenzyl)oxy]-1-methyl-3,4-dihydro-2-naphthalenyl}methyl)-3-azetidinecarboxylic acid hydrochloride TLC: Rf 0.20 (n-butanol:acetic acid:water=20:4:1);
$^1$H-NMR (CD$_3$OD): δ 7.24-7.43 (m, 3H), 7.15 (d, J=8.1 Hz, 2H), 6.73-6.94 (m, 2H), 5.04 (s, 2H), 4.16 (s, 2H), 4.06-4.47 (m, 4H), 3.60-3.82 (m, 1H), 2.73 (t, J=8.4 Hz, 2H), 2.48 (d, J=7.1 Hz, 2H), 2.13-2.31 (m, 5H), 1.69-1.98 (m, 1H), 0.90 (d, J=6.6 Hz, 6H).

EXAMPLE 31-62

1-({6-[(4-tert-butylbenzyl)oxy]-1-methyl-3,4-dihydro-2-naphthalenyl}methyl)-3-azetidinecarboxylic acid hydrochloride TLC: Rf 0.20 (n-butanol:acetic acid:water=20:4:1);
$^1$H-NMR (CD$_3$OD): δ 7.37-7.43 (m, 2H), 7.29-7.36 (m, 3H), 6.84 (dd, J=8.4, 2.7 Hz, 1H), 6.80 (d, J=2.7 Hz, 1H), 5.04 (s, 2H), 4.19-4.43 (m, 4H), 4.16 (s, 2H), 3.62-3.78 (m, 1H), 2.69-2.77 (m, 2H), 2.21 (s, 3H), 2.19-2.29 (m, 2H), 1.31 (s, 9H).

EXAMPLE 31-63

1-({1-methyl-6-[3-(2-methylphenyl)propoxy]-3,4-dihydro-2-naphthalenyl}methyl)-3-azetidinecarboxylic acid hydrochloride TLC: Rf 0.22 (n-butanol:acetic acid:water=20:4:1);
$^1$H-NMR (CD$_3$OD): δ 7.33 (d, J=8.6 Hz, 1H), 7.02-7.15 (m, 4H), 6.77 (dd, J=8.6, 2.6 Hz, 1H), 6.73 (d, J=2.6 Hz, 1H), 4.21-4.42 (m, 4H), 4.16 (s, 2H), 3.98 (t, J=6.0 Hz, 2H), 3.63-3.77 (m, 1H), 2.68-2.84 (m, 4H), 2.30 (s, 3H), 2.22 (s, 3H), 2.19-2.32 (m, 2H), 1.96-2.07 (m, 2H);
Melting point: 160-165° C.

EXAMPLE 31-64

1-({1-methyl-6-[(4-phenylbutyl)sulfanyl]-3,4-dihydro-2-naphthalenyl}methyl)-3-azetidinecarboxylic acid hydrochloride TLC: Rf 0.17 (chloroform:methanol:aqueous ammonia=20:5:1);
$^1$H-NMR (CD$_3$OD): δ 7.31 (d, J=8.2 Hz, 1H), 7.05-7.27 (m, 7H), 4.23-4.42 (m, 4H), 4.18 (s, 2H), 3.62-3.77 (m, 1H), 2.95 (t, J=7.0 Hz, 2H), 2.67-2.78 (m, 2H), 2.61 (t, J=7.4 Hz, 2H), 2.22 (s, 3H), 2.20-2.30 (m, 2H), 1.57-1.81 (m, 4H).

EXAMPLE 31-65

1-{[1-methyl-6-(2-naphthylmethoxy)-3,4-dihydro-2-naphthalenyl]methyl}-3-azetidinecarboxylic acid hydrochloride TLC: Rf 0.32 (chloroform:methanol:aqueous ammonia=80:20:4);
$^1$H-NMR (CD$_3$OD): δ 7.81-7.91 (m, 4H), 7.54 (dd, J=8.50, 1.50 Hz, 1H), 7.44-7.51 (m, 2H), 7.35 (d, J=8.50 Hz, 1H), 6.91 (dd, J=8.50, 2.50 Hz, 1H), 6.87 (d, J=2.50 Hz, 1H), 5.26 (s, 2H), 4.19-4.45 (m, 4H), 4.16 (s, 2H), 3.64-3.77 (m, 1H), 2.74 (t, J=8.00 Hz, 2H), 2.20-2.29 (m, 5H).

EXAMPLE 31-66

1-{[1-methyl-6-(2-quinolinylmethoxy)-3,4-dihydro-2-naphthalenyl]methyl}-3-azetidinecarboxylic acid dihydrochloride TLC: Rf 0.29 (chloroform:methanol:aqueous ammonia=80:20:4);
$^1$H-NMR (CD$_3$OD): δ 9.17 (d, J=8.50 Hz, 1H), 8.32-8.41 (m, 2H), 8.15-8.24 (m, 2H), 7.95-8.03 (m, 1H), 7.44 (d, J=9.00 Hz, 1H), 7.03-7.07 (m, 2H), 5.73 (s, 2H), 4.38-4.49 (m, 2H), 4.16-4.34 (m, 4H), 3.65-3.82 (m, 1H), 2.80 (t, J=8.00 Hz, 2H), 2.23-2.34 (m, 5H).

EXAMPLE 31-67

1-{[6-(1-benzothien-2-ylmethoxy)-1-methyl-3,4-dihydro-2-naphthalenyl]methyl}-3-azetidinecarboxylic acid hydrochloride TLC: Rf 0.31 (chloroform:methanol:aqueous ammonia=80:20:4);
$^1$H-NMR (CD$_3$OD): δ 7.80-7.84 (m, 1H), 7.73-7.79 (m, 1H), 7.27-7.39 (m, 4H), 6.91 (dd, J=8.50, 2.50 Hz, 1H), 6.86 (d, J=2.50 Hz, 1H), 5.38 (d, J=1.00 Hz, 2H), 4.18-4.43 (m, 4H), 4.16 (s, 2H), 3.63-3.77 (m, 1H), 2.75 (t, J=8.00 Hz, 2H), 2.20-2.29 (m, 5H).

EXAMPLE 31-68

1-({6-[3-(3,4-difluorophenyl)propoxy]-1-methyl-3,4-dihydro-2-naphthalenyl}methyl)-3-azetidinecarboxylic acid hydrochloride TLC: Rf 0.32 (chloroform:methanol:aqueous ammonia=80:20:4);
$^1$H-NMR (CD$_3$OD): δ 7.33 (d, J=8.50 Hz, 1H), 7.07-7.18 (m, 2H), 6.96-7.03 (m, 1H), 6.76 (dd, J=8.50, 2.50 Hz, 1H), 6.72 (d, J=2.50 Hz, 1H), 4.18-4.47 (m, 4H), 4.16 (s, 2H), 3.96 (t, J=6.00 Hz, 2H), 3.66-3.78 (m, 1H), 2.68-2.82 (m, 4H), 2.20-2.30 (m, 5H), 2.00-2.10 (m, 2H);
Melting point: 132-133° C.

EXAMPLE 31-69

1-{[6-(4-butylphenoxy)-1-methyl-3,4-dihydronaphthalen-2-yl]methyl}azetidine-3-carboxylic acid hydrochloride TLC: Rf 0.14 (n-butanol:acetic acid:water=20:4:1);
$^1$H-NMR (CD$_3$OD): δ 7.38 (d, J=8.6 Hz, 1H), 7.17 (d, J=8.6 Hz, 2H), 6.85-6.98 (m, 2H), 6.73-6.83 (m, 2H), 4.20-4.45 (m, 4H), 4.17 (s, 2H), 3.58-3.81 (m, 1H), 2.67-2.79 (m, 2H), 2.60 (t, J=7.8 Hz, 2H), 2.23 (s, 3H), 2.17-2.32 (m, 2H), 1.52-1.66 (m, 2H), 1.29-1.44 (m, 2H), 0.94 (t, J=7.3 Hz, 3H).

EXAMPLE 31-70

1-{[6-(1-benzofuran-2-ylmethoxy)-1-methyl-3,4-dihydro-2-naphthalenyl]methyl}-3-azetidinecarboxylic acid hydrochloride TLC: Rf 0.28 (chloroform:methanol:aqueous ammonia=80:20:4);
$^1$H-NMR (CD$_3$OD): δ 7.55-7.59 (m, 1H), 7.44-7.49 (m, 1H), 7.36 (d, J=8.50 Hz, 1H), 7.25-7.32 (m, 1H), 7.18-7.24 (m, 1H), 6.92 (dd, J=8.50, 2.50 Hz, 1H), 6.85-6.88 (m, 2H), 5.20 (s, 2H), 4.20-4.45 (m, 4H), 4.16 (s, 2H), 3.66-3.78 (m, 1H), 2.75 (t, J=7.50 Hz, 2H), 2.19-2.29 (m, 5H).

EXAMPLE 31-71

1-({1-methyl-6-[(3-phenyl-1,2,4-oxadiazol-5-yl)methoxy]-3,4-dihydro-2-naphthalenyl}methyl)-3-azetidinecarboxylic acid hydrochloride TLC: Rf 0.27 (chloroform:methanol:aqueous ammonia=80:20:4);
$^1$H-NMR (CD$_3$OD): δ 8.03-8.09 (m, 2H), 7.47-7.57 (m, 3H), 7.39 (d, J=8.50 Hz, 1H), 6.90-6.97 (m, 2H), 5.46 (s, 2H), 4.20-4.43 (m, 4H), 4.16 (s, 2H), 3.63-3.76 (m, 1H), 2.77 (t, J=7.50 Hz, 2H), 2.20-2.31 (m, 5H).

EXAMPLE 31-72

1-[(1-methyl-6-{[(2E)-3-phenyl-2-propenyl]oxy}-3,4-dihydro-2-naphthalenyl)methyl]-3-azetidinecarboxylic acid hydrochloride TLC: Rf 0.28 (chloroform:methanol:aqueous ammonia=80:20:4);
$^1$H-NMR (CD$_3$OD): δ 7.37-7.45 (m, 2H), 7.27-7.38 (m, 3H), 7.19-7.26 (m, 1H), 6.85 (dd, J=8.50, 2.50 Hz, 1H), 6.81 (d, J=2.50 Hz, 1H), 6.74 (dt, J=16.00, 1.50 Hz, 1H), 6.44 (dt, J=16.00, 5.50 Hz, 1H), 4.71 (dd, J=5.50, 1.50 Hz, 2H), 4.19-4.44 (m, 4H), 4.16 (s, 2H), 3.65-3.76 (m, 1H), 2.72-2.79 (m, 2H), 2.20-2.30 (m, 5H).

EXAMPLE 31-73

1-({6-[3-(3-fluorophenyl)propoxy]-1-methyl-3,4-dihydro-2-naphthalenyl}methyl)-3-azetidinecarboxylic acid hydrochloride TLC: Rf 0.28 (chloroform:methanol:aqueous ammonia=80:20:4);

¹H-NMR (CD₃OD): δ 7.33 (d, J=8.50 Hz, 1H), 7.21-7.30 (m, 1H), 7.02 (d, J=8.00 Hz, 1H), 6.84-6.98 (m, 2H), 6.76 (dd, J=8.50, 2.50 Hz, 1H), 6.72 (d, J=2.50 Hz, 1H), 4.20-4.43 (m, 4H), 4.16 (s, 2H), 3.96 (t, J=6.00 Hz, 2H), 3.64-3.78 (m, 1H), 2.81 (t, J=7.50 Hz, 2H), 2.73 (t, J=8.00 Hz, 2H), 2.19-2.29 (m, 5H), 2.01-2.12 (m, 2H);

Melting point: 157-161° C.

EXAMPLE 31-74

1-({6-[3-(2,4-dichlorophenyl)propoxy]-1-methyl-3,4-dihydronaphthalen-2-yl}methyl)azetidine-3-carboxylic acid hydrochloride TLC: Rf 0.14 (n-butanol:acetic acid:water=20:4:1);
¹H-NMR (CD₃OD): δ 7.41 (d, J=2.2 Hz, 1H), 7.33 (d, J=8.6 Hz, 1H), 7.28 (d, J=8.4 Hz, 1H), 7.22 (dd, J=8.4, 2.2 Hz, 1H), 6.76 (dd, J=8.6, 2.4 Hz, 1H), 6.71 (d, J=2.4 Hz, 1H), 4.19-4.42 (m, 4H), 4.16 (s, 2H), 3.99 (t, J=6.0 Hz, 2H), 3.62-3.76 (m, 1H), 2.87-2.96 (m, 2H), 2.69-2.78 (m, 2H), 2.22 (s, 3H), 2.18-2.29 (m, 2H), 2.00-2.12 (m, 2H);

Melting point: 121-126° C.

EXAMPLE 31-75

1-({6-[3-(2,4-dimethylphenyl)propoxy]-1-methyl-3,4-dihydrbonaphthalen-2-yl}methyl)azetidine-3-carboxylic acid hydrochloride TLC: Rf 0.16 (n-butanol:acetic acid:water=20:4:1);
¹H-NMR (CD₃OD): δ 7.32 (d, J=8.6 Hz, 1H), 6.99 (d, J=7.5 Hz, 1H), 6.93 (s, 1H), 6.88 (d, J=7.5 Hz, 1H), 6.76 (dd, J=8.6, 2.6 Hz, 1H), 6.72 (d, J=2.6 Hz, 1H), 4.19-4.43 (m, 4H), 4.16 (s, 2H), 3.96 (t, J=6.1 Hz, 2H), 3.62-3.77 (m, 1H), 2.67-2.80 (m, 4H), 2.25 (s, 3H), 2.24 (s, 3H), 2.22 (s, 3H), 2.15-2.32 (m, 2H), 1.91-2.04 (m, 2H);

Melting point: 132-136° C.

EXAMPLE 31-76

1-({6-[(4-ethylbenzyl)oxy]-1-methyl-3,4-dihydronaphthalen-2-yl}methyl)azetidine-3-carboxylic acid hydrochloride TLC: Rf 0.16 (n-butanol:acetic acid:water=20:4:1);
¹H-NMR (CD₃OD): δ 7.29-7.37 (m, 3H), 7.20 (d, J=8.1 Hz, 2H), 6.84 (dd, J=8.5, 2.8 Hz, 1H), 6.80 (d, J=2.8 Hz, 1H), 5.04 (s, 2H), 4.22-4.42 (m, 4H), 4.15 (s, 2H), 3.63-3.78 (m, 1H), 2.70-2.79 (m, 2H), 2.64 (q, J=7.6 Hz, 2H), 2.21 (s, 3H), 2.19-2.30 (m, 2H), 1.22 (t, J=7.6 Hz, 3H).

EXAMPLE 31-77

1-({6-[(4-cyclohexylbenzyl)oxy]-1-methyl-3,4-dihydronaphthalen-2-yl}methyl)azetidine-3-carboxylic acid hydrochloride TLC: Rf 0.14 (n-butanol:acetic acid:water=20:4:1);
¹H-NMR (CD₃OD): δ 7.27-7.41 (m, 3H), 7.20 (d, J=7.8 Hz, 2H), 6.84 (dd, J=8.4, 2.6 Hz, 1H), 6.80 (d, J=2.6 Hz, 1H), 5.03 (s, 2H), 4.20-4.43 (m, 4H), 4.15 (s, 2H), 3.62-3.77 (m, 1H), 2.66-2.78 (m, 2H), 2.45-2.57 (m, 1H), 2.21 (s, 3H), 2.17-2.29 (m, 2H), 1.70-1.90 (m, 5H), 1.34-1.54 (m, 5H);

Melting point: 154-158° C.

EXAMPLE 31-78

1-({6-[3-(4-chlorophenyl)propoxy]-1-ethyl-3,4-dihydronaphthalen-2-yl}methyl)azetidine-3-carboxylic acid hydrochloride TLC: Rf 0.27 (chloroform:methanol:aqueous ammonia=80:5:1);
¹H-NMR (CD₃OD): δ 7.34 (d, J=8.60 Hz, 1H), 7.23-7.28 (m, 2H), 7.17-7.22 (m, 2H), 6.77 (dd, J=8.60, 2.56 Hz, 1H), 6.72 (d, J=2.56 Hz, 1H), 4.15 (s, 2H), 4.09-4.54 (m, 4H), 3.96 (t, J=6.13 Hz, 2H), 3.63-3.78 (m, 1H), 2.64-2.85 (m, 6H), 2.20 (t, J=7.80 Hz, 2H), 1.96-2.13 (m, 2H), 1.11 (t, J=7.50 Hz, 3H);

Melting-point: 102-105° C.

EXAMPLE 31-79

1-{[3-methyl-6-(4-phenylbutoxy)-1-benzofuran-2-yl]methyl}azetidine-3-carboxylic acid TLC: Rf 0.30 (chloroform:methanol:aqueous ammonia=80:20:4);
¹H-NMR (DMSO-D₆): δ 7.36 (d, J=8.60 Hz, 1H), 7.13-7.32 (m, 5H), 7.06 (d, J=2.20 Hz, 1H), 6.82 (dd, J=8.60, 2.20 Hz, 1H), 3.97-4.03 (m, 2H), 3.60 (s, 2H), 3.36-3.44 (m, 2H), 3.25 (t, J=6.68 Hz, 2H), 3.08-3.20 (m, 1H), 2.60-2.70 (m, 2H), 2.15 (s, 3H), 1.68-1.79 (m, 4H).

EXAMPLE 31-80

1-({6-[3-(2,4-difluorophenyl)propoxy]-1-methyl-3,4-dihydro-2-naphthalenyl}methyl)-3-azetidinecarboxylic acid hydrochloride TLC: Rf 0.20 (chloroform:methanol:aqueous ammona=80:20:4);
¹H-NMR (CD₃OD): δ 7.33 (d, J=8.50 Hz, 1H), 7.21-7.30 (m, 1H), 6.82-6.92 (m, 2H), 6.76 (dd, J=8.50, 2.50 Hz, 1H), 6.72 (d, J=2.50 Hz, 1H), 4.18-4.44 (m, 4H), 4.16 (s, 2H), 3.97 (t, J=6.00 Hz, 2H), 3.66-3.77 (m, 1H), 2.81 (t, J=7.50 Hz, 2H), 2.69-2.77 (m, 2H), 2.20-2.29 (m, 5H), 1.99-2.10 (m, 2H);

Melting point: 126-129° C.

EXAMPLE 31-81

1-({6-[2-(2,3-dihydro-1H-inden-2-yl)ethoxy]-1-methyl-3,4-dihydro-2-naphthalenyl}methyl)-3-azetidinecarboxylic acid hydrochloride TLC: Rf 0.20 (chloroform:methanol:aqueous ammonia=80:20:4);
¹H-NMR(CD₃OD): δ 7.34 (d, J=8.50 Hz, 1H), 7.12-7.17 (m, 2H), 7.03-7.10 (m, 2H), 6.80 (dd, J=8.50, 2.50 Hz, 1H), 6.75 (d, J=2.50 Hz, 1H), 4.19-4.43 (m, 4H), 4.16 (s, 2H), 4.08 (t, J=6.50 Hz, 2H), 3.64-3.77 (m, 1H), 2.99-3.14 (m, 2H), 2.60-2.79 (m, 5H), 2.20-2.30 (m, 5H), 1.92-2.02 (m, 2H);

Melting point: 129-132° C.

EXAMPLE 31-82

1-{[6-(2,3-dihydro-1H-inden-2-ylmethoxy)-1-methyl-3,4-dihydro-2-naphthalenyl]methyl}-3-azetidinecarboxylic acid hydrochloride TLC: Rf 0.20 (chloroform:methanol:aqueous ammonia=80:20:4);

$^1$H-NMR (CD$_3$OD): δ 7.33 (d, J=8.50 Hz, 1H), 7.15-7.21 (m, 2H), 7.07-7.13 (m, 2H), 6.79 (dd, J=8.50, 2.50 Hz, 1H), 6.74 (d, J=2.50 Hz, 1H), 4.21-4.41 (m, 4H), 4.15 (s, 2H), 3.97 (d, J=7.00 Hz, 2H), 3.63-3.76 (m, 1H), 3.06-3.18 (m, 2H), 2.78-2.99 (m, 3H), 2.69-2.77 (m, 2H), 2.19-2.29 (m, 5H).

EXAMPLE 31-83

1-{[6-(bicyclo[4.2.0]octa-1,3,5-trien-7-ylmethoxy)-1-methyl-3,4-dihydro-2-naphthalenyl]methyl}-3-azetidinecarboxylic acid hydrochloride TLC: Rf 0.20 (chloroform:methanol:aqueous ammonia=80:20:4);

$^1$H-NMR (CD$_3$OD): δ 7.33 (d, J=8.50 Hz, 1H), 7.05-7.24 (m, 4H), 6.81 (dd, J=8.50, 2.50 Hz, 1H), 6.77 (d, J=2.50 Hz, 1H), 4.24-4.43 (m, 4H), 4.20 (d, J=7.00 Hz, 2H), 4.16 (s, 2H), 3.85-3.95 (m, 1H), 3.64-3.77 (m, 1H), 3.38 (dd, J=14.00, 5.00 Hz, 1H), 2.96 (dd, J=14.00, 2.50 Hz, 1H), 2.70-2.78 (m, 2H), 2.20-2.29 (m, 5H).

EXAMPLE 31-84

1-[(1-methyl-6-{3-[3-(trifluoromethyl)phenyl]propoxy}-3,4-dihydronaphthalen-2-yl)methyl]azetidine-3-carboxylic acid TLC: Rf 0.26 (chloroform:methanol:aqueous ammonia=20:5:1);

$^1$H-NMR (CD$_3$OD): δ 7.42-7.54 (m, 4H), 7.31 (d, J=8.60 Hz, 1H), 6.76 (dd, J=8.60, 2.75 Hz, 1H); 6.71 (d, J=2.7-5 Hz, 1H) 4.11-4.27 (m, 4H), 4.08 (s, 2H), 3.97 (t, J=6.13 Hz, 2H), 3.33-3.51 (m, 1H), 2.89 (t, J=7.87 Hz, 2H), 2.72 (t, J=8.05 Hz, 2H), 2.18-2.29 (m, 2H), 2.20 (s, 3H), 2.00-2.16 (m, 2H);

Melting point: 125-133° C.

EXAMPLE 31-85

1-({1-methyl-6-[3-(3-methylphenyl)propoxy]-3,4-dihydronaphthalen-2-yl}methyl)azetidine-3-carboxylic acid TLC: Rf 0.26 (chloroform:methanol:aqueous ammonia=20:5:1);

$^1$H-NMR (CD$_3$OD): δ 7.30 (d, J=8.60 Hz, 1H), 7.06-7.19 (m, 1H), 6.92-7.04 (m, 3H), 6.74 (dd, J=8.60, 2.74 Hz, 1H), 6.70 (d, J=2.74 Hz, 1H), 4.07-4.24 (m, 4H), 4.05 (s, 2H), 3.94 (t, J=6.22 Hz, 2H), 3.33-3.49 (m, 1H), 2.64-2.81 (m, 4H), 2.28 (s, 3H), 2.19 (s, 3H), 2.16-2.29 (m, 2H), 1.95-2.10 (m, 2H);

Melting point: 148-153° C.

EXAMPLE 31-86

1-({6-[3-(3-chlorophenyl)propoxy]-1-methyl-3,4-dihydronaphthalen-2-yl}methyl)azetidine-3-carboxylic acid TLC: Rf 0.26 (chloroform:methanol:aqueous ammonia=20:5:1);

$^1$H-NMR (CD$_3$OD): δ 7.31 (d, J=8.60 Hz, 1H), 7.20-7.28 (m, 2H), 7.08-7.20 (m, 2H), 6.75 (dd, J=8.60, 2.74 Hz, 1H), 6.71 (d, J=2.74 Hz, 1H), 4.10-4.26 (m, 4H), 4.07 (s, 2H), 3.96 (t, J=6.13 Hz, 2H), 3.34-3.51 (m, 1H), 2.79 (t, J=7.87 Hz, 2H), 2.66-2.75 (m, 2H), 2.20 (s, 3H), 2.16-2.28 (m, 2H), 1.98-2.11 (m, 2H);

Melting point: 151-153° C.

EXAMPLE 31-87

1-({6-[3-(3,4-dichlorophenyl)propoxy]-1-methyl-3,4-dihydronaphthalen-2-yl}methyl)azetidine-3-carboxylic acid TLC: Rf 0.26 (chloroform:methanol:aqueous ammonia=20:5:1);

$^1$H-NMR (CD$_3$OD): δ 7.39 (d, J=8.23 Hz, 1H), 7.36-7.39 (m, 1H), 7.30 (d, J=8.42 Hz, 1H), 7.14 (dd, J=8.23, 2.20 Hz, 1H), 6.75 (dd, J=8.42, 2.65 Hz, 1H), 6.70 (d, J=2.65 Hz, 1H), 4.06-4.25 (m, 4H), 4.04 (s, 2H), 3.96 (t, J=6.13 Hz, 2H), 3.33-3.47 (m, 1H), 2.79 (t, J=8.05 Hz, 2H), 2.67-2.75 (m, 2H), 2.19 (s, 3H), 2.16-2.28 (m, 2H), 1.99-2.12 (m, 2H);

Melting point: 74-81° C.

EXAMPLE 31-88

1-({6-[2-(4-ethylphenyl)ethoxy]-1-methyl-3,4-dihydronaphthalen-2-yl}methyl)azetidine-3-carboxylic acid TLC: Rf 0.28 (chloroform:methanol:aqueous ammonia=20:5:1);

$^1$H-NMR (CD$_3$OD): δ 7.30 (d, J=8.42 Hz, 1H), 7.19 (d, J=7.80 Hz, 2H), 7.12 (d, J=7.80 Hz, 2H), 6.76 (dd, J=8.42, 2.56 Hz, 1H), 6.71 (d, J=2.56 Hz, 1H), 4.07-4.27 (m, 6H), 4.08 (s, 2H), 3.34-3.48 (m, 1H), 3.01 (t, J=6.86 Hz, 2H), 2.66-2.76 (m, 2H), 2.60 (q, J=7.75 Hz, 2H), 2.18-2.27 (m, 2H), 2.19 (s, 3H), 1.20 (t, J=7.68 Hz, 3H);

Melting point: 158-163° C.

EXAMPLE 31-89

1-({6-[2-(4-isopropylphenyl)ethoxy]-1-methyl-3,4-dihydronaphthalen-2-yl}methyl)azetidine-3-carboxylic acid TLC: Rf 0.30 (chloroform:methanol:aqueous ammonia=20:5:1);

$^1$H-NMR (CD$_3$OD): δ 7.30 (d, J=8.42 Hz, 1H), 7.20 (d, J=8.24 Hz, 2H), 7.15 (d, J=8.24 Hz, 2H), 6.76 (dd, J=8.42, 2.65 Hz, 1H), 6.71 (d, J=2.65 Hz, 1H), 4.10-4.27 (m, 6H), 4.07 (s, 2H), 3.33-3.49 (m, 1H), 3.01 (t, J=6.86 Hz, 2H), 2.77-2.93 (m, 1H), 2.62-2.77 (m, 2H), 2.19 (s, 3H), 2.15-2.29 (m, 2H), 1.22 (d, J=6.95 Hz, 6H);

Melting point: 148-152° C.

EXAMPLE 31-90

1-[(1-methyl-6-{3-[3-(trifluoromethoxy)phenyl]propoxy}-3,4-dihydronaphthalen-2-yl)methyl]azetidine-3-carboxylic acid TLC: Rf 0.28 (chloroform:methanol:aqueous ammonia=20:5:1);

$^1$H-NMR (CD$_3$OD): δ 7.28-7.40 (m, 2H), 7.18-7.25 (m, 1H), 7.02-7.15 (m, 2H), 6.76 (dd, J=8.60, 2.75 Hz, 1H), 6.71 (d, J=2.75 Hz, 1H), 4.12-4.28 (m, 4H), 4.08 (s, 2H), 3.97 (t, J=6.13 Hz, 2H), 3.35-3.52 (m, 1H), 2.84 (t, J=7.86 Hz, 2H), 2.65-2.78 (m, 2H), 2.21 (s, 3H), 2.16-2.31 (m, 2H), 1.97-2.14 (m, 2H);

Melting point: 136-139° C.

EXAMPLE 31-91

1-{[1-methyl-6-(3-phenylbutoxy)-3,4-dihydro-2-naphthalenyl]methyl}-3-azetidinecarboxylic acid hydrochloride TLC: Rf 0.30 (chloroform:methanol:aqueous ammonia=80:20:4);

$^1$H-NMR (CD$_3$OD): δ 7.10-7.34 (m, 6H), 6.68 (dd, J=8.50, 2.50 Hz, 1H), 6.64 (d, J=2.50 Hz, 1H), 4.18-4.46 (m, 4H), 4.15 (s, 2H), 3.65-3.94 (m, 3H), 2.91-3.04 (m, 1H), 2.67-2.75 (m, 2H), 2.18-2.28 (m, 5H), 1.93-2.12 (m, 2H), 1.30 (d, J=7.00 Hz, 3H);

Melting point: 127-133° C.

EXAMPLE 31-92

1-{[1-methyl-6-(2-methyl-3-phenylpropoxy)-3,4-dihydro-2-naphthalenyl]methyl}-3-azetidinecarboxylic acid hydrochloride TLC: Rf 0.30 (chloroform:methanol:aqueous ammonia=80:20:4);

$^1$H-NMR (CD$_3$OD): δ 7.32 (d, J=8.50 Hz, 1H), 7.21-7.28 (m, 2H), 7.12-7.19 (m, 3H), 6.75 (dd, J=8.50, 2.50 Hz, 1H), 6.70 (d, J=2.50 Hz, 1H), 4.36-4.48 (m, 2H), 4.19-4.33 (m, 2H), 4.16 (s, 2H), 3.65-3.86 (m, 3H), 2.84 (dd, J=13.00, 6.50 Hz, 1H), 2.73 (t, J=8.00 Hz, 2H), 2.55 (dd, J=13.00, 7.50 Hz, 1H), 2.15-2.29 (m, 6H), 1.01 (d, J=7.00 Hz, 3H);

Melting point: 105-110° C.

EXAMPLE 31-93

1-{[1-methyl-6-(1-methyl-3-phenylpropoxy)-3,4-dihydro-2-naphthalenyl]methyl}-3-azetidinecarboxylic acid hydrochloride TLC: Rf 0.30 (chloroform:methanol:aqueous ammonia=80:20:4);

$^1$H-NMR (CD$_3$OD): δ 7.31 (d, J=8.50 Hz, 1H), 7.20-7.27 (m, 2H), 7.10-7.18 (m, 3H), 6.72 (dd, J=8.50, 2.50 Hz, 1H), 6.65 (d, J=2.50 Hz, 1H), 4.20-4.47 (m, 5H), 4.16 (s, 2H), 3.64-3.80 (m, 1H), 2.66-2.79 (m, 4H), 2.19-2.31 (m, 5H), 1.80-2.09 (m, 2H), 1.29 (d, J=6.00 Hz, 3H).

EXAMPLE 31-94

1-({6-[1-(4-isobutylphenyl)ethoxy]-1-methyl-3,4-dihydronaphthalen-2-yl}methyl)azetidine-3-carboxylic acid hydrochloride TLC: Rf 0.18 (n-butanol:acetic acid:water=20:4:1);

$^1$H-NMR (CD$_3$OD): δ 7.19-7.29 (m, 3H), 7.09 (d, J=7.9 Hz, 2H), 6.65-6.75 (m, 2H), 5.37 (q, J=6.4 Hz, 1H), 4.18-4.40 (m, 4H), 4.12 (s, 2H), 3.60-3.75 (m, 1H), 2.59-2.73 (m, 2H), 2.43 (d, J=7.1 Hz, 2H), 2.16 (s, 3H), 2.11-2.25 (m, 2H), 1.75-1.88 (m, 1H), 1.57 (d, J=6.4 Hz, 3H), 0.87 (d, J=6.6 Hz, 6H).

EXAMPLE 32

3-[methyl({6-[(5-phenylpentyl)oxy]-2-naphthyl}methyl)amino]propanoic acid

To methyl({6-[(5-phenylpentyl)oxy]-2-naphthyl}methyl)amine (15 mg), acrylic acid (6.2 μl) was added. Further, methanol was added thereto to give a total volume of 390 μL, followed by stirring at 60° C. for 24 hours. After concentrating the reaction mixture, the residue was purified by preparative TLC (chloroform:methanol:aqueous ammonia=80:20:4) to give an invention compound (11.2 mg) having the following physical properties.

TLC: Rf 0.35 (chloroform:methanol:aqueous ammonia=80:20:4);

$^1$H-NMR (CD$_3$OD): δ 7.79 (s, 1H) 7.77 (d, J=8.51 Hz, 1H) 7.76 (d, J=8.97 Hz, 1H) 7.46 (dd, J=8.51, 1.74 Hz, 1H) 7.03-7.31 (m, 7H) 4.01-4.11 (m, 4H) 3.09 (t, J=7.04 Hz, 2H) 2.63 (t, J=7.50 Hz, 2H) 2.53 (s, 3H) 2.48-2.57 (m, 2H) 1.77-1.93 (m, 2H) 1.63-1.77 (m, 2H) 1.43-1.62 (m, 2H).

EXAMPLES 32-01 to 32-12

The procedure of example 32 was similarly carried out, except for using a corresponding amine compound a substitute for methyl({6-[(5-phenylpentyl)oxy]-2-naphthyl}methyl)amine to thereby give invention compounds having the following physical properties.

EXAMPLE 32-01

3-[ethyl({6-[(5-phenylpentyl)oxy]-2-naphthyl}methyl)amino]propanoic acid

TLC: Rf 0.43 (chloroform:methanol:aqueous ammonia=80:20:4);

$^1$H-NMR (CD$_3$OD) δ 7.84 (s, 1H) 7.72-7.82 (m, 2H) 7.47 (dd, J=8.42, 1.83 Hz, 1H) 7.06-7.29 (m, 7H) 4.22 (s, 2H) 4.05 (t, J=6.31 Hz, 2H) 3.20 (t, J=6.86 Hz, 2H) 3.00 (q, J=7.20 Hz, 2H) 2.62 (t, J=7.50 Hz, 2H) 2.53 (t, J=6.86 Hz, 2H) 1.76-1.93 (m, 2H) 1.62-1.75 (m, 2H) 1.43-1.61 (m, 2H) 1.25 (t, J=7.20 Hz, 3H).

EXAMPLE 32-02

3-[({6-[(5-phenylpentyl)oxy]-2-naphthyl}methyl)(propyl)amino]propanoic acid

TLC: Rf 0.24 (chloroform:methanol:aqueous ammonia=80:20:4);

$^1$H-NMR (CD$_3$OD): δ 7.89 (s, 1H) 7.84 (d, J=8.78 Hz, 1H) 7.80 (d, J=9.15 Hz, 1H) 7.49 (dd, J=8.42, 1.65 Hz, 1H) 7.06-7.30 (m, 7H) 4.39 (s, 2H) 4.08 (t, J=6.40 Hz, 2H) 3.26-

3.40 (m, 2H) 2.93-3.13 (m, 2H) 2.64 (t, J=7.68 Hz, 2H) 2.59 (t, J=6.31 Hz, 2H) 1.80-1.94 (m, 2H) 1.62-1.79 (m, 4H) 1.46-1.62 (m, 2H) 0.90 (t, J=7.41 Hz, 3H).

EXAMPLE 32-03

3-[isopropyl({6-[(5-phenylpentyl)oxy]-2-naphthyl}methyl)amino]propanoic acid

TLC: Rf 0.54 (chloroform:methanol:aqueous ammonia=80:20:4);
$^1$H-NMR (CD$_3$OD): δ 7.79 (s, 1H) 7.75 (d, J=8.60 Hz, 1H) 7.73 (d, J=9.15 Hz, 1H) 7.48 (dd, J=8.60, 1.74 Hz, 1H) 7.04-7.29 (m, 7H) 4.07 (t, J=6.31 Hz, 2H) 4.01-4.13 (m, 2H) 2.93-3.13 (m, 2H) 2.65 (t, J=7.50 Hz, 2H) 2.44 (t, J=6.68 Hz, 2H) 1.79-1.94 (m, 2H) 1.64-1.79 (m, 2H) 1.47-1.63 (m, 2H) 1.25-1.34 (m, 1H) 1.21 (d, J=6.59 Hz, 6H).

EXAMPLE 32-04

3-[(2-hydroxyethyl)({6-[(5-phenylpentyl)oxy]-2-naphthyl}methyl)amino]propanoic acid TLC: Rf 0.28 (chloroform:methanol:aqueous ammonia=80:10:1);
$^1$H-NMR (CD$_3$OD): δ 7.90 (s, 1H) 7.75-7.87 (m, 2H) 7.52 (dd, J=8.32, 1.74 Hz, 1H) 7.05-7.30 (m, 7H) 4.46 (s, 2H) 4.09 (t, J=6.40 Hz, 2H) 3.83 (t, J=5.20 Hz, 2H) 3.37 (t, J=6.31 Hz, 2H) 3.20 (t, J=5.20 Hz, 2H) 2.65 (t, J=7.55 Hz, 2H) 2.60 (t, J=6.31 Hz, 2H) 1.80-1.95 (m, 2H) 1.64-1.79 (m, 2H) 1.46-1.63 (m, 2H).

EXAMPLE 32-05

3-{4-methoxy-4-[4-(3-phenylpropoxy)phenyl]-1-piperidinyl}propanoic acid

TLC: Rf 0.29 (chloroform:methanol:aqueous ammonia=80:20:4);
$^1$H-NMR (CD$_3$OD): δ 7.33 (d, J=8.97 Hz, 2H) 7.09-7.29 (m, 5H) 6.93 (d, J=8.97 Hz, 2H) 3.97 (t, J=6.31 Hz, 2H) 3.38-3.52 (m, 2H) 3.17-3.38 (m, 4H) 2.95 (s, 3H) 2.79 (t, J=7.55 Hz, 2H) 2.57 (t, J=6.59 Hz, 2H) 2.26-2.41 (m, 2H) 1.98-2.24 (m, 4H).

EXAMPLE 32-06

3-{4-[4-(3-phenylpropoxy)phenyl]-1-piperidinyl}propanoic acid trifluoroacetate

TLC: Rf 0.29 (chloroform:methanol:aqueous ammonia=80:20:4);
$^1$H-NMR (CD$_3$OD): δ 7.09-7.30 (m, 7H) 6.86 (d, J=8.78 Hz, 2H) 3.93 (t, J=6.31 Hz, 2H) 3.60-3.74 (m, 2H) 3.44 (t, J=7.04 Hz, 2H) 3.06-3.23 (m, 2H) 2.84 (t, J=7.04 Hz, 2H) 2.78 (t, J=7.04 Hz, 2H) 2.71-2.91 (m, 1H) 1.98-2.17 (m, 4H) 1.86-1.98 (m, 2H).

EXAMPLE 32-07

3-[5-methyl-4-[4-(3-phenylpropoxy)phenyl]-3,6-dihydropyridin-1(2H)-yl]propanoic acid TLC: Rf 0.23 (chloroform:methanol:aqueous ammonia=80:20:4);
$^1$H-NMR (CD$_3$OD): δ 7.13-7.31 (m, 5H), 7.11 (d, J=8.78 Hz, 2H), 6.90 (d, J=8.78 Hz, 2H), 3.95 (t, J=6.22 Hz, 2H), 3.64 (s, 2H), 3.26-3.37 (m, 4H), 2.79 (t, J=7.50 Hz, 2H), 2.52-2.69 (m, 4H), 1.95-2.13 (m, 2H), 1.64 (s, 3H).

EXAMPLE 32-08

3-{4-[4-(3-phenylpropoxy)phenyl]-1-piperadinyl}propanoic acid dihydrochloride

TLC: Rf 0.18 (chloroform:methanol:aqueous ammonia=80:20:4);
$^1$H-NMR (CD$_3$OD): δ 7.10-7.33 (m, 5H) 6.97-7.10 (m, 2H) 6.88 (d, J=7.32 Hz, 2H) 3.92 (t, J=6.31 Hz, 2H) 3.52 (t, J=7.23 Hz, 2H) 3.34-3.78 (m, 8H) 2.89 (t, J=7.23 Hz, 2H) 2.78 (t, J=7.59 Hz, 2H) 1.93-2.14 (m, 2H).

EXAMPLE 32-09

3-[6-(3-phenylpropoxy)-3,4-dihydro-2(1H)-isoquinolinyl]propanoic acid hydrochloride TLC: Rf 0.18 (chloroform:methanol:aqueous ammonia=80:20:4);
$^1$H-NMR (CD$_3$OD): δ 6.99-7.37 (m, 6H) 6.85 (dd, J=8.60, 2.74 Hz, 1H) 6.79 (d, J=2.74 Hz, 1H) 4.21-4.66 (m, 2H) 3.95 (t, J=6.31 Hz, 2H) 3.55 (t, J=7.04 Hz, 2H) 3.35-3.85 (m, 2H) 3.03-3.26 (m, 2H) 2.93 (t, J=7.04 Hz, 2H) 2.78 (t, J=7.59 Hz, 2H) 1.96-2.15 (m, 2H).

EXAMPLE 32-10

3-[6-[(5-phenylpentyl)oxy]-3,4-dihydro-2(1H)-isoquinolinyl]propanoic acid hydrochloride TLC: Rf 0.22 (chloroform:methanol:aqueous ammonia=80:20:4);
$^1$H-NMR (CD$_3$OD): δ 7.01-7.32 (m, 6H) 6.83 (dd, J=8.42, 2.56 Hz, 1H) 6.79 (d, J=2.56 Hz, 1H) 4.40 (s, 2H) 3.95 (t, J=6.31 Hz, 2H) 3.51-3.68 (m, 2H) 3.54 (t, J=7.04 Hz, 2H) 3.09-3.23 (m, 2H) 2.91 (t, J=7.04 Hz, 2H) 2.63 (t, J=7.55 Hz, 2H) 1.73-1.90 (m, 2H) 1.59-1.73 (m, 2H) 1.36-1.59 (m, 2H).

EXAMPLE 32-11

3-{(3Z)-3-[4-(3-phenylpropoxy)benzylidene]-1-piperidinyl}propanoic acid hydrochloride TLC: Rf 0.35 (chloroform:methanol:aqueous ammonia=80:20:4);
$^1$H-NMR (CD$_3$OD): δ 7.15-7.30 (m, 5H) 7.13 (d, J=8.78 Hz, 2H) 6.91 (d, J=8.78 Hz, 2H) 6.67 (s, 1H) 3.95 (t, J=6.31 Hz, 2H) 3.87-3.96 (m, 2H) 3.31-3.35 (m, 2H) 3.21 (t, J=6.68 Hz, 2H) 2.79 (t, J=7.50 Hz, 2H) 2.45-2.54 (m, 2H) 2.42 (t, J=6.68 Hz, 2H) 2.00-2.14 (m, 2H) 1.88-2.01 (m, 2H).

EXAMPLE 32-12

3-{(3E)-3-[4-(3-phenylpropoxy)benzylidene]-1-piperidinyl}propanoic acid hydrochloride TLC: Rf 0.26 (chloroform:methanol:aqueous ammonia=80:20:4);
$^1$H-NMR (CD$_3$OD): δ 7.06-7.30 (m, 7H) 6.89 (d, J=8.78 Hz, 2H) 6.61 (s, 1H) 3.96 (t, J=6.22 Hz, 2H) 3.84 (s, 2H) 3.19-3.40 (m, 4H) 2.79 (t, J=7.50 Hz, 2H) 2.58-2.68 (m, 2H) 2.58 (t, J=6.68 Hz, 2H) 1.98-2.12 (m, 2H) 1.79-1.96 (m, 2H).

EXAMPLE 33

3-[(3-{4-[3-(4-methylphenyl)propoxy]phenyl}propyl)amino]propanoic acid hydrochloride To a solution of the compound (48 mg) prepared in Example 5 in tetrahydrofuran (3 mL), 3-(4-methylphenyl)propanol (19 mg), diethyl azodicarboxylate (60 mg) and polymer supported triphenylphosphine (2.3 mmol/g, 60 mg) were added, followed by stirring at room temperature for 2 days. After filtering off insoluble matters and concentrating the mixture, the residue was purified by silica gel column chromatography (hexane:ethyl acetate=3:1) to give an ether compound. To a solution of the obtained compound in 1,4-dioxane (2 mL), a 4N hydrogen chloride/1,4-dioxane solution (0.8 mL) was added, followed by stirring at 40° C. for 1 hour. The reaction mixture was concentrated and washed with ethyl acetate to thereby give an invention compound (32.5 mg) having the following physical properties.

TLC: Rf 0.29 (n-butanol:acetic acid:water=20:4:1);
$^1$H-NMR (CD$_3$OD): δ 7.01-7.17 (m, 6H), 6.76-6.91 (m, 2H), 3.90 (t, J=6.31 Hz, 2H), 3.24 (t, J=6.59 Hz, 2H), 2.93-3.08 (m, 2H), 2.57-2.80 (m, 6H), 2.28 (s, 3H), 1.87-2.10 (m, 4H).

EXAMPLE 34

[6-(4-phenylbutoxy)-3,4-dihydronaphthalen-1(2H)-ylidene]acetonitrile (E/Z mixture)

To a solution of 6-(4-phenylbutoxy)-3,4-dihydronaphthalen-1(2H)-one (300 mg) in tetrahydrofuran (10 mL), diethyl cyanomethylphosphonate (199 mg) and sodium hydride (60%, 97.8 mg) were added, followed by stirring at room temperature for 24 hours. After adding water, the reaction mixture was extracted with ethyl acetate. The organic layer was washed with a saturated aqueous sodium chloride solution, concentrated and then purified by silica gel column chromatography (hexane:ethyl acetate=3:1) to thereby give the title compound (E/Z mixture, 207 mg) having the following physical properties.

TLC: Rf 0.68 (hexane:ethyl acetate=3:1).

EXAMPLE 35

3-({2-[6-(4-phenylbutoxy)-3,4-dihydro-1-naphthalenyl]ethyl}amino)propanoic acid hydrochloride To a solution of the compound (205 mg) prepared in Example 34 in tetrahydrofuran (6.5 mL), a 1M diisobutyl aluminum hydride/toluene solution (1.4 mL) was added at 0° C., followed by stirring at room temperature for 3 hours. After adding 2N hydrochloric acid, the reaction mixture was stirred for 15 minutes and extracted with ethyl acetate. The organic layer was washed with saturated aqueous sodium chloride solution, concentrated and purified by silica gel column chromatography (hexane:ethyl acetate=3:1) to give an aldehyde compound. Then, the procedure of Example 29 was similarly carried out, except for using the aldehyde compound thus obtained as a substitute for (2E)-3-[4-(3-phenylpropoxy)phenyl]but-2-enal to thereby give an invention compound having the following physical properties.

TLC: Rf 0.25 (n-butanol:acetic acid:water=20:4:1);
$^1$H-NMR (CD$_3$OD): δ 7.08-7.32 (m, 6H) 6.67-6.82 (m, 2H) 5.89 (t, J=4.57 Hz, 1H) 3.89-4.07 (m, 2H) 3.23-3.40 (m, 2H) 3.19 (t, J=7.50 Hz, 2H) 2.83 (t, J=7.59 Hz, 2H) 2.62-2.77 (m, 6H) 2.19-2.29 (m, 2H) 1.72-1.85 (m, 4H).

EXAMPLES 36-1 to 36-2

The procedures of Example 1 and Example 2 as described in WO 02/092068 were followed in this order but using a corresponding amine compound as a substitute for methyl 2-methoxy-5-aminobenzoate to thereby give invention compounds having the following physical properties.

EXAMPLE 36-1

{3-[(3-{4-[(5-phenylpentyl)oxy]phenyl}propanoyl)amino]phenyl}aceetic acid

HPLC retention time (minute: measurement conditions of HPLC are described in Example 26): 4.31;
MS (m/z): 891 (2M+H)$^+$, 446 (M+H)$^+$.

EXAMPLE 36-2

{4-[(3-{4-[(5-phenylpentyl)oxy]phenyl}propanoyl)amino]phenyl}aceetic acid

HPLC retention time (minute: measurement conditions of HPLC are described in Example 26): 4.27;
MS (m/z): 891 (2M+H)$^+$, 446 (M+1)$^+$.

EXAMPLES 37-01 to 37-32

The procedure of Example 29 was similarly carried out, except for using a corresponding amine compound as a substitute for β-alanine and a corresponding aldehyde compound as a substitute for (2E)-3-[4-(3-phenylpropoxy)phenyl]but-2-enal to thereby give invention compounds having the following physical properties.

EXAMPLE 37-01

1-[(1-methyl-6-{[(1R,2R)-2-phenylcyclopropyl]methoxy}-3,4-dihydronaphthalen-2-yl)methyl]azetidine-3-carboxylic acid TLC: Rf 0.26(chloroform:methanol:aqueous ammonia=80:20:4);
$^1$H-NMR(CD$_3$OD): δ 7.31 (d, J=8.60 Hz, 1H), 7.17-7.26 (m, 2H), 7.04-7.16 (m, 3H), 6.79 (dd, J=8.60, 2.74 Hz, 1H), 6.74 (d, J=2.74 Hz, 1H), 4.11-4.28 (m, 4H), 4.09 (s, 2H), 3.90-4.08 (m, 2H), 3.36-3.50 (m, 1H), 2.65-2.78 (m, 2H), 2.15-2.30 (m, 5H), 1.86-2.02 (m, 1H), 1.44-1.64 (m, 1H), 1.03 (t, J=6.68 Hz, 2H);

Melting point: 70-84° C.

EXAMPLE 37-02

1-({6-[3-(4-fluoro-3-methylphenyl)propoxy]-1-methyl-3,4-dihydronaphthalen-2-yl}methyl)azetidine-3-carboxylic acid TLC: Rf 0.26(chloroform:methanol:aqueous ammonia=80:20:4);

$^1$H-NMR (CD$_3$OD): δ 7.30 (d, J=8.60 Hz, 1H), 6.95-7.1 (m, 2H), 6.81-6.94(m, 1H), 6.75 (dd, J=8.60, 2.75 Hz, 1H), 6.70 (d, J=2.75 Hz, 1H), 4.11-4.27 (m, 4H), 4.08 (s, 2H), 3.94 (t, J=6.22 Hz, 2H), 3.35-3.48 (m, 1H), 2.66-2.78 (m, 4H), 2.15-2.31 (m, 8H), 1.94-2.10 (m, 2H).

Melting point: 149-152° C.

EXAMPLE 37-03

1-{[1-methyl-6-(quinolin-7-ylmethoxy)-3,4-dihydronaphthalen-2-yl]methyl}azetidine-3-carboxylic acid TLC: Rf 0.23 (chloroform:methanol:aqueous ammonia=80:20:4);

$^1$H-NMR(CD$_3$OD): δ 8.83 (dd, J=4.5, 1.0 Hz, 1H), 8.36 (dd, J=8.5, 1.0 Hz, 1H), 8.07 (s, 1H), 7.96 (d, J=8.5 Hz, 1H), 7.68 (d, J=8.5 Hz, 1H), 7.52 (dd, J=8.5, 4.5 Hz, 1H), 7.33 (d, J=8.5 Hz, 1H), 6.83-6.97 (m, 2H), 5.33 (s, 2H), 4.11-4.28 (m, 4H), 4.08 (s, 2H), 3.34-3.52 (m, 1H), 2.66-2.79 (m, 2H), 2.13-2.28 (m, 5H).

EXAMPLE 37-04

1-({6-[3-(2,6-difluorophenyl)propoxy]-1-methyl-3,4-dihydronaphthalen-2-yl}methyl)azetidine-3-carboxylic acid TLC: Rf 0.23 (chloroform:methanol:aqueous ammonia=50:10:1);

$^1$H-NMR(CD$_3$OD): δ 7.31 (d, J=8.6 Hz, 1H), 7.14-7.29 (m, 1H), 6.85-6.95 (m, 2H), 6.74 (dd, J=8.6, 2.6 Hz, 1H), 6.69 (d, J=2.6 Hz, 1H), 4.12-4.27 (m, 4H), 4.10 (s, 2H), 3.99 (t, J=6.0 Hz, 2H), 3.34-3.52 (m, 1H), 2.87 (t, J=7.3 Hz, 2H), 2.72 (t, J=7.2 Hz, 2H), 2.17-2.28 (m, 5H), 1.95-2.10 (m, 2H);

Melting point: 144-150° C.

EXAMPLE 37-05

1-[(1-methyl-6-{3-[2-(trifluoromethyl)phenyl]propoxy}-3,4-dihydronaphthalen-2-yl)methyl]azetidine-3-carboxylic acid TLC: Rf 0.18 (chloroform:methanol:aqueous ammonia=50:10:1);

$^1$H-NMR(CD$_3$OD): δ 7.64 (d, J=7.7 Hz, 1H), 7.49-7.57 (m, 1H), 7.44 (d, J=7.8 Hz, 1H), 7.30-7.39 (m, 2H), 6.78 (dd, J=8.5, 2.7 Hz, 1H), 6.73 (d, J=2.7 Hz, 1H), 4.13-4.26 (m, 4H), 4.10 (s, 2H), 4.02 (t, J=6.2 Hz, 2H), 3.34-3.50 (m, 1H), 2.98 (t, J=7.8 Hz, 2H), 2.73 (t, J=8.1 Hz, 2H), 2.18-2.29 (m, 5H), 1.99-2.14 (m, 2H);

Melting point: 125-127° C.

EXAMPLE 37-06

1-({6-[3-(3,4-dimethylphenyl)propoxy]-1-methyl-3,4-dihydronraphthalen-2-yl}methyl)azetidine-3-carboxylic acid TLC: Rf 0.17 (chloroform:methanol:aqueous ammonia=50:10:1);

$^1$H-NMR(CD$_3$OD): δ 7.31 (d, J=8.4 Hz, 1H), 7.00 (d, J=7.5 Hz, 1H), 6.95 (d, J=1.5 Hz, 1H), 6.89 (dd, J=7.5, 1.5 Hz, 1H), 6.75 (dd, J=8.4, 2.4 Hz, 1H), 6.70 (d, J=2.4 Hz, 1H), 4.12-4.28 (m, 4H), 4.10 (s, 2H), 3.94 (t, J=6.3 Hz, 2H), 3.33-3.49 (m, 1H), 2.66-2.76 (m, 4H), 2.15-2.28 (m, 11H), 1.89-2.09 (m, 2H);

Melting point: 167-172° C.

EXAMPLE 37-07

1-{[1-methyl-6-(1,2,3,4-tetrahydronaphthalen-2-ylmethoxy)-3,4-dihydronaphthalen-2-yl]methyl}azetidine-3-carboxylic acid TLC: Rf 0.31 (chloroform:methanol:aqueous ammonia=80:20:4);

$^1$H-NMR(CD$_3$OD): δ 7.33 (d, J=8.50 Hz, 1H), 7.04-7.06 (m, 4H), 6.81 (dd, J=8.50, 2.50 Hz, 1H), 6.77 (d, J=2.50 Hz, 1H), 4.11-4.24 (m, 4H), 4.08 (s, 2H), 3.96 (d, J=6.50 Hz, 2H), 3.35-3.47 (m, 1H), 2.96 (dd, J=16.00, 5.00 Hz, 1H), 2.80-2.88 (m, 2H), 2.70-2.77 (m, 2H), 2.61 (dd, J=16.00, 10.50 Hz, 1H), 2.19-2.28 (m, 6H), 2.06-2.14 (m, 1H), 1.53-1.64 (m, 1H).

EXAMPLE 37-08

1-({6-[(4'-fluoro-1,1'-biphenyl-4-yl)methoxy]-1-methyl-3,4-dihydronaphthalen-2-yl}methyl)azetidine-3-carboxylic acid TLC: Rf 0.29 (chloroform:methanol:aqueous ammonia=80:20:4);

$^1$H-NMR(DMSO-d$_6$): δ 7.63-7.73 (m, 4H), 7.51 (d, J=8.00 Hz, 2H), 7.28 (t, J=9.00 Hz, 2H), 7.17 (d, J=9.50 Hz, 1H), 6.81-6.85 (m, 2H), 5.13 (s, 2H), 3.13-3.56 (m, 7H), 2.53-2.65 (m, 2H), 2.10-2.21 (m, 2H), 2.01 (s, 3H).

EXAMPLE 37-09

1-({6-[3,3-bis(4-fluorophenyl)propoxy]-1-methyl-3,4-dihydronaphthalen-2-yl}methyl)azetidine-3-carboxylic acid TLC: Rf 0.32 (chloroform:methanol:aqueous ammonia=80:20:4);

$^1$H-NMR(CD$_3$OD): δ 7.25-7.32 (m, 5H), 6.99 (t, J=9.00 Hz, 4H), 6.69 (dd, J=8.50, 2.50 Hz, 1H), 6.65 (d, J=2.50 Hz, 1H), 4.14-4.31 (m, 5H), 4.10 (s, 2H), 3.87 (t, J=6.00 Hz, 2H), 3.38-3.49 (m, 1H), 2.66-2.74 (m, 2H), 2.42-2.51 (m, 2H), 2.17-2.27 (m, 5H).

EXAMPLE 37-10

1-{[1-methyl-6-(5-phenylpentyloxy)-3,4-dihydro-2-naphthalenyl]methyl}-3-azetidinecarboxylic acid TLC: Rf 0.25 (chloroform:methanol:aqueous ammonia=80:20:4)

$^1$H-NMR(CD$_3$OD): δ 7.30 (d, J=8.50 Hz, 1H), 7.20-7.27 (m, 2H), 7.09-7.19 (m, 3H), 6.74 (dd, J=8.50, 2.50 Hz, 1H), 6.70 (d, J=2.50 Hz, 1H), 4.12-4.26 (m, 4H), 4.09 (s, 2H), 3.96 (t, J=6.50 Hz, 2H), 3.36-3.49 (m, 1H), 2.67-2.76 (m, 2H), 2.63 (t, J=8.00 Hz, 2H), 2.17-2.28 (m, 5H), 1.73-1.84 (m, 2H), 1.62-1.72 (m, 2H), 1.43-1.55 (m, 2H);

Melting point: 129-133° C.

EXAMPLE 37-11

1-[(6-{3-[4-chloro-2-(trifluoromethyl)phenyl]propoxy}-1-methyl-3,4-dihydronaphthalen-2-yl)methyl]azetidine-3-carboxylic acid TLC: Rf 0.24(chloroform:methanol:aqueous ammonia=80:20:4);

$^1$H-NMR(CD$_3$OD): δ 7.64 (d, J=2.56 Hz, 1H), 7.55 (dd, J=8.23, 2.56 Hz, 1H), 7.46 (d, J=8.23 Hz, 1H), 7.32 (d, J=8.23 Hz, 1H), 6.77 (dd, J=8.23, 2.74 Hz, 1H), 6.72 (d, J=2.74 Hz, 1H), 4.09-4.24 (m, 4H), 4.06 (s, 2H), 4.03 (t, J=6.04 Hz, 2H), 3.33-3.49 (m, 1H), 2.88-3.03 (m, 2H), 2.64-2.79 (m, 2H), 2.16-2.30 (m, 5H), 1.98-2.14 (m, 2H);

Melting point: 127-128° C.

EXAMPLE 37-12

1-{[6-(1,1'-biphenyl-3-ylmethoxy)-1-methyl-3,4-dihydronaphthalen-2-yl]methyl}azetidine-3-carboxylic acid hydrochloride TLC: Rf 0.15 (n-butanol:acetic acid:water=20:4:1);

$^1$H-NMR(CD$_3$OD): δ 7.67 (s, 1H), 7.54-7.62 (m, 3H), 7.39-7.47 (m, 4H), 7.30-7.36 (m, 2H), 6.89 (dd, J=8.70, 2.38 Hz, 1H), 6.85 (d, J=2.38 Hz, 1H), 5.17 (s, 2H), 4.21-4.43 (m, 4H), 4.16 (s, 2H), 3.63-3.81 (m, 1H), 2.69-2.78 (m, 2H), 2.14-2.30 (m, 5H);

Melting point: 119-120° C.

EXAMPLE 37-13

1-[(6-{3-[2,5-bis(trifluoromethyl)phenyl]propoxy}-1-methyl-3,4-dihydronaphthalen-2-yl)methyl]azetidine-3-carboxylic acid TLC: Rf 0.25(chloroform:methanol:aqueous ammonia=80:20:4);

$^1$H-NMR(CD$_3$OD): δ 7.87 (d, J=8.23 Hz, 1H), 7.77 (s, 1H), 7.68 (d, J=8.23 Hz, 1H), 7.32 (d, J=8.60 Hz, 1H), 6.77 (dd, J=8.60, 2.38 Hz, 1H), 6.72 (d, J=2.38 Hz, 1H), 4.12-4.27 (m, 4H), 4.09 (s, 2H), 4.04 (t, J=5.95 Hz, 2H), 3.35-3.48 (m, 1H), 3.03-3.11 (m, 2H), 2.69-2.77 (m, 2H), 2.20-2.29 (m, 5H), 2.03-2.17 (m, 2H);

Melting point: 119-124° C.

EXAMPLE 37-14

1-({1-methyl-6-[3-(2,4,5-trifluorophenyl)propoxy]-3,4-dihydronaphthalen-2-yl}methyl)azetidine-3-carboxylic acid TLC: Rf 0.26(chloroform:methanol:aqueous ammonia=80:20:4);

$^1$H-NMR(CD$_3$OD): δ 7.30 (d, J=8.60 Hz, 1H), 7.14-7.26 (m, 1H), 7.02-7.13 (m, 1H), 6.75 (dd, J=8.60, 2.56 Hz, 1H), 6.70 (d, J=2.56 Hz, if), 4.04-4.22 (m, 4H), 4.02 (s, 2H), 3.98 (t, J=6.04 Hz, 2H), 3.32-3.46 (m, 1H), 2.80 (t, J=7.59 Hz, 2H), 2.66-2.75 (m, 2H), 2.15-2.29 (m, 5H), 1.96-2.11 (m, 2H);

Melting point: 159-164° C.

EXAMPLE 37-15

1-[(6-{3-[4-fluoro-3-(trifluoromethyl)phenyl]propoxy}-1-methyl-3,4-dihydronaphthalen-2-yl)methyl]azetidine-3-carboxylic acid TLC: Rf 0.29(chloroform:methanol:aqueous ammonia=80:20:4);

$^1$H-NMR(CD$_3$OD): δ 7.45-7.55 (m, 2H), 7.31 (d, J=8.60 Hz, 1H), 7.21 (t, J=10.43 Hz, 1H), 6.77 (dd, J=8.60, 2.65 Hz, 1H), 6.70 (d, J=2.65 Hz, 1H), 4.11-4.27 (m, 4H), 4.08 (s, 2H), 3.97 (t, J=6.13 Hz, 2H), 3.33-3.50 (m, 1H), 2.80-2.91 (m, 2H), 2.66-2.78 (m, 2H), 2.16-2.29 (m, 5H), 2.00-2.13 (m, 2H).

EXAMPLE 37-16

1-[(6-{3-[4-fluoro-2-(trifluoromethyl)phenyl]propoxy}-1-methyl-3,4-dihydronaphthalen-2-yl)methyl]azetidine-3-carboxylic acid TLC: Rf 0.26(chloroform:methanol:aqueous ammonia=80:20:4);

$^1$H-NMR(CD$_3$OD): δ 7.48 (dd, J=8.60, 5.49 Hz, 1H), 7.39 (dd, J=9.24, 2.65 Hz, 1H), 7.24-7.34 (m, 2H), 6.77 (dd, J=8.60, 2.56 Hz, 1H), 6.72 (d, J=2.56 Hz, 1H), 4.11-4.27 (m, 4H), 4.08 (s, 2H), 4.02 (t, J=6.04 Hz, 2H), 3.33-3.49 (m, 1H), 2.90-3.03 (m, 2H), 2.66-2.78 (m, 2H), 2.16-2.32 (m, 5H), 1.93-2.13 (m, 2H);

Melting point: 126-128° C.

EXAMPLE 37-17

1-({1-methyl-6-[3-(2,3,4-trifluorophenyl)propoxy]-3,4-dihydronaphthalen-2-yl}methyl)azetidine-3-carboxylic acid TLC: Rf 0.25(chloroform:methanol:aqueous ammonia=80:20:4);

$^1$H-NMR(DMSO-d$_6$): δ 7.09-7.30 (m, 3H), 6.65-6.75 (m, 2H), 3.94 (t, J=6.13 Hz, 2H), 3.38 (s, 2H), 3.09-3.22 (m, 5H), 2.78 (t, J=7.50 Hz, 2H), 2.53-2.62 (m, 2H), 2.10-2.19 (n, 2H), 1.92-2.04 (m, 5H);

Melting point: 151-155° C.

EXAMPLE 37-18

1-({1-methyl-6-[3-(3,4,5-trifluorophenyl)propoxy]-3,4-dihydronaphthalen-2-yl}methyl)azetidine-3-carboxylic acid TLC: Rf 0.29(chloroform:methanol:aqueous ammonia=80:20:4); δ

$^1$H-NMR(CD$_3$OD): δ 7.31 (d, J=8.42 Hz, 1H), 6.93-7.03 (dd, J=9.00, 7.00 Hz, 2H), 6.76 (dd, J=8.42, 2.74 Hz, 1H), 6.71 (d, J=2.74 Hz, 1H), 4.09-4.26 (m, 4H), 4.07 (s, 2H), 3.97 (t, J=6.04 Hz, 2H), 3.33-3.51 (m, 1H), 2.75-2.84 (m, 2H), 2.72 (t, J=8.41 Hz, 2H), 2.17-2.29 (m, 5H), 1.98-2.13 (m, 2H);

Melting point: 140-144° C.

EXAMPLE 37-19

1-({6-[3-(4-fluoro-2,6-dimethylphenyl)propoxy]-1-methyl-3,4-dihydronaphthalen-2-yl}methyl)azetidine-3-carboxylic acid TLC: Rf 0.24(chloroform:methanol:aqueous ammonia=80:20:4);

$^1$H-NMR(CD$_3$OD): δ 7.32 (d, J=8.60 Hz, 1H), 6.78 (dd, J=8.60, 2.84 Hz, 1H), 6.74 (d, J=2.84 Hz, 1H), 6.71 (d, J=9.15 Hz, 2H), 4.11-4.25 (m, 4H), 4.07 (s, 2H), 4.02 (t, J=5.85 Hz, 2H), 3.35-3.49 (m, 1H), 2.77-2.86 (m, 2H), 2.69-2.76 (m, 2H), 2.31 (s, 6H), 2.17-2.28 (m, 5H), 1.81-1.98 (m, 2H);

Melting point: 144-146° C.

EXAMPLE 37-20

1-({6-[3-(3-chloro-4-fluorophenyl)propoxy]-1-methyl-3,4-dihydronaphthalen-2-yl}methyl)azetidine-3-carboxylic acid TLC: Rf 0.25(chloroform:methanol:aqueous ammonia=80:20:4);

$^1$H-NMR(CD$_3$OD): δ 7.27-7.34 (m, 2H), 7.05-7.20 (m, 2H), 6.75 (dd, J=8.51, 2.65 Hz, 1H), 6.70 (d, J=2.65 Hz, 1H), 4.11-4.27 (m, 4H), 4.08 (s, 2H), 3.96 (t, J=6.13 Hz, 2H), 3.34-3.48 (m, 1H), 2.67-2.83 (m, 4H), 2.20-2.29 (m, 5H), 1.98-2.10 (m, 2H);

Melting point: 118-119° C.

EXAMPLE 37-21

1-({6-[3-(4-chloro-3-fluorophenyl)propoxy]-1-methyl-3,4-dihydronaphthalen-2-yl}methyl)azetidine-3-carboxylic acid TLC: Rf 0.26(chloroform:methanol:aqueous ammonia=80:20:4)

$^1$H-NMR(CD$_3$OD): δ 7.30-7.37 (m, 2H), 7.10 (dd, J=10.43, 2.01 Hz, 1H), 7.02 (dd, J=7.96, 2.01 Hz, 1H), 6.75 (dd, J=8.60, 2.65 Hz, 1H), 6.71 (d, J=2.65 Hz, 1H), 4.10-4.26 (m, 4H), 4.07 (s, 2H), 3.97 (t, J=6.22 Hz, 2H), 3.36-3.50 (m, 1H), 2.77-2.86 (m, 2H), 2.66-2.76 (m, 2H), 2.16-2.30 (m, 5H), 1.99-2.12 (m, 2H);

Melting point: 126-128° C.

EXAMPLE 37-22

1-({6-[3-(4-chloro-2-fluorophenyl)propoxy]-1-methyl-3,4-dihydronaphthalen-2-yl}methyl)azetidine-3-carboxylic acid TLC: Rf 0.24(chloroform:methanol:aqueous ammonia=80:20:4);

$^1$H-NMR(CD$_3$OD): δ 7.31 (d, J=8.42 Hz, 1H), 7.24 (t, J=8.42 Hz, 1H), 7.06-7.16 (m, 2H), 6.75 (dd, J=8.42, 2.47 Hz, 1H), 6.70 (d, J=2.47 Hz, 1H), 4.10-4.27 (m, 4H), 4.07 (s, 2H), 3.97 (t, J=6.13 Hz, 2H), 3.35-3.50 (m, 1H), 2.78-2.87 (m, 2H), 2.67-2.76 (m, 2H), 2.15-2.32 (m, 5H), 1.96-2.12 (m, 2H);

Melting point: 160-162° C.

EXAMPLE 37-23

1-[(6-{3-[4-chloro-3-(trifluoromethyl)phenyl]propoxy}-1-methyl-3,4-dihydronaphthalen-2-yl)methyl]azetidine-3-carboxylic acid hydrochloride TLC: Rf 0.20 (n-butanol:acetic acid:water=20:4:1)

$^1$H-NM(CD$_3$OD): δ 7.60 (d, J=1.10 Hz, 1H), 7.41-7.53 (m, 2H), 7.32 (d, J=8.60 Hz, 1H), 6.75 (dd, J=8.60, 2.38 Hz, 1H), 6.70 (d, J=2.38 Hz, 1H), 4.20-4.45 (m, 4H), 4.16 (s, 2H), 3.98 (t, J=6.04 Hz, 2H), 3.59-3.78 (m, 1H), 2.88 (t, J=7.80 Hz, 2H), 2.67-2.77 (m, 2H), 2.18-2.30 (m, 5H), 2.00-2.14 (m, 2H);

Melting point: 120-124° C.

EXAMPLE 37-24

1-({6-[3-(2-chloro-4-fluorophenyl)propoxy]-1-methyl-3,4-dihydronaphthalen-2-yl}methyl)azetidine-3-carboxylic acid hydrochloride TLC: Rf 0.17 (n-butanol:acetic acid:water=20:4:1)

$^1$H-NMR(CD$_3$OD): δ 7.26-7.36 (m, 2H), 7.17 (dd, J=8.78, 2.74 Hz, 1H), 6.98 (td, J=8.42, 2.74 Hz, 1H), 6.77 (dd, J=8.40, 2.38 Hz, 1H), 6.72 (d, J=2.38 Hz, 1H), 4.21-4.41 (m, 4H), 4.16 (s, 2H), 3.99 (t, J=6.13 Hz, 2H), 3.62-3.77 (m, 1H), 2.91 (t, J=7.50 Hz, 2H), 2.73 (t, J=6.30 Hz, 2H), 2.19-2.29 (m, 5H), 2.00-2.12 (m, 2H);

Melting point: 125-127° C.

EXAMPLE 37-25

1-({6-[3-(2-chloro-3,6-difluorophenyl)propoxy]-1-methyl-3,4-dihydronaphthalen-2-yl}methyl)azetidine-3-carboxylic acid TLC: Rf 0.23(chloroform:methanol:aqueous ammonia=80:20:4);

$^1$H-NMR(DMSO-d$_6$): δ 7.35 (td, J=9.01, 4.94 Hz, 1H), 7.26 (td, J=9.01, 4.67 Hz, 1H), 7.14 (d, J=8.23 Hz, 1H), 6.65-6.72 (m, 2H), 3.97 (t, J=5.95 Hz, 2H), 3.38 (s, 2H), 3.13-3.20 (m, 5H), 2.86-2.97 (m, 2H), 2.52-2.62 (m, 2H), 2.09-2.20 (m, 2H), 1.89-2.00 (m, 5H);

Melting point: 156-159° C.

EXAMPLE 37-26

1-({1-methyl-6-[3-(2,4,6-trifluorophenyl)propoxy]-3,4-dihydronaphthalen-2-yl}methyl)azetidine-3-carboxylic acid TLC: Rf 0.21(chloroform:methanol:aqueous ammonia=80:20:4);

$^1$H-NMR(CD$_3$OD): δ 7.30 (d, J=8.50 Hz, 1H), 6.80 (dd, J=9.00, 8.00 Hz, 2H), 6.73 (dd, J=8.50, 2.50 Hz, 1H), 6.68 (d, J=2.50 Hz, 1H), 4.11-4.25(m, 4H), 4.07(s, 2H), 3.98(t, J=6.00 Hz, 2H), 3.35-3.48 (m, 1H), 2.84 (t, J=7.50 Hz, 2H), 2.68-2.76 (m, 2H), 2.18-2.28 (m, 5H), 1.97-2.08 (m, 2H);

Melting point: 159-162° C.

EXAMPLE 37-27

1-{[6-(2,2-dimethyl-3-phenylpropoxy)-1-methyl-3,4-dihydronaphthalen-2-yl]methyl}azetidine-3-carboxylic acid hydrochloride TLC: Rf 0.19 (n-butanol:acetic acid:water=20:4:1)
$^1$H-NMR(CD$_3$OD): δ 7.34 (d, J=8.23 Hz, 1H), 7.03-7.26 (m, 5H), 6.70-6.85 (m, 2H), 4.20-4.50 (m, 4H), 4.17 (s, 2H), 3.60-3.81 (m, 1H), 3.54 (s, 2H), 2.67-2.81 (m, 4H), 2.20-2.32 (m, 5H), 1.01 (s, 6H);
Melting point: 124-127° C.

EXAMPLE 37-28

1-({1-methyl-6-[2-(1,2,3,4-tetrahydronaphthalen-1-yl)ethoxy]-3,4-dihydronaphthalen-2-yl}methyl)azetidine-3-carboxylic acid TLC: Rf 0.37(chloroform:methanol:aqueous ammonia=80:20:4);
$^1$H-NMR(CD$_3$OD): δ 7.33 (d, J=8.50 Hz, 1H), 7.09-7.1.5 (m, 1H), 7.01-7.08 (m, 3H), 6.79 (dd, J=8.50, 2.50 Hz, 1H), 6.74 (d, J=2.50 Hz 1H), 4.03-4.25 (m, 8H), 3.34-3.49 (m, 1H), 3.01-3.10 (m, 1H), 2.69-2.80 (m, 4H), 2.09-2.29 (m, 6H), 1.70-2.03 (m, 5H);
Melting point: 99-107° C.

EXAMPLE 37-29

1-({6-[2-(2,3-dihydro-1H-inden-1-yl)ethoxy]-1-methyl-3,4-dihydronaphthalen-2-yl}methyl)azetidine-3-carboxylic acid TLC: Rf 0.32(chloroform:methanol:aqueous ammonia=80:20:4);
$^1$H-NMR(CD$_3$OD): δ 7.33 (d, J=8.50 Hz, 1H), 7.16-7.22 (m, 2H), 7.08-7.13 (m, 2H), 6.79 (dd, J=8.50, 2.50 Hz, 1H), 6.75 (d, J=2.50 Hz, 1H), 4.14-4.25 (m, 4H), 4.07-4.14 (m, 4H), 3.35-3.48 (m, 1H), 3.28-3.32 (m, 1H), 2.69-3.01 (m, 4H), 2.19-2.39 (m, 7H), 1.71-1.91 (m, 2H);
Melting point: 163-167° C.

EXAMPLE 37-30

1-({6-[2-(5-fluoro-2,3-dihydro-1H-inden-1-yl)ethoxy]-1-methyl-3,4-dihydronaphthalen-2-yl}methyl)azetidine-3-carboxylic acid TLC: Rf 0.29(chloroform:methanol:aqueous ammonia=80:20:4);
$^1$H-NMR(CD$_3$OD): δ 7.32 (d, J=8.50 Hz, 1H), 7.16 (dd, J=8.50, 5.00 Hz, 1H), 6.91 (dd, J=9.00, 2.50 Hz, 1H), 6.76-6.87 (m, 2H), 6.74 (d, J=2.50 Hz, 1H), 4.05-4.24 (m, 8H), 3.34-3.47 (m, 1H), 3.28-3.32 (m, 1H), 2.69-3.02 (m, 4H), 2.19-2.43 (m, 7H), 1.76-1.92 (m, 2H);
Melting point: 149-153° C.

EXAMPLE 37-31

1-({6-[2-(4-isobutylphenyl)ethyl]-1-methyl-3,4-dihydronaphthalen-2-yl}methyl)azetidine-3-carboxylic acid hydrochloride TLC: Rf0.19 (n-butanol:acetic acid:water=20:4:1)
$^1$H-NMR(CD$_3$OD): δ 7.29 (d, J=7.87 Hz, 1H), 6.99-7.10 (m, 5H), 6.94 (s, 1H), 4.24-4.46 (m, 4H), 4.17 (s, 2H), 3.53-3.86 (m, 1H), 2.84-2.86 (m, 4H), 2.63-2.75 (m, 2H), 2.41 (d, J=7.14 Hz, 2H), 2.15-2.30 (m, 5H), 1.68-1.90 (m, 1H), 0.87 (d, J=6.77 Hz, 6H);
Melting point: 154-157° C.

EXAMPLE 37-32

1-{[9-methyl-3-(4-phenylbutoxy)-6,7-dihydro-5H-benzo[7]annulen-8-yl]methyl}azetidine-3-carboxylic acid

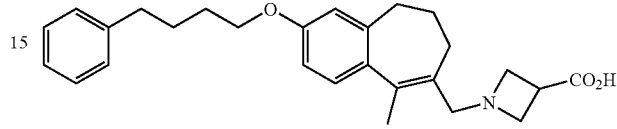

TLC: Rf 0.42(chloroform:methanol:aqueous ammonia=80:20:4);
MS (m/z): 420 (M+H)$^+$, 319, 187.

REFERENCE EXAMPLE 01

6-(benzyloxy)-3,4-dihydronaphthalen-1(2H)-one

To a solution of 6-hydroxy-3,4-dihydronaphthalen-1(2H)-one (24.3 g) in acetone (160 mL), benzyl bromide (29.4 mL) and potassium carbonate (31.1 g) were added at room temperature, followed by stirring at 40° C. for 3.5 hours. After filtering off the insoluble matters and concentrating the mixture, the residue was washed with a mixed solvent of tert-butyl methyl ether-hexane (1:4) to thereby give the title compound (34.5 g) having the following physical properties.
TLC: Rf 0.38 (hexane:ethyl acetate=3:1).

REFERENCE EXAMPLE 02

7-(benzyloxy)-4-methyl-1,2-dihydronaphthalene

To a solution of the compound (34.5 g) prepared in Reference Example 01 in tetrahydrofuran (300 mL), methyl magnesium bromide (3 M diethyl ether solution, 55 mL) was added at 0° C., followed by stirring at room temperature for 1 hour. Then, the reaction mixture was cooled to 0° C. and poured into ice-saturated aqueous ammonium chloride. After adding 2 N hydrochloric acid, the mixture was stirred at room temperature for 3 hours. Then, the mixture was extracted with ethyl acetate and the organic layer was successively washed with water and a saturated aqueous sodium chloride solution, dried and concentrated. The residue thus obtained was purified by silica gel column chromatography (hexane:ethyl acetate=10:1) to thereby give the title compound (24.8 g) having the following physical properties.
TLC: Rf 0.57 (hexane:ethyl acetate=15:1).

REFERENCE EXAMPLE 03

6-(benzyloxy)-1-methyl-3,4-dihydronaphthalene-2-carboaldehyde

To phosphorus oxychloride (26.7 g), N,N-dimethylformamide (60 mL) was dropped at 0° C., followed by stirring for 20 minutes. Then, a solution of the compound (24.8 g) prepared in Reference Example 02 in dichloromethane (60 mL) was slowly added dropwise thereto, followed by stirring at room temperature for 90 minutes. The reaction mixture was cooled to 0° C., poured into ice and then allowed to stand for a while. Next, the mixture was extracted with a mixed solvent of hexane-ethyl acetate (1:2). The organic layer was successively washed with water and a saturated aqueous sodium chloride solution, dried and concentrated. The solid thus obtained was washed with tert-butyl methyl ether to thereby give the title compound (19.9 g) having the following physical properties.

TLC: Rf 0.50 (hexane:ethyl acetate=3:1).

REFERENCE EXAMPLE 04

6-hydroxy-1-methyl-3,4-dihydronaphthalene-2-carboaldehyde

To thioanisole (35 mL), trifluoroacetic acid (140 mL) was added at 0° C. Then, the compound (9.17 g) prepared in Reference Example 03 was added in portions thereto, followed by stirring at room temperature for 4 hours. The reaction mixture was poured into ice and then a 5 N aqueous sodium hydroxide solution was added. After washing tert-butyl methyl ether, 1 N hydrochloric acid was added to the aqueous layer, followed by extraction with ethyl acetate. The organic layer was dried and concentrated. The obtained residue was purified by silica gel column chromatography (hexane:ethyl acetate=5:1 to 2:1) to thereby give the title compound (6.03 g) having the following physical properties.

TLC: Rf 0.26 (hexane:ethyl acetate=3:1).

REFERENCE EXAMPLE 05

6-[3-(4-fluorophenyl)propoxy]-1-methyl-3,4-dihydronaphthalene-2-carboaldehyde

The procedure of Reference Example 01 was similarly carried out, except for using the compound prepared in Reference Example 04 as a substitute for 6-hydroxy-3,4-dihydronaphthalen-1(2H)-one and 1-bromo-3-(4-fluorophenyl)propane as a substitute for benzyl bromide to thereby give the title compound having the following physical properties.

TLC: Rf 0.40 (hexane:ethyl acetate=3:1);
$^1$H-NMR (CDCl$_3$): δ 10.32 (s, 1H), 7.48 (d, J=8.50 Hz, 1H), 7.16 (dd, J=8.50, 5.50 Hz, 2H), 6.97 (t, J=8.50 Hz, 2H), 6.78 (dd, J=8.50, 2.50 Hz, 1H), 6.73 (d, J=2.50 Hz, 1H), 3.99 (t, J=6.00 Hz, 2H), 2.79 (t, J=7.50 Hz, 2H), 2.69-2.75 (m, 2H), 2.47-2.56 (m, 5H), 2.04-2.14 (m, 2H).

REFERENCE EXAMPLE 06

5-oxo-5,6,7,8-tetrahydronaphthalen-2-yl trifluoromethanesulfonate

To a solution of 6-hydroxy-3,4-dihydronaphthalen-1(2H)-one (2.0 g) in dichloromethane (20 mL), triethylamine (5.16 mL) and trifluoromethanesulfonic anhydride (2.49 mL) were added at −78° C., followed by stirring at 0° C. for 1 hour. After adding a saturated aqueous sodium hydrogencarbonate solution, the mixture was stirred and extracted with diethyl ether. The organic layer was successively washed with 1 N hydrochloric acid, a saturated aqueous sodium hydrogencarbonate solution and a saturated aqueous sodium chloride solution, dried and concentrated. The residue thus obtained was purified by silica gel column chromatography (hexane:ethyl acetate=9:1) to thereby give the title compound (2.34 g) having the following physical properties.

TLC: Rf 0.34 (hexane:ethyl acetate=85:15).

REFERENCE EXAMPLE 07

6-[(4-isobutylphenyl)ethynyl]-3,4-dihydronaphthalen-1(2H)-one

To cuprous iodide (48 mg), a solution of the compound (353 mg) prepared in Reference Example 06 in N,N-dimethylformamide (3 mL), triethylamine (279 µl) and a solution of 1-ethynyl-4-isobutylbenzene (158 mg) in N,N-dimethylformamide (5 mL) were added, followed by stirring at room temperature for 5 minutes. Next, tetrakis(triphenylphosphine) palladium (0) (58 mg) was added thereto, followed by stirring for 19 hours. After adding 1 N hydrochloric acid, the mixture was extracted with ethyl acetate. The organic layer was successively washed with 1 N hydrochloric acid, a saturated aqueous sodium hydrogencarbonate solution and a saturated aqueous sodium chloride solution, dried and concentrated. The residue thus obtained was purified by silica gel column chromatography (hexane:ethyl acetate=95:5) to thereby give the title compound (209 mg) having the following physical properties.

TLC: Rf 0.35 (hexane:ethyl acetate=9:1).

REFERENCE EXAMPLE 08

6-[(4-isobutylphenyl)ethynyl]-1-methyl-1,2,3,4-tetrahydronaphthalen-1-ol

To a solution of the compound (200 mg) prepared in Reference Example 07 in tetrahydrofuran (5 mL), methyl magnesium bromide (3 M diethyl ether solution, 0.33 mL) was added at 0° C., followed by stirring for 30 minutes. After adding water, the reaction mixture was extracted with ethyl acetate. The organic layer was washed with a saturated aqueous sodium chloride solution, dried and concentrated. The residue thus obtained was purified by silica gel column chromatography (hexane:ethyl acetate=87:13) to thereby give the title compound (154 mg) having the following physical properties.

TLC: Rf 0.36 (hexane:ethyl acetate=4:1).

REFERENCE EXAMPLE 09

6-[(4-isobutylphenyl)ethyl]-1-methyl-1,2,3,4-tetrahydronaphthalen-1-ol

To a solution of the compound (150 mg) prepared in Reference Example 08 in ethanol (4 mL), 10% palladium on carbon (15 mg) was added, followed by stirring under a hydrogen gas stream for 15 minutes. After filtering off the catalyst through Celite, the filtrate was concentrated to thereby give the title compound (153 mg) having the following physical properties.

TLC: Rf 0.40 (hexane:ethyl acetate=4:1).

REFERENCE EXAMPLE 10

7-[2-(4-isobutylphenyl)ethyl]-4-methyl-1,2-dihydronaphthalene

To a solution of the compound (150 mg) prepared in Reference Example 09 in dichloromethane (3 mL), p-toluenesulfonic acid monohydrate (1 mg) was added, followed by stirring at room temperature for 2 hours. The reaction mixture was concentrated and purified by silica gel column chromatography (hexane) to thereby give the title compound (129 mg) having the following physical properties.

TLC: Rf 0.35 (hexane).

REFERENCE EXAMPLE 11

6-[2-(4-isobutylphenyl)ethyl]-1-methyl-3,4-dihydronaphthalene-2-carboaldehyde

The procedure of Reference Example 03 was similarly carried out, except for using the compound prepared in Reference Example 10 as a substitute for the compound prepared in Reference Example 02 to thereby give the title compound having the following physical properties.

TLC: Rf 0.66 (hexane:ethyl acetate=3:1);

$^1$H-NMR (CDCl$_3$): δ 10.35 (s, 1H), 7.46 (d, J=7.87 Hz, 1H), 7.00-7.14 (m, 6H), 2.90 (s, 4H), 2.71 (t, J=7.32 Hz, 2H), 2.42-2.56 (m, 7H), 1.76-1.93 (m, 1H), 0.90 (d, J=6.59 Hz, 6H).

REFERENCE EXAMPLE 12

3-(methoxymethoxy)benzaldehyde

To a solution of 3-hydroxybenzaldehyde (5.0 g) in acetone (120 mL), potassium carbonate (8.5 g) and methoxymethyl chloride (4.0 g) were added, followed by stirring at 50° C. for 6 hours. The reaction mixture was concentrated and water was added thereto, followed by extraction with ethyl acetate. The organic layer was washed with a saturated aqueous sodium chloride solution, dried and concentrated. The residue thus obtained was purified by silica gel column chromatography (hexane:ethyl acetate=10:1) to thereby give the title compound (6.0 g) having the following physical properties.

TLC: Rf 0.56(hexane:ethyl acetate=3:1).

REFERENCE EXAMPLE 13 ethyl 5-(3-hydroxyphenyl)pentanoate

To a solution of vinyl magnesium bromide (1 M tetrahydrofuran solution, 24.4 mL) in tetrahydrofuran (50 mL), the compound (2.7 g) prepared in Reference Example 12 was added at −20° C., followed by stirring for 1 hour. After adding water, the reaction mixture was concentrated. Further, a saturated aqueous ammonium chloride solution was added thereto and the mixture was extracted with ethyl acetate. The organic layer was washed with a saturated aqueous sodium chloride solution, dried and concentrated. To a solution of the obtained residue in toluene (50 mL), triethyl orthoacetate (14.9 mL) and propionic acid (122 μL) were added, followed by stirring at 130° C. for 2 hours. The reaction mixture was concentrated and the obtained residue was purified by silica gel column chromatography (hexane:ethyl acetate=9:1). To a solution of the compound thus obtained in methanol (60 mL), 10% palladium on carbon (285 mg) was added, followed by stirring under a hydrogen gas stream for 2 hours. After filtering off the catalyst through Celite, the filtrate was concentrated. To a solution of the compound thus obtained in ethanol (40 mL), conc. hydrochloric acid (4 mL) was added, followed by stirring at 70° C. for 1 hour. By concentrating the reaction mixture, the title compound (2.37 g) having the following physical properties was obtained.

TLC: Rf 0.37 (hexane:ethyl acetate=3:1).

REFERENCE EXAMPLE 14

5-[3-(4-phenylbutoxy)phenyl]pentanoic acid

The procedure of Reference Example 01 was similarly carried out, except for using the compound (1.13 g) prepared in Reference Example 13 as a substitute for 6-hydroxy-3,4-dihydronaphthalen-1(2H)-one while using 1-bromo-4-phenylbutane (1.63 g) as a substitute for benzyl bromide. A solution of the compound thus obtained in a mixed solvent of methanol (2 mL)-tetrahydrofuran (10 mL), 5 N sodium hydroxide (10 mL) was added, followed by stirring for 3 days. After adding 5 N hydrochloric acid, the mixture was extracted with dichloromethane. The organic layer was dried and concentrated to thereby give the title compound (1.45 g) having the following physical properties.

TLC: Rf 0.56 (hexane:ethyl acetate=1:1).

REFERENCE EXAMPLE 15

2-(4-phenylbutoxy)-6,7,8,9-tetrahydro-5H-benzo[7]annulen-5-one

To a solution of the compound (100 mg) prepared in Reference Example 14 in dichloromethane (1 mL), a catalytic amount of N,N-dimethylformamide and oxalyl chloride (40 μL) were added, followed by stirring for 30 minutes. The reaction mixture was concentrated. To a solution of the residue thus obtained in toluene (2 mL), stannic chloride (43 μL) was added, followed by stirring at room temperature for 1 hour. After adding water, the reaction mixture was extracted with ethyl acetate. The organic layer was dried and concentrated and the obtained residue was purified by silica gel column chromatography (hexane:ethyl acetate=8:1 to 6:1) to thereby give the title compound (88 mg) having the following physical properties.

TLC: Rf 0.34 (hexane:ethyl acetate=6:1).

REFERENCE EXAMPLE 16

9-methyl-3-(4-phenylbutoxy)-6,7-dihydro-5H-benzo[7]annulene-8-carboaldehyde

The procedures of Reference Example 2 and Reference Example 3 were followed in this order but using the compound prepared in Reference Example 15 as a substitute for the compound prepared in Reference Example 1 to thereby give the title compound having the following physical properties.

TLC: Rf 0.47 (hexane:ethyl acetate=6:1).

BIOLOGICAL EXAMPLES

The pharmacological action of the present invention compounds have been confirmed by the following Biological Examples. All operations were carried out by conventional methods by preparing gene-highly expressing cells based on the fundamental genetic engineering techniques. Also, the measuring methods in the present invention for evaluating the compounds of the present invention were carried out, for example, by improving measuring methods, measuring accuracy and/or measuring sensitivity. The details are described below. The preparation of histological preparation was also carried out by conventional methods based on the fundamental genetic engineering techniques with an appropriate modification.

Biological Example 1

Measurement of Inhibitory Activity of the Present Invention Compound on Binding of [$^3$H]-S1P to EDG-6

Method:

Firstly, EDG-6-overexpressing cells were seeded at a density of 2×10$^5$ cells/well into a 12-well plate. After 12 hours, the cells were washed with 0.5 mL of an assay buffer twice. In a saturation binding test for determining the $K_D$ value and the $B_{max}$ value, the cells were incubated in 0.4 mL of an assay buffer containing D-erythro-sphingosine-3-[$^3$H]-1-phosphate at various concentrations and 2 µL of 0.01 N NaOH for 60 minutes on ice. Then, the wells were washed with 0.8 mL of the assay buffer twice and the whole cells were disrupted by adding 0.1 mL of 0.5% TCA (trichloroacetic acid), 0.4 mL of a lysis buffer (2% Na$_2$CO$_3$, 4% NaOH, 0.1% SDS) and 0.1 mL of 1 N hydrochloric acid. Then, 0.5 mL of the lysed solution was collected in a glass vial (Packard) with a pipette. After adding 7 mL of ACSII (Amersham), the mixture was thoroughly stirred and the radioactivity was measured with a liquid scintillation counter (TR1-CARB 2900TR Packard), thereby determining the $K_D$ value. The value of the nonspecific binding was determined by adding unlabeled S1P at a final concentration of 25 µM as a substitute for 0.01 N NaOH. In a competitive binding test for determining the $K_i$ value based on the $K_D$ value thus determined, cells were incubated in 0.4 mL of an assay buffer containing 5 nM of D-erythro-sphingosine-3-[$^3$H]-1-phosphate and 0 to 1 µM of a test compound for 60 minutes on ice. The subsequent procedures following washing were carried out as in the saturation binding test and the radioactivity was measured as described above.

Results:

The present invention compounds showed inhibitory activities of 50% or higher on the binding of S1P to EDG-6 at 100 µmol/L. For example, the $K_i$ value of 3-[3-(4-(5-phenylpentyloxy)phenyl)propylamino]propanoic acid was 0.352 µmol/L.

Biological Example 2

Measurement of Inhibitory Activity of the Present Invention Compound on Binding of [$^3$H]-PhS1P to EDG-6

Method:

A similar experiment was carried out by using cell membrane fraction of an EDG-6-overexpressing CHO. Using 1 mg protein/mL of the membrane fraction, reaction was carried out in a 96-well plate. Into each well, 80 µL of a vehicle (DMSO) solution diluted with 2× binding buffer (100 mmol/L Tris pH 7.5, 200 mM NaCl, 30 mM NaF, 1% BSA) or a ligand solution having a twice higher concentration and 40 µL of 10 nmol/L [$^3$H]-PhS1P (5,5,6,6,-tetralithium phytosphingosine 1 phosphate: This was prepared in the following manner. A compound (anti-7: tert-butyl (4S)-4-[(1S,2R)-1-(benzyloxy)-2-hydroxyhexadec-3-yn-1-yl]-2,2-dimethyl-1,3-oxazolizine-3-carboxylate) prepared in accordance with a method reported in a document (*Tetrahedron Lett.*, 38(34), 6027-6030 (1997)) was reacted with benzyl bromide in tetrahydrofuran in the presence of potassium hexamethyldisilylamide to thereby protect the hydroxy group. Then, it was treated in hydrogen chloride/methanol to removal of acetonide group. The compound thus obtained was reacted with N,N-diethyl-1,5-dihydro-2,4,3-benzodioxaphosphepin-3-amine in dichloromethane in the presence of tetrazole and then oxidized with m-chloroperbenzoic acid. Then, it was reacted in the presence of ASCA-2 catalyst (manufactured by NE Chemcat, 4.5% palladium-0.5% platinum catalyst carried on active carbon, see, Fine Chemical, Oct. 1, 2002, pages 5 to 14) in methanol under a tritium atmosphere. The obtained compound was treated with a 4 N hydrogen chloride/1,4-dioxane solution in dichloromethane to thereby give the desired compound) were added. Further, 40 µl of the membrane fraction solution was added and reacted at room temperature for 60 minutes. After the completion of the reaction, the reaction mixture was filtered by aspiration with a 96-well Unifilter, washed with 50 mL of a washing buffer (50 mmol/L Tris pH7.5, 0.5% BSA) thrice and dried at 60° C. for 45 minutes. Then, 50 µl/well of Micro Scint 20 was added and the plate was covered with Top Seal-P. Next, the radioactivity was measured with Top Count (Perkin Elmer).

Results:

The present invention compounds showed inhibitory activities of 50% or higher on the binding of S1P to EDG-6 at 100 µmol/L.

Biological Example 3

Evaluation of an Agonistic Activity Against EDG of the Present Invention Compound by Monitoring Changes in Intracellular Calcium Ion Concentration [Ca$^{2+}$]$_i$

Method:

Human EDG-1, EDG-3, EDG-5 or EDG-8 gene overexpressing Chinese Hamster Ovary (CHO) cells were cultured in Ham's F12 medium (manufactured by GIBCO BRL) containing 10% FBS (fetal bovine serum), penicillin/streptomycin and blasticidin (5 µg/ml). The cultured cells were incubated in a 5 µM Fura2-AM solution (Ham's F12 medium containing 10% of FBS, 20 mM HEPES buffer (pH7.4) and 2.5 mM probenecid) at 37° C. for 60 minutes. After washing once with Hanks solution containing 20 mM HEPES buffer (pH7.4) and 2.5 mM probenecid, the plate was soaked in the same solution until assay. Then, the plate was set on a fluorescent drug screening system (FDSS 6000; Hamamatsu Photonics) and the intracellular calcium ion concentration was measured without stimulation for 30 seconds. A test compound (final concentration: 1 nM to 10 µM, dimethylsulfoxide (DMSO) solution) was added and S1P (final concentration: 100 nM) was added 5 minutes thereafter. Then, the increase in the intracellular calcium ion concentration was measured before and after the addition of S1P at intervals of 3 seconds (excitation wavelength: 340 nm and 380 nm, fluorescence wavelength: 500 nm).

The agonistic activity of the present invention compound against each EDG was determined by using the peak value due to S1P-stimulation in a well containing DMSO as a substitute for the test compound as a control value (A), comparing the value before the addition of the test compound with the increased value (B) in the fluorescent ratio after the addition, and calculating the increase ratio (%) in the intracellular calcium ion concentration [Ca$^{2+}$]$_i$ as: increase ratio (%)=(B/A)×100. Increase ratios of the test compound at individual concentrations were determined and the EC$_{50}$ was calculated.

Results:

For example, the $EC_{50}$ of 3-[3-(4-(5-phenylpentyloxy)phenyl)propylamino]propanoic acid for EDG-1 was 0.255 µmol/L.

Biological Example 4

Counting the Number of Lymphocyte in Blood (1)

Method:

Test compounds were orally administered to male Sprague-Dawley rats (Charles Riber Laboratories, Japan, Ltd., 6-week-old at using). Four to 72 hours after the administration, the blood was collected from the aorta abdominalis under ether anesthesia. Using a portion of the thus collected blood, the number of blood cells were counted and the number of lymphocyte, neutrophil and platelet were counted. Each group had 4 or 5 animals.

Results:

It was indicated that the present invention compounds lowered the number of lymphocyte in blood, thereby showing a strong lymphocyte homing effect. It was also found out that the effects of lymphopenia of the present invention compounds were sustained even 72 hours after the administration. For example, 3-[3-(4-(5-phenylpentyloxy)phenyl)propylamino]propanoic acid concentration-dependently lowered the number of lymphocyte in blood at 10, 30 and 100 mg/kg 4 hours after the administration.

It is found out that the present invention compounds have an agonistic activity against EDG-1 and an ability to bind to EDG-6 and, moreover, an effect of lymphopenia over a long period of time.

Biological Example 5

Counting the Number of Lymphocyte in Blood (2)

Method:

Test compounds were orally administered to male BALB/c mice. Four to 72 hours after the administration, the blood was collected from the aorta abdominalis under ether anesthesia. The number of the total leucocyte count, the lymphocyte count, the neutrophil count, the erythrocyte count, the platelet count in blood and the hematocrit value were measured with a multipurpose automatic blood cell counter (SF-3000, Sysmex). Evaluation was made by referring the average blood cell count in a vehicle-administered group (vehicle group) as to 100% and calculating the percentage of vehicle from the average blood cell count of each test compound-administered group. Based on the test compound doses and percentages of vehicle, a calibration curve is formed and the dose of the compound required for lowering the blood cell count to 50% was calculated as $ED_{50}$.

Biological Example 6

Counting the Number of Lymphocyte in Blood (3)

Method:

Test compounds of the present invention or a vehicle were orally administered everyday to male Sprague-Dawley rats (Charles Riber Laboratories, Japan, Ltd., 6-week-old at using). Then, the administration of the test compounds or the vehicle was ceased and the recovery speed of the lymphocyte count in blood was monitored with time lapse. For example, the rats were divided into 10 groups and a test compound was administered for 10 days to 5 groups while the vehicle was administered for 10 days to the other 5 groups. After the administration for 10 days, the lymphocytes in blood were counted by using rats of one of the vehicle groups and one of the test compound-administered groups on the days 1, 2, 3, 4 and 5 after cease. The whole blood was collected from the aorta abdominalis under ether anesthesia. Using a portion of the thus collected blood, the number of the blood cells were counted and the lymphocyte count, the neutrophil count and the platelet count were determined by using a multipurpose automatic blood cell counter (SF-3000, Sysmex). Each group had 4 or 5 animals.

Biological Example 7

Study on Effect of Invention Compound of Promoting Lymphocyte Homing into Lymphatic Organ (1: Histological Stain of Lymph Nod)

Method:

Lymph nods were taken out from the Sprague-Dawley rats (Charles Riber Laboratories, Japan, 6-week-old at using) used in Biological Example 4 to which the test compounds or the vehicle had been administered. According to a method commonly used in the art, the tissues were formalin-fixed and tissue pieces were prepared. By using the double staining method with hematoxylin and eosin, the conditions in the lymph tissues, i.e., the cortex, medulla, marginal sinus and lymphatic sinus parts, etc. were observed.

Biological Example 8

Study on Effect of Invention Compound of Promoting Lymphocyte Homing into Lymphatic Organ (1: Count the Lymphocyte in Lymph Organ)

Method:

To male BALB/c mice, test compounds were orally administered. Twenty hours thereafter, the mice were killed by exsanguination under ether anesthesia. Immediately thereafter, various lymph organs such as Peyer's patch and thymus were taken out. Then, lymphocytes were obtained therefrom and subjected to the subsequent analysis. Namely, the cells were stained with the use of anti-CD3 antibody, anti-CD4 antibody, anti-CD8, anti-B220 antibody, etc. and various positive cells were measured by using a flow cytometer.

Biological Example 9

Chemotaxis Assay

Method:

The spleen or lymph nod was taken out from mice and lymphocytes were obtained therefrom in accordance with a method commonly used in the art (*J. Immunol.*, 171, 3500-3507 (2003)). The lymphocytes (for example, $1 \times 10^7$ cells/mL) thus obtained were put on the upper layer of a chemotactic chamber, while S1P or various chemokines such as CCL-5 and CCL-21 were put on the lower layer. Test compounds (either alone or simultaneously) are added to the lower layer or the upper layer and thus the inhibitory or promoting effects on the lymphocyte migration were observed.

Biological Example 10

Phenotype Analysis of Blood Cells

Method:

The whole blood was collected from rats to which test compounds or a vehicle alone had been administered. Then, cells were stained with the use of anti-CD3 antibody, anti-CD45RA antibody, anti-CD4 antibody, anti-CD8a antibody, anti-CD161a antibody and the like. Thus, the effects of the test compounds on the phenotype of blood cells were observed. For example, cells were suspended in a Spitz type test tube and 7-AAD viability dye, FITC-labeled anti-CD3 antibody, FITC-labeled anti-CD45RA antibody, FITC-labeled anti-CD8b antibody, PE-labeled anti-CD4 antibody and FITC-labeled anti-CD161a antibody were added and mixed. Then, the mixture was allowed to stand at room temperature in a dark place for 15 minutes. Next, a hemolytic reagent IO Test 3 Lysing Solution was added, followed by stirring and then they were allowed to stand at room temperature in a dark place for 10 minutes. Next, the mixture was centrifuged at 1300 rpm (320 g) for 5 minutes. The precipitate was suspended in 1 mL of DPBS and 10,000 or more cells were measured with a flow cytometer EPICS XL (Beackman Coulter).

Biological Example 11

Internalization Analysis of EDG-1 Protein

Method:

By using EDG-1-overexpressing CHO cells, the internalization of EDG-1 protein due to the stimulation with test compounds was observed in accordance with a method reported in *FASEB*, 18, 551-553 (2004).

FORMULATION EXAMPLES

Formulation Examples carried out in the present invention are shown below.

Formulation Example 1

3-[3-(4-(5-Phenylpentyloxy)phenyl)propylamino]propanoic acid (100 g), calcium carboxymethylcellulose (disintegrant, 20.0 g), magnesium stearate (lubricant, 10.0 g) and microcrystalline cellulose (870 g) were mixed in a conventional manner, punched them out to give 10,000 tablets each containing 10 mg of the active ingredient.

Formulation Example 2

3-[3-(4-(5-Phenylpentyloxy)phenyl)propylamino]propanoic acid (200 g), mannitol (2 kg) and distilled water (50 L) were mixed in a conventional manner. Then the solution was filtered through a dustproofing filter, and then 5 ml aliquots were charged into ampoules, which were autoclaved to give 10,000 ampoules each containing 20 mg of the active ingredient.

INDUSTRIAL APPLICABILITY

The present invention is applicable to drugs as will be described below.

The present invention compounds represented by formula (I), salts thereof, solvates thereof or prodrugs thereof are compounds having an ability to bind to an S1P receptor, in particular EDG-6 and exhibit prolonged pharmacological action. Therefore, they are useful as preventives and/or remedies in mammals, in particular, humans for rejection in transplantation, rejection of a transplanted organ, transplantation versus host disease, autoimmune diseases (systemic lupus erythematosus, rheumatoid arthritis, myasthenia gravis and the like), allergic diseases (atopic dermatitis, asthma and the like), inflammation, infection, ulcer, lymphoma, malignant tumor, leukemia, diseases associated with lymphocyte infiltration into a tissue and the like.

In addition to the ability to bind to EDG-6, some of the present invention compounds have an agonistic activity against EDG-1 and, therefore, show an immunosuppressant effect and prolonged pharmacological action. Due to these characteristics, they are more useful as preventives and/or remedies for rejection in transplantation, transplantation versus host disease, autoimmune diseases, allergic diseases and the like.

The invention claimed is:
1. A compound represented by formula (IA-2-1):

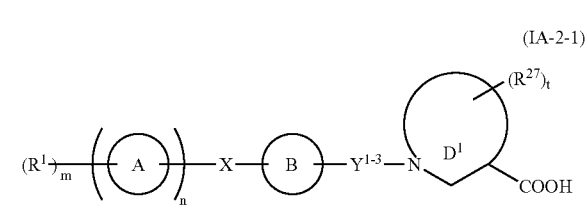

wherein ring A represents a cyclic group;
ring B represents a dihydronaphthalene group, an indene group, or a 6,7-dihydro-5H-benzo[7]annulene group which may further have a substituent(s);
X represents —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —O—, —$CH_2$—O—, —$(CH_2)_2$—O—, —$(CH_2)_3$—O—, —$(CH_2)_4$—O—, —$(CH_2)_5$—O—, —CH=CH—$CH_2$—O— or -cyclopropylene-$CH_2$—O—, which each may be substituted, in which the right side of each group is bound to ring B;
ring $D^1$ represents a nitrogen-containing heterocyclic group;
$Y^{1-3}$ represents methylene which may have a substituent(s), ethylene which may have a substituent(s), propylene which may have a substituent(s) or propenylene which may have a substituent(s);
$R^{27}$ represents a hydrogen atom, a halogen atom, or C1-4 alkyl which may be substituted with 1 to 3 halogen atoms;
t is 0 or an integer of 1 to 5;
$R^1$ represents a substituent of ring A;
n represents 1;
m is 0 or an integer of 1 to 7, and when m is 2 or more, plural $R^1$s are the same or different;
when X is —O— or —$CH_2$—O— and ring A is phenyl, m is an integer of 1 to 5, or a salt thereof.

2. The compound according to claim 1, wherein ring A is a benzene, indane, indene or naphthalene ring.

3. The compound according to claim 1, wherein $Y^{1-3}$ is —$CH_2$—, —$(CH_2)_2$—, or —$(CH_2)_3$—, which each may be substituted.

4. The compound according to claim 1, wherein the substituent represented by $R^1$ is a halogen atom, C1-20 alkyl which may be substituted, or C1-20 alkyloxy which may be substituted.

5. The compound according to claim 4, wherein the substituent represented by $R^1$ is fluoro, chloro, bromo, methyl, ethyl, propyl, butyl, trifluoromethyl or methoxy.

6. The compound according to claim 1, which is a compound represented by
formula (I-S-7a):

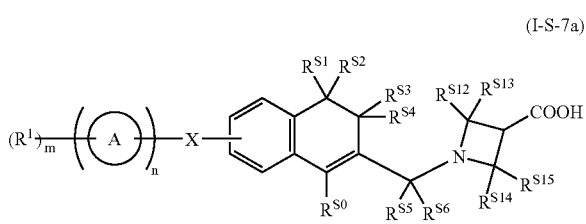

(I-S-7a)

wherein $R^{S0}$, $R^{S1}$, $R^{S2}$, $R^{S3}$, $R^{S4}$, $R^{S5}$ and $R^{S6}$ each independently represents a hydrogen atom, a halogen atom, or C1-4 alkyl which may be substituted with 1 to 3 halogen atom; $R^{S12}$, $R^{S13}$, $R^{S14}$ and $R^{S15}$ each independently represents a hydrogen atom, a halogen atom, or C1-4 alkyl which may be substituted with 1 to 3 halogen atoms; and other symbols have the same meanings as described in claim 1.

7. The compound according to claim 1, which is
(11) 1- {[1-methyl-6-(4-phenylbutoxy)-3,4-dihydro-2-naphthalenyl]methyl}-3-azetidinecarboxylic acid,
(14) 1-({6-[3-(4-chlorophenyl)propoxy]-1-methyl-3,4-dihydro-2-naphthalenyl}methyl)-3-azetidinecarboxylic acid, or
(15) 1-({6-[3-(4-chlorophenyl)propoxy]-1-methyl-3,4-dihydro-2-naphthalenyl}methyl)-3-azetidinecarboxylic acid.

8. A pharmaceutical composition which comprises a compound represented by formula (IA-2-1) in claim 1, or a salt thereof.

9. The pharmaceutical composition according to claim 8, which is an S1P receptor binding agent.

10. The pharmaceutical composition according to claim 9, which is an EDG-6 binding agent which may have an ability to bind to EDG-1.

11. The pharmaceutical composition according to claim 10, wherein the EDG-6 binding agent which may have an ability to bind to EDG-1 is an EDG-6 agonist which may have an agonistic activity against EDG-1.

12. The pharmaceutical composition according to claim 8, which is an agent for preventing and/or treating a disease related to EDG-1 and/or EDG-6.

13. The pharmaceutical composition according to claim 12, wherein the disease related to EDG-1 and/or EDG-6 is rejection in transplantation, autoimmune disease and/or allergic disease.

14. The pharmaceutical composition according to claim 12, wherein the disease related to EDG-1 and/or EDG-6 is rejection in transplantation of kidney, liver, heart, lung, dermal graft, cornea, bone, bone marrow cells and/or pancreatic islet cells, collagen disease, systemic lupus erythematosus, rheumatoid arthritis, multiple sclerosis, psoriasis, inflammatory bowel disease, Crohn's disease, autoimmune diabetes, lung fibrosis, atopic dermatitis and/or asthma.

15. The pharmaceutical composition according to claim 8, which is an immunosuppressant agent.

16. The pharmaceutical composition according to claim 8, which is an agent causing lymphopenia.

17. A medicament comprising the compound represented by formula (IA-2-1) according to claim 1, or a salt thereof in combination with one or at least two selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent and an antifungal agent.

18. An immunosuppressant agent and/or an agent causing lymphopenia, which comprises a compound represented by formula (IA-2-1) according to claim 1 or a salt thereof which has an ability to bind to EDG-6 and may have an ability to bind to EDG-1.

19. The immunosuppressant agent and/or the agent causing lymphopenia according to claim 18, which is an agent for preventing and/or treating rejection in transplantation, autoimmune disease and/or allergic disease.

20. A method for treating a disease related to EDG-1 and/or EDG-6 in a mammal, which comprises administering to the mammal an effective amount of the compound represented by formula (IA-2-1) according to claim 1, or a salt thereof wherein the disease is rejection in transplantation of kidney, liver, heart, lung, dermal graft, cornea, bone, bone marrow cells, pancreatic islet cells, collagen disease, systemic lupus erythematosus, rheumatoid arthritis, multiple sclerosis, lupus nephritis, lymphoma, malignant tumor, psoriasis, inflammatory bowel disease, Crohn's disease, autoimmune diabetes, lung fibrosis, atopic dermatitis and/or asthma.

21. A method for immune suppression and/or lymphopenia in a mammal, which comprises administering to the mammal an effective amount of the compound represented by formula (IA-2-1) according to claim 1, or a salt thereof.

* * * * *